United States Patent
Bravo-Altamirano et al.

(10) Patent No.: US 10,182,568 B2
(45) Date of Patent: Jan. 22, 2019

(54) USE OF PICOLINAMIDE COMPOUNDS AS FUNGICIDES

(71) Applicant: Dow AgroSciences LLC, Indianapolis, IN (US)

(72) Inventors: Karla Bravo-Altamirano, Indianapolis, IN (US); Yu Lu, Indianapolis, IN (US); Brian A. Loy, Indianapolis, IN (US); Zachary A. Buchan, Indianapolis, IN (US); David M. Jones, Indianapolis, IN (US); Jeremy Wilmot, Indianapolis, IN (US); Jared W. Rigoli, Indianapolis, IN (US); Kyle A. Dekorver, Indianapolis, IN (US); John F. Daeuble, Sr., Indianapolis, IN (US); Jessica Herrick, Indianapolis, IN (US); Xuelin Wang, Indianapolis, IN (US); Chenglin Yao, Indianapolis, IN (US); Kevin G. Meyer, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/036,316

(22) PCT Filed: Dec. 18, 2015

(86) PCT No.: PCT/US2015/066764
§ 371 (c)(1),
(2) Date: May 12, 2016

(87) PCT Pub. No.: WO2016/109257
PCT Pub. Date: Jul. 7, 2016

(65) Prior Publication Data
US 2017/0295792 A1 Oct. 19, 2017

Related U.S. Application Data

(60) Provisional application No. 62/098,120, filed on Dec. 30, 2014, provisional application No. 62/098,122, filed on Dec. 30, 2014.

(51) Int. Cl.
| | | |
|---|---|---|
| A01N 47/12 | (2006.01) |
| A01N 43/40 | (2006.01) |
| A01N 37/44 | (2006.01) |
| A01N 43/10 | (2006.01) |
| A01N 25/00 | (2006.01) |
| C07D 313/00 | (2006.01) |
| A01N 43/16 | (2006.01) |
| C07C 229/08 | (2006.01) |
| C07C 229/20 | (2006.01) |
| C07C 229/22 | (2006.01) |
| C07C 235/52 | (2006.01) |
| C07C 271/22 | (2006.01) |
| C07D 213/81 | (2006.01) |
| C07D 311/82 | (2006.01) |
| C07D 333/16 | (2006.01) |
| C07D 405/12 | (2006.01) |
| C07D 409/14 | (2006.01) |

(52) U.S. Cl.
CPC ............ *A01N 47/12* (2013.01); *A01N 25/00* (2013.01); *A01N 37/44* (2013.01); *A01N 43/10* (2013.01); *A01N 43/16* (2013.01); *A01N 43/40* (2013.01); *C07C 229/08* (2013.01); *C07C 229/20* (2013.01); *C07C 229/22* (2013.01); *C07C 235/52* (2013.01); *C07C 271/22* (2013.01); *C07D 213/81* (2013.01); *C07D 311/82* (2013.01); *C07D 313/00* (2013.01); *C07D 333/16* (2013.01); *C07D 405/12* (2013.01); *C07D 409/14* (2013.01)

(58) Field of Classification Search
CPC .................................................. C07C 313/00
See application file for complete search history.

(56) References Cited

U.S. PATENT DOCUMENTS

| | | |
|---|---|---|
| 4,051,173 A | 9/1977 | Schact et al. |
| 4,588,735 A | 5/1986 | Spatz |
| 5,342,835 A | 8/1994 | Pepin et al. |
| 5,401,871 A | 3/1995 | Feldmann-Krane et al. |
| 5,475,132 A | 12/1995 | Pepin et al. |
| 5,563,165 A | 10/1996 | Talley |
| 5,760,068 A | 6/1998 | Talley |
| 5,852,042 A | 12/1998 | Jakobi et al. |
| 6,355,660 B1 | 3/2002 | Ricks et al. |

(Continued)

FOREIGN PATENT DOCUMENTS

| | | |
|---|---|---|
| CL | 2015001862 | 10/2015 |
| CN | 101530104 | 9/2009 |

(Continued)

OTHER PUBLICATIONS

Gisi, U., The American Phytopathological Society, vol. 86, No. 11, 1996, p. 1273.

(Continued)

*Primary Examiner* — Paul V Ward
(74) *Attorney, Agent, or Firm* — Faegre Baker Daniels LLP

(57) ABSTRACT

This disclosure relates to picolinamides of Formula I and their use as fungicides.

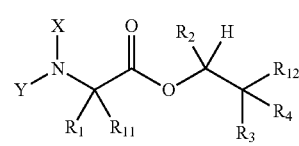

19 Claims, No Drawings

(56) References Cited

U.S. PATENT DOCUMENTS

| | | |
|---|---|---|
| 6,436,421 B1 | 4/2002 | Schindler et al. |
| 6,410,572 B1 | 6/2002 | Schelberger et al. |
| 6,521,622 B1 | 2/2003 | Ricks et al. |
| 6,706,740 B2 | 3/2004 | Ricks et al. |
| 6,861,390 B2 | 3/2005 | Meyer et al. |
| 6,916,932 B2 | 7/2005 | Meyer et al. |
| 6,927,225 B2 | 8/2005 | Ricks et al. |
| 6,953,807 B2 | 10/2005 | Hutin |
| 7,034,035 B2 | 4/2006 | Ricks et al. |
| 7,183,278 B1 | 2/2007 | Imamura et al. |
| 7,250,389 B1 | 7/2007 | Sakanaka et al. |
| RE39,991 E | 1/2008 | Ricks et al. |
| 7,442,672 B2 | 10/2008 | Muller et al. |
| 8,008,231 B2 | 8/2011 | Leatherman |
| 8,465,562 B2 | 6/2013 | Chen |
| 8,470,840 B2 | 6/2013 | Klittich et al. |
| 8,476,193 B2 | 7/2013 | Keeney et al. |
| 8,580,959 B2 | 11/2013 | Devasthale et al. |
| 8,604,215 B2 | 12/2013 | Phiasivongsa et al. |
| 8,785,479 B2 | 7/2014 | Meyer et al. |
| 8,835,462 B2 | 9/2014 | Meyer et al. |
| 8,883,811 B2 | 11/2014 | Owen et al. |
| 8,916,579 B2 | 12/2014 | Boebel et al. |
| 9,006,259 B2 | 4/2015 | Boebel et al. |
| 9,084,418 B2 | 7/2015 | Ehr et al. |
| 9,131,690 B2 | 9/2015 | Meyer et al. |
| 9,144,239 B2 | 9/2015 | Meyer et al. |
| 9,156,816 B2 | 10/2015 | Ito et al. |
| 9,179,674 B2 | 11/2015 | Martin et al. |
| 9,185,911 B2 | 11/2015 | Inami et al. |
| 9,198,419 B2 | 12/2015 | Owen et al. |
| 9,247,741 B2 | 2/2016 | DeLorbe et al. |
| 9,265,253 B2 | 2/2016 | Li et al. |
| 9,265,255 B2 | 2/2016 | Funke |
| 9,271,496 B2 | 3/2016 | Kemmitt |
| 9,271,497 B2 | 3/2016 | Lorsbach |
| 9,439,422 B2 | 9/2016 | Martin et al. |
| 9,482,661 B2 | 11/2016 | Ross |
| 9,549,555 B2 | 1/2017 | DeLorbe et al. |
| 9,549,556 B2 | 1/2017 | DeKorver et al. |
| 9,629,365 B2 | 4/2017 | Li et al. |
| 9,681,664 B2 | 6/2017 | LaLonde et al. |
| 9,686,984 B2 | 6/2017 | DeKorver et al. |
| 9,700,047 B2 | 7/2017 | Lu |
| 9,750,248 B2 | 9/2017 | Ouimette et al. |
| 9,840,475 B2 | 12/2017 | Lorsbach |
| 9,936,697 B2 | 4/2018 | Hopkins |
| 9,955,690 B2 | 5/2018 | Owen |
| 9,955,691 B2 | 5/2018 | Boebel |
| 9,974,304 B2 | 5/2018 | DeKorver |
| 2002/0119979 A1 | 8/2002 | Degenhardt et al. |
| 2002/0177578 A1 | 11/2002 | Ricks et al. |
| 2003/0018012 A1 | 1/2003 | Ricks et al. |
| 2003/0018052 A1 | 1/2003 | Ricks et al. |
| 2003/0022902 A1 | 1/2003 | Ricks et al. |
| 2003/0022903 A1 | 1/2003 | Ricks et al. |
| 2004/0034025 A1 | 2/2004 | Ricks et al. |
| 2004/0048864 A1 | 3/2004 | Ricks et al. |
| 2004/0171838 A1 | 9/2004 | Meyer et al. |
| 2004/0186296 A1 | 9/2004 | Niyaz et al. |
| 2004/0192924 A1 | 9/2004 | Meyer et al. |
| 2005/0239873 A1 | 10/2005 | Hockenbery et al. |
| 2006/0040995 A1 | 2/2006 | Bacque et al. |
| 2006/0167281 A1 | 7/2006 | Meijer |
| 2007/0010401 A1 | 1/2007 | Noon |
| 2007/0060579 A1 | 3/2007 | Wachendorff-Neumann et al. |
| 2007/0066629 A1 | 3/2007 | Tormo i Biasco et al. |
| 2008/0070985 A1 | 3/2008 | Derrer et al. |
| 2008/0293798 A1 | 11/2008 | Dietz |
| 2008/0318785 A1 | 12/2008 | Koltzenburg |
| 2009/0203770 A1 | 8/2009 | Hockenberry et al. |
| 2009/0306142 A1 | 12/2009 | Carson et al. |
| 2010/0016163 A1 | 1/2010 | Keiper et al. |
| 2011/0034493 A1 | 2/2011 | Boebel et al. |
| 2011/0053891 A1 | 3/2011 | Boebel et al. |
| 2011/0053966 A1 | 3/2011 | Klittich et al. |
| 2011/0070278 A1 | 3/2011 | Lopez |
| 2011/0082039 A1 | 4/2011 | Keeney et al. |
| 2011/0082160 A1 | 4/2011 | Owen |
| 2011/0082162 A1 | 4/2011 | Lorsbach et al. |
| 2011/0306644 A1 | 12/2011 | Hoekstra et al. |
| 2012/0035054 A1 | 2/2012 | Ehr et al. |
| 2012/0245031 A1 | 9/2012 | Gewehr et al. |
| 2013/0090298 A1 | 4/2013 | Lee et al. |
| 2013/0296371 A1 | 11/2013 | Meyer et al. |
| 2013/0296372 A1 | 11/2013 | Owen et al. |
| 2013/0296373 A1 | 11/2013 | Meyer |
| 2013/0296374 A1 | 11/2013 | Owen et al. |
| 2013/0296375 A1 | 11/2013 | Meyer et al. |
| 2014/0128411 A1 | 5/2014 | Ogawa et al. |
| 2014/0187587 A1 | 7/2014 | Ouimette et al. |
| 2014/0187588 A1 | 7/2014 | Lalonde et al. |
| 2014/0187590 A1 | 7/2014 | Ouimette et al. |
| 2014/0275171 A1 | 9/2014 | Meyer, Jr. et al. |
| 2014/0357713 A1 | 12/2014 | Damaj et al. |
| 2015/0065529 A1 | 3/2015 | Owen, Jr. et al. |
| 2015/0181868 A1 | 7/2015 | DeKorver et al. |
| 2015/0289508 A1 | 10/2015 | Meyer et al. |
| 2015/0322051 A1 | 11/2015 | Lu et al. |
| 2016/0007601 A1 | 1/2016 | Boebel et al. |
| 2016/0037774 A1 | 2/2016 | Schultz |
| 2016/0183526 A1 | 6/2016 | Hopkins et al. |
| 2016/0183527 A1 | 6/2016 | Hopkins et al. |
| 2016/0183528 A1 | 6/2016 | Hopkins et al. |
| 2017/0183324 A1 | 6/2017 | Li et al. |
| 2017/0360038 A1 | 6/2017 | Yao |
| 2017/0273303 A1 | 9/2017 | DeKorver et al. |
| 2017/0273306 A1 | 9/2017 | LaLonde et al. |
| 2017/0290333 A1 | 10/2017 | Bravo-Altamirano et al. |
| 2017/0369421 A1 | 12/2017 | Yao |
| 2018/0000075 A1 | 1/2018 | Bravo-Altamirano et al. |
| 2018/0000080 A1 | 1/2018 | Buchan et al. |
| 2018/0000084 A1 | 1/2018 | Yao |
| 2018/0000085 A1 | 1/2018 | Bravo-Altamirano et al. |
| 2018/0002288 A1 | 1/2018 | Buchan |
| 2018/0002319 A1 | 1/2018 | Wilmot |
| 2018/0002320 A1 | 1/2018 | Wilmot |
| 2018/0037541 A1 | 2/2018 | Yao |

FOREIGN PATENT DOCUMENTS

| | | |
|---|---|---|
| CN | 102638989 | 8/2012 |
| EP | 1054011 | 11/2000 |
| EP | 1516874 | 3/2005 |
| FR | 2649699 | 1/1991 |
| JP | 19940026884 | 9/1995 |
| JP | 1998053583 | 2/1998 |
| JP | H10-045747 | 2/1998 |
| WO | 1996010016 | 4/1996 |
| WO | 199637472 | 11/1996 |
| WO | 1997019908 | 6/1997 |
| WO | 199741103 | 11/1997 |
| WO | 1998018751 | 5/1998 |
| WO | 1999011127 | 11/1999 |
| WO | 2000076979 | 12/2000 |
| WO | WO 2001/014365 | 3/2001 |
| WO | WO 200114339 | 3/2001 |
| WO | WO 03/011857 | 2/2003 |
| WO | WO 03/035617 | 5/2003 |
| WO | 2005121069 | 12/2005 |
| WO | WO 2007017416 | 2/2007 |
| WO | 2008079387 | 7/2008 |
| WO | WO 2009040397 | 9/2008 |
| WO | WO 2011028657 | 3/2011 |
| WO | WO 2011044213 | 4/2011 |
| WO | WO 2011069893 | 6/2011 |
| WO | 2012020777 | 2/2012 |
| WO | WO 2012/016972 | 2/2012 |
| WO | WO 2012016989 | 2/2012 |
| WO | WO 2012070015 | 5/2012 |
| WO | WO 2013/110002 | 7/2013 |
| WO | WO 2013/116251 | 8/2013 |
| WO | 2014105844 | 7/2014 |
| WO | WO 2015/103161 | 7/2015 |

(56) References Cited

FOREIGN PATENT DOCUMENTS

| WO | 2016007525 | 1/2016 |
|---|---|---|
| WO | 2016109288 | 7/2016 |
| WO | 2016109289 | 7/2016 |
| WO | 2016109290 | 7/2016 |
| WO | 2016109291 | 7/2016 |
| WO | 2016109300 | 7/2016 |
| WO | 2016109301 | 7/2016 |
| WO | 2016109302 | 7/2016 |
| WO | 2016109303 | 7/2016 |
| WO | 2016109304 | 7/2016 |
| WO | 2016109305 | 7/2016 |
| WO | 2015005355 | 3/2017 |

OTHER PUBLICATIONS

Cantacuzene, D., "Optimization of the papain catalyzed esterification of amino acids by alcohols and diols," Tetrahedron, vol. 45, Issue 3 (1989), pp. 741-748.

Washburn, W.N., "Identification of a nonbasic melanin hormone receptor 1 antagonist as an antiobesity clinical candidate," Journal of Medicinal Chemistry, 57, 18 (Aug. 28, 2014), pp. 7509-7522.

Koyanagi et al., "Bioisoterism, etc.," Synthesis and Chemistry of Agrochemicals IV; Baker, D. et al., 1995, 15-24.

Masashi Ueki et al., "UK-2A, B, C, and D, Novel Antifungal Antibiotics from *Streptomyces* sp. 517-02 I. Fermentation, Isolation, and Biological Properties," The Journal of Antibiotics, vol. 49, No. 7, Jul. 1996, pp. 639-634.

K. Tani et al., Journal of Antibiotics, vol. 55, No. 3, Mar. 2002, pp. 315-321.

Y. Usuki et al., Journal of Antibiotics, vol. 55, No. 6, Jun. 2002, pp. 607-610.

Anonymous, Synergistic Fungicidal Composition of Heterocyclic Aromatic Amides and Triazoles, ip.com, Electronic Publication, 2004, 11 pages.

Anonymous, Synergistic Fungicidal Composition of Heterocyclic Aromatic Amides and Triazoles, ip.com Journal, ip.com, Inc., West Henrietta, NY, US, Jul. 2004, 10 pages.

Z. Hu et al., Synthesis of Novel Analogues of Antimycin A3, Tetrahedron Letters 49 (2008), pp. 5192-5195.

Usuki, et al., "Semi-synthesis and biological evaluation of analogues of UK-2A, a novel antifungal antibiotic from *Steptomyces* sp. 517-02," Bioorganic & Medicinal Chemistry Letters, Pergamon, Amsterdam, KL, vol. 15, No. 8, Apr. 15, 2005, pp. 2011-2014, XP027801790.

Pubchem, Substance Record for SID 74383515. Deposit Date Jun. 11, 2009 [retrieved on May 25, 2016] Retrieved from internet. <URL:https://pubchem.ncbi.nlm.nih.gov/substance/74383515#section=Top>.

International Searching Authority, International Search Report and Written Opinion for PCT/2015/066760, dated Apr. 14, 2016, 11 pages.

International Searching Authority, International Search Report and Written Opinion for PCT/2015/066764, dated Apr. 28, 2016, 11 pages.

BASF New Fungicide Xemium Got Full Approval in EU. Agronews. Jul. 18, 2012 [retrieved on Feb. 4, 2014]. Retrieved from the Internet: ,URL:http://news.agropages.com/News/NewsDetail---7386.htm.

Bolton, MD et al., Wheat leaf rust caused by Puccinia triticina. Molecular Plant Pathology, vol. 9, No. 5, 2008, pp. 563-575 [online] [retrieved on Feb. 3, 2016]. Retrieved from the Internet URL: https://www.researchgate.net/profile/Melvin_Bolton/publication/23483068_Wheat_leaf_rust_caused_by_Puccinia_triticina/links/0046352d94b8d5f2c9000000.pdf.

Davari, M. et al. ""Quantum Chemical Investigation of Intramolecular Thione-Thiol Tautomerism of 1, 2, 4-triazole-3-thione and its disubstituted derivatives,"" Journal of Molecular Modeling, Sep. 2009, 16(5), pp. 841-855.

FRAC Code List: Fungicides Sorted by Mode of Action (including FRAC Code numbering), Dec. 2008, pp. 1-10.

Fungicidal Mixtures, IP.com Prior Art Database Technical Disclosure, (Jul. 5, 2005), pp. 1-10, XP055073888, DOI: http://ip.com/pdf/ipcompad/IPCOM000126160D.pdf.

Kissling, Crop Protection Pipeline Value Jumps to Euro 2.4 Billion. BASF. Mar. 11, 2010 [retrieved on Feb. 4, 2014], Retrieved from the internet: ,URL:http://agro.basf.com/agri/AP-Internet/en/content/news_room/news/basf-crop-protection-pipeline-value.

Parker, J.E., et al., ""Mechanism of Binding of Prothioconazole to Mycosphaerella graminicola CYP51 Differs from That of Other Azole Antifungals,"" Applied and Environmental Microbiology, Feb. 2011, pp. 1460-1465.

Science for a Better Life, Bayer Cropscience, Jun. 2008, p. 22.

Sulfonate (http://www.hichem.com/product/showproduct.php?id=334639) Mar. 28, 2013, p. 1-4.

The Merck Index, Twelfth Edition, S. Budavari, Ed. Merck and Co., Whitehouse Station, NJ, 1996 pp. 2220, 3666, 7937 and 7946.

Websters New World Dictionary, 2nd college edition, The World Publishing Co., New York, p. 1127 (1972).

Wilson, C.L. et al. "Fruit Volatiles Inhibitory to Monilinia Fruiticola and Botrytis cinerea," 1987, Plant Disease 71: 316-319.

Huang, et al., Synergistic Interactions between Chitinase ChiCW and Fungicides Against Plant Fungal Pathogens, J. Microbiol. Biotechnol., 2008, 18(4) 784-787.

Backman, P., Fungicide Formulation: Relationship to Biological Activity, 1978, 16, 211-237.

Latin, et al, Re-Examining Fungicide Synergism for Dollar Spot Control, GCM, 2008, 84-87.

O'Sullivan, et al., Fungicide Resistance—an Increasing Problem, Proceedings of National Tillage Conference 2007, Published by Crop Research Centre Oak Park Carlow, date Jan. 31, 2007, 14 pages.

Guseynov et al: "Study of the reaction of aminoacetic acid with dihydric alcohols and production of epoxy esters" Chemical Problems, 2009 (1), pp. 188-190. English Machine Translation attached.

International Searching Authority, International Search Report PCT/US2000/021523 dated Jul. 7, 2001, 7 pages.

Database Chemabs Online, Chemical Abstracts Service, Columbus Ohio, US: accession No. CA63:16300d XP002164206 (Cited in International Search Report for PCT/US2000/021523).

Amiri et al. "Sensitivity of Botrytis cinerea field isolates to the novel succinate dehydrogenase inhibitors fluopyram, penthiopyrad, and fluxapuroxad". Annual Meeting of the American Phytopathological Society, Phytopathology, vol. 102 (2012).(Submitted in 3 Parts due to size limitations).

Cooke et al. "The effect of fungicide programmes based on epoxiconazole on the control and DMI sensitivity of Rhynchosporium secalis in winter barley." Crop Protection, vol. 23, No. 5, pp. 393-406 (2004).

Fujita T, Ed. "Quantitative structure-activity analysis and database-aided bioisosteric structural transformation procedure as methodologies of agrochemical design"; Classical and Three Dimensional QSAR in Agrochemistry, American Chemical Society Symposium Series, Washington, D.C. vol. 606, pp. 13-34 (1995).

Goellner et al. "Phakopsora pachyrhizi, the causal agent of Asian soybean rust." Molecular Plant Pathology, vol. 11, No. 2, pp. 169-177 (2010).

Kendall, S. et al. "Changes in sensitivity to DMI fungicides in Rhynchosporium secalis". Crop Protection, vol. 12, No. 5, pp. 357-362 (1993).

Lippard, S. "The Art of Chemistry". Nature, vol. 416, p. 587 (2002).

Patani et al. Biosterism: A rational approach in drug design. Chemical Reviews, vol. 96, No. 8, pp. 3147-3176 (1996).

Shimano et al. "Total synthesis of the antifungal dilactones UK-2A and UK-3A: The determination of their relative and absolute configurations, analog synthesis and antifungal activities". Tetrahedron, vol. 54, pp. 12745-12774 (1998).

Hanafi et al. "UK2A, B, C, and D, Novel Antifungal Antibiotics from *Streptomyces* sp 517-02 II. Structural Elucidation." The Journal of Antibiotics, vol. 49, Issue 12, pp. 1226-1231 (1996).

(56) References Cited

OTHER PUBLICATIONS

Shibata et al. "UK1, A Novel Cytotoxic Metabolite from *Streptomyces* sp. 517-02 II. Structural Elucidation." The Journal of Antibiotics, vol. 46, Issue 7, pp. 1095-1100 (1993).
Shimano et al. "Enantioselective Total Synthesis of the Antifungal Dilactone, UK-2A: The Determination of the Relative and Absolute Configurations". Tetrahedron Letters, vol. 39, pp. 4363-4366 (1998).
Ueki et al. "UK-3A, A Novel Antifungal Antibiotic from *Streptomyces* sp. 517-02: Fermentation, Isolation, Structural Elucidation and Biological Properties". The Journal of Antibiotics, vol. 50, Issue 7, pp. 551-555 (1997).
Ueki et al. "The mode of action of UK-2A and UK-3A, Novel antifungal antibiotics from *Streptomyces* sp. 517-02". The Journal of Antibiotics, vol. 50, Issue 12, pp. 1052-1057 (1997).
Ueki, M., et al., "UK-1, A Novel Cytotoxic Metabolite from *Streptomyces* sp. 517-02 I. Taxonomy, Fermentation, Isolation, Physico-chemical and Biological Properties." The Journal of Antibiotics, vol. 46, No. 7, pp. 1089-1094 (1993).
Stephenson, G., et al. "Glossary of terms relating to pesticides". Pure and Applied Chemistry, vol. 78, No. 11, pp. 2075-2154, International Union of Pure and Applied Chemistry (2006).
Chitwood, D. "Nematicides". Encyclopedia of Agrochemicals (3), pp. 1104-1115, John Wiley & Sons, New York, NY, http://naldc.nal.usda.gov/download/43874/PDF (2003).
International Searching Authority, International Search Report and Written Opinion for PCT/US14/58061 dated Dec. 15, 2014, 9 pages.
International Searching Authority, International Search Report and Written Opinion for PCT/US1458065 dated Dec. 22, 2014, 9 pages.
International Searching Authority, International Search Report and Written Opinion for PCT/US1528407 dated Aug. 5, 2015, 8 pages.
International Searching Authority, International Search Report and Written Opinion for PCT/US1539407 dated Sep. 30, 2015, 9 pages.
International Searching Authority, International Search Report and Written Opinion for PCT/US1544383 dated Mar. 16, 2016, 11 pages.
International Searching Authority, International Search Report and Written Opinion for PCT/US1567111 dated Mar. 11, 2016, 11 pages.
International Searching Authority, International Search Report and Written Opinion for PCT/US1567113 dated Mar. 11, 2016, 10 pages.
International Searching Authority, International Search Report and Written Opinion for PCT/US1567116 dated Mar. 7, 2016, 8 pages.
International Searching Authority, International Search Report and Written Opinion for PCT/US1567199 dated Mar. 11, 2016, 9 pages.
International Searching Authority, International Search Report and Written Opinion for PCT/US1567200 dated Mar. 10, 2016, 10 pages.
International Searching Authority, International Search Report and Written Opinion for PCT/US1567204 dated Mar. 7, 2016, 10 pages.
International Searching Authority, International Search Report and Written Opinion for PCT/US1567201 dated Mar. 11, 2016, 8 pages.
International Searching Authority, International Search Report and Written Opinion for PCT/US1567206 dated Mar. 7, 2016, 8 pages.
International Searching Authority, International Search Report and Written Opinion for PCT/US1567207 dated Mar. 11, 2016, 12 pages.
International Searching Authority, International Search Report and Written Opinion for PCT/US2013039726 dated Sep. 17, 2013, 9 pages.
International Searching Authority, International Search Report and Written Opinion for PCT/US2013039735 dated Oct. 18, 2013, 8 pages.
International Searching Authority, International Search Report and Written Opinion for PCT/US2013077472 dated Apr. 16, 2014, 9 pages.
International Searching Authority, International Search Report and Written Opinion for PCT/US2013077537 dated Apr. 16, 2014, 11 pages.
International Searching Authority, International Search Report and Written Opinion for PCT/US2014071692 dated Apr. 20, 2015, 6 pages.
International Searching Authority, International Search Report and Written Opinion for PCT/US2014071695 dated Apr. 17, 2015, 9 pages.
International Searching Authority, International Search Report and Written Opinion for PCT/US2014071699 dated Apr. 20, 2015, 6 pages.
International Searching Authority, International Search Report and Written Opinion for PCT/US2014071700 dated Apr. 17, 2015, 9 pages.
International Searching Authority, International Search Report and Written Opinion for PCT/US2015066760 dated Apr. 14, 2016, 11 pages.
International Searching Authority, International Search Report and Written Opinion for PCT/US2015066764 dated Apr. 28, 2016, 11 pages.
International Searching Authority, International Search Report and Written Opinion for PCT/US20150051598 dated Dec. 6, 2010, 5 pages.
International Searching Authority, International Search Report for PCT/US14/058067, dated Dec. 22, 2014, 4 pages.
International Searching Authority, Written Opinion for PCT/US14/058067, dated Dec. 22, 2014, 5 pages.
International Searching Authority, International Search Report for PCT/US14/058070, dated Dec. 15, 2014, 4 pages.
International Searching Authority, Written Opinion for PCT/US14/058070, dated Dec. 15, 2014, 5 pages.
International Searching Authority, International Search Report and Written Opinion for PCT/US2015/067115, dated Mar. 11, 2016, 6 pages.
International Searching Authority, International Search Report and Written Opinion for PCT/US1539409 dated Oct. 5, 2015, 10 pages.

USE OF PICOLINAMIDE COMPOUNDS AS FUNGICIDES

CROSS-REFERENCE TO RELATED APPLICATIONS

This application is a U.S. National Phase Patent Application based on International Application No. PCT/US2015/066764 filed Dec. 18, 2015, which claims the benefit of U.S. Provisional Patent Application Serial Nos. 62/098,120 filed Dec. 30, 2014 and 62/098,122 filed Dec. 30, 2014, which are expressly incorporated by reference herein.

BACKGROUND & SUMMARY

Fungicides are compounds, of natural or synthetic origin, which act to protect and/or cure plants against damage caused by agriculturally relevant fungi. Generally, no single fungicide is useful in all situations. Consequently, research is ongoing to produce fungicides that may have better performance, are easier to use, and cost less.

The present disclosure relates to picolinamides and their use as fungicides. The compounds of the present disclosure may offer protection against ascomycetes, basidiomycetes, deuteromycetes and oomycetes.

One embodiment of the present disclosure may include compounds of Formula I:

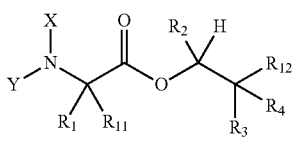

I in which: X is hydrogen or $C(O)R_5$;
Y is hydrogen, $C(O)R_5$, or Q;
Q is

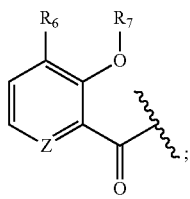

wherein: Z is N or CH;
$R_1$ is hydrogen or alkyl, each optionally substituted with 0, 1 or multiple $R_8$;
$R_2$ is methyl;
$R_3$ is chosen from aryl or heteroaryl, each optionally substituted with 0, 1 or multiple $R_8$;
$R_4$ is chosen from hydrogen, halo, hydroxyl, alkyl or alkoxy;
$R_5$ is chosen from alkoxy or benzyloxy, each optionally substituted with 0, 1, or multiple $R_8$;
$R_6$ is chosen from hydrogen, alkoxy, or halo, each optionally substituted with 0, 1, or multiple $R_8$;
$R_7$ is chosen from hydrogen, —$C(O)R_9$, or —$CH_2OC(O)R_9$;
$R_8$ is chosen from hydrogen, alkyl, aryl, acyl, halo, alkenyl, alkenyl, alkoxy, cyano or heterocyclyl, each optionally substituted with 0, 1, or multiple $R_{10}$;
$R_9$ is chosen from alkyl, alkoxy, or aryl, each optionally substituted with 0, 1, or multiple $R_8$;
$R_{10}$ is chosen from hydrogen, alkyl, aryl, acyl, halo, alkenyl, alkoxy, or heterocyclyl;
$R_{11}$ is chosen from hydrogen or alkyl, substituted with 0, 1, or multiple $R_8$;
$R_{12}$ is chosen from aryl or heteroaryl, each optionally substituted with 0, 1 or multiple $R_8$.

Another embodiment of the present disclosure may include a fungicidal composition for the control or prevention of fungal attack comprising the compounds described above and a phytologically acceptable carrier material.

Yet another embodiment of the present disclosure may include a method for the control or prevention of fungal attack on a plant, the method including the steps of applying a fungicidally effective amount of one or more of the compounds described above to at least one of the fungus, the plant, and an area adjacent to the plant.

It will be understood by those skilled in the art that the following terms may include generic "R"-groups within their definitions, e.g., "the term alkoxy refers to an —OR substituent". It is also understood that within the definitions for the following terms, these "R" groups are included for illustration purposes and should not be construed as limiting or being limited by substitutions about Formula I.

The term "alkyl" refers to a branched, unbranched, or saturated cyclic carbon chain, including, but not limited to, methyl, ethyl, propyl, butyl, isopropyl, isobutyl, tertiary butyl, pentyl, hexyl, cyclopropyl, cyclobutyl, cyclopentyl, cyclohexyl, and the like.

The term "alkenyl" refers to a branched, unbranched or cyclic carbon chain containing one or more double bonds including, but not limited to, ethenyl, propenyl, butenyl, isopropenyl, isobutenyl, cyclobutenyl, cyclopentenyl, cyclohexenyl, and the like.

The term "alkynyl" refers to a branched or unbranched carbon chain containing one or more triple bonds including, but not limited to, propynyl, butynyl, and the like.

The terms "aryl" and "Ar" refer to any aromatic ring, mono- or bi-cyclic, containing 0 heteroatoms.

The term "heterocyclyl" refers to any aromatic or non-aromatic ring, mono- or bi-cyclic, containing one or more heteroatoms.

The term "alkoxy" refers to an —OR substituent.
The term "acyloxy" refers to an —OC(O)R substituent.
The term "cyano" refers to a —C≡OH substituent.
The term "hydroxyl" refers to an —OH substituent.
The term "amino" refers to a —$N(R)_2$ substituent.
The term "arylalkoxy" refers to —$O(CH_2)_n Ar$ where n is an integer selected from the list 1, 2, 3, 4, 5, or 6.
The term "haloalkoxy" refers to an ORX substituent, wherein X is Cl, F, Br, or I, or any combination thereof.
The term "haloalkyl" refers to an alkyl, which is substituted with Cl, F, I, or Br or any combination thereof.
The term "halogen" or "halo" refers to one or more halogen atoms, defined as F, Cl, Br, and I.
The term "nitro" refers to a —$NO_2$ substituent.
The term thioalkyl refers to an —SR substituent.

Throughout the disclosure, reference to the compounds of Formula I is read as also including all stereoisomers, for example diastereomers, enantiomers, and mixtures thereof. In another embodiment, Formula I is read as also including salts or hydrates thereof. Exemplary salts include, but are not limited to: hydrochloride, hydrobromide, hydroiodide, trifluoroacetate, and trifluoromethane sulfonate.

It is also understood by those skilled in the art that additional substitution is allowable, unless otherwise noted, as long as the rules of chemical bonding and strain energy are satisfied and the product still exhibits fungicidal activity.

Another embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, and/or roots.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

DETAILED DESCRIPTION

The compounds of the present disclosure may be applied by any of a variety of known techniques, either as the compounds or as formulations comprising the compounds. For example, the compounds may be applied to the roots or foliage of plants for the control of various fungi, without damaging the commercial value of the plants. The materials may be applied in the form of any of the generally used formulation types, for example, as solutions, dusts, wettable powders, flowable concentrate, or emulsifiable concentrates.

Preferably, the compounds of the present disclosure are applied in the form of a formulation, comprising one or more of the compounds of Formula I with a phytologically acceptable carrier. Concentrated formulations may be dispersed in water, or other liquids, for application, or formulations may be dust-like or granular, which may then be applied without further treatment. The formulations can be prepared according to procedures that are conventional in the agricultural chemical art.

The present disclosure contemplates all vehicles by which one or more of the compounds may be formulated for delivery and use as a fungicide. Typically, formulations are applied as aqueous suspensions or emulsions. Such suspensions or emulsions may be produced from water-soluble, water-suspendible, or emulsifiable formulations which are solids, usually known as wettable powders; or liquids, usually known as emulsifiable concentrates, aqueous suspensions, or suspension concentrates. As will be readily appreciated, any material to which these compounds may be added may be used, provided it yields the desired utility without significant interference with the activity of these compounds as antifungal agents.

Wettable powders, which may be compacted to form water-dispersible granules, comprise an intimate mixture of one or more of the compounds of Formula I, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the cornpound(s) and milled.

Emulsifiable concentrates of the compounds of Formula I may comprise a convenient concentration, such as from about 1 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulfonic acids, oil-soluble salts or sulfated polyglycol ethers and appropriate salts of phosphated polyglycol ether.

Representative organic liquids which may be employed in preparing the emulsifiable concentrates of the compounds of the present disclosure are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, the methyl ether of triethylene glycol, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tuna oil and the like; esters of the above vegetable oils; and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 1 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle.

The compounds of Formula I can also be applied as granular formulations, which are particularly useful for applications to the soil. Granular formulations generally contain from about 0.5 to about 10 weight percent, based on the total weight of the granular formulation of the compounds), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting, and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulfosuccinic acids, ethoxylated organosilicones, ethoxylated fatty amines, blends of surfactants with mineral or vegetable oils, crop oil concentrate (mineral oil (85%)+emulsifiers (15%)); nonylphenol ethoxylate, benzyl-cocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrrate; emulsified methylated seed oil; tridecyl alcohol (synthetic) ethoxylate (8EO); tallow amine ethoxylate (15 EO); PEG(400) dioleate-99. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present disclosure in the medium selected for application, and not antagonistic to the activity of the present compounds. Accordingly, in such embodiments, the other pesticidal compound is employed as a supplemental toxicant for the same or for a different pesticidal use. The compounds of Formula I and the pesticidal compound in the combination can generally be present in a weight ratio of from 1:100 to 100:1.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank-mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, Ampelomyces quisqualis, azaconazole, azoxystrobin, *Bacillus subtilis, Bacillus subtilis* strain QST713, benalaxyl, benomyl, benthiavalicarb-isopropyl, benzovindiflupyr, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), coumoxystrobin, cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dipymetitrone, dithianon, dodemorph, dodemorph acetate, dodine, dodine free base, edifenphos, enestrobin, enestroburin, enoxastrobin, epoxiconazole, ethaboxam, ethoxyquin, etridiazole, famoxadone, fenamidone, fenaminostrobin, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flufenoxystrobin, flumorph, fluopicolide, fluopyram, fluoroimide, fluoxastrobin, fluquinconazole, flusilazole flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isofetamid, isoprothiolane, isopyrazam, isotianil, kasugamycin, kasugamycin hydrochloride hydrate, kresoxim-methyl, laminarin, mancopper, mancozeb, mandestrobin, mandipropamid, maneb, mefenoxam, mepanipyrim, mepronil, meptyl-dinocap, mercuric chloride; mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxathiapiprolin, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picarbutrazox, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyraziflumid, pyrazophos, pyribencarb, pyributicarb, pyrifenox, pyrimethanil, pyriofenone, pyrisoxazole, pyroquilon, quinoclamine, quinoxyfen, quintozene, *Reynouiria sachalinensis* extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofos-methyl, tolprocarb, tolylfluanid, triadimefon, triadimenol, triazoxide, triclopyricarb, tricyclazole, tridemorph, trilloxystrobin, triflumizole, triforine, triticonazole, validamycin, valifenalate, valiphenal, vinclozolin, zineb, ziram, zoxamide, *Candida aleophila, Fusarium oxysporum, Gliocladium* spp., *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithiine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme, ampropylfos, anilazine, azithiram, barium polysulfide, Bayer 32394, benodanil, benquinox, bentaluron, benzamacril, benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb, prothiocarb hydrochloride, pyracarbolid, pyridinitril, pyroxychlor, pyroxyfur, quinacetol, quinacetol sulfate, quinazamid, quinconazole, rabenzazole, salicylanilide SSF-109, sultropen, tecoram, thiadifluor, thicyofen, thiochloifenphim, thiophanate, thioquinox, tioxymid, triamiphos, triarimol, triazbutil, trichlamide, urbacid, zarilamid, and any combinations thereof.

Additionally, the compounds described herein may be combined with other pesticides, including insecticides, nematocides, miticides, arthropodicides, bactericides or combinations thereof that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank-mixed with the other pesticide(s) or applied sequentially with the other pesticide(s). Typical insecticides include, but are not limited to: 1,2-dichloropropane, abamectin, acephate, acetamiprid, acethion, acetoprole, acrinathrin, acrylonitrile, afidopyropen, alanycarb, aldicarb, aldoxycarb, aldrin, allethrin, allosarnidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluron, borax, boric acid, broflanilide, bromfenvinfos, brornocycien, bromo-DDT, brotnophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chloifenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, clacyfos, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclaniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicloromezotiaz, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepallethrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flometoquin, flonicamid, flubendiamide, flucofuron, flucycloxuron, flucythrinate, flufenerim, flufenoxuron, flufenprox, flufiprole, fluhexafon, flupyradifurone, fluvalinate, fonofos, formetanate, formetanate hydrochloride, formothion, formparanate, formparanate hydrochloride, fosmethilan, fospirate, fosthietan, furathiocarb, furethrin, gamma-cyhalothrin, gamma-HCH, halfenprox, halofenozide, HCH, HEOD, heptachlor, heptafluthrin, heptenophos, heterophos, hexaflurmuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kappa-bifenthrin, kappa-tefluthrin, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, momfluorothrin, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, promacyl, promecarb, propaphos, propetamphos, propoxur, prothidathion, prothiotos, prothoate, protrifenbute, pyflubumide, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyriminostrobin, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupitimfos, teflubenzuron, tefluthrin, temephos, TEPP, terallethrin, terbufos, tetrachloroethane, tetrachlorvinphos, tetramethrin, tetramethylfluthrin, tetraniliprole, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tioxazafen, tolfenpyrad, tralomethrin, transfluthrin, transpermethrin, triarathene, triazamate, triazophos, trichlorfon, trichlormetaphos-3, trichloronat, trifenofos, triflumezopyrim, triflumuron, trimethacarb, triprene, vamidothion, vaniliprole, XMC, xylylcarb, zeta-cypermethrin, zolaprofos, and any combinations thereof.

Additionally, the compounds described herein may be combined with herbicides that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank-mixed with the herbicide(s) or applied sequentially with the herbicide(s). Typical herbicides include, but are not limited to: 4-CPA; 4-CPB; 4-CPP; 2,4-D; 3,4-DA; 2,4-DB, 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclopyrimorate, cyclosulfamuron, cycloxydim, cycluron, cyhalofop, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosaur, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenquinotrione, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfron, fosamine, furyloxyfen, glufosinate, glufosinate-P, glyphosate, halauxifen, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, napropamide-M, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thiobencarb, tiafenacil, tiocarbazil, tioclorim, tolpyralate, topramezone, tralkoxydim, triafamone, tri-allate, triasulfuron, triaziflam, tribenuron, tricamba, triclopyr, tridiphane, truietazine, trifloxysulfuron, trifludimoxazin, trifluralin, triflusulfuron, trifop, trifopsime, trihydroxytriazine, trimeturon, tripropindan, tritac, tritosulfuron, vernolate, and xylachlor.

Another embodiment of the present disclosure is a method for the control or prevention of fungal attack. This method comprises applying to the soil, plant, roots, foliage, or locus of the fungus, or to a locus in which the infestation is to be prevented (for example applying to cereal or grape plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants.

It will be understood by those skilled in the art that the efficacy of the compound for the foregoing fungi establishes the general utility of the compounds as fungicides.

The compounds have broad ranges of activity against fungal pathogens. Exemplary pathogens may include, but are not limited to, causing agent of wheat leaf blotch (*Zymoseptoria tritici*), wheat brown rust (*Puccinia triticina*), wheat stripe rust (*Puccinia striiformis*), scab of apple (*Venturia inaequalis*), powdery mildew of grapevine (*Uncinula necator*), barley scald (*Rhynchosporium secalis*), blast of rice (*Pyricularia oryzae*), rust of soybean (*Phakopsora pachyrhizi*), glume blotch of wheat (*Leptosphaeria nodorum*), powdery mildew of wheat (*Blumeria graminis* f. sp. *tritici*), powdery mildew of barley (*Blumeria graminis* f. sp. *hordei*), powdery mildew of cucurbits (*Erysiphe cichoracearum*), anthracnose of cucurbits (*Colletotrichum lagenarium*), leaf spot of beet (*Cercospora beticola*), early blight of tomato (*Alternaria solani*), and spot blotch of barley (*Cochliobolus sativus*). The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, $g/m^2$).

Any range or desired value given herein may be extended or altered without losing the effects sought, as is apparent to the skilled person for an understanding of the teachings herein.

The compounds of Formula I may be made using well-known chemical procedures. Intermediates not specifically mentioned in this disclosure are either commercially available, may be made by routes disclosed in the chemical literature, or may be readily synthesized from commercial starting materials utilizing standard procedures.

GENERAL SCHEMES

The following schemes illustrate approaches to generating picolinamide compounds of Formula I. The following descriptions and examples are provided for illustrative purposes and should not be construed as limiting in terms of substituents or substitution patterns.

Compounds of Formula 1.1, wherein $R_3$ and $R_{12}$ are as originally defined and are equivalent, can be prepared by the methods shown in Scheme 1, step a. The compound of Formula 1.0 can be treated with an organometallic nucleophile such as phenylmagnesium bromide (PhMgBr) in a polar aprotic solvent such as tetrahydrofuran (THF) at a temperature of about 0° C. to 23° C. to afford compounds of Formula 1.1, wherein $R_3$ and $R_{12}$ are as previously defined, as shown in a.

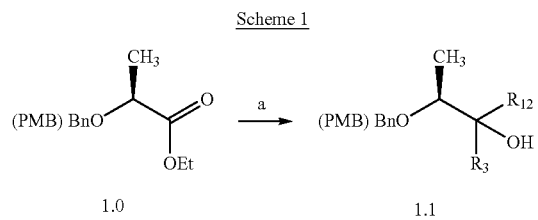

Scheme 1

Compounds of Formula 2.2, wherein $R_3$ is as originally defined and may or may not be equal to $R_{12}$, can be prepared by the methods shown in Scheme 2, steps a-c. Compounds of Formula 2.2, wherein $R_3$ and $R_{12}$ are as previously defined but not an electron-deficient aryl or heteroaryl group and may or may not be equivalent, can be obtained by treating the compounds of Formula 2.0, wherein $R_3$ and $R_{12}$ are as previously defined but not an electron-deficient aryl or heteroaryl group and may or may not be equivalent, with a mixture of a hydride reagent, such as triethylsilane (Et₃SiH), and an acid, such as 2,2,2-trifluoroacetic acid (TFA) in a halogenated solvent such as dichloromethane (DCM) at a temperature of about 0° C. to 23° C., as depicted in a. Alternatively, compounds of Formula 2.1, wherein $R_3$ and $R_{12}$ are an electron-deficient aryl or heteroaryl group and may or may not be equivalent, can be obtained by treating the compounds of Formula 2.0, wherein $R_3$ and $R_{12}$ are an electron-deficient aryl or heteroaryl group and may or may not be equivalent, with a base, such as sodium hydride (NaH), and a catalyst, such as imidazole, in a polar aprotic solvent such as THF at a temperature of about 23° C., followed by sequential addition of carbon disulfide (CS₂) and an alkyl iodide, such as iodomethane (MeI), as depicted in b. Compounds of Formula 2.2, wherein $R_3$ and $R_{12}$ are an electron-deficient aryl or heteroaryl group and may or may not be equivalent, can be obtained by treating the compounds of Formula 2.1, wherein $R_3$ and $R_{12}$ are as previously defined and may or may not be equivalent, with a tin reagent, such as tributyltin hydride, and a radical initiator, such as azobisisobutyronitrile (AIBN), in a nonpolar solvent such as toluene at a temperature of about 115° C., as depicted in c.

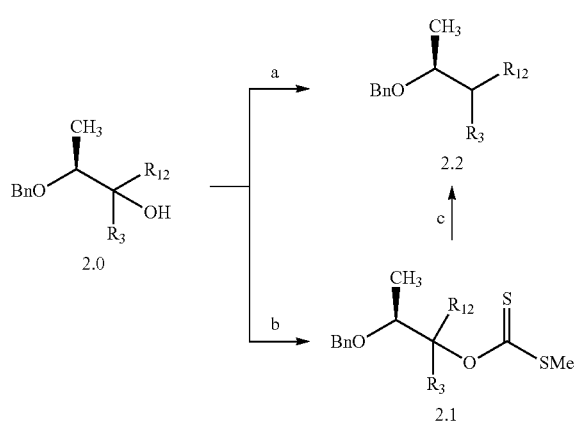

Compounds of Formula 3.1, wherein $R_3$ and $R_{12}$ are as originally defined and may or may not be equivalent, can be prepared according to the method outlined in Scheme 3, step a. Compounds of Formula 3.1, wherein $R_3$ and $R_{12}$ are as originally defined and may or may not be equivalent, can be prepared from compounds of Formula 3.0, wherein $R_3$ and $R_{12}$ are as previously defined and may or may not be equivalent, by treating with a base, such as NaH and an alkyl halide, such as MeI, in a polar aprotic solvent like N,N-dimethylformamide (DMF) at a temperature of about 0° C. to 23° C., as depicted in a.

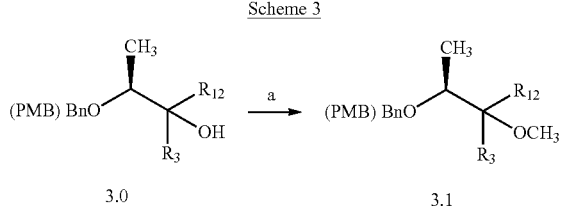

Compounds of Formula 4.1, wherein $R_3$ and $R_{12}$ are as originally defined and may or may not be equivalent, can be prepared according to the method outlined in Scheme 4, step a. Compounds of Formula 4.1, wherein $R_3$ and $R_{12}$ are as originally defined and may or may not be equivalent, can be prepared from compounds of Formula 4.0, wherein $R_3$ and $R_{12}$ are as previously defined and may or may not be equivalent, by treating with a fluorination reagent, such as (diethylamino)sulfur trifluoride (DAST), in a halogenated solvent such as DCM at a temperature of about 0° C. to 23° C., as depicted in a.

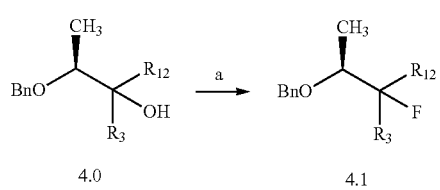

Compounds of Formula 5.3, wherein $R_3$, $R_4$, and $R_{12}$ are as originally defined and $R_3$ may or may not be equivalent to $R_{12}$, can be prepared according to the methods outlined in Scheme 5, steps a-c. Compounds of Formula 5.3, wherein $R_3$, $R_4$, and $R_{12}$ are as originally defined and $R_3$ may or may not be equivalent to $R_{12}$, can be prepared from compounds of Formula 5.0, wherein $R_3$, $R_4$, and $R_{12}$ are as originally defined and $R_3$ may or may not be equivalent to $R_{12}$, by treating with a catalyst such as palladium on carbon (Pd/C) in a mixture of an unsaturated hydrocarbon solvent, such as cyclohexene, and a polar protic solvent, such as ethanol (EtOH), at an elevated temperature of about 65° C., as shown in a. Alternatively, compounds of Formula 5.3, wherein $R_3$ and $R_{12}$ are an electron-deficient aryl or heteroaryl group and may or may not be equivalent and $R_4$ is hydroxyl (OH) or alkoxy, can be obtained by treating compounds of Formula 5.1, wherein $R_3$, $R_4$, and $R_{12}$ are as previously defined and $R_3$ may or may not be equivalent to $R_{12}$, with a mixture of a hydride reagent, such as Et₃SiH, and an acid, such as TFA in a halogenated solvent such as DCM at a temperature of about 0° C. to 23° C., as indicated in b. Additionally, compounds of Formula 5.3, wherein $R_3$ and $R_{12}$ are as originally defined but not an electron-deficient aryl or heteroaryl group and may or may not be equivalent, and $R_4$ is a proton (H), can be obtained by treating the compounds of Formula 5.2, wherein $R_3$, $R_4$, and $R_{12}$ are previously defined and $R_3$ may or may not be equivalent to $R_{12}$, with a mixture of a hydride reagent, such as and an acid, such as TFA in a halogenated solvent such as DCM at a temperature of about 0° C. to 23° C., as depicted in c.

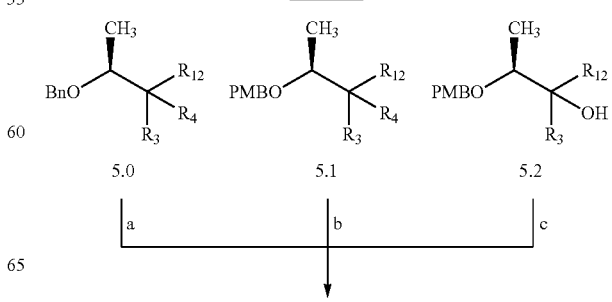

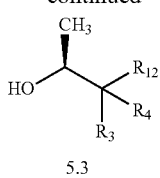

5.3

Compounds of Formula 6.2, wherein $R_3$ and $R_{12}$ are an electron-deficient aryl or heteroaryl group and equivalent, can be prepared according to the methods outlined in Scheme 6, steps a-b. Compounds of Formula 6.1, wherein $R_3$ and $R_{12}$ are as described previously, can be prepared from compound of Formula 6.0, by treating with an aryl bromide, such as 4-bromobenzonitrile, in the presence of a Pd catalyst, such as XPhos Pd G3 (CAS #1445085-55-1, commercially available from Sigma-Aldrich), in a polar aprotic solvent such as THF at a temperature of about 55° C., as indicated in a. Compounds of Formula 6.2, wherein $R_3$ and $R_{12}$ are as described previously, can be prepared from compound of Formula 6.1, wherein $R_3$ and $R_{12}$ are as described previously, by treating with a hydride reagent, such as borane dimethyl sulfide complex, in the presence of a catalyst, such as (R)-(+)-2-Methyl-CBS-oxazaborolidine, in a polar protic solvent, such as methanol (MeOH), at a temperature of about 0° C., as indicated in b.

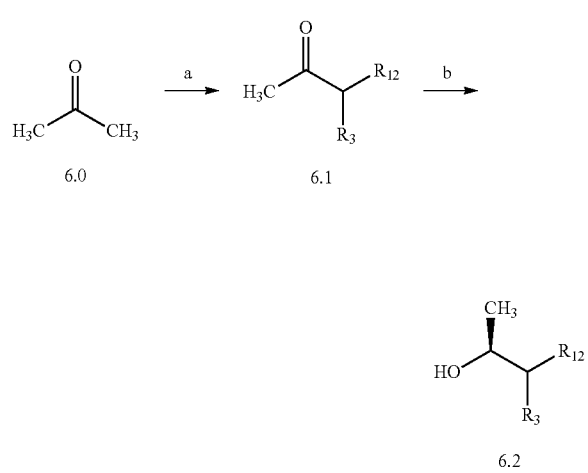

Compounds of Formula 7.2, wherein $R_3$ and $R_{12}$ are as originally defined and equivalent, can be prepared according to the methods outlined in Scheme 7, steps a-b. Compounds of Formula 7.1, wherein $R_3$ and $R_{12}$ are as described previously, can be prepared from compounds of Formula 7.0, by treating with a catalyst, such as $SbCl_5$, in a halogenated solvent such as DCM at a temperature of about 23° C., as indicated in a. Compounds of Formula 7.2, wherein $R_3$ and $R_{12}$ are as described previously, can be prepared from compound of Formula 7.1, wherein $R_3$ and $R_{12}$ are as described previously, by treating with a hydride reagent, such as borane dimethyl sulfide complex, in the presence of a catalyst, such as (R)-(+)-2-Methyl-CBS-oxazaborolidine, in a polar protic solvent, such as methanol (MeOH), at a temperature of about 23° C., as indicated in b.

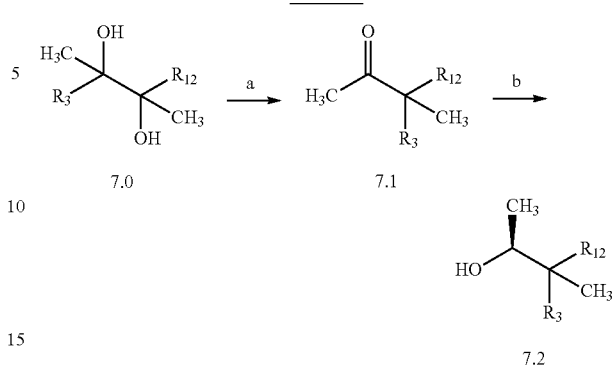

Compounds of Formula 8.1, wherein n is either 0 or 1, and W is either $CH_2$ or O, can be prepared according to the method outlined in Scheme 8, step a. Compounds of Formula 8.1, wherein n is either 0 or 1, and W is either $CH_2$ or O, can be prepared from compounds of Formula 8.0, wherein n is either 0 or 1, and W is either $CH_2$ or O, by treating with a base, such as n-butyllithium (n-BuLi), and an aldehyde, such as acetaldehyde, in a polar aprotic solvent such as THF at a temperature of about −78° C., to 23° C., as indicated in a.

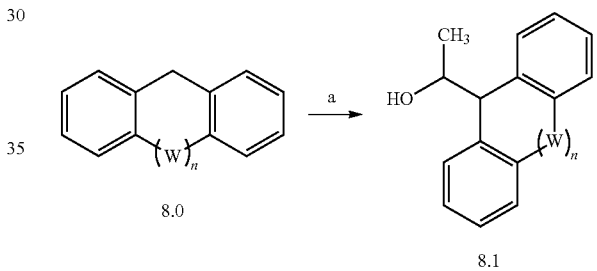

Compounds of Formula 9.1, wherein $R_3$ and $R_{12}$ are as originally defined, can be prepared according to the method outlined in Scheme 9, step a. Compounds of Formula 9.1, wherein $R_3$ and $R_{12}$ are as originally defined, can be prepared from compounds of Formula 9.0, wherein $R_3$ is as originally defined (Formula 9.0 is either commerically available, or could be prepared from asymmetric Shi epoxidation of the corresponding E-olefin precursor, as reported in Wang, Z.-X.; Tu, Y.; Frohn, M.; Zhang, Shi, Y. *J. Am. Chem. Soc.* 1997, 119, 11224), by treating with a pre-mixed suspension of a copper(I) salt, such as copper iodide (CuI), and an organometallic nucleophile, such as 4-(trifluoromethyl)phenylmagnesium bromide in a polar aprotic solvent such as THF, at a temperature of about −78° C. to 23° C., as shown in a.

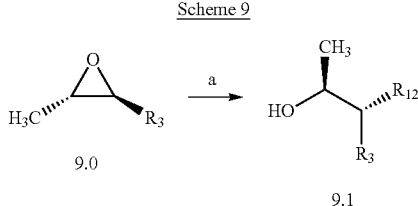

Compounds of Formula 10.2, wherein $R_1$, $R_2$, $R_3$, $R_4$ and $R_{12}$ are as originally defined, can be prepared according to the method outlined in Scheme 10, step a. Compounds of Formula 10.0, wherein $R_1$ is as originally defined, can be treated with alcohols of Formula 10.1, wherein $R_2$, $R_3$, $R_4$ and $R_{12}$ are as originally defined, and a coupling reagent such as 3-(ethyliminomethyleneamino)-N,N-dimethylpropan-1-amine hydrochloride (EDC), and a catalyst such as N,N-dimethylpyridin-4-amine (DMAP) in a halogenated solvent like DCM to afford compounds of Formula 10.2, wherein $R_1$, $R_2$, $R_3$, $R_4$ and $R_{12}$ are as previously defined, as shown in a.

Scheme 10

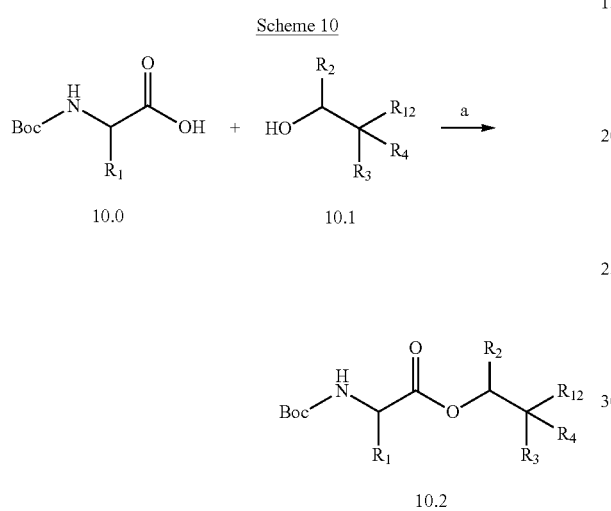

Compounds of Formula 11.2, wherein $R_1$, $R_2$, $R_3$, $R_4$, $R_6$, $R_{12}$ and Z are as originally defined, can be prepared according to the methods outlined in Scheme 11, steps a-b. As depicted in a, compounds of Formula 11.2, wherein $R_1$, $R_2$, $R_3$, $R_4$ and $R_{12}$ are as originally defined, can be subjected to an acid, such as a 4 normal (N) solution of hydrogen chloride (HCl) in dioxane, in a halogenated solvent such as DCM to afford compounds of Formula 9.0, wherein $R_1$, $R_2$, $R_3$, $R_4$ and $R_{12}$ are as originally defined, as shown in a.

Compounds of Formula 11.0, wherein $R_1$, $R_2$, $R_3$, $R_4$ and $R_{12}$ are as originally defined, can be treated with compounds of Formula 11.1, wherein $R_6$ and Z are as originally defined, in the presence of a base, such as diisopropylethylamine (DIPEA), and a peptide coupling reagent, such as benzotriazol-1-yl-oxytripyrrolidinophosphonium hexafluorophosphate (PyBOP), in an halogenated solvent like DCM, to afford compounds of Formula 11.2, wherein $R_1$, $R_2$, $R_3$, $R_4$, $R_6$, $R_{12}$ and Z are as originally defined, as shown in b.

Scheme 11

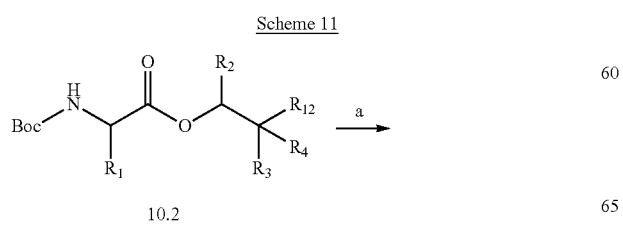

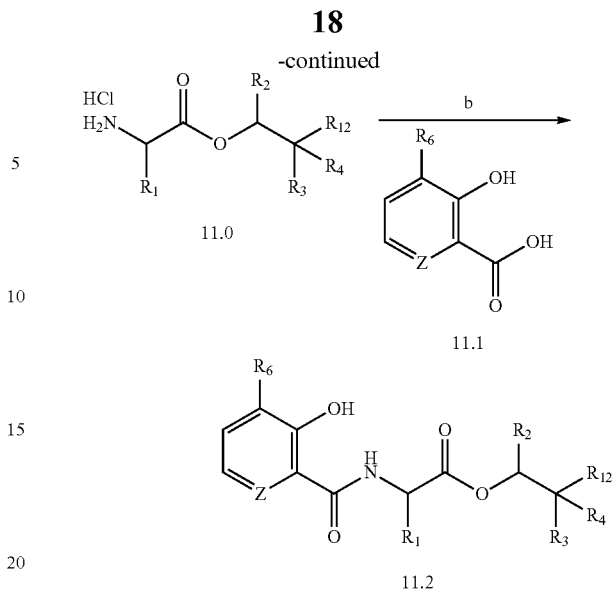

Compounds of Formula 12.0, wherein $R_1$, $R_2$, $R_3$, $R_4$, $R_6$, $R_7$, $R_{12}$ and Z are as originally defined, can be prepared according to the method outlined in Scheme 12, step a. As shown in a, compounds of Formula 11.2, wherein $R_1$, $R_2$, $R_3$, $R_4$, $R_6$, $R_{12}$ and Z are as originally defined, can be treated with an appropriate alkyl halide with or without a reagent such as sodium iodide (NaI) and an alkali carbonate base, such as sodium carbonate ($Na_2CO_3$) or potassium carbonate ($K_2CO_3$), in a solvent like acetone at a temperature of about 55° C., or by treatment with an acyl halide in the presence of an amine base, such as pyridine, triethylamine ($Et_3N$), DMAP, or mixtures thereof, in an aprotic solvent such as DCM, at a temperature of about 23° C., to afford compounds of Formula 12.0 wherein $R_1$, $R_2$, $R_3$, $R_4$, $R_6$, $R_7$, $R_{12}$ and Z are as originally defined.

Scheme 12

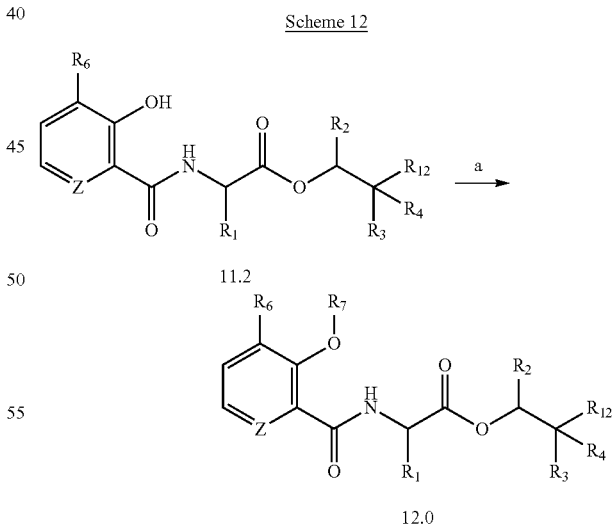

EXAMPLES

The chemistry in the following examples may be conducted using either enantiomer of 2-((tert-butoxycarbonyl)amino)propanoic acid (Boc-Ala-OH) or either protected (PMB or Bn) or unprotected enantiomer of ethyl lactate.

Example 1: Preparation of (S)-2-(benzyloxy)-1,1-bis(4-fluorophenyl)propan-1-ol

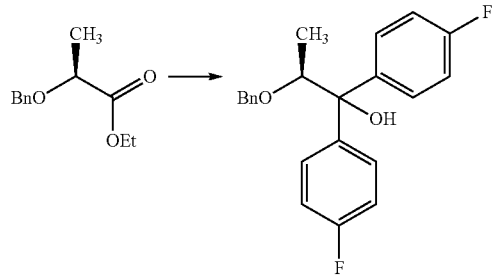 [SMILES: CCOC(=O)[C@H](C)OCc1ccccc1 ; C[C@H](OCc1ccccc1)C(O)(c1ccc(F)cc1)c1ccc(F)cc1]

To a solution of (S)-ethyl 2-(benzyloxy)propanoate (2.08 grams (g), 10.0 millimoles (mmol)) in tetrahydrofuran (THF; 20 milliliters (mL)) at 0° C. was slowly added (4-fluorophenyl)magnesium bromide (31.3 mL, 25.0 mmol, 0.8 molar (M) in THF) over a 10 minute (min) period. The reaction vessel was allowed to warm slowly to room temperature over 2 hours (h), and the reaction mixture was quenched by careful addition of saturated (sat.) aqueous (aq.) ammonium chloride ($NH_4Cl$; 50 mL). The mixture was diluted with diethyl ether ($Et_2O$; 50 mL), the phases were separated, and the aq. phase was extracted with $Et_2O$ (2×50 mL). The combined organic phases were washed with sat. aq. sodium chloride (NaCl, brine; 100 mL), dried over sodium sulfate ($Na_2SO_4$), filtered, and concentrated. The resulting oil was purified by flash column chromatography (silica gel ($SiO_2$), 0→5% acetone in hexanes) to afford the title compound (3.28 g, 93%) as a colorless oil: $^1$H NMR (300 MHz, $CDCl_3$) δ 7.47-7.38 (m, 2H), 7.38-7.27 (m, 5H), 7.17-7.09 (m, 2H), 7.04-6.89 (m, 4H), 4.64 (dd, J=11.4, 0.7 Hz, 1H), 4.51-4.38 (m, 2H), 3.12 (s, 1H), 1.11 (d, J=6.1 Hz, 3H); $^{19}$F NMR (376 MHz, $CDCl_3$) δ −116.19, −116.41; ESIMS m/z 377 ([M+Na]$^+$).

Example 2A: Preparation of (S)-4,4'-(2-(benzyloxy)propane-1,1-diyl)bis(fluorobenzene)

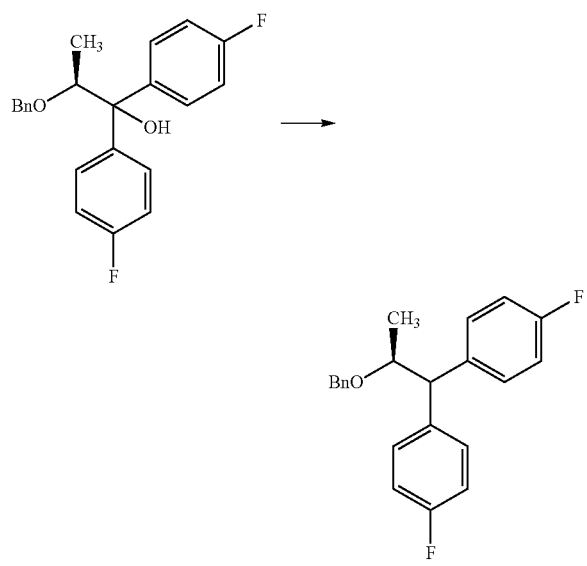

To a solution of (S)-2-(benzyloxy)-1,1-bis(4-fluorophenyl)propan-1-ol (709 milligrams (mg), 2.00 mmol) in dichloromethane (DCM; 20 mL) at 0° C. was added triethylsilane ($Et_3SiH$; 3.19 mL, 20.0 mmol) followed by 2,2,2-trifluoroacetic acid (TFA; 1.53 mL, 20.0 mmol). The mixture was stirred at 0° C. for 1 h. The resulting solution was quenched by careful addition of sat. aq. sodium bicarbonate ($NaHCO_3$; 20 mL). The phases were separated, and the aq. phase was extracted with DCM (2×30 mL). The combined organic phases were washed with brine (50 mL), dried over $Na_2SO_4$, filtered, and concentrated. The resulting oil was purified by flash column chromatography ($SiO_2$, 0→10% acetone in hexanes) to afford the title compound (627 mg, 92%) as a white solid: $^1$H NMR (400 MHz, $CDCl_3$) δ 7.31-7.22 (m, 5H), 7.21-7.16 (m, 2H), 7.10-7.03 (m, 2H), 7.00-6.91 (m, 4H), 4.54 (dd, J=11.5, 0.7 Hz, 1H), 4.31 (dd, J=11.6, 0.8 Hz, 1H), 4.14 (dq, J=8.1, 6.1 Hz, 3.93 (d, J=8.1 Hz, 1H), 1.18 (d, J=6.0 Hz, 3H); $^{19}$F NMR (376 MHz, $CDCl_3$) δ −116.60, −117.10; ESIMS (m/z) 361 ([M+Na]$^+$).

Example 2B: Preparation of (S)-(2-(benzyloxy)-1-methoxypropane-1,1-diyl)dibenzene

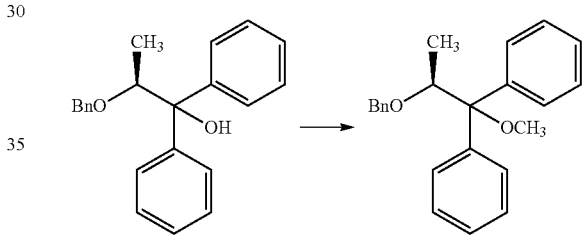

To a suspension of sodium hydride (NaH; 52.0 mg, 1.30 mmol, 60% weight per weight (w/w) in mineral oil) in N,N-dimethylformamide (DMF; 3 mL) at 0° C. was added a solution of (S)-2-(benzyloxy)-1,1-diphenylpropan-1-ol (318 mg, 1 mmol) in DMF (1 mL). The reaction mixture was stirred at room temperature for 30 min and then cooled to 0° C. Iodomethane (MeI; 93.0 microliters (μL), 1.50 mmol) was added, and the reaction mixture was stirred at room temperature for 1 h. The resulting solution was quenched by careful addition of sat. aq. $NaHCO_3$ (10 mL), The mixture was diluted with diethyl ether ($Et_2O$; 10 mL), the phases were separated, and the aq. phase was extracted with $Et_2O$ (2×10 mL). The combined organic phases were washed with brine (20 mL), dried over $Na_2SO_4$, filtered, and concentrated. The resulting oil was purified by flash column chromatography ($SiO_2$, 0→5% acetone in hexanes) to afford the title compound (295 mg, 89%) as a colorless oil: $^1$H NMR (400 MHz, $CDCl_3$) δ 7.47-7.41 (m, 2H), 7.40-7.35 (m, 2H), 7.33-7.18 (m, 11H), 4.69 (d, J=11.9 Hz, 1H), 4.54 (d, J=12.3 Hz, 1H), 4.50 (q, J=6.1 Hz, 1H), 3.13 (s, 3H), 1.10 (d, 6.1 Hz, 3H); $^{13}$C NMR (101 MHz, $CDCl_3$) δ 142.96, 141.31, 138.79, 129.13, 128.54, 128.14, 127.61, 127.16, 127.08, 126.95, 126.69, 99.99, 85.35, 78.13, 70.80, 52.46, 13.65; ESIMS (m/z) 333 ([M+H]$^+$).

Example 2C: Preparation of (S)-(2-(benzyloxy)-1-fluoropropane-1,1-diyl)dibenzene

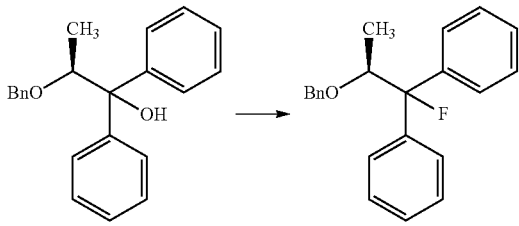 [SMILES: C[C@H](OCc1ccccc1)C(O)(c1ccccc1)c1ccccc1 ; C[C@H](OCc1ccccc1)C(F)(c1ccccc1)c1ccccc1]

To a solution of (S)-2-(benzyloxy)-1,1-diphenylpropan-1-ol (300 mg, 0.942 mmol) in DCM (5 mL) at 0° C. was added (diethylamino)sulfur trifluoride (DAST; 1.88 mL, 1.88 mmol, 1 M in DCM). The reaction was slowly warmed to room temperature over 3 h. The resulting solution was quenched by careful addition of sat. aq. NaHCO$_3$ (5 mL), The phases were separated, and the aq. phase was extracted with DCM (2×10 mL). The combined organic phases were washed with brine (10 mL), dried over Na$_2$SO$_4$, filtered, and concentrated. The resulting oil was purified by flash column chromatography (SiO$_2$, 0→10% acetone in hexanes) to afford the title compound (300 mg, 98%) as a colorless oil: $^1$H NMR (400 MHz, CDCl$_3$) δ 7.58-7.49 (m, 2H), 7.43-7.37 (m, 2H), 7.36-7.20 (m, 9H), 7.09-6.99 (m, 2H), 4.47 (d, J=11.7 Hz, 1H), 4.37-4.25 (m, 2H), 1.26 (dd, J=6.3, 1.3 Hz, 3H); $^{13}$C NMR (101 MHz, CDCl$_3$) δ 142.2.3 (d, J=22.7 Hz), 141.00 (d, J=23.5 Hz), 138.03, 128.21, 128.16, 127.90 (d, J=1.5 Hz), 127.80, 127.72 (d, J=1.7 Hz), 127.52, 127.42 (d, J=1.3 Hz), 126.2.3 (d, J=9.6 Hz), 125.93 (d, J=8.7 Hz), 99.96 (d, J=180.8 Hz), 78.91 (d, J=26.9 Hz), 71.68, 14.47 (d, J=3.6 Hz); $^{19}$F NMR (376 MHz, CDCl$_3$) δ −159.80.

Example 2D, Step 1: Preparation of (S)—O-(2-(benzyloxy)-1,1-bis(3,4,5-trifluorophenyl)propyl) S-methyl Carbonodithioate

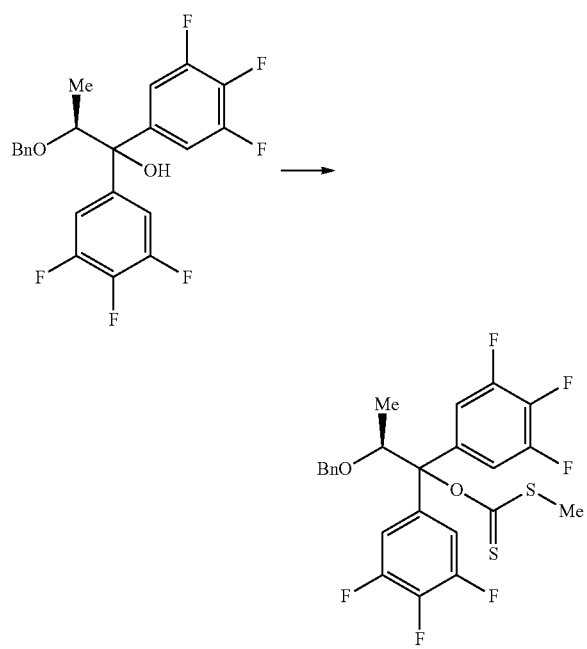

To a solution of (S)-2-(benzyloxy)-1,1-bis(3,4,5-trifluorophenyl)propan-1-ol (496 mg, 1.16 mmol) in anhydrous THF (5.8 mL) was added NeH (93.0 mg, 2.33 mmol), followed by imidazole (3.96 mg, 0.0580 mmol), and the reaction mixture was stirred at ambient temperature for 1 h. Carbon disulfide (562 µL, 9.30 mmol) was added via syringe in one portion, followed by MeI (579 µL, 9.30 mmol), and the reaction mixture was stirred at ambient temperature for 2 h. The reaction mixture was diluted with Et$_2$O (5 mL) and quenched with sat. aq, NH$_4$Cl (10 mL). The layers were separated, and the aq. layer was extracted with Et$_2$O (3×10 mL). The combined organic layers were dried over magnesium sulfate (MgSO$_4$), filtered and concentrated to afford an orange/brown oil. The crude oil was purified by flash column chromatography (SiO$_2$, 0→50% ethyl acetate (EtOAc) in hexanes) to afford the title compound (627 mg, 94%) as a clear, bright yellow colored oil: $^1$H NMR (400 MHz, CDCl$_3$) δ 7.40-7.27 (m, 3H), 7.24-7.16 (m, 2H), 7.02 (dd, J=9.1, 6.6 Hz, 2H), 6.96 (dd, J=8.8, 6.5 Hz, 2H), 5.44 (q, J=6.1 Hz, 1H), 4.66 (d, J=11.6 Hz, 1H), 4.51 (d, J=11.6 Hz, 1H), 2.49 (s, 3H), 1.16 (d, J=6.1 Hz, 3H); $^{19}$F NMR (376 MHz, CDCl$_3$) δ −133.89 (d, J=20.7 Hz), −134.73 (d, J=20.6 Hz), −159.83 (t, J=20.6 Hz), −160.56 (t, J=20.7 Hz); (Thin film) 2922, 1721, 1622, 1595, 1526, 1436, 1344, 1241, 1217, 1197, 1119, 1088, 1040, 965, 908, 861, 822, 730, 712, 697, 672 cm$^1$.

Example 2D, Step 2: Preparation of (S)-5,5'-(2-(benzyloxy)propane-1,1-diyl)bis(1,2,3-trifluorobenzene)

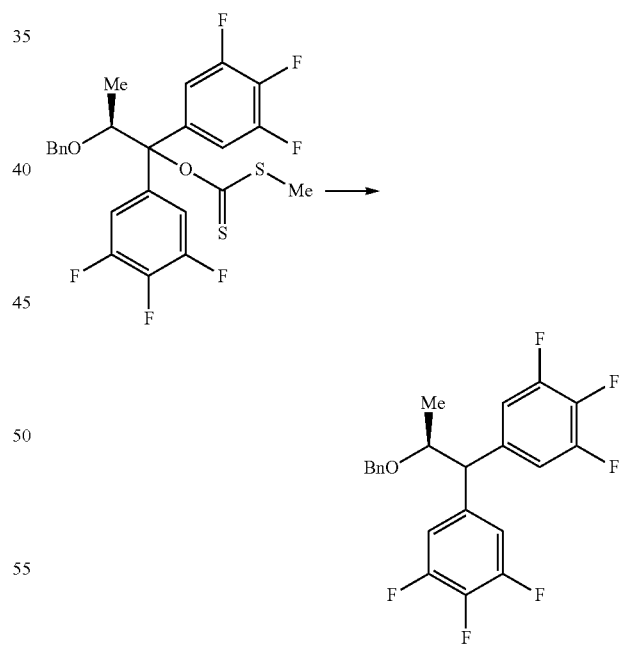

A solution of (S)—O-(2-(benzyloxy)-1,1-bis(3,4,5-trifluorophenyl)propyl) S-methyl carbonodithioate (598 mg, 1.16 mmol) in toluene (200 mL) was degassed by a freeze-pump-thaw procedure (3 cycles using liquid nitrogen (N$_2$)) under an atmosphere of N$_2$. Tributyltin hydride (3.12 mL, 11.6 mmol) was then added, the reaction flask was fitted with a reflux condenser, and the reaction mixture was heated to a light reflux (115° C.). A solution of azobisisobutyronitrile (AIBN; 0.200 g, 1.22 mmol) in degassed toluene (3 cycles via liquid N$_2$; 32 mL) was added via syringe down the reflux condenser over 3 h. Once slow addition of the AIBN was complete, the reaction mixture was stirred at reflux overnight. The solvent was removed in vacuo to provide a pale yellow oil. The crude oil was purified by flash column chromatography (SiO$_2$, 0→30% EtOAc in hexanes) to afford the title compound (358 mg, 72%) as a clear, colorless oil: $^1$H NMR (400 MHz, CDCl$_3$) 7.28 (d, J=6.6 Hz, 3H), 7.17-7.06 (m, 2H), 6.92 (dd, J8.5, 6.5 Hz, 2H), 6.79 (dd, J=8.3, 6.4 Hz, 2H), 4.59 (d, J=11.7 Hz, 1H), 4.31 (d, J=11.7 Hz, 1H), 4.02 (p, J=6.2 Hz, 1H), 3.76 (d, J=6.8 Hz, 1H), 1.19 (d, J=6.1 Hz, 3H); $^{19}$F NMR (376 MHz, CDCl$_3$) δ −133.80 (d, J=20.5 Hz), −134.34 (d, J=20.5 Hz), −162.54 (t, J=20.5 Hz), −162.84 (t, J=20.5 Hz); (Thin film) 2871, 1621, 1526, 1445, 1345, 1262, 1235, 1116, 1096, 1043, 859, 802, 728, 698, 679 cm$^{-1}$.

Example 3A: Preparation of (S)-1,1-bis(4-fluorophenyl)propan-2-ol

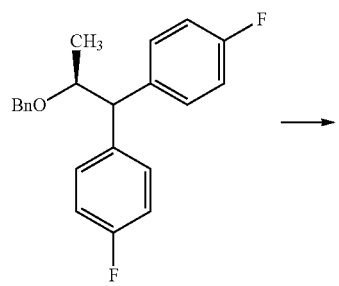

To a solution of (S)-4,4'-(2-(benzyloxy)propane-1,1-diyl) bis(fluorobenzene) (575 mg, 1.70 mmol) in ethanol (EtOH; 11 mL) and cyclohexene (5.5 mL) at room temperature was added palladium on carbon (Pd/C; 362 mg, 0.0850 mmol, 2.5% w/w of Pd). The reaction mixture was stirred at 65° C. for 2 h, cooled to room temperature, filtered through a plug of Celite®, and concentrated to afford the title compound (415 mg, 98%) as a colorless oil: $^1$H NMR (400 MHz, CDCl$_3$) δ 7.36-7.29 (m, 2H), 7.25-7.18 (m, 2H), 7.09-6.93 (m, 4H), 4.47 (dqd, J=8.2, 6.1, 3.3 Hz, 1H), 3.80 (d, J=8.3 Hz, 1H), 1.55 (d, J=3.3 Hz, 1H), 1.19 (d, J=6.1 Hz, 3H); $^{13}$C NMR (101 MHz, CDCl$_3$) δ 162.90 (d, J=23.1 Hz), 160.46 (d, J=23.1 Hz), 138.15 (d, J=3.1 Hz), 136.94 (d, J=3.6 Hz), 130.14 (d, J=7.8 Hz), 129.55 (d, J=7.8 Hz), 115.70 (d, J=18.8 Hz), 115.49 (d, J=18.8 Hz), 70.07, 58.61, 21.63; $^{19}$F NMR (376 MHz, CDCl$_3$) δ −115.84, −116.19.

Example 3B: Preparation of (S)-1,1-bis(2-fluorophenyl)propane-1,2-diol

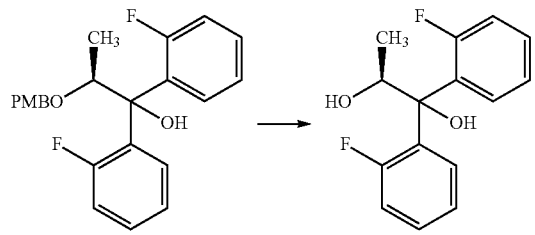

To a solution of (S)-1,1-bis(2-fluorophenyl)-2-((4-methoxybenzyl)oxy)propan-1-ol (790 mg, 2.06 mmol) in DCM (20 mL) at 0° C. was added Et$_3$SiH (3.28 mL, 20.6 mmol) followed by TFA (1.57 mL, 20.6 mmol). The mixture was stirred at 0° C. for 1 h. The resulting solution was quenched by careful addition of sat. aq, NaHCO$_3$ (20 mL). The phases were separated, and the aq. phase was extracted with DCM (2×30 mL). The combined organic phases were washed with brine (50 mL), dried over Na$_2$SO$_4$, filtered, and concentrated. The resulting oil was purified by flash column chromatography (SiO$_2$, 0→10% acetone in hexanes) to afford the title compound (388 mg, 71%) as a colorless oil: $^1$H NMR (400 MHz, CDCl$_3$) δ 7.90-7.77 (m, 1H), 7.70 (tt, J=8.2, 1.5 Hz, 1H), 7.31-7.10 (m, 4H), 6.97 (ddd, J=12.7, 8.1, 1.3 Hz, 1H), 6.88 (ddd, J=11.8, 8.0, 1.4 Hz, 1H), 5.11 (qd, J=6.3, 2.3 Hz, 1H), 3.49 (s, 1H), 2.27 (s, 1H), 1.09 (d, J=6.3 Hz, 3H); $^{19}$F NMR (376 MHz, CDCl$_3$) δ −112.90 (d, J=8.3 Hz), −113.92 (d, J=8.4 Hz); ESIMS (m/z) 551 ([2M+Na]$^+$).

Example 3C: Preparation of (S)-1,1-bis(4-bromophenyl)propan-2-ol

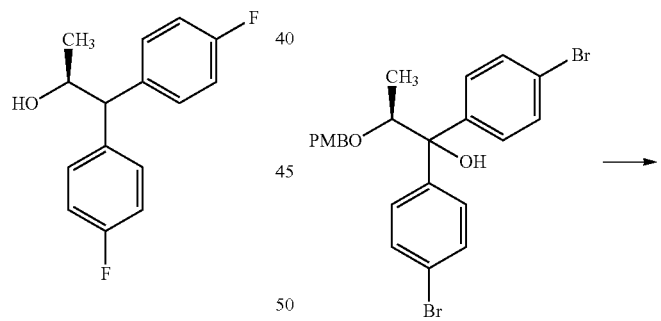

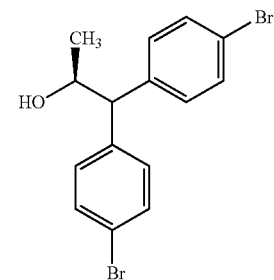

To a solution of (S)-1,1-bis(4-bromophenyl)-2-((4-methoxybenzyl)oxy)propan-1-ol (1.80 g, 3.56 mmol) in DCM (18 mL) at 0° C. was added. Et$_3$SiH (5.68 mL, 35.6 mmol) followed by TFA (2.72 mL, 35.6 mmol), The mixture was warmed slowly to room temperature over 3 h. The resulting solution was quenched by careful addition of sat. aq. NaHCO$_3$ (20 mL). The phases were separated, and the aq. phase was extracted with DCM (2×30 mL). The combined organic phases were washed with brine (50 mL), dried over Na$_2$SO$_4$, filtered, and concentrated. The resulting oil was purified by flash column chromatography (SiO$_2$, 0→10% acetone in hexanes) to afford the title compound (742 mg, 56%) as a colorless oil: $^1$H NMR (300 MHz, CDCl$_3$) δ 7.51-7.36 (m, 4H), 7.25-7.17 (m, 2H), 7.18-7.06 (m, 2H), 4.48 (dq, J=8.2, 6.1 Hz, 1H), 3.76 (d, J=8.2 Hz, 1H), 2.80 (s, 1H), 1.19 (d, J=6.2 Hz, 3H); $^{13}$C NMR (75 MHz, CDCl$_3$) δ 140.94, 139.85, 131.98, 131.85, 130.39, 129.84, 121.06, 120.72, 69.82, 58.91, 21.65; (Thin film) 3390, 3024, 2969, 2900, 1486, 1072 cm$^{-1}$.

Example 3D, Step 1: Preparation of (S)-1,1-bis(4-((trimethylsilyl)ethynyl)-phenyl)propan-2-ol

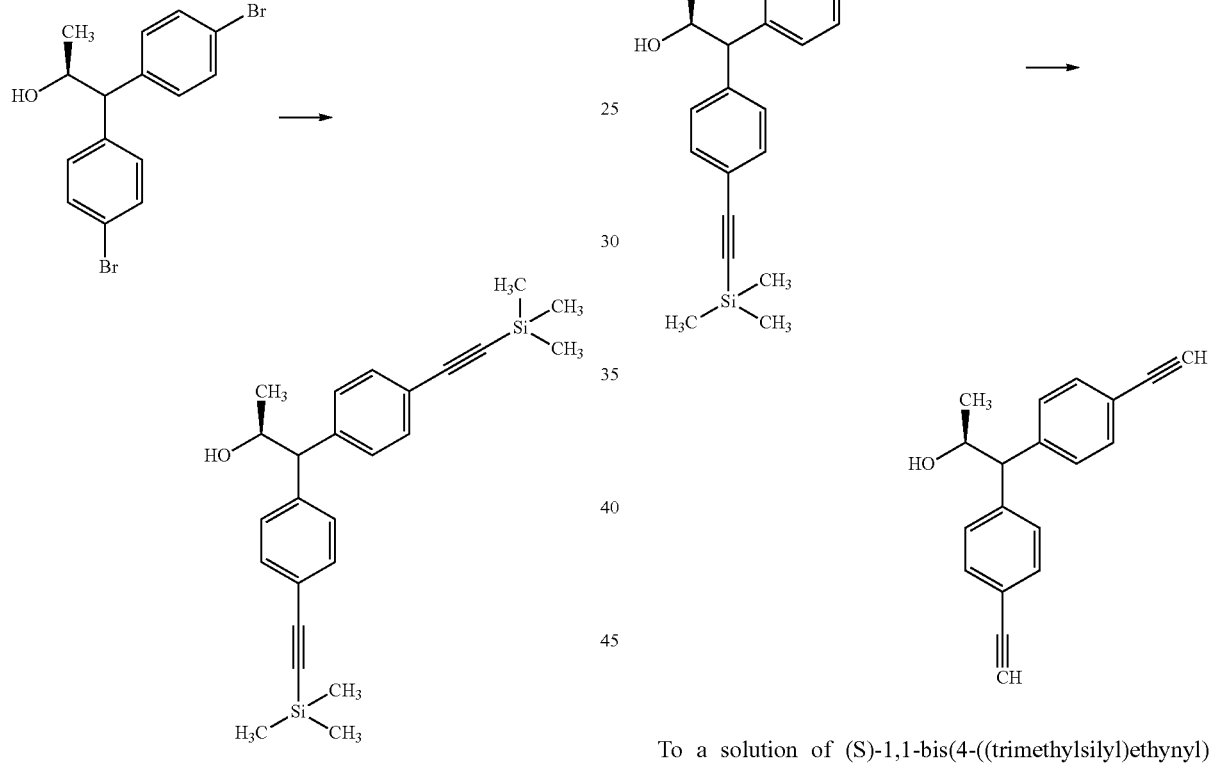

To a solution of (S)-1,1-bis(4-bromophenyl)propan-2-ol (1.01 g, 2.72 mmol) in THF (9 mL) was added bis(triphenylphosphine)palladium dichloride (0.095 g, 0.136 mmol) and copper(I) iodide (CuI; 0.026 g, 0.136 mmol). The mixture was sparged with N$_2$ for 20 min, and triethylamine (Et$_3$N; 4.53 mL) was added dropwise. To the resulting mixture was added ethynyltrimethylsilane (1.15 mL, 8.15 mmol) dropwise, and the mixture was heated to reflux and stirred overnight. The mixture was cooled to room temperature, and the reaction was quenched with sat. aq. NaHCO$_3$. The products were extracted with EtOAc (2×), and the combined organic layers were washed with brine, dried over Na$_2$SO$_4$, filtered and concentrated. The crude residue was then purified by flash column chromatography (SiO$_2$, 0→20% acetone in hexanes) to provide the title compound (495 mg, 45%) as a brown foam: $^1$H NMR (400 MHz, CDCl$_3$) δ 7.48-7.42 (m, 2H), 7.42-7.37 (m, 2H), 7.33-7.27 (m, 2H), 7.24-7.17 (m, 2H), 4.51 (dqd, J=12.2, 6.1, 3.5 Hz, 1H), 3.81 (d, J=8.3 Hz, 1H), 1.60 (d, J=3.8 Hz, 1H), 1.18 (d, J=6.1 Hz, 3H), 0.26 (s, 9H), 0.26 (s, 9H); $^{13}$C NMR (101 MHz, CDCl$_3$) δ 142.55, 141.48, 132.42, 132.29, 128.69, 128.15, 121.90, 121.57, 104.76, 104.71, 94.49, 94.33, 69.76, 59.96, 21.55, 0.00; (Thin film) 3397, 2960, 2156, 1501, 1248, 861, 840 cm$^{-1}$; HRMS-ESI (m/z) [M+H]$^+$ calcd for C$_{25}$H$_{33}$OSi$_2$, 405.2064; found, 405.2070.

Example 3D, Step 2: Preparation of (S)-1,1-bis(4-ethynylphenyl)propan-2-ol

To a solution of (S)-1,1-bis(4-((trimethylsilyl)ethynyl)phenyl)propan-2-ol (0.470 g, 1.16 mmol) in methanol (MeOH; 5.8 mL) was added potassium carbonate (K$_2$CO$_3$; 0.482 g, 3.48 mmol). The mixture was stirred for 1 h at room temperature and then filtered through Celite®. The filter cake was washed with MeOH, and the filtrate was concentrated. The crude material was purified by flash column chromatography (SiO$_2$, 0→20% acetone in hexanes) to provide the title compound (288 mg, 95%) as a yellow oil: $^1$H NMR (300 MHz, CDCl$_3$) δ 7.48-7.43 (m, 2H), 7.43-7.39 (m, 2H), 7.35-7.29 (m, 2H), 7.24-7.19 (m, 2H), 4.51 (dqd, J=8.3, 6.1, 3.7 Hz, 1H), 3.82 (d, J=8.3 Hz, 1H), 3.05 (s, 1H), 3.04 (s, 1H), 1.63-1.55 (m, 1H), 1.18 (d, J=6.1 Hz, 3H); $^{13}$C NMR (101 MHz, CDCl$_3$) δ 142.84, 141.82, 132.60, 132.48, 128.74, 128.22, 120.87, 120.57, 83.31, 83.29, 77.39, 77.29, 69.73, 59.96, 21.66; (Thin film) 3436, 3280, 2968, 2106, 1499, 1075, 825 cm$^{-1}$; HRMS-ESI (m/z) [M+H]$^+$ calcd for C$_{19}$H$_{17}$O, 261.1274; found, 261.1272.

Example 3D, Step 3: Preparation of (S)-1,1-bis(4-ethylphenyl)propan-2-ol

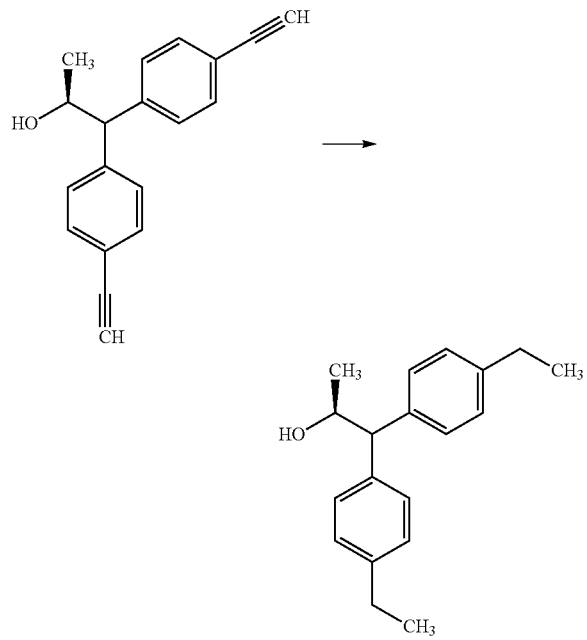

To a solution of (S)-1,1-bis(4-ethynylphenyl)propan-2-ol (0.144 g, 0.553 mmol) in EtOAc (2.8 mL) was added palladium (5% weight (wt) on carbon, dry basis; 0.235 g, 0.055 mmol). The mixture was stirred under a balloon of hydrogen overnight. The mixture was filtered through Celite®, and the filter cake was washed with EtOAc. The combined filtrate was then concentrated, and the crude residue was purified by flash column chromatography (SiO$_2$, 0→25% acetone in hexanes) to provide the title compound (97.0 mg, 65%) as a clear oil: $^1$H NMR (400 MHz, CDCl$_3$) δ 7.33-7.25 (m, 2H), 7.22-7.15 (m, 2H), 7.18-7.11 (m, 2H), 7.10 (d, J=8.1 Hz, 2H), 4.51 (dqd, J=8.7, 6.1, 2.5 Hz, 1H), 3.74 (d, J=8.9 Hz, 1H), 2.65-2.53 (m, 4H), 1.68 (d, J=2.8 Hz, 1H), 1.23-1.14 (m, 9H); $^{13}$C NMR (101 MHz, CDCl$_3$) δ 142.74, 142.33, 139.94, 138.91, 128.48, 128.40, 128.07, 128.02, 70.19, 60.02, 28.41, 28.39, 21.37, 15.47, 15.46; (Thin film) 3421, 2963, 1510, 1110, 821 cm$^{-1}$; HRMS-ESI (m/z) ([M+Na]$^+$) calcd for C$_{19}$H$_{24}$NaO, 291.1719; found, 291.1725.

Example 3E: Preparation of 1-(9H-xanthen-9-yl)ethanol

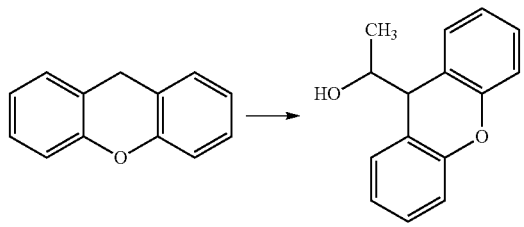 [SMILES: c1ccc2c(c1)Cc1ccccc1O2 ; CC(O)C1c2ccccc2Oc2ccccc21]

To a solution of 9H-xanthene (364 mg, 2.00 mmol) in THF (10 mL) at −78° C. was added n-butyllithium (2.5 M in hexanes; 0.880 mL, 2.20 mmol). The mixture was stirred at −78° C. for 30 min. Acetaldehyde (0.226 mL, 4.00 mmol) was added, and the reaction mixture was warmed slowly to room temperature overnight. The resulting solution was quenched by careful addition of sat. aq. NH$_4$Cl (10 mL). The phases were separated, and the aq. phase was extracted with Et$_2$O (2×15 mL). The combined organic phases were washed with brine (20 mL), dried over Na$_2$SO$_4$, filtered, and concentrated. The resulting oil was purified by flash column chromatography (SiO$_2$, 0→10% acetone in hexanes) to afford the title compound (216 mg, 48%) as a colorless oil: $^1$H NMR (400 MHz, CDCl$_3$) δ 7.33-7.22 (m, 4H), 7.17-7.04 (m, 4H), 3.99 (d, J=5.1 Hz, 1H), 3.96-3.82 (m, 1H), 1.54 (d, J=6.0 Hz, 1H), 1.00 (d, J=6.3 Hz, 3H); $^{13}$C NMR (101 MHz, CDCl$_3$) δ 152.94, 152.65, 129.54, 129.30, 128.19, 128.17, 123.18, 123.14, 122.48, 121.73, 116.59, 116.41, 73.07, 47.06, 18.81; ESIMS (m/z) 475 ([2M+Na]$^+$).

Example 3F: Preparation of (1S,2S)-1-phenyl-1-(4-(trifluoromethyl)phenyl)propan-2-ol

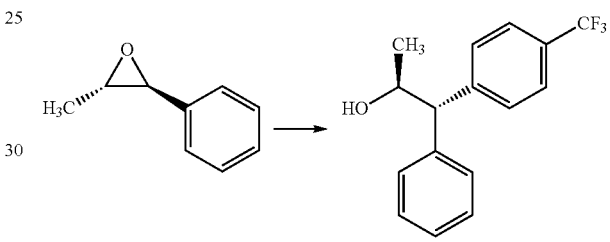

To a mixture of magnesium turnings (102 mg, 4.20 mmol) in Et$_2$O (4 mL) was added 1-bromo-4-(trifluoromethyl)benzene (0.588 mL, 4.20 mmol) at room temperature, followed by MeI (5 μL). Upon warming to a gentle boil using a heat gun, the mixture turned a yellow/brown color. The reaction was then stirred in a water bath at room temperature for 30 min until almost all the magnesium was consumed. This was added to a suspension of copper(I) iodide (CuI; 400 mg, 2.10 mmol) in Et$_2$O (4 mL) at −78° C. The reaction was stirred at −20° C. for 30 min, then cooled to −78° C., and (2S,3S)-2-methyl-3-phenyloxirane (0.201 mL, 1.50 mmol) was added. The resulting mixture was warmed slowly to room temperature overnight. The resulting solution was quenched by careful addition of sat. aq. NH$_4$Cl (10 mL). The phases were separated, and the aq. phase was extracted with Et$_2$O (2×1.5 mL). The combined organic phases were washed with brine (20 mL), dried over Na$_2$SO$_4$, filtered, and concentrated. The resulting oil was purified by flash column chromatography (SiO$_2$, 0→10% acetone in hexanes) to afford the title compound (390 mg, 94%) as a light yellow oil: $^1$H NMR (400 MHz, CDCl$_3$) δ 7.60-7.50 (m, 2H), 7.48-7.38 (m, 2H), 7.38-7.33 (m, 4H), 7.30-7.23 (m, 1H), 4.58 (dqd, J=8.4, 6.1, 3.5 Hz, 1H), 3.88 (d, J=8.5 Hz, 1H), 1.65 (d, J=3.6 Hz, 1H), 1.20 (d, J=6.1 Hz, 3H); $^{19}$F NMR (376 MHz, CDCl$_3$) δ −62.49; ESIMS (m/z) 263 ([M−OH]$^+$).

Example 3G, Step 1: Preparation of 4,4'-(2-oxopropane-1,1-diyl)dibenzonitrile

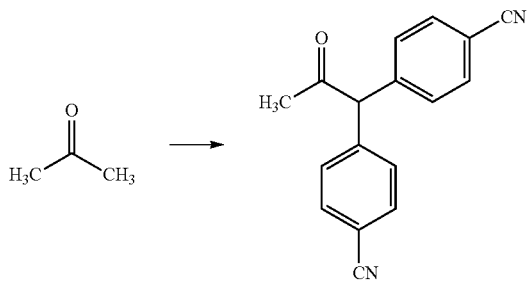

To a suspension of 4-bromobenzonitrile (546 mg, 3.00 mmol) and cesium carbonate (977 mg, 3.00 mmol) in THF (10 mL) under an $N_2$ atmosphere was added acetone (1.10 mL, 15.00 mmol), followed by X-Phos Pd G3 (50.8 mg, 0.060 mmol). Then, the vial was sealed and heated to 55° C. for 4 days. The reaction was diluted with EtOAc (30 mL) and washed with sat. $NH_4Cl$ (3×10 mL), water (15 mL), and brine (15 mL). Then the organic phase was dried over $Na_2SO_4$, filtered, and concentrated. The resulting oil was purified by flash column chromatography ($SiO_2$, 0→40% EtOAc in hexanes) to afford the title compound (174 mg, 22%) as a colorless oil: $^1$H NMR (400 MHz, $CDCl_3$) δ 7.66 (d, J=8.4 Hz, 4H), 7.34 (d, J=8.3 Hz, 4H), 5.21 (s, 1H), 2.29 (s, 3H); $^{13}$C NMR (101 MHz, $CDCl_3$) δ 203.68, 142.15, 132.75, 129.64, 118.21, 112.00, 64.25, 30.43; ESIMS m/z 261 ([M+H]$^+$).

Example 3G, Step 2: Preparation of (S)-4,4'-(2-hydroxypropane-1,1-diyl)dibenzonitrile

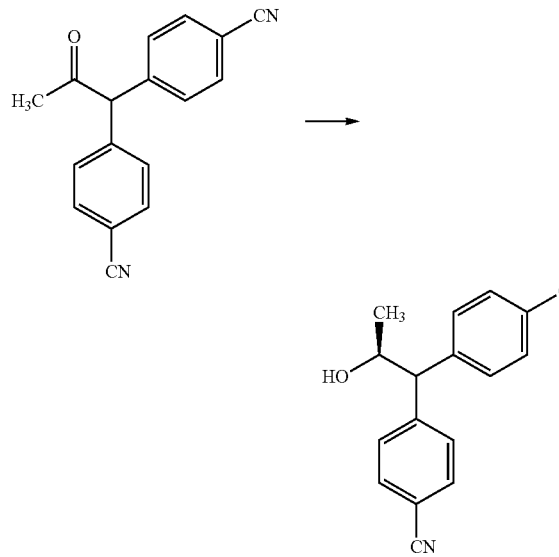

To a solution of 4,4'-(2-oxopropane-1,1-diyl)dibenzonitrile (174 mg, 0.668 mmol) in toluene (4.5 mL) was added (R)-1-methyl-3,3-diphenylhexahydropyrrolo[1,2-c][1,3,2]oxazaborole (1 M solution in toluene, 66.8 μL, 0.067 mmol). Then, the reaction was cooled to 0° C. and a solution of $BH_3$-DMS (69.8 μL, 0.735 mmol) in 0.5 mL toluene was added over 2 min. The flask was left to stir at 0° C. After 2 h, the reaction was quenched with methanol (0.5 mL), diluted with EtOAc and added water. Phases were separated and the aqueous phase was extracted with EtOAc×2. The combined organic phases were washed with brine (20 mL), dried over $Na_2SO_4$, filtered, and concentrated. The resulting oil was purified by flash column chromatography ($SiO_2$, 0→50% EtOAc in hexanes) to afford the title compound (99.7 mg, 57%) as a colorless oil: $^1$H NMR (400 MHz, $CDCl_3$) δ d 7.60 (dd, J=8.4, 6.8 Hz, 4H), 7.51-7.46 (m, 2H), 7.43-7.37 (m, 2H), 4.63-4.47 (m, 1H), 3.97 (d, J=7.5 Hz, 1H), 1.97 (d, J=3.8 Hz, 1H), 1.21 (d, J=6.2 Hz, 3H); $^{13}$C NMR (101 MHz, $CDCl_3$) δ 146.91, 145.86, 132.60, 132.45, 129.90, 129.19, 118.58, 118.51, 110.96, 110.92, 69.19, 59.56, 22.27; ESIMS m/z 263 ([M+H]$^+$).

Example 3H, Step 1: Preparation of 3,3-diphenylbutan-2-one

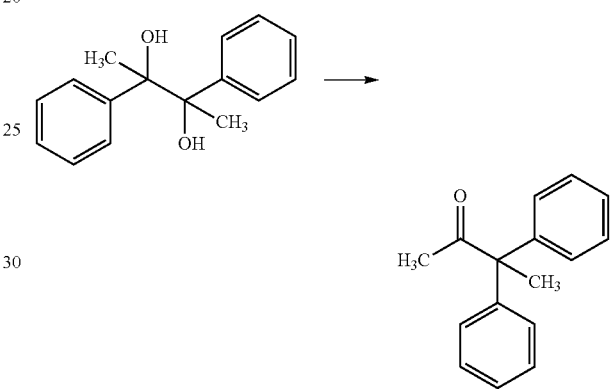

To a magnetically stirred mixture of 2,3-diphenylbutane-2,3-diol (500 mg, 2.06 mmol) in DCM (10 mL) was added antimony pentachloride (26.5 μL, 0.206 mmol) under air atmosphere. The reaction mixture was stirred at 25° C. for 1 h and then was quenched by slow addition of sat. aq. $NaHCO_3$. The resulting mixture was diluted with water and additional DCM, and the organic layer was separated by passing through a phase separator. The resulting oil was purified by flash column chromatography ($SiO_2$, 0→5% acetone in hexanes) to afford the title compound (330 mg, 71%) as a colorless oil: $^1$H NMR (400 MHz, $CDCl_3$) δ 7.36-7.31 (m, 4H), 7.30-7.25 (m, 2H), 7.23-7.15 (m, 4H), 2.11 (s, 3H), 1.87 (s, 3H); $^{13}$C NMR (101 MHz, $CDCl_3$) δ 209.16, 143.59, 128.36, 126.91, 62.32, 27.62, 26.42; ESIMS m/z 225 ([M+H]$^+$).

Example 3H, Step 2: Preparation of (S)-3,3-diphenylbutan-2-ol

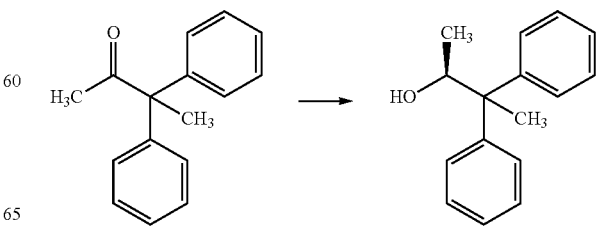

To a solution of 3,3-diphenylbutan-2-one (150 mg, 0.669 mmol) in toluene (4.5 mL) was added (R)-1-methyl-3,3-diphenylhexahydropyrrolo[1,2-c][1,3,2]oxazaborole (1 M solution in toluene, 134 µL, 0.134 mmol). Then, a solution of BH$_3$-DMS (70.2 µL, 0.702 mmol) in 0.5 mL of toluene was added to the reaction mixture over 2 min. The flask was left to stir at room temperature. After 1 h, the reaction was quenched with methanol (0.5 mL). DCM and water were added, and the phases were separated. The aqueous phase was extracted with DCM (2×). The combined organic phases were washed with brine (20 mL), dried over Na$_2$SO$_4$, filtered, and concentrated. The resulting oil was purified by flash column chromatography (SiO$_2$, 0→20% acetone in hexanes) to afford the title compound (150 mg, 99%) as a colorless oil: $^1$H NMR, (400 MHz, CDCl$_3$) δ d 7.39-7.17 (m, 10H), 4.70-4.61 (m, 1H), 1.67 (s, 3H), 1.51 (d, J=4.9 Hz, 1H), 1.11 (d, J=6.3 Hz, 3H); $^{13}$C NMR (101 MHz, CDCl$_3$) δ 147.30, 145.86, 128.40, 128.15, 128.05, 127.79, 126.20, 126.01, 72.28, 51.77, 23.26, 18.39; ESIMS m/z 227 ([M+H]$^+$).

Example 3I, Step 1: Preparation of (S)-1,1-bis(2,3-dimethoxyphenyl)propane-1,2-diol

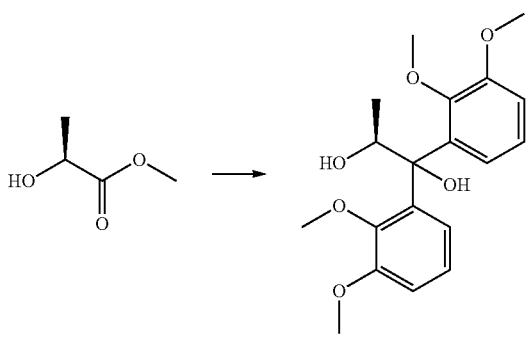

To a solution of isopropylmagnesium lithium chloride (1.3 M in THF, 6.1 mL, 8.00 mmol) was added. THF (2 mL) and 1-bromo-2,3-dimethoxybenzene (1.74 g, 8.00 mmol). The resulting brown solution was heated to a gentle reflux (75° C. external temp) for 2.5 h, then cooled to 0° C. in an ice water bath. (S)-methyl 2-hydroxypropanoate (0.191 ml, 2 mmol) was then added dropwise via syringe. The reaction was stirred at 0° C. for 1 h, then removed from the cold bath and stirred overnight at rt. The reaction was cooled to 0° C. in an ice water bath, diluted with water (20 mL), brine (20 mL), and Et$_2$O (40 mL), and was quenched with 1 N HCl (8 mL). The phases were separated, and the aqueous phase was extracted with Et$_2$O (20 mL). The organic phases were combined, dried over MgSO$_4$, filtered, and concentrated to provide an oil. Purification by automated silica gel column chromatography (5-50% EtOAc in hexanes) provided the title compound (568 mg, 82%) as a yellow, crystalline solid: $^1$H NMR (300 MHz, CDCl$_3$) δ 7.43 (td, J=8.0, 1.5 Hz, 2H), 7.11 (td, J=8.1, 4.9 Hz, 2H), 6.83 (dd, J=8.1, 1.4 Hz, 2H), 5.06-4.82 (m, 1H), 4.74 (d, J=1.2 Hz, 1H), 3.81 (s, 3H), 3.80 (s, 3H), 3.20 (s, 3H), 3.04 (s, 3H), 2.86 (d, J=9.5 Hz, 1H), 0.97 (d, J=6.4 Hz, 3H); $^{13}$C NMR (126 MHz, CDCl$_3$) δ 152.89, 152.82, 146.94, 145.53, 139.56, 138.92, 123.32, 123.26, 122.01, 119.01, 111.30, 79.20, 77.22, 60.07, 59.26, 55.77, 55.64, 18.34; HRMS-ESI (m/z)([M+Na]$^+$) calcd for C$_{19}$H$_{24}$O$_6$Na, 371.1465; found, 371.1456.

Example 3I, Step 2: Preparation of 1,1-bis(2,3-dimethoxyphenyl)propan-2-one

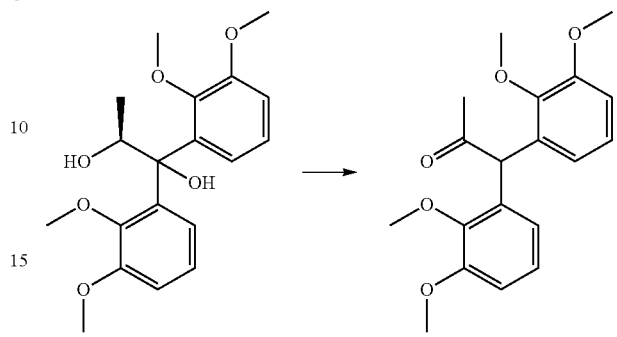

To a solution of (S)-1,1-bis(2,3-dimethoxyphenyl)propane-1,2-diol (560 mg, 1.61 mmol) in anhydrous CH$_2$Cl$_2$ (8 mL) at 0° C. was added triethylsilane (770 µl, 4.82 mmol) and trifluoroacetic acid (TFA, 124 µL, 1.61 mmol). The resulting solution was stirred at 0° C. for 2 h, then removed from the cold bath and stirred for 2 h. TEN (248 µL, 3.2 mmol) was added, and the reaction was then stirred overnight at rt. The reaction was diluted with water (25 mL) and extracted with CH$_2$Cl$_2$ (3×25 mL). The organic extracts were dried over Na$_2$SO$_4$, filtered, and concentrated to provide an oil. Purification by automated silica gel column chromatography (5-25% acetone in hexanes) provided the title compound (396 mg, 75%) as a white solid: $^1$H NMR (300 MHz, CDCl$_3$) δ 6.99 (t, J=8.0 Hz, 2H), 6.87 (dd, J=8.2, 1.5 Hz, 2H), 6.67-6.54 (m, 2H), 5.86 (s, 1H), 3.87 (s, 6H), 3.75 (s, 6H), 2.25 (s, 3H); $^{13}$C NMR (126 MHz, CDCl$_3$) δ 207.18, 152.69, 147.02, 132.23, 123.74, 121.61, 111.64, 60.36, 55.74, 51.96, 29.80; HRMS-ESI (m/z) ([M+Na]$^+$) calcd for C$_{19}$H$_{22}$O$_5$Na, 353.1359; found, 353.1353.

Example 3I, Step 3: Preparation of 1,1-bis(2,3-dimethoxyphenyl)propan-2-ol

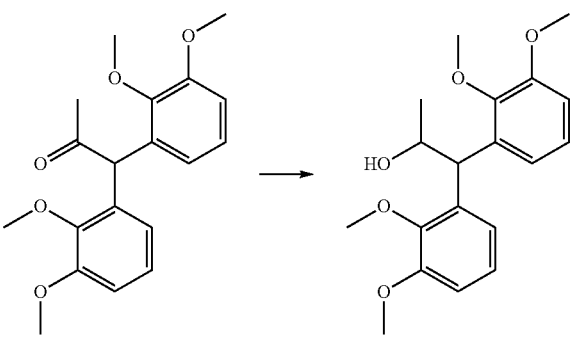 [SMILES: COc1cccc(C(C(C)=O)c2cccc(OC)c2OC)c1OC ; COc1cccc(C(c2cccc(OC)c2OC)C(C)O)c1OC]

To a solution of 1,1-bis(2,3-dimethoxyphenyl)propan-2-one (356 mg, 1.08 mmol) in methanol (3.5 mL) was added sodium borohydride (61 mg, 1.6 mmol). The resulting solution was stirred at rt for 20 h, then was quenched with sat'd NH$_4$Cl (1 mL), diluted with water (20 mL) and extracted with CH$_2$Cl$_2$ (3×20 mL), The organic extracts were combined, dried over Na$_2$SO$_4$, filtered, and concentrated to provide the title compound (360 mg, 100%) as an oil: $^1$H NMR (300 MHz, CDCl$_3$) δ 7.16-6.88 (m, 4H), 6.79

(ddd, J=9.6, 7.8, 1.9 Hz, 2H), 4.81 (d, J=8.3 Hz, 1H), 4.53-4.32 (m, 1H), 3.84 (s, 3H), 3.84 (s, 3H), 3.77 (s, 3H), 3.76 (s, 3H), 2.04 (d, J=4.2 Hz, 1H), 1.22 (d, J=6.2 Hz, 3H); $^{13}$C NMR (126 MHz, CDCl$_3$) δ 152.98, 152.83, 147.71, 147.04, 136.17, 135.33, 123.94, 123.62, 120.96, 120.84, 110.76, 110.48, 70.32, 60.26, 60.20, 55.66, 55.63, 45.11, 21.80; IR (neat film) 3451, 2935, 2833, 1582, 1473, 1428, 1266, 1215, 1167, 1125, 1088, 1068, 1004, 964, 908, 835, 809, 787, 748, 728.

Example 4A: Preparation of (S)—(S)-1,1-diphenyl-propan-2-yl 2-((tert-butoxycarbonyl)amino)-propanoate

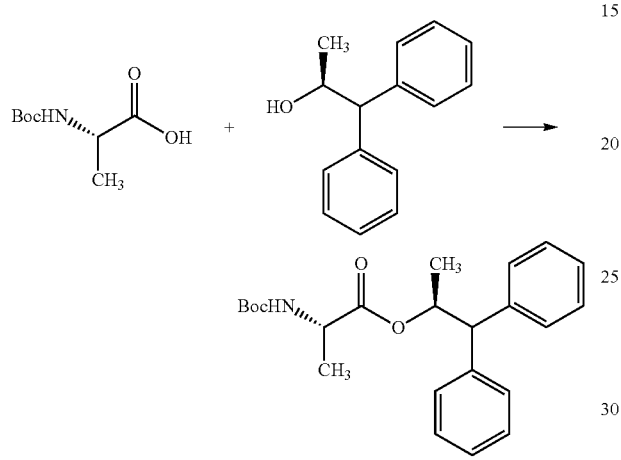

To a solution of (S)-1,1-diphenylpropan-2-ol (317 mg, 1.493 mmol) in DCM (15 mL) at 0° C. were added (S)-2-((tert-butoxycarbonyl)amino)propanoic acid (Boc-Ala-OH; 311 mg, 1.64 mmol) and N,N-dimethylpyridin-4-amine (DMAP; 18.2 mg, 0.149 mmol) followed by N$^1$-((ethyl-imino)methylene)-N$^3$,N$^3$-dimethylpropane-1,3-diamine hydrochloride (EDC; 573 mg, 2.99 mmol), and the reaction mixture was stirred at room temperature overnight and concentrated to give a yellow oil. The crude material was purified by flash column chromatography (SiO$_2$, 1→10% acetone in hexanes) to afford the title compound (433 mg, 75%) as a colorless oil: $^1$H NMR (400 MHz, CDCl$_3$) δ 7.42-7.07 (m, 10H), 5.80 (dq, J=10.1, 6.1 Hz, 1H), 4.97 (d, J=8.0 Hz, 1H), 4.19-4.06 (m, 1H), 4.03 (d, J=10.1 Hz, 1H), 1.41 (s, 9H), 1.23 (d, J=6.1 Hz, 3H), 0.76 (d, J=7.2 Hz, 3H); $^{13}$C NMR (101 MHz, CDCl$_3$) δ 172.83, 154.96, 141.52, 141.26, 128.79, 128.50, 128.10, 128.08, 126.91, 126.67, 79.62, 73.10, 57.98, 49.21, 28.33, 19.31, 17.98; ESIMS m/z 384 ([M+H]$^+$).

Example 5, Step 1: Preparation of (S)-1-(((S)-1,1-diphenylpropan-2-yl)oxy)-1-oxopropan-2-aminium chloride

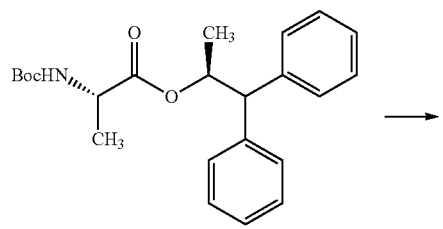

To a solution of (S)—(S)-1,1-diphenylpropan-2-yl 2-((tert-butoxycarbonyl)amino)propanoate (Cmpd 2; 433 mg, 11.3 mmol) in DCM (6 mL) was added a 4 N solution of HCl in dioxane (2.8 mL, 11.3 mmol), and the mixture was stirred for 3 h at room temperature. The solvent was evaporated under a stream of N$_2$ to provide the title compound (360 mg, 100%) as a white solid: ESIMS (m/z) 284 ([M+H]$^+$).

Example 5, Step 2: Preparation of (S)—(S)-1,1-diphenylpropan-2-yl 2-(3-hydroxy-4-methoxypico-linamido)propanoate

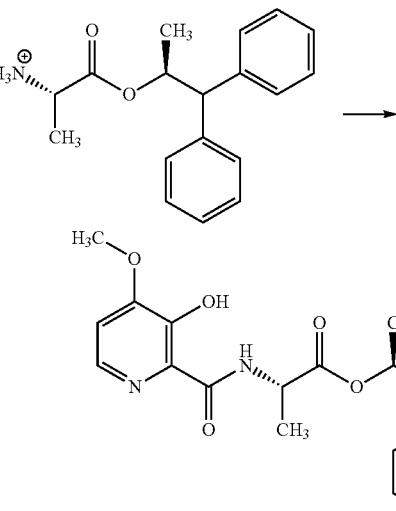

To a solution of (S)-1-(((S)-1,1-diphenylpropan-2-yl)oxy)-1-oxopropan-2-aminium chloride (Cmpd 46; 361 mg, 1.13 mmol) and 3-hydroxy-4-methoxypicolinic acid (210 mg, 1.24 mmol) in DCM (11 mL) were added benzotriazol-1-yl-oxytripyrrolidinophosphonium hexafluorophosphate (PyBOP; 646 mg, 1.24 mmol) and N-ethyl-N-isopropylpropan-2-amine (DIPEA; 0.651 mL, 3.72 mmol), and the reaction mixture was stirred for 2 h at room temperature. The solvent was evaporated and the crude oil was purified by flash column chromatography (SiO$_2$, 1→50% acetone in hexanes) to afford the title compound (340 mg, 70%) as a white foam: $^1$H NMR (400 MHZ, CDCl$_3$) δ 12.10 (s, 1H), 8.34 (d, J=8.0 Hz, 1H), 7.98 (d, J=5.2 Hz, 1H), 7.38-7.06 (m, 10H), 6.86 (d, J=5.3, 1H), 5.83 (dq, J=10.1, 6.1 Hz, 1H), 4.52 (dq, J=8.1, 7.2 Hz, 1H), 4.06 (d, J=10.2 Hz, 1H), 3.93 (s, 3H), 1.26 (d, J=6.1 Hz, 3H), 0.97 (d, J=7.2 Hz, 3H); $^{13}$C NMR (101 MHz, CDCl$_3$) δ 171.67, 168.53, 155.34, 148.72, 141.38, 141.13, 140.40, 130.48, 128.80, 128.50, 128.10, 128.03, 126.95, 126.70, 109.39, 73.57, 57.93, 56.07, 47.85, 19.24, 17.61; HRMS-ESI (m/z) ([M+H]$^+$) calcd for C$_{25}$H$_{27}$N$_2$O$_5$, 435.1920; found, 435.1925.

Example 6A: Preparation of (S)—(S)-1,1-diphenyl-propan-2-yl 2-(3-acetoxy-4-methoxypicolinamido)propanoate

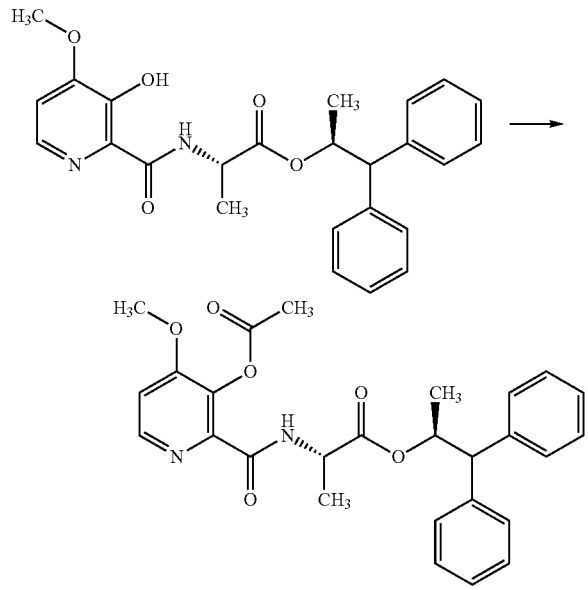

To a solution of (S)—(S)-1,1-diphenylpropan-2-yl 2-(3-hydroxy-4-methoxypicolinamido)-propanoate (Cmpd 90; 70.0 mg, 0.161 mmol) Et$_3$N (44.9 μL, 0.332 mmol), and DMAP (3.94 mg, 0.032 mmol) in DCM (3.2 mL) was added acetyl chloride (17.2 μt, 0.242 mmol) at room temperature, and the reaction mixture was stirred for 2 h. The solvent was evaporated, and the resulting crude oil was purified by flash column chromatography (SiO$_2$, 1→40% acetone in hexanes) to afford the title compound (75.0 mg, 97%) as a colorless oil: $^1$H NMR (400 MHz, CDCl$_3$) δ 8.41 (d, J=7.8 Hz, 1H), 8.30 (d, J=: 5.4 Hz, 1 Hz), 7.38-7.10 (m, 10H), 6.97 (d, J=5.4 Hz, 1H), 5.82 (dq, J=10.0, 6.2 Hz, 1H), 4.52 (dt, J=8.2, 7.1 Hz, 1H), 4.05 (d, J=10.1 Hz, 1H), 3.87 (s, 3H), 2.37 (s, 3H), 1.24 (d, J=6.1 Hz, 3H), 0.89 (d, J=7.1 Hz, 3H); $^{13}$C NMR (101 MHZ, CDCl$_3$) δ 172.23, 168.89, 162.28, 159.42, 146.66, 141.55, 141.44, 141.25, 137.45, 128.77, 128.50, 128.13, 128.11, 126.89, 126.67, 109.73, 73.32, 57.90, 56.27, 47.85, 20.75, 19.25, 17.92; HRMS-ESI (m/z) ([M+H]$^+$) calcd for C$_{27}$H$_{29}$N$_2$O$_6$, 477.2025; found, 477.2019.

Example 6B: Preparation of (S)—(S)-1,1-diphenyl-propan-2-yl 2-(3-(acetoxymethoxy)-4-methoxypicolinamido)propanoate

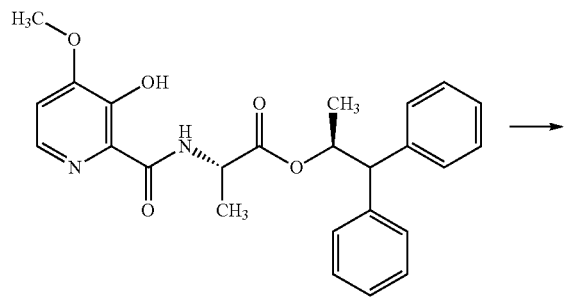

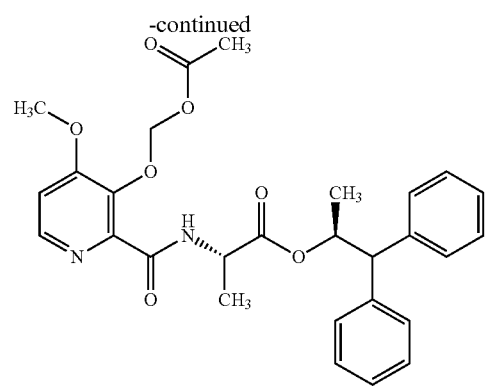

To a suspension of (S)—(S)-1,1-diphenylpropan-2-yl 2-(3-hydroxy-4-methoxypicolinamido)-propanoate (Cmpd 90; 100 mg, 0.230 mmol) and K$_2$CO$_3$ (63.6 mg, 0.460 mmol) in acetone (4.6 mL) was added bromomethyl acetate (33.9 μL, 0.345 mmol) at room temperature, and the mixture was heated to 55° C. for 3 h and then cooled to room temperature. The solvent was evaporated and the resulting crude material was purified by flash column chromatography (SiO$_2$, 1→40% acetone in hexanes) to afford the title compound (94.0 mg, 80% yield) as a colorless oil: $^1$H NMR (400 MHz, CDCl$_3$) δ 8.25 (d, J=5.4 Hz, 1H), 8.22 (d, J=7.9 Hz, 1H), 7.34-7.09 (m, 10H), 6.92 (d, J=5.4 Hz, 1H), 5.83 (dq, J=10.1, 6.2 Hz, 1H), 5.72 (d, J=0.7 Hz, 2H), 4.60-4.49 (m, 1H), 4.06 (d, J=10.1 Hz, 1H), 3.88 (s, 3H), 2.05 (s, 3H), 1.25 (d, J=6.1 Hz, 3H), 0.91 (d, J=7.2 Hz, 3H); $^{13}$C NMR (101 MHZ, CDCl$_3$) δ 172.33, 170.25, 162.88, 160.24, 145.70, 143.91, 142.54, 141.48, 141.25, 128.76, 128.49, 128.12, 128.09, 126.89, 126.65, 109.56, 89.50, 73.27, 57.92, 56.17, 48.07, 20.86, 19.25, 17.73; HRMS-ESI (m/z) [M+H]$^+$ calcd for C$_{28}$H$_{31}$N$_2$O$_7$, 507.2131; found, 507.2125.

Example 6C: Preparation of (S)—(S)-1,1-diphenyl-propan-2-yl 2-(3-((isobutyryloxy)methoxy)-4-methoxypicolinamido)propanoate

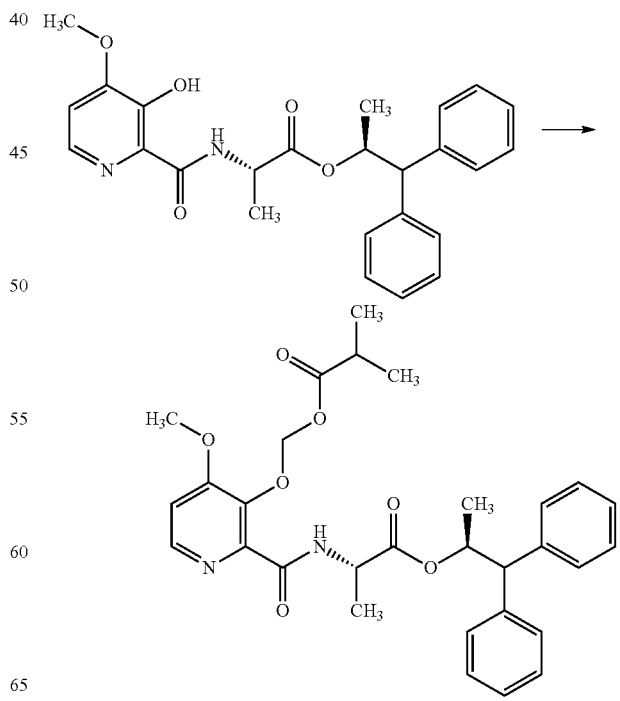

To a solution of (S)—(S)-1,1-diphenylpropan-2-yl 2-(3-hydroxy-4-methoxypicolinamido)-propanoate (Cmpd 90; 100 mg, 0.230 mmol) in acetone (4.6 mL) were added sodium carbonate ($Na_2CO_3$; 73.2 mg, 0.690 mmol), sodium iodide (NaI; 6.90 mg, 0.046 mmol) and chloromethyl 2-ethoxyacetate (62.9 mg, 0.460 mmol). The mixture was heated to 55° C. overnight and then cooled to room temperature, and the solvent was evaporated. The resulting residue was purified by flash column chromatography ($SiO_2$, 2→30% acetone in hexanes) to afford the title compound (79.0 mg, 64% as a colorless oil: $^1$H NMR (400 MHz, $CDCl_3$) δ 8.28 (d, J=7.9 Hz 1H), 8.25 (d, J=5.3 Hz, 7.36-7.08 (m, 10H), 6.92 (d, J=5.4 Hz, 1H), 5.83 (dq, J=10.1, 6.2 Hz, 1H), 5.79-5.69 (m, 2H), 4.62-4.44 (m, 1H), 4.06 (d, J=10.1 Hz, 1H), 3.86 (s, 3H), 2.53 (hept, J=7.0 Hz, 1H), 1.25 (d, J=6.2 Hz, 3H), 1.13 (d, J=7.0 Hz, 6H), 0.91 (d, J=7.2 Hz, 3H); $^{13}$C NMR (101 MHz, $CDCl_3$) δ 176.22, 172.34, 162.85, 160.23, 145.55, 144.16, 142.18, 141.48, 141.26, 128.76, 128.49, 128.12, 128.09, 126.89, 126.65, 109.48, 89.90, 73.26, 57.93, 56.12, 48.07, 33.85, 19.26, 18.68, 17.74; HRMS-ESI (m/z) ([M+H]$^+$) calcd for $C_{30}H_{35}N_2O_7$, 535.2444; found, 535.2431.

Example A: Evaluation of Fungicidal Activity: Leaf Blotch of Wheat (*Zymoseptoria tritici*; Bayer Code SEPTTR)

Technical grades of materials were dissolved in acetone, which were then mixed with nine volumes of water ($H_2O$) containing 110 ppm Triton X-100. The fungicide solutions were applied onto wheat seedlings using an automated booth sprayer to run-off. All sprayed plants were allowed to air dry prior to further handling. All fungicides were evaluated using the aforementioned method for their activity vs. all target diseases, unless stated otherwise. Wheat leaf blotch and brown rust activity were also evaluated using track spray applications, in which case the fungicides were formulated as EC formulations, containing 0.1% Trycol 5941 in the spray solutions.

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Zymoseptoria tritici* either prior to or after fungicide treatments. After inoculation the plants were kept in 100% relative humidity (one day in a dark dew chamber followed by two to three days in a lighted dew chamber at 20° C.) to permit spores to germinate and infect the leaf. The plants were then transferred to a greenhouse set at 20° C. for disease to develop. When disease symptoms were fully expressed on the 1$^{st}$ leaves of untreated plants, infection levels were assessed on a scale of 0 to 100 percent disease severity. Percent disease control was calculated using the ratio of disease severity on treated plants relative to untreated plants.

Example B: Evaluation of Fungicidal Activity: Wheat Brown Rust (*Puccinia friticina*; Synonym: *Puccinia recondita* f. Sp. *Tritici*; Bayer Code PUCCRT)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Puccinia triticina* either prior to or after fungicide treatments. After inoculation the plants were kept in a dark dew room at 22° C. with 100% relative humidity overnight to permit spores to germinate and infect the leaf. The plants were then transferred to a greenhouse set at 24° C. for disease to develop. Fungicide formulation, application and disease assessment followed the procedures as described in the Example A.

Example C: Evaluation of Fungicidal Activity: Wheat Glume Blotch (*Leptasphaeria nodorum*; Bayer Code LEPTNO)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Leptosphaeria nodorum* 24 h after fungicide treatments. After inoculation the plants were kept in 100% relative humidity (one day in a dark dew chamber followed by two days in a lighted dew chamber at 20° C.) to permit spores to germinate and infect the leaf. The plants were then transferred to a greenhouse set at 20° C. for disease to develop. Fungicide formulation, application and disease assessment followed the procedures as described in the Example A.

Example D: Evaluation of Fungicidal Activity: Apple Scab (*Venturia inaequalis*; Bayer Code VENTIN)

Apple seedlings (variety McIntosh) were grown in soil-less Metro mix, with one plant per pot. Seedlings with two expanding young leaves at the top (older leaves at bottom of the plants were trimmed) were used in the test. Plants were inoculated with a spore suspension of *Venturia inaequalis* 24 h after fungicide treatment and kept in a 22° C. dew chamber with 100% relative humidity for 48 h, and then moved to a greenhouse set at 20° C. for disease to develop. Fungicide formulation, application and disease assessment on the sprayed leaves followed the procedures as described in the Example A.

Example E: Evaluation of Fungicidal Activity: Leaf Spot of Sugar Beets *Cercaspora beticola*; Bayer Code CERCBE)

Sugar beet plants (variety HH88) were grown in soil-less Metro mix and trimmed regularly to maintain a uniform plant size prior to test. Plants were inoculated with a spore suspension 24 h after fungicide treatments. Inoculated plants were kept in a dew chamber at 22° C. for 48 h then incubated in a greenhouse set at 24° C. under a clear plastic hood with bottom ventilation until disease symptoms were fully expressed. Fungicide formulation, application and disease assessment on the sprayed leaves followed the procedures as described in the Example A.

Example F: Evaluation of Fungicidal Activity: Asian Soybean Rust (*Phakopsora pachyrhizi*; Bayer Code PHAKPA)

Technical grades of materials were dissolved in acetone, which were then mixed with nine volumes of $H_2O$ containing 0.011% Tween 20. The fungicide solutions were applied onto soybean seedlings using an automated booth sprayer to run-off. All sprayed plants were allowed to air dry prior to further handling.

Soybean plants (variety Williams 82) were grown in soil-less Metro mix, with one plant per pot. Two weeks old seedlings were used for testing. Plants were inoculated either 3 days prior to or 1 day after fungicide treatments. Plants were incubated for 24 h in a dark dew room at 22° C. and 100% relative humidity then transferred to a growth room at 23° C. for disease to develop. Disease severity was assessed on the sprayed leaves.

Example: G: Evaluation of: Fungicidal Activity: Barley Scald (*Rhyncosporium secalis*; Bayer Code RHYNSE)

Barley seedlings (variety Harrington) were propagated in soil-less Metro mix, with each pot having 8 to 12 plants, and used in the test when the first leaf was fully emerged. Test plants were inoculated by an aqueous spore suspension of *Rhyncovorium secahs* 24 h after fungicide treatments. After inoculation the plants were kept in a dew room at 22° C. with 100% relative humidity for 48 h. The plants were then transferred to a greenhouse set at 20° C. for disease to develop. Fungicide formulation, application and disease assessment on the sprayed leaves followed the procedures as described in the Example A.

Example H: Evaluation of Fungicidal Activity: Rice Blast (*Pyricularia olyzae*; Bayer Code PYRIOR)

Rice seedlings (variety *Japonica*) were propagated in soil-less Metro mix, with each pot having 8 to 14 plants, and used in the test when 12 to 14 days old. Test plants were inoculated with an aqueous spore suspension of *Pyricularia oryzae* 24 h after fungicide treatments. After inoculation the plants were kept in a dew room at 22° C. with 100% relative humidity for 48 h to permit spores to germinate and infect the leaf. The plants were then transferred to a greenhouse set at 24° C. for disease to develop. Fungicide formulation, application and disease assessment on the sprayed leaves followed the procedures as described in the Example A.

Example I: Evaluation of Fungicidal Activity: Tomato Early Blight (*Alternaria solani*; Bayer Code ALTESO)

Tomato plants (variety Outdoor Girl) were propagated in soil-less Metro mix, with each pot having one plant, and used when 12 to 14 days Old. Test plants were inoculated with an aqueous spore suspension of *Alternaria solani* 24 h after fungicide treatments. After inoculation the plants were kept in a dew room at 22° C. with 100% relative humidity for 48 h to permit spores to germinate and infect the leaf. The plants were then transferred to a growth room at 22° C. for disease to develop. Fungicide formulation, application and disease assessment on the sprayed leaves followed the procedures as described in the Example A.

Example J: Evaluation of Fungicidal Activity: Cucumber Anthracnose (*Colletotrichum lagenarium*; Bayer Code COLLLA)

Cucumber seedlings (variety Bush Pickle) were propagated in soil-less Metro mix, with each pot having one plant, and used in the test when 12 to 14 days old. Test plants were inoculated with an aqueous spore suspension of *Colletotrichum lagenarium* 24 hr after fungicide treatments. After inoculation the plants were kept in a dew room at 22° C. with 100% relative humidity for 48 hr to permit spores to germinate and infect the leaf. The plants were then transferred to a growth room set at 22° C. for disease to develop. Fungicide formulation, application and disease assessment on the sprayed leaves followed the procedures as described in the Example A.

TABLE 1

Compound Structure, Preparation Method, and Appearance

| *Cmpd. No. | Structure | Prepared According To Example | Appearance |
|---|---|---|---|
| 1 | (structure) | Example 1; Example 3A; Example 4A | White Solid |
| 2 | (structure) | Example 1; Example 2A; Example 3A; Example 4A | Colorless Oil |

TABLE 1-continued

Compound Structure, Preparation Method, and Appearance

| *Cmpd. No. | Structure | Prepared According To Example | Appearance |
|---|---|---|---|
| 3 | 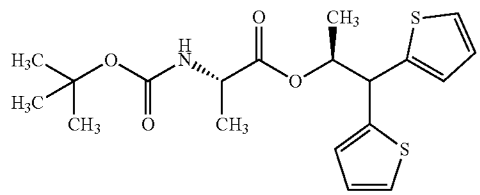 [SMILES: C[C@H](NC(=O)OC(C)(C)C)C(=O)O[C@@H](C)C(c1cccs1)c1cccs1] | Example 1; Example 2A; Example 3A; Example 4A | Colorless Oil |
| 4 | 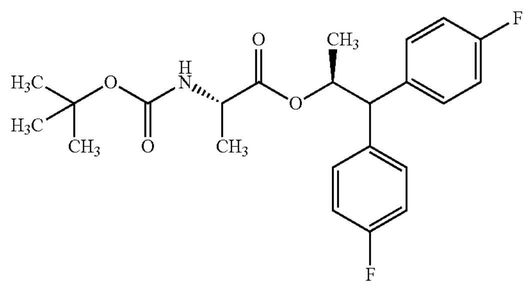 [SMILES: C[C@H](NC(=O)OC(C)(C)C)C(=O)O[C@@H](C)C(c1ccc(F)cc1)c1ccc(F)cc1] | Example 1; Example 2A; Example 3A; Example 4A | Clear, Colorless Oil |
| 5 | 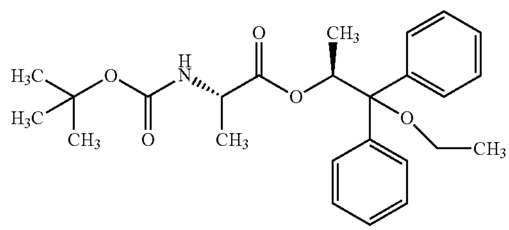 [SMILES: CCOC(c1ccccc1)(c1ccccc1)[C@H](C)OC(=O)[C@H](C)NC(=O)OC(C)(C)C] | Example 1; Example 2B; Example 3A; Example 4A | Colorless Oil |
| 6 | 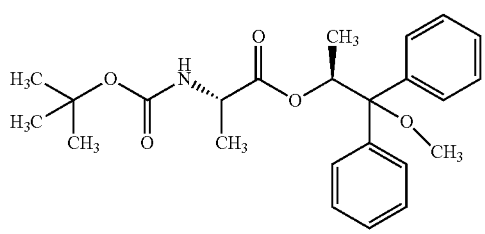 [SMILES: COC(c1ccccc1)(c1ccccc1)[C@H](C)OC(=O)[C@H](C)NC(=O)OC(C)(C)C] | Example 1; Example 2B; Example 3A; Example 4A | Colorless Oil |
| 7 | 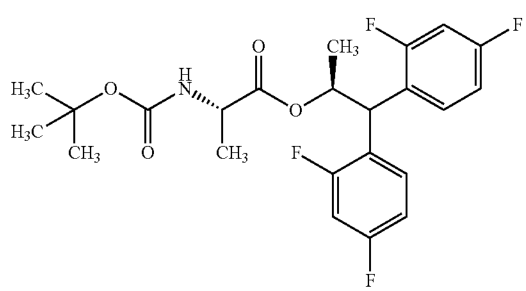 [SMILES: C[C@H](NC(=O)OC(C)(C)C)C(=O)O[C@@H](C)C(c1ccc(F)cc1F)c1ccc(F)cc1F] | Example 1; Example 2A; Example 3A; Example 4A | Colorless Oil |
| 8 | 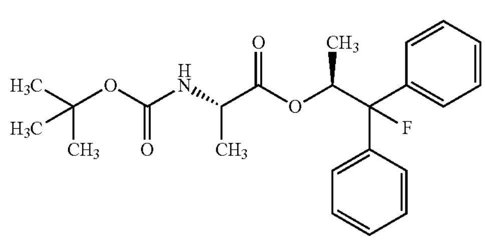 [SMILES: C[C@H](NC(=O)OC(C)(C)C)C(=O)O[C@@H](C)C(F)(c1ccccc1)c1ccccc1] | Example 1; Example 2C; Example 3A; Example 4A | Colorless Oil |

TABLE 1-continued

Compound Structure, Preparation Method, and Appearance

| *Cmpd. No. | Structure | Prepared According To Example | Appearance |
| --- | --- | --- | --- |
| 9 | 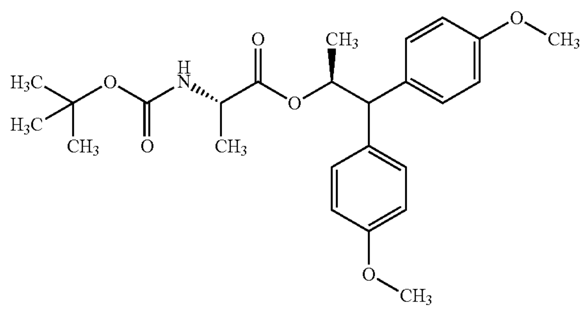 [SMILES: COc1ccc(C(c2ccc(OC)cc2)[C@H](C)OC(=O)[C@H](C)NC(=O)OC(C)(C)C)cc1] | Example 1; Example 2A; Example 3A; Example 4A | Colorless Oil |
| 10 | 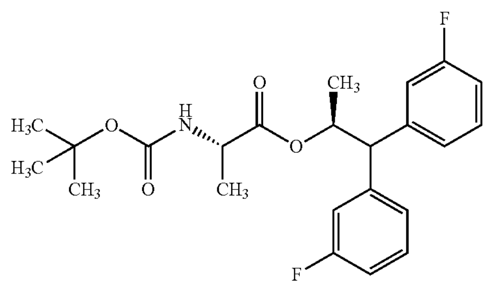 [SMILES: C[C@H](NC(=O)OC(C)(C)C)C(=O)O[C@@H](C)C(c1cccc(F)c1)c1cccc(F)c1] | Example 1; Example 2A; Example 3A; Example 4A | Colorless Oil |
| 11 | 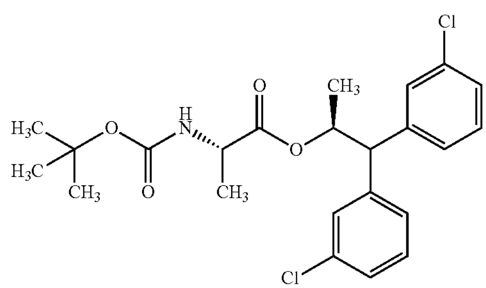 [SMILES: C[C@H](NC(=O)OC(C)(C)C)C(=O)O[C@@H](C)C(c1cccc(Cl)c1)c1cccc(Cl)c1] | Example 1; Example 2A; Example 3A; Example 4A | Colorless Oil |
| 12 | 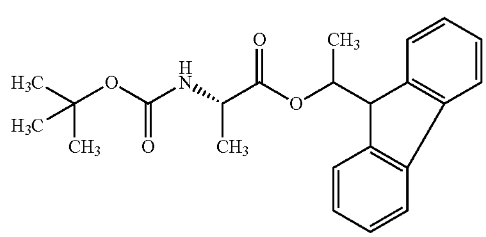 [SMILES: CC(OC(=O)[C@H](C)NC(=O)OC(C)(C)C)C1c2ccccc2-c2ccccc21] | Example 3E; Example 4A | Colorless Oil |
| 13 | 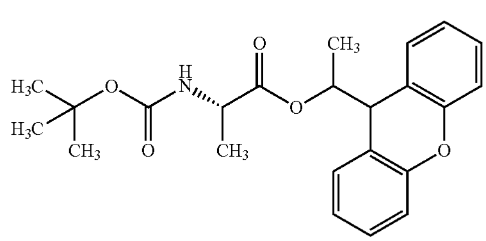 [SMILES: CC(OC(=O)[C@H](C)NC(=O)OC(C)(C)C)C1c2ccccc2Oc2ccccc21] | Example 3E; Example 4A | Colorless Oil |

TABLE 1-continued

Compound Structure, Preparation Method, and Appearance

| *Cmpd. No. | Structure | Prepared According To Example | Appearance |
|---|---|---|---|
| 14 | 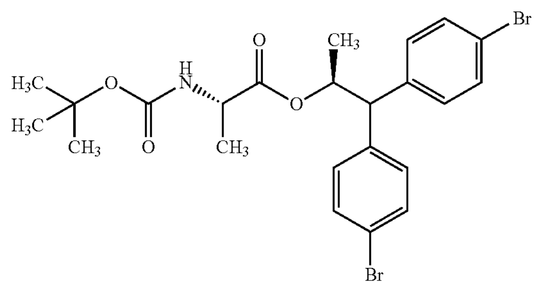 [SMILES: C[C@H](NC(=O)OC(C)(C)C)C(=O)O[C@@H](C)C(c1ccc(Br)cc1)c1ccc(Br)cc1] | Example 1; Example 3C; Example 4A | Colorless Oil |
| 15 | 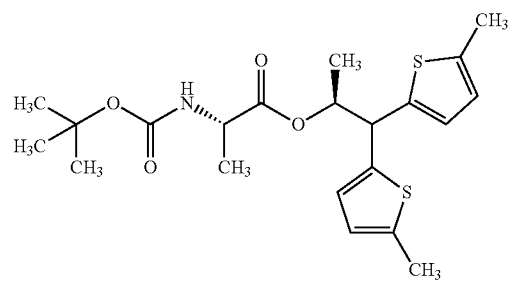 [SMILES: Cc1ccc(C(c2ccc(C)s2)[C@H](C)OC(=O)[C@H](C)NC(=O)OC(C)(C)C)s1] | Example 1; Example 3C; Example 4A | Colorless Oil |
| 16 | 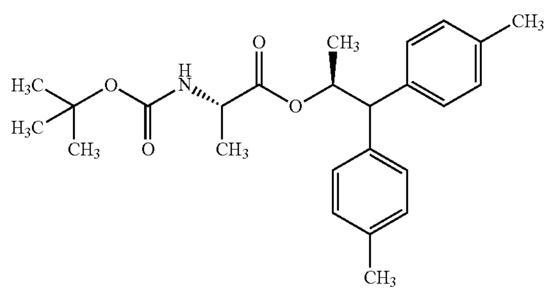 [SMILES: Cc1ccc(C(c2ccc(C)cc2)[C@H](C)OC(=O)[C@H](C)NC(=O)OC(C)(C)C)cc1] | Example 1; Example 2A; Example 3A; Example 4A | Colorless Oil |
| 18 | 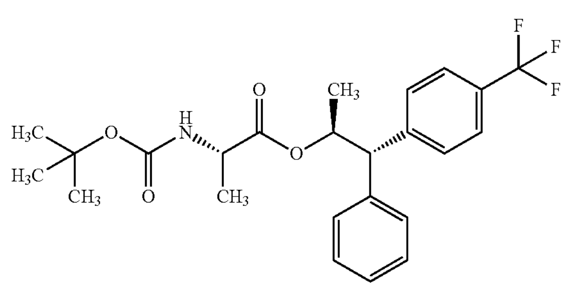 [SMILES: C[C@H](NC(=O)OC(C)(C)C)C(=O)O[C@@H](C)[C@@H](c1ccccc1)c1ccc(C(F)(F)F)cc1] | Example 3F; Example 4A | Colorless Oil |
| 19 | 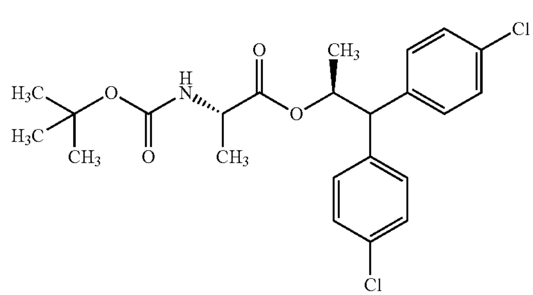 [SMILES: C[C@H](NC(=O)OC(C)(C)C)C(=O)O[C@@H](C)C(c1ccc(Cl)cc1)c1ccc(Cl)cc1] | Example 1; Example 2A; Example 3A; Example 4A | Colorless Oil |

TABLE 1-continued

Compound Structure, Preparation Method, and Appearance

| *Cmpd. No. | Structure | Prepared According To Example | Appearance |
|---|---|---|---|
| 20 | 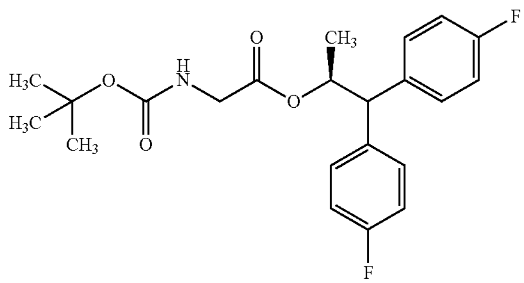 [SMILES: C[C@H](OC(=O)CNC(=O)OC(C)(C)C)C(c1ccc(F)cc1)c1ccc(F)cc1] | Example 1; Example 2A; Example 3A; Example 4A | Clear Oil |
| 21 | 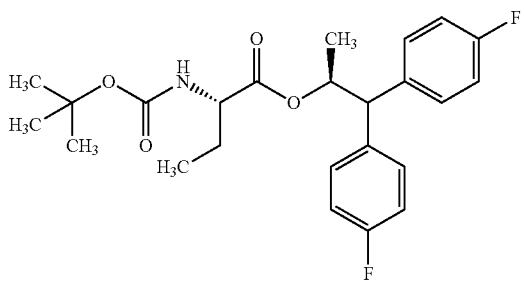 [SMILES: CC[C@H](NC(=O)OC(C)(C)C)C(=O)O[C@@H](C)C(c1ccc(F)cc1)c1ccc(F)cc1] | Example 1; Example 2A; Example 3A; Example 4A | Clear Oil |
| 22 | 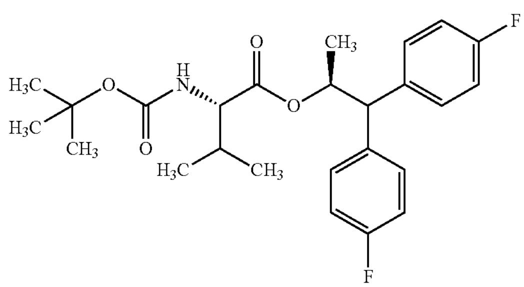 [SMILES: CC(C)[C@H](NC(=O)OC(C)(C)C)C(=O)O[C@@H](C)C(c1ccc(F)cc1)c1ccc(F)cc1] | Example 1; Example 2A; Example 3A; Example 4A | Clear Oil |
| 23 | 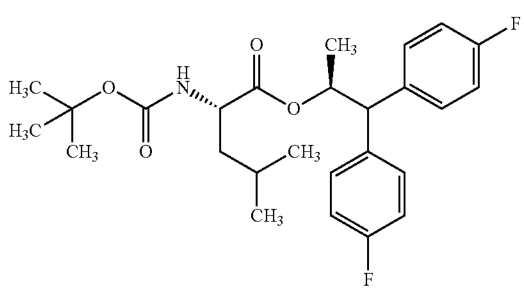 [SMILES: CC(C)C[C@H](NC(=O)OC(C)(C)C)C(=O)O[C@@H](C)C(c1ccc(F)cc1)c1ccc(F)cc1] | Example 1; Example 2A; Example 3A; Example 4A | Clear Oil |
| 24 | 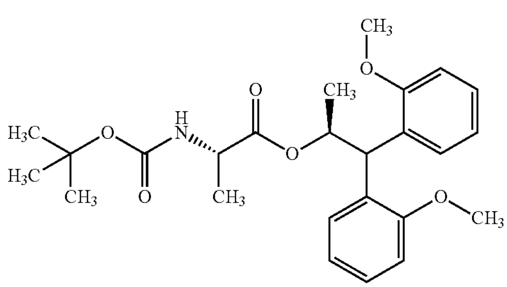 [SMILES: COc1ccccc1C(c1ccccc1OC)[C@H](C)OC(=O)[C@H](C)NC(=O)OC(C)(C)C] | Example 1; Example 3C; Example 4A | Sticky Wax |

TABLE 1-continued

Compound Structure, Preparation Method, and Appearance

| *Cmpd. No. | Structure | Prepared According To Example | Appearance |
|---|---|---|---|
| 25 | 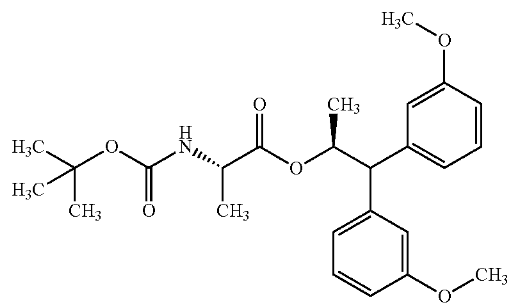 [SMILES: COc1cccc(C(c2cccc(OC)c2)[C@H](C)OC(=O)[C@H](C)NC(=O)OC(C)(C)C)c1] | Example 1; Example 3C; Example 4A | Sticky Wax |
| 26 | 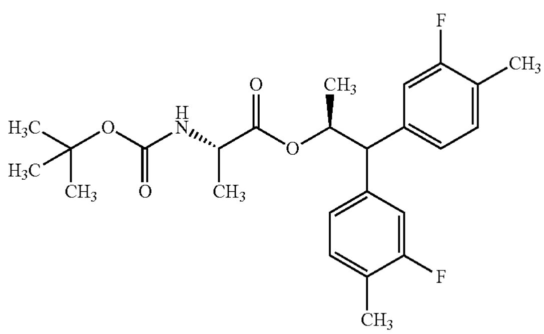 [SMILES: Cc1ccc(C(c2ccc(C)c(F)c2)[C@H](C)OC(=O)[C@H](C)NC(=O)OC(C)(C)C)cc1F] | Example 1; Example 3C; Example 4A | Sticky Wax |
| 27 | 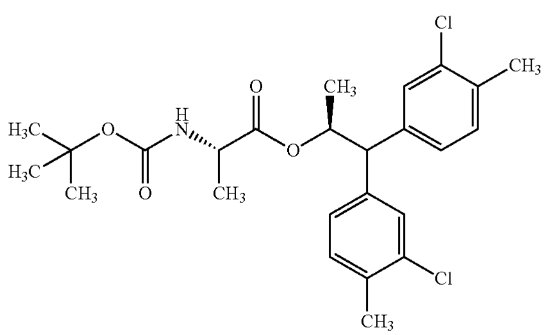 [SMILES: Cc1ccc(C(c2ccc(C)c(Cl)c2)[C@H](C)OC(=O)[C@H](C)NC(=O)OC(C)(C)C)cc1Cl] | Example 1; Example 3C; Example 4A | Sticky Wax |
| 28 | 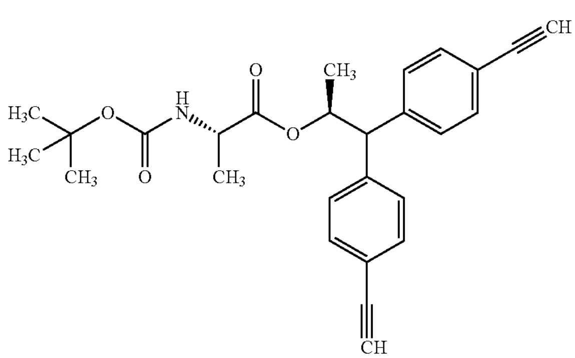 [SMILES: C#Cc1ccc(C(c2ccc(C#C)cc2)[C@H](C)OC(=O)[C@H](C)NC(=O)OC(C)(C)C)cc1] | Example 1; Example 3C; Example 3D, Steps 1-2; Example 4A | White Foam |

TABLE 1-continued

Compound Structure, Preparation Method, and Appearance

| *Cmpd. No. | Structure | Prepared According To Example | Appearance |
| --- | --- | --- | --- |
| 29 | 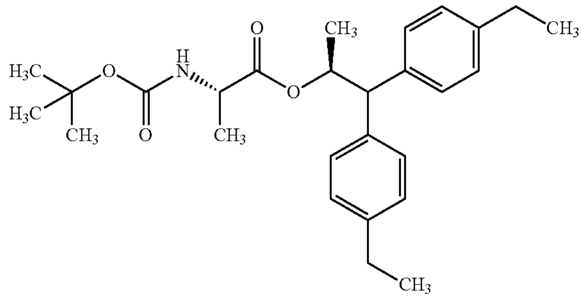 [SMILES: CCc1ccc(C(c2ccc(CC)cc2)[C@H](C)OC(=O)[C@H](C)NC(=O)OC(C)(C)C)cc1] | Example 1; Example 3C; Example 3D, Steps 1-3; Example 4A | Sticky Wax |
| 31 | 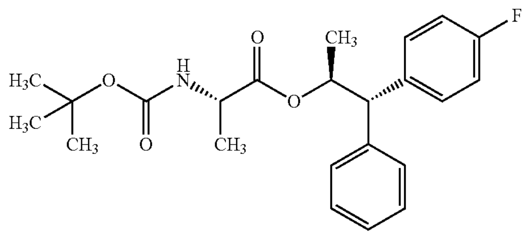 [SMILES: C[C@H](NC(=O)OC(C)(C)C)C(=O)O[C@@H](C)[C@@H](c1ccccc1)c1ccc(F)cc1] | Example 3F; Example 4A | Clear Oil |
| 33 | 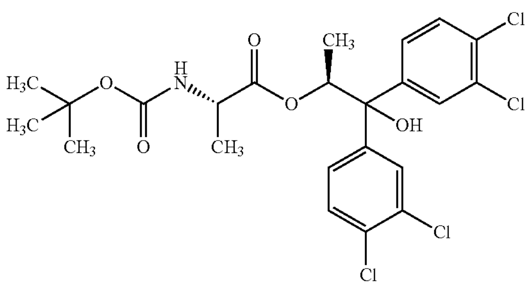 [SMILES: C[C@H](NC(=O)OC(C)(C)C)C(=O)O[C@@H](C)C(O)(c1ccc(Cl)c(F)c1)c1ccc(Cl)c(F)c1] | Example 1; Example 3B; Example 4A | White Solid |
| 34 | 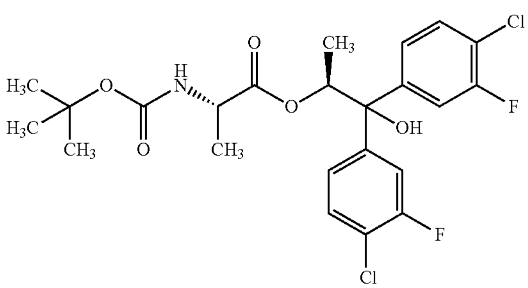 | Example 1; Example 3B; Example 4A | White Solid |
| 35 | 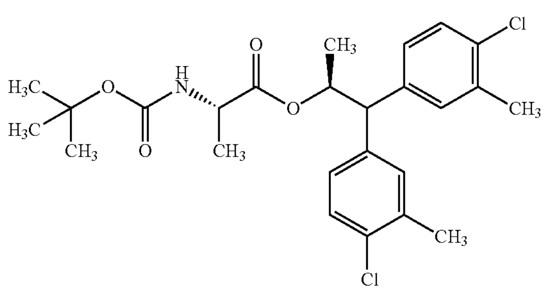 [SMILES: Cc1cc(C(c2ccc(Cl)c(C)c2)[C@H](C)OC(=O)[C@H](C)NC(=O)OC(C)(C)C)ccc1Cl] | Example 1; Example 2A; Example 3A; Example 4A | White Solid |

TABLE 1-continued

Compound Structure, Preparation Method, and Appearance

| *Cmpd. No. | Structure | Prepared According To Example | Appearance |
|---|---|---|---|
| 36 | 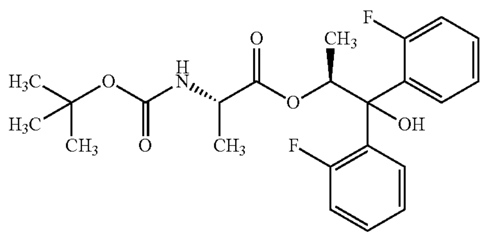 [SMILES: C[C@H](NC(=O)OC(C)(C)C)C(=O)O[C@@H](C)C(O)(c1ccccc1F)c1ccccc1F] | Example 1; Example 3B; Example 4A | White Foam |
| 37 | 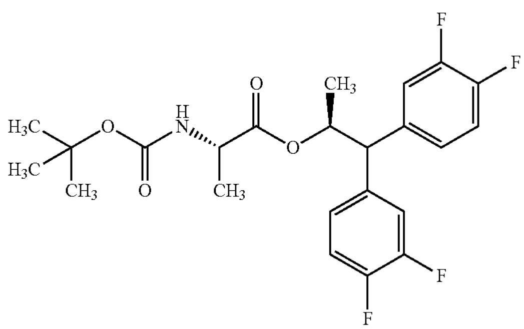 [SMILES: C[C@H](NC(=O)OC(C)(C)C)C(=O)O[C@@H](C)C(c1ccc(F)c(F)c1)c1ccc(F)c(F)c1] | Example 1; Example 2A; Example 3A; Example 4A | Clear, Colorless Oil |
| 38 | 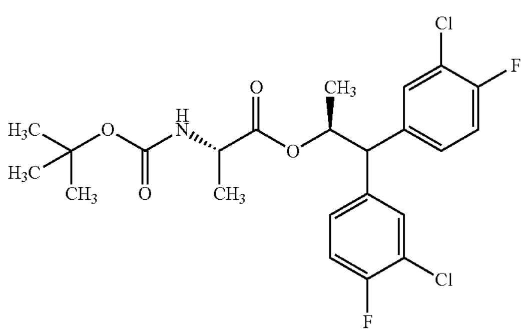 [SMILES: C[C@H](NC(=O)OC(C)(C)C)C(=O)O[C@@H](C)C(c1ccc(F)c(Cl)c1)c1ccc(F)c(Cl)c1] | Example 1; Example 2A; Example 3A; Example 4A | Clear, Colorless Oil |
| 39 | 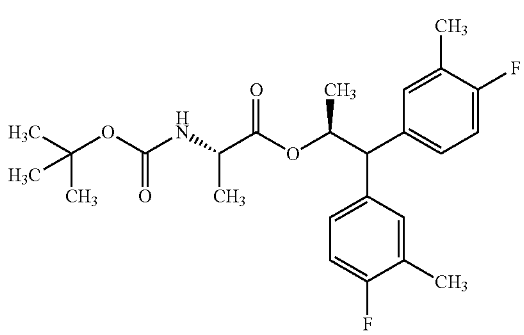 [SMILES: Cc1cc(C(c2ccc(F)c(C)c2)[C@H](C)OC(=O)[C@H](C)NC(=O)OC(C)(C)C)ccc1F] | Example 1; Example 2A; Example 3A; Example 4A | Clear, Colorless Oil |

TABLE 1-continued

Compound Structure, Preparation Method, and Appearance

| *Cmpd. No. | Structure | Prepared According To Example | Appearance |
|---|---|---|---|
| 40 | 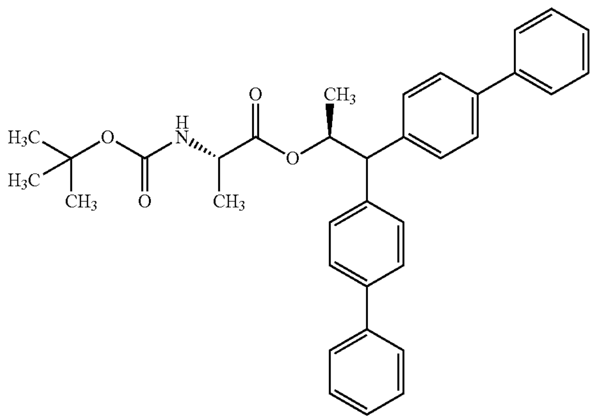 [SMILES: C[C@H](NC(=O)OC(C)(C)C)C(=O)O[C@@H](C)C(c1ccc(-c2ccccc2)cc1)c1ccc(-c2ccccc2)cc1] | Example 1; Example 2A; Example 3A; Example 4A | White Foam |
| 43 | 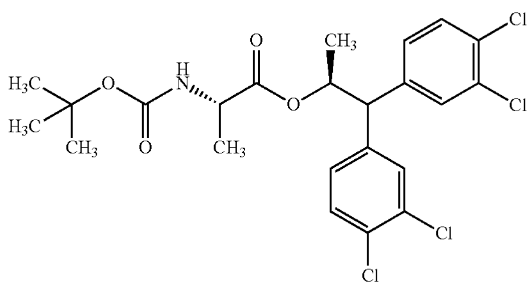 [SMILES: C[C@H](NC(=O)OC(C)(C)C)C(=O)O[C@@H](C)C(c1ccc(Cl)c(Cl)c1)c1ccc(Cl)c(Cl)c1] | Example 1; Example 2A; Example 3A; Example 4A | White Solid |
| 44 | 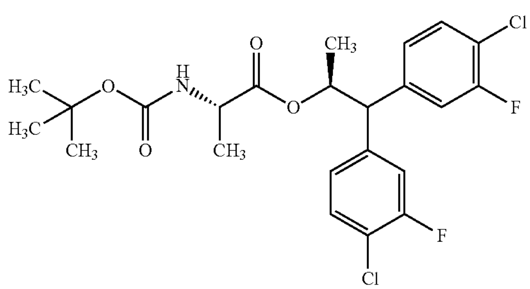 | Example 1; Example 2A; Example 3A; Example 4A | White Solid |
| 45 | 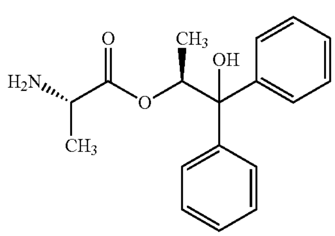 [SMILES: C[C@H](N)C(=O)O[C@@H](C)C(O)(c1ccccc1)c1ccccc1] | Example 5, Step 1 | White Solid |
| 46 | 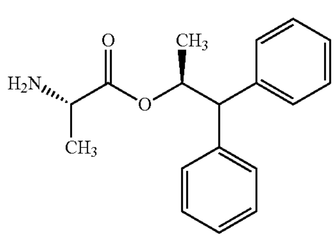 [SMILES: C[C@H](N)C(=O)O[C@@H](C)C(c1ccccc1)c1ccccc1] | Example 5, Step 1 | Colorless Oil |

TABLE 1-continued

Compound Structure, Preparation Method, and Appearance

| *Cmpd. No. | Structure | Prepared According To Example | Appearance |
|---|---|---|---|
| 47 | 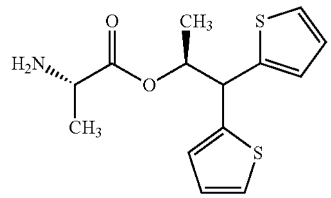 [SMILES: C[C@H](N)C(=O)O[C@@H](C)C(c1cccs1)c1cccs1] | Example 5, Step 1 | Colorless Oil |
| 48 | 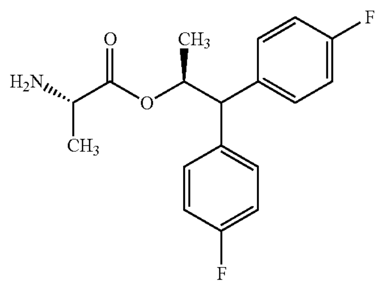 [SMILES: C[C@H](N)C(=O)O[C@@H](C)C(c1ccc(F)cc1)c1ccc(F)cc1] | Example 5, Step 1 | Pale Yellow Oil |
| 49 | 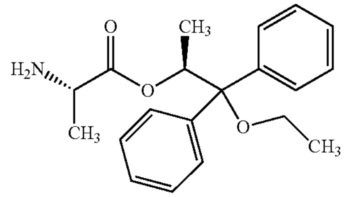 [SMILES: CCOC(c1ccccc1)(c1ccccc1)[C@H](C)OC(=O)[C@H](C)N] | Example 5, Step 1 | Colorless Oil |
| 50 | 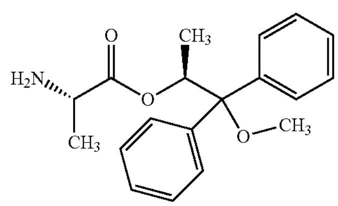 [SMILES: COC(c1ccccc1)(c1ccccc1)[C@H](C)OC(=O)[C@H](C)N] | Example 5, Step 1 | Colorless Oil |
| 51 | 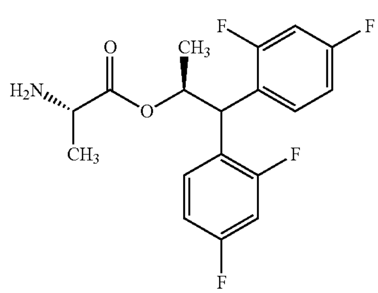 [SMILES: C[C@H](N)C(=O)O[C@@H](C)C(c1ccc(F)cc1F)c1ccc(F)cc1F] | Example 5, Step 1 | Colorless Oil |
| 52 | 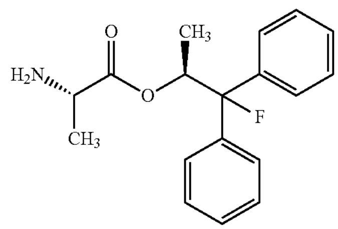 [SMILES: C[C@H](N)C(=O)O[C@@H](C)C(F)(c1ccccc1)c1ccccc1] | Example 5, Step 1 | Colorless Oil |

TABLE 1-continued

Compound Structure, Preparation Method, and Appearance

| *Cmpd. No. | Structure | Prepared According To Example | Appearance |
|---|---|---|---|
| 53 | 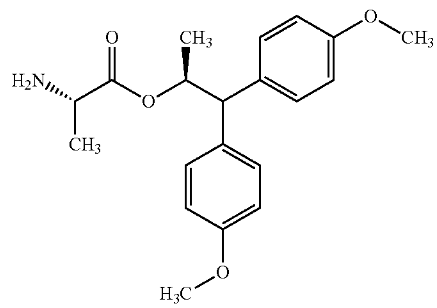 [SMILES: COc1ccc(C(c2ccc(OC)cc2)[C@H](C)OC(=O)[C@H](C)N)cc1] | Example 5, Step 1 | Colorless Oil |
| 54 | 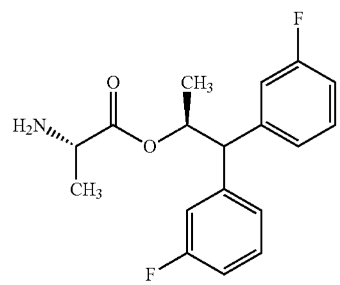 [SMILES: C[C@H](N)C(=O)O[C@@H](C)C(c1cccc(F)c1)c1cccc(F)c1] | Example 5, Step 1 | Colorless Oil |
| 55 | 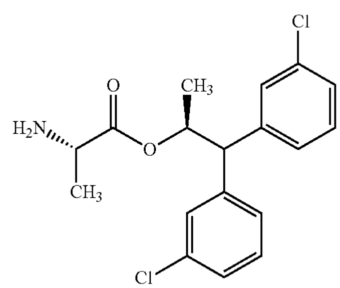 [SMILES: C[C@H](N)C(=O)O[C@@H](C)C(c1cccc(Cl)c1)c1cccc(Cl)c1] | Example 5, Step 1 | Colorless Oil |
| 56 | 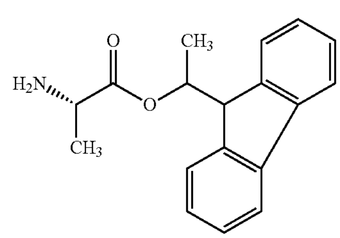 [SMILES: CC(OC(=O)[C@H](C)N)C1c2ccccc2-c2ccccc21] | Example 5, Step 1 | Colorless Oil |
| 57 | 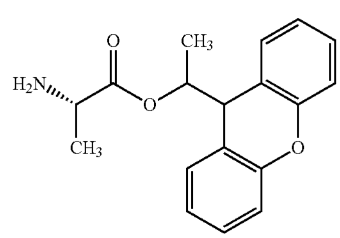 [SMILES: CC(OC(=O)[C@H](C)N)C1c2ccccc2Oc2ccccc21] | Example 5, Step 1 | Colorless Oil |

TABLE 1-continued

Compound Structure, Preparation Method, and Appearance

| *Cmpd. No. | Structure | Prepared According To Example | Appearance |
|---|---|---|---|
| 58 | 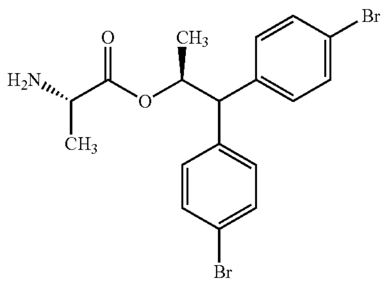 [SMILES: C[C@H](N)C(=O)O[C@@H](C)C(c1ccc(Br)cc1)c1ccc(Br)cc1] | Example 5, Step 1 | Colorless Oil |
| 59 | 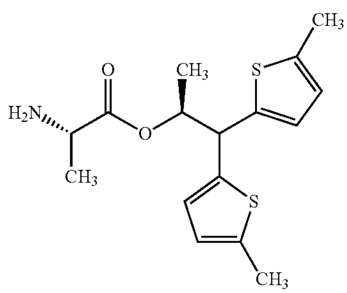 [SMILES: Cc1ccc(C(c2ccc(C)s2)[C@H](C)OC(=O)[C@H](C)N)s1] | Example 5, Step 1 | Colorless Oil |
| 60 | 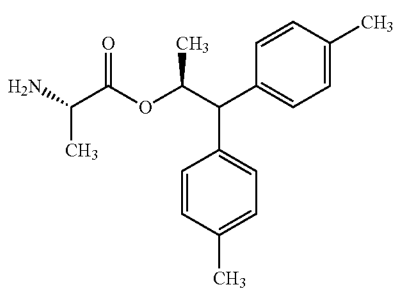 [SMILES: Cc1ccc(C(c2ccc(C)cc2)[C@H](C)OC(=O)[C@H](C)N)cc1] | Example 5, Step 1 | Colorless Oil |
| 61 | 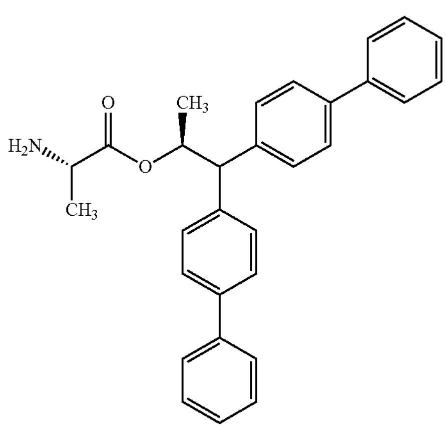 [SMILES: C[C@H](N)C(=O)O[C@@H](C)C(c1ccc(-c2ccccc2)cc1)c1ccc(-c2ccccc2)cc1] | Example 5, Step 1 | White Solid |

TABLE 1-continued

Compound Structure, Preparation Method, and Appearance

| *Cmpd. No. | Structure | Prepared According To Example | Appearance |
|---|---|---|---|
| 63 | 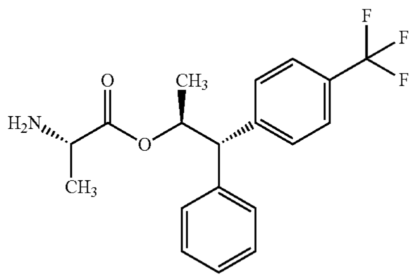 [SMILES: C[C@H](N)C(=O)O[C@@H](C)[C@@H](c1ccccc1)c1ccc(C(F)(F)F)cc1] | Example 5, Step 1 | Colorless Oil |
| 64 | 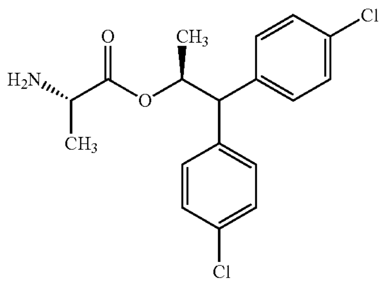 [SMILES: C[C@H](N)C(=O)O[C@@H](C)C(c1ccc(Cl)cc1)c1ccc(Cl)cc1] | Example 5, Step 1 | Colorless Oil |
| 65 | 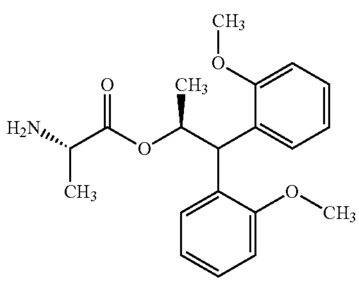 [SMILES: COc1ccccc1C(c1ccccc1OC)[C@H](C)OC(=O)[C@H](C)N] | Example 5, Step 1 | Sticky Oil |
| 66 | 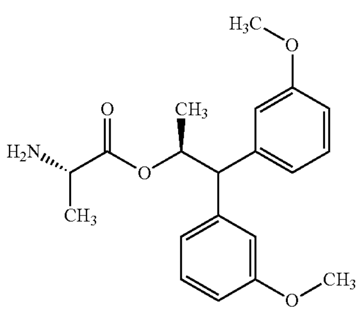 [SMILES: COc1cccc(C(c2cccc(OC)c2)[C@H](C)OC(=O)[C@H](C)N)c1] | Example 5, Step 1 | Sticky Oil |
| 67 | 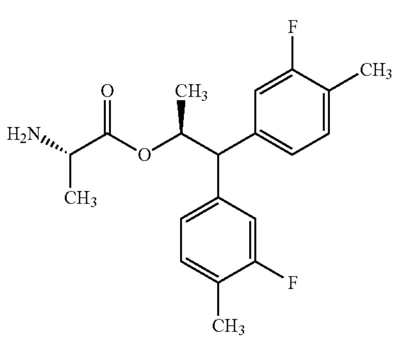 [SMILES: Cc1ccc(C(c2ccc(C)c(F)c2)[C@H](C)OC(=O)[C@H](C)N)cc1F] | Example 5, Step 1 | Sticky Oil |

TABLE 1-continued

Compound Structure, Preparation Method, and Appearance

| *Cmpd. No. | Structure | Prepared According To Example | Appearance |
|---|---|---|---|
| 68 | 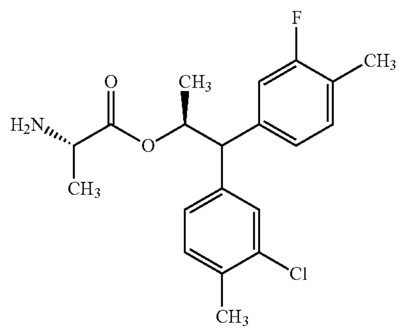 [SMILES: Cc1ccc(C(c2ccc(C)c(Cl)c2)[C@H](C)OC(=O)[C@H](C)N)cc1F] | Example 5, Step 1 | Sticky Wax |
| 69 | 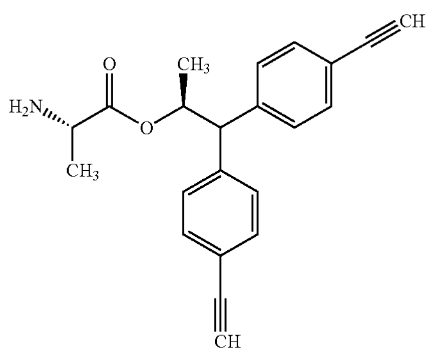 [SMILES: C#Cc1ccc(C(c2ccc(C#C)cc2)[C@H](C)OC(=O)[C@H](C)N)cc1] | Example 5, Step 1 | Sticky Wax |
| 70 | 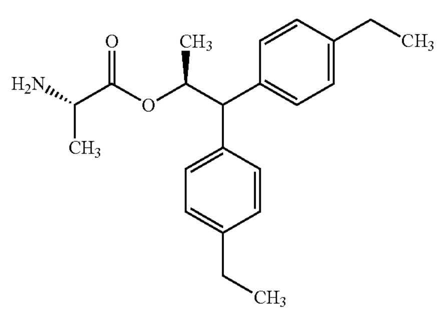 [SMILES: CCc1ccc(C(c2ccc(CC)cc2)[C@H](C)OC(=O)[C@H](C)N)cc1] | Example 5, Step 1 | Sticky Wax |
| 71 | 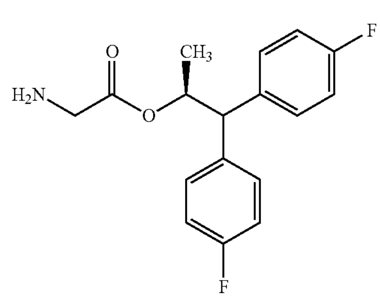 [SMILES: C[C@H](OC(=O)CN)C(c1ccc(F)cc1)c1ccc(F)cc1] | Example 5, Step 1 | White Solid |

TABLE 1-continued

Compound Structure, Preparation Method, and Appearance

| *Cmpd. No. | Structure | Prepared According To Example | Appearance |
|---|---|---|---|
| 72 | 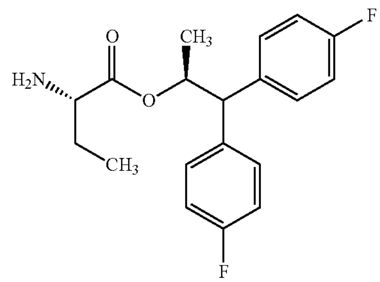 [SMILES: CC[C@H](N)C(=O)O[C@@H](C)C(c1ccc(F)cc1)c1ccc(F)cc1] | Example 5, Step 1 | White Solid |
| 73 | 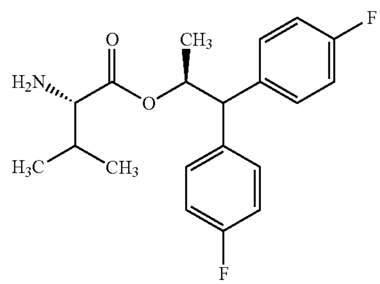 [SMILES: CC(C)[C@H](N)C(=O)O[C@@H](C)C(c1ccc(F)cc1)c1ccc(F)cc1] | Example 5, Step 1 | White Solid |
| 74 | 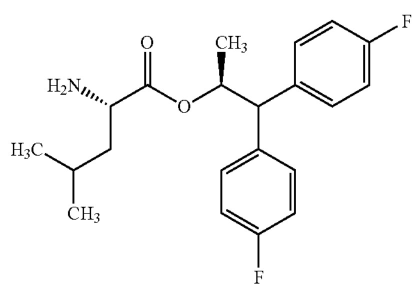 [SMILES: CC(C)C[C@H](N)C(=O)O[C@@H](C)C(c1ccc(F)cc1)c1ccc(F)cc1] | Example 5, Step 1 | White Solid |
| 75 | 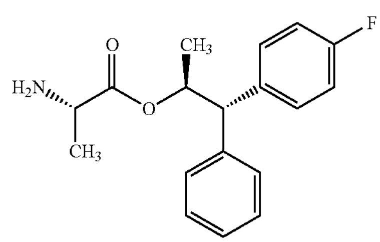 [SMILES: C[C@H](N)C(=O)O[C@@H](C)[C@@H](c1ccccc1)c1ccc(F)cc1] | Example 5, Step 1 | White Solid |
| 77 | 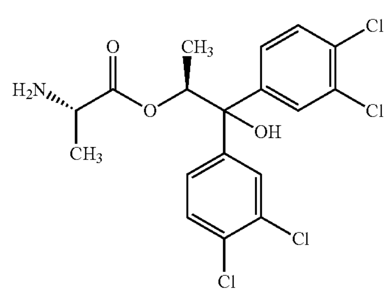 [SMILES: C[C@H](N)C(=O)O[C@@H](C)C(O)(c1ccc(Cl)c(Cl)c1)c1ccc(Cl)c(Cl)c1] | Example 5, Step 1 | White Solid |

TABLE 1-continued

Compound Structure, Preparation Method, and Appearance

| *Cmpd. No. | Structure | Prepared According To Example | Appearance |
|---|---|---|---|
| 78 | 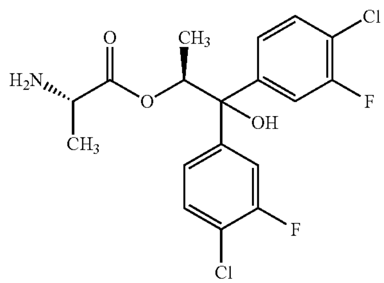 | Example 5, Step 1 | White Solid |
| 79 | 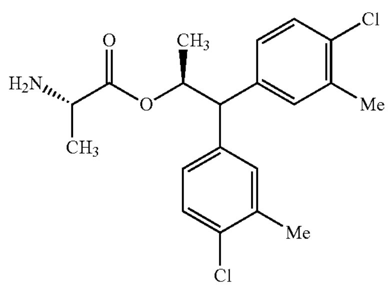 [SMILES: Cc1cc(C(c2ccc(Cl)c(C)c2)[C@H](C)OC(=O)[C@H](C)N)ccc1Cl] | Example 5, Step 1 | White Solid |
| 80 | 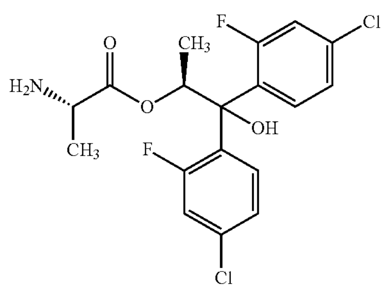 [SMILES: C[C@H](N)C(=O)O[C@@H](C)C(O)(c1ccc(Cl)cc1F)c1ccc(Cl)cc1F] | Example 1; Example 3B; Example 4A; Eample 5, Step 1 | Sticky Oil |
| 81 | 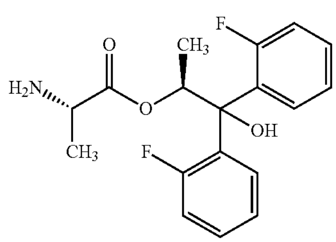 [SMILES: C[C@H](N)C(=O)O[C@@H](C)C(O)(c1ccccc1F)c1ccccc1F] | Example 5, Step 1 | Sticky Oil |
| 83 | 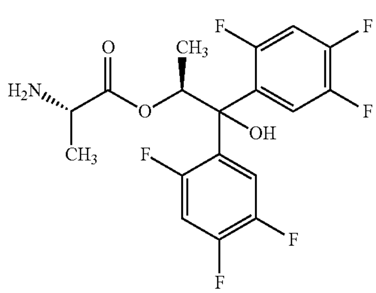 [SMILES: C[C@H](N)C(=O)O[C@@H](C)C(O)(c1cc(F)c(F)cc1F)c1cc(F)c(F)cc1F] | Example 5, Step 1 | Colorless Oil |

TABLE 1-continued

Compound Structure, Preparation Method, and Appearance

| *Cmpd. No. | Structure | Prepared According To Example | Appearance |
|---|---|---|---|
| 84 | 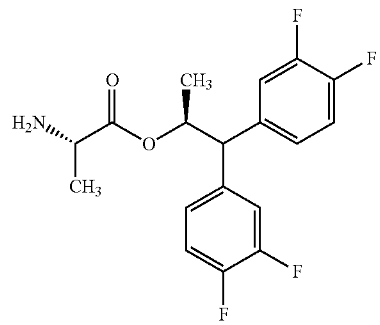 [SMILES: C[C@H](N)C(=O)O[C@@H](C)C(c1ccc(F)c(F)c1)c1ccc(F)c(F)c1] | Example 5, Step 1 | Clear, Colorless Oil |
| 85 | 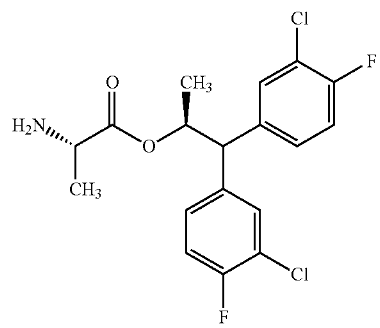 [SMILES: C[C@H](N)C(=O)O[C@@H](C)C(c1ccc(F)c(Cl)c1)c1ccc(F)c(Cl)c1] | Example 5, Step 1 | Clear, Colorless Oil |
| 86 | 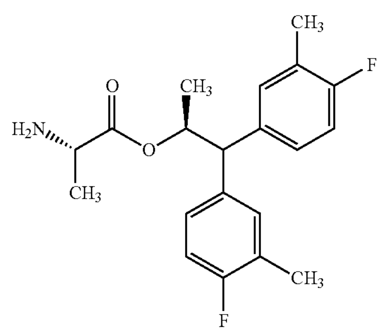 [SMILES: Cc1cc(C(c2ccc(F)c(C)c2)[C@H](C)OC(=O)[C@H](C)N)ccc1F] | Example 5, Step 1 | White Solid |
| 87 | 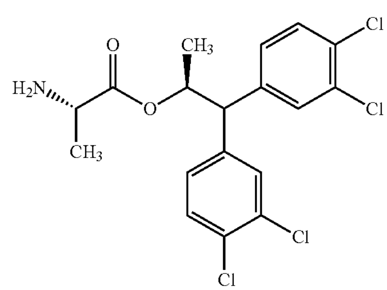 [SMILES: C[C@H](N)C(=O)O[C@@H](C)C(c1ccc(Cl)c(Cl)c1)c1ccc(Cl)c(Cl)c1] | Example 5, Step 1 | White Solid |

TABLE 1-continued

Compound Structure, Preparation Method, and Appearance

| *Cmpd. No. | Structure | Prepared According To Example | Appearance |
|---|---|---|---|
| 88 | 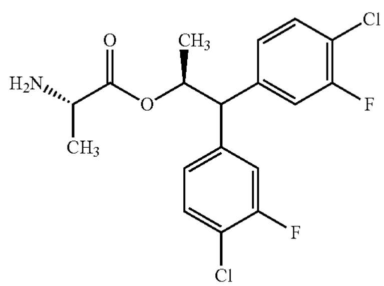 | Example 5, Step 1 | White Solid |
| 89 | 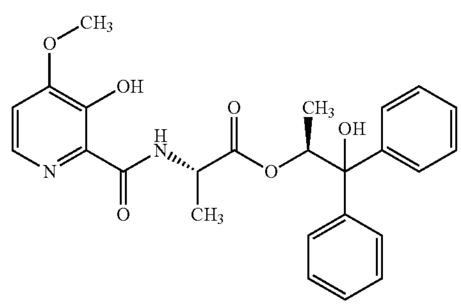 [SMILES: COc1ccnc(C(=O)N[C@@H](C)C(=O)O[C@@H](C)C(O)(c2ccccc2)c2ccccc2)c1O] | Example 5, Step 2 | White Solid |
| 90 | 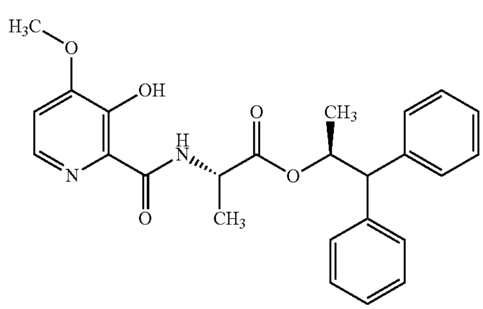 [SMILES: COc1ccnc(C(=O)N[C@@H](C)C(=O)O[C@@H](C)C(c2ccccc2)c2ccccc2)c1O] | Example 5, Step 2 | White Foam |
| 91 | 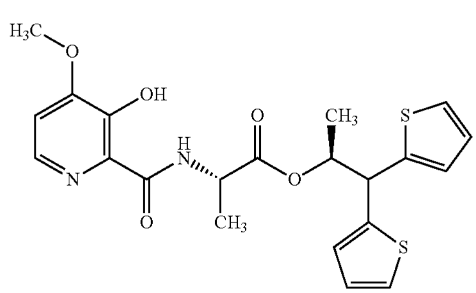 [SMILES: COc1ccnc(C(=O)N[C@@H](C)C(=O)O[C@@H](C)C(c2cccs2)c2cccs2)c1O] | Example 5, Step 2 | Colorless Oil |

TABLE 1-continued
Compound Structure, Preparation Method, and Appearance
| *Cmpd. No. | Structure | Prepared According To Example | Appearance |
|---|---|---|---|
| 92 | 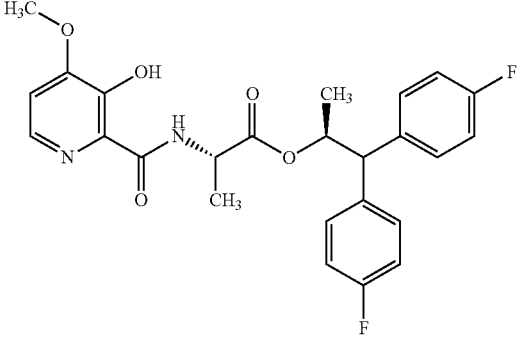 [SMILES: COc1ccnc(C(=O)N[C@@H](C)C(=O)O[C@@H](C)C(c2ccc(F)cc2)c2ccc(F)cc2)c1O] | Example 5, Step 2 | White Foam |
| 93 | 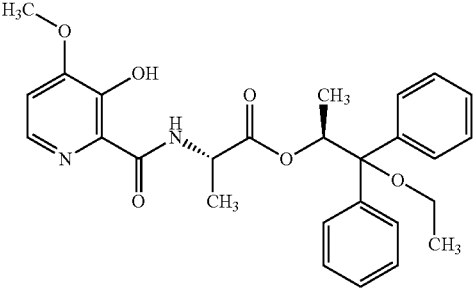 [SMILES: CCOC(c1ccccc1)(c1ccccc1)[C@H](C)OC(=O)[C@H](C)NC(=O)c1nccc(OC)c1O] | Example 5, Step 2 | White Foam |
| 95 | 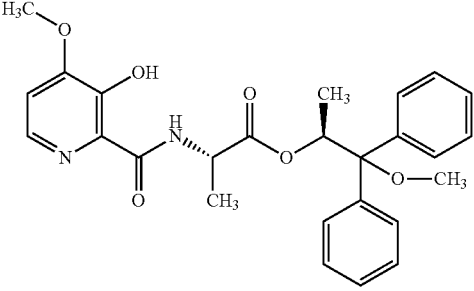 [SMILES: COc1ccnc(C(=O)N[C@@H](C)C(=O)O[C@@H](C)C(OC)(c2ccccc2)c2ccccc2)c1O] | Example 5, Step 2 | Colorless Oil |
| 96 | 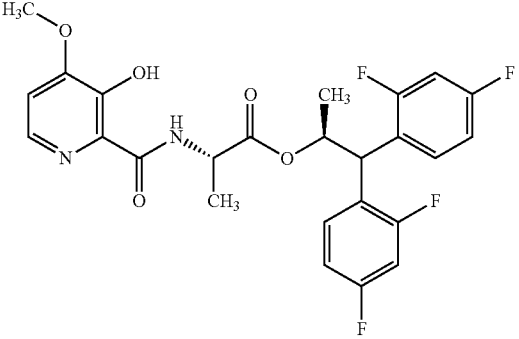 [SMILES: COc1ccnc(C(=O)N[C@@H](C)C(=O)O[C@@H](C)C(c2ccc(F)cc2F)c2ccc(F)cc2F)c1O] | Example 5, Step 2 | White Foam |

TABLE 1-continued

Compound Structure, Preparation Method, and Appearance

| *Cmpd. No. | Structure | Prepared According To Example | Appearance |
|---|---|---|---|
| 97 | 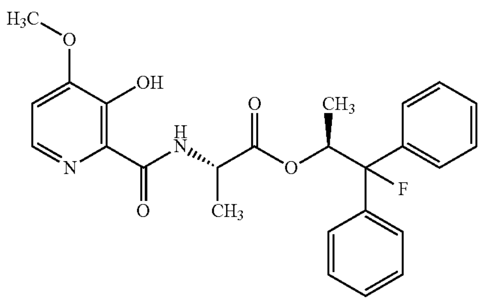 [SMILES: COc1ccnc(C(=O)N[C@@H](C)C(=O)O[C@@H](C)C(F)(c2ccccc2)c2ccccc2)c1O] | Example 5, Step 2 | Colorless Oil |
| 98 | 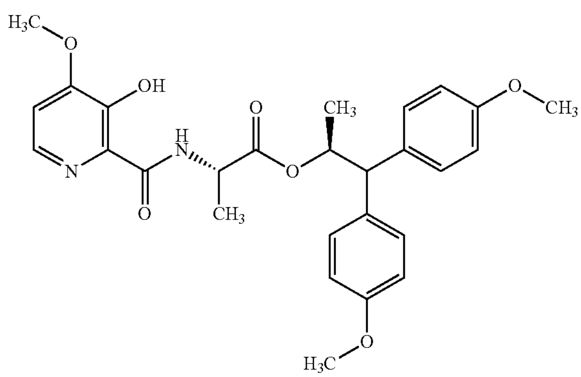 [SMILES: COc1ccc(C(c2ccc(OC)cc2)[C@H](C)OC(=O)[C@H](C)NC(=O)c2nccc(OC)c2O)cc1] | Example 5, Step 2 | Colorless Oil |
| 99 | 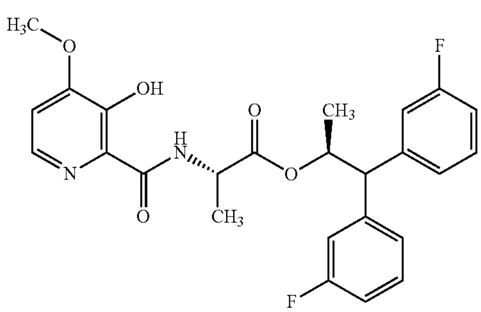 [SMILES: COc1ccnc(C(=O)N[C@@H](C)C(=O)O[C@@H](C)C(c2cccc(F)c2)c2cccc(F)c2)c1O] | Example 5, Step 2 | Colorless Oil |
| 100 | 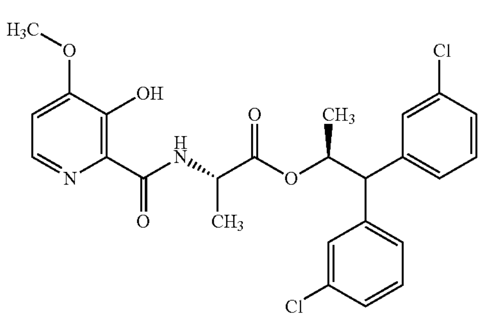 [SMILES: COc1ccnc(C(=O)N[C@@H](C)C(=O)O[C@@H](C)C(c2cccc(Cl)c2)c2cccc(Cl)c2)c1O] | Example 5, Step 2 | Colorless Oil |

TABLE 1-continued

Compound Structure, Preparation Method, and Appearance

| *Cmpd. No. | Structure | Prepared According To Example | Appearance |
| --- | --- | --- | --- |
| 101 | 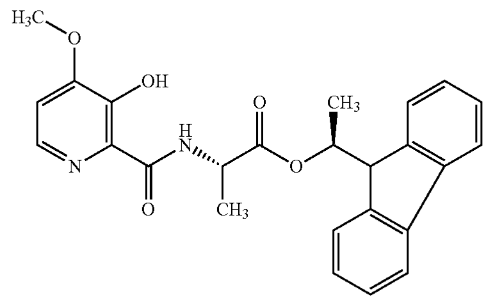 [SMILES: COc1ccnc(C(=O)N[C@@H](C)C(=O)O[C@@H](C)C2c3ccccc3-c3ccccc32)c1O] | Example 5, Step 2 | Colorless Oil |
| 102 | 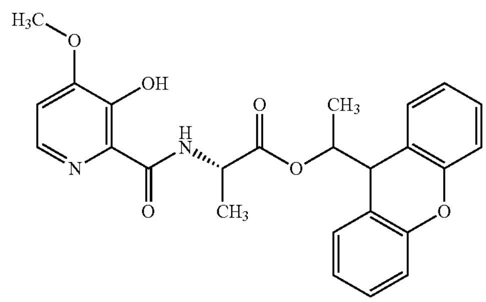 [SMILES: COc1ccnc(C(=O)N[C@@H](C)C(=O)OC(C)C2c3ccccc3Oc3ccccc32)c1O] | Example 5, Step 2 | Colorless Oil |
| 103 | 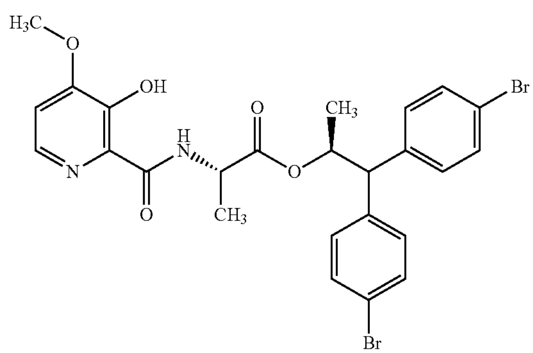 [SMILES: COc1ccnc(C(=O)N[C@@H](C)C(=O)O[C@@H](C)C(c2ccc(Br)cc2)c2ccc(Br)cc2)c1O] | Example 5, Step 2 | Colorless Oil |
| 104 | 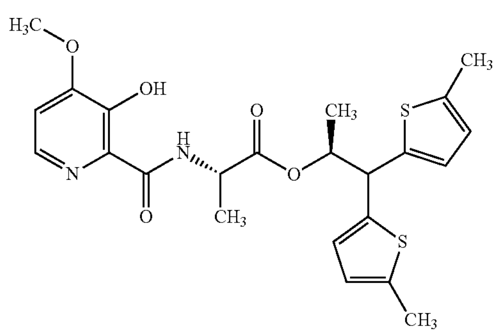 [SMILES: COc1ccnc(C(=O)N[C@@H](C)C(=O)O[C@@H](C)C(c2ccc(C)s2)c2ccc(C)s2)c1O] | Example 5, Step 2 | Colorless Oil |

TABLE 1-continued

Compound Structure, Preparation Method, and Appearance

| *Cmpd. No. | Structure | Prepared According To Example | Appearance |
|---|---|---|---|
| 105 | 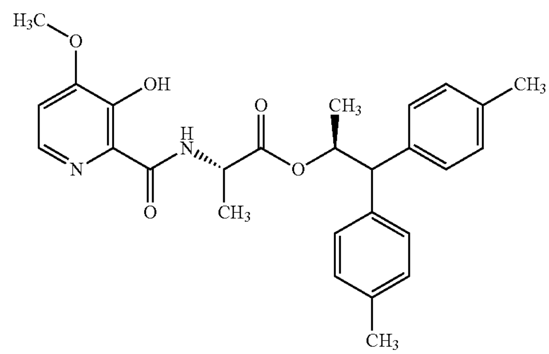 [SMILES: COc1ccnc(C(=O)N[C@@H](C)C(=O)O[C@@H](C)C(c2ccc(C)cc2)c2ccc(C)cc2)c1O] | Example 5, Step 2 | Colorless Oil |
| 106 | 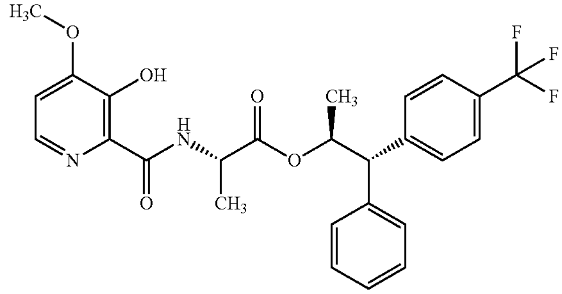 [SMILES: COc1ccnc(C(=O)N[C@@H](C)C(=O)O[C@@H](C)[C@@H](c2ccccc2)c2ccc(C(F)(F)F)cc2)c1O] | Example 5, Step 2 | Colorless Gel |
| 107 | 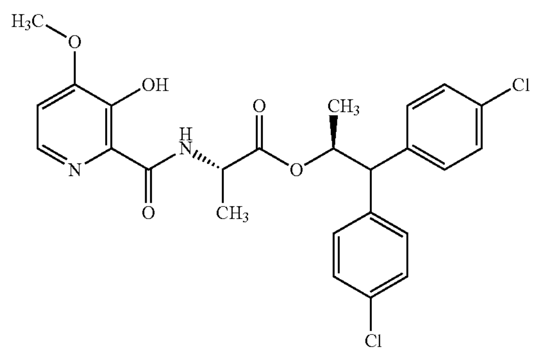 [SMILES: COc1ccnc(C(=O)N[C@@H](C)C(=O)O[C@@H](C)C(c2ccc(Cl)cc2)c2ccc(Cl)cc2)c1O] | Example 5, Step 2 | Colorless Gel |
| 109 | 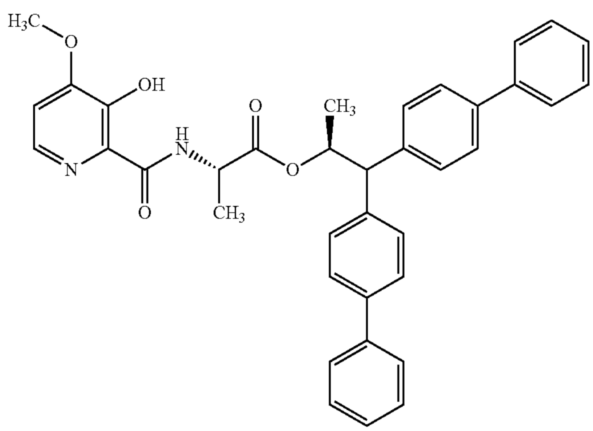 [SMILES: COc1ccnc(C(=O)N[C@@H](C)C(=O)O[C@@H](C)C(c2ccc(-c3ccccc3)cc2)c2ccc(-c3ccccc3)cc2)c1O] | Example 5, Step 2 | Colorless Oil |

TABLE 1-continued

Compound Structure, Preparation Method, and Appearance

| *Cmpd. No. | Structure | Prepared According To Example | Appearance |
|---|---|---|---|
| 110 | 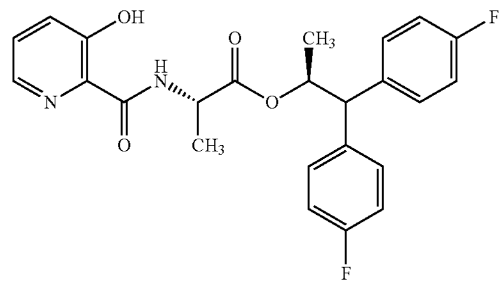 [SMILES: C[C@H](NC(=O)c1ncccc1O)C(=O)O[C@@H](C)C(c1ccc(F)cc1)c1ccc(F)cc1] | Example 5, Step 2 | Clear, Colorless Oil |
| 111 | 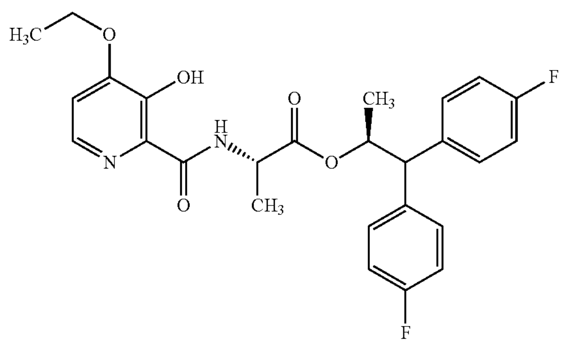 [SMILES: CCOc1ccnc(C(=O)N[C@@H](C)C(=O)O[C@@H](C)C(c2ccc(F)cc2)c2ccc(F)cc2)c1O] | Example 5, Step 2 | Clear, Colorless Oil |
| 112 | 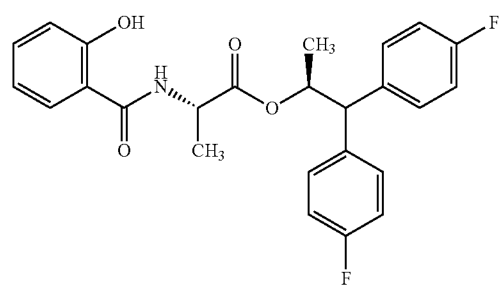 [SMILES: C[C@H](NC(=O)c1ccccc1O)C(=O)O[C@@H](C)C(c1ccc(F)cc1)c1ccc(F)cc1] | Example 5, Step 2 | Clear, Colorless Oil |
| 113 | 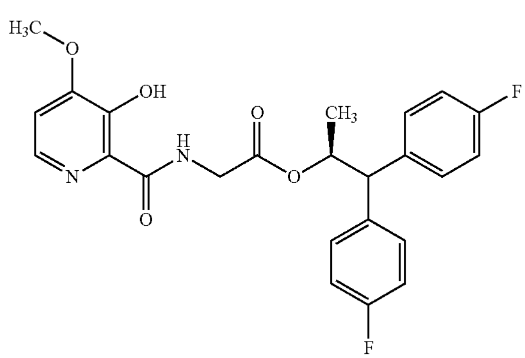 [SMILES: COc1ccnc(C(=O)NCC(=O)O[C@@H](C)C(c2ccc(F)cc2)c2ccc(F)cc2)c1O] | Example 5, Step 2 | White Solid |

TABLE 1-continued

Compound Structure, Preparation Method, and Appearance

| *Cmpd. No. | Structure | Prepared According To Example | Appearance |
|---|---|---|---|
| 114 | 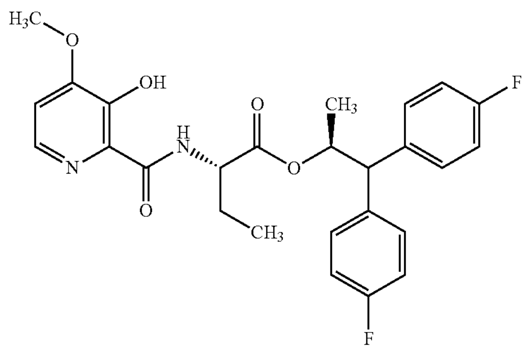 [SMILES: CC[C@H](NC(=O)c1nccc(OC)c1O)C(=O)O[C@@H](C)C(c1ccc(F)cc1)c1ccc(F)cc1] | Example 5, Step 2 | White Solid |
| 115 | 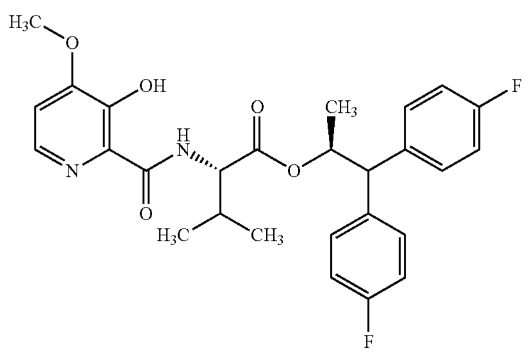 [SMILES: COc1ccnc(C(=O)N[C@H](C(=O)O[C@@H](C)C(c2ccc(F)cc2)c2ccc(F)cc2)C(C)C)c1O] | Example 5, Step 2 | White Solid |
| 116 | 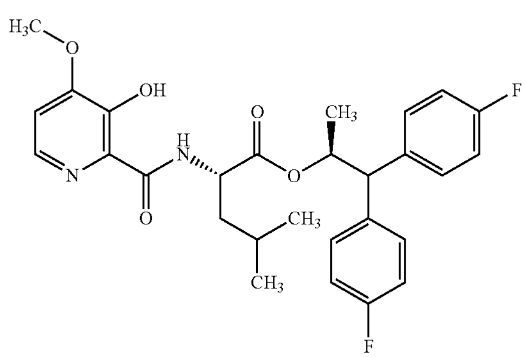 [SMILES: COc1ccnc(C(=O)N[C@@H](CC(C)C)C(=O)O[C@@H](C)C(c2ccc(F)cc2)c2ccc(F)cc2)c1O] | Example 5, Step 2 | White Solid |
| 117 | 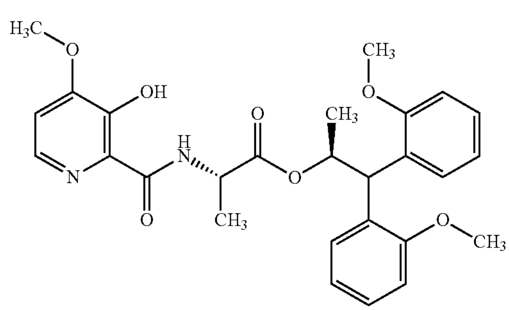 [SMILES: COc1ccccc1C(c1ccccc1OC)[C@H](C)OC(=O)[C@H](C)NC(=O)c1nccc(OC)c1O] | Example 5, Step 2 | White Foam |

TABLE 1-continued

Compound Structure, Preparation Method, and Appearance

| *Cmpd. No. | Structure | Prepared According To Example | Appearance |
| --- | --- | --- | --- |
| 118 | 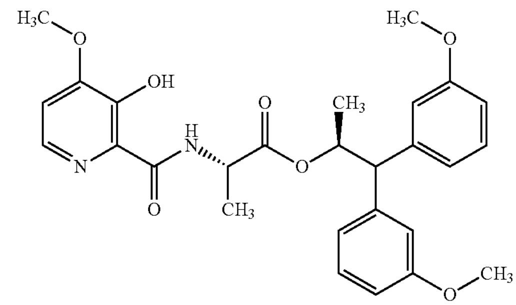 [SMILES: COc1cccc(C(c2cccc(OC)c2)[C@H](C)OC(=O)[C@H](C)NC(=O)c2nccc(OC)c2O)c1] | Example 5, Step 2 | White Foam |
| 119 | 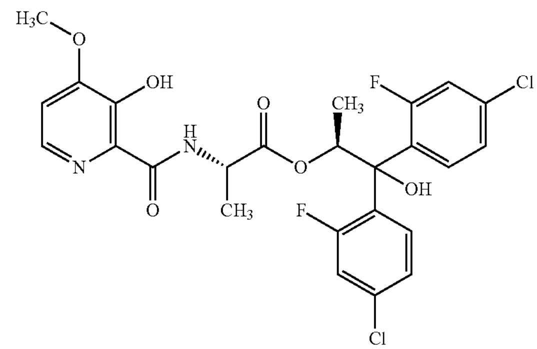 [SMILES: COc1ccnc(C(=O)N[C@@H](C)C(=O)O[C@@H](C)C(O)(c2ccc(Cl)cc2F)c2ccc(Cl)cc2F)c1O] | Example 5, Step 2 | White Foam |
| 120 | 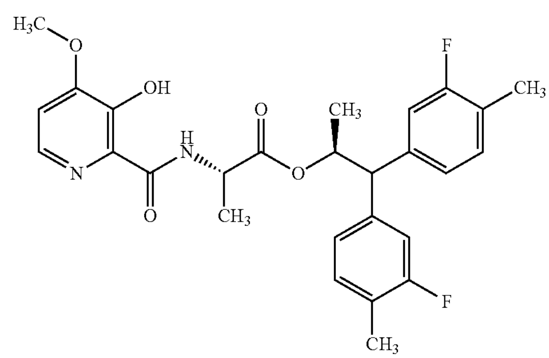 | Example 5, Step 2 | White Foam |
| 121 | 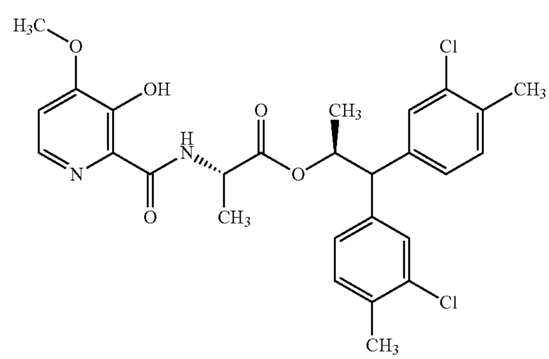 [SMILES: COc1ccnc(C(=O)N[C@@H](C)C(=O)O[C@@H](C)C(c2ccc(C)c(Cl)c2)c2ccc(C)c(Cl)c2)c1O] | Example 5, Step 2 | White Foam |

TABLE 1-continued

Compound Structure, Preparation Method, and Appearance

| *Cmpd. No. | Structure | Prepared According To Example | Appearance |
| --- | --- | --- | --- |
| 122 | 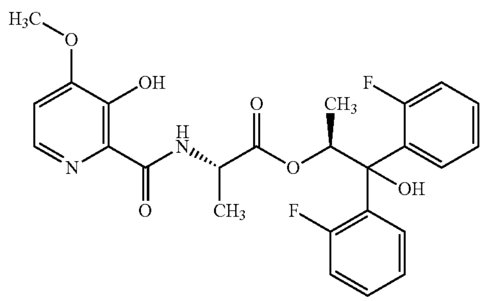 [SMILES: COc1ccnc(C(=O)N[C@@H](C)C(=O)O[C@@H](C)C(O)(c2ccccc2F)c2ccccc2F)c1O] | Example 5, Step 2 | White Foam |
| 123 | 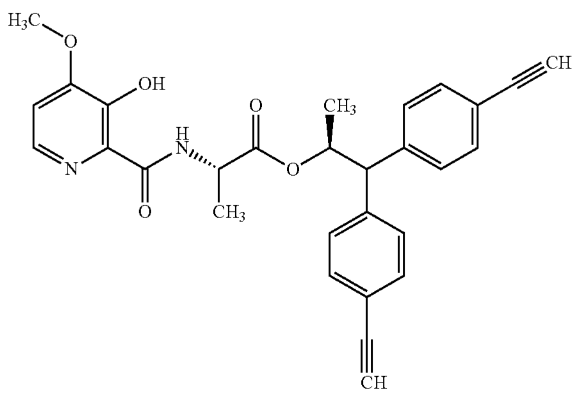 [SMILES: C#Cc1ccc(C(c2ccc(C#C)cc2)[C@H](C)OC(=O)[C@H](C)NC(=O)c2nccc(OC)c2O)cc1] | Example 5, Step 2 | White Foam |
| 124 | 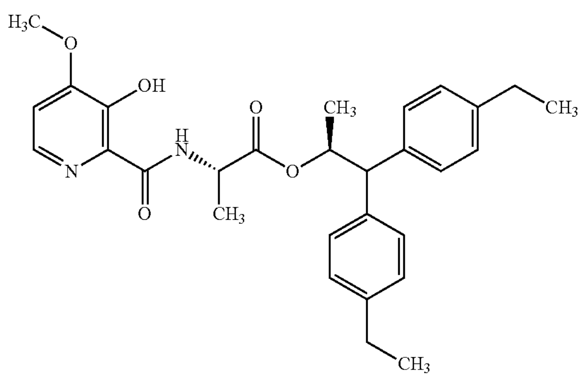 [SMILES: CCc1ccc(C(c2ccc(CC)cc2)[C@H](C)OC(=O)[C@H](C)NC(=O)c2nccc(OC)c2O)cc1] | Example 5, Step 2 | White Foam |
| 125 | 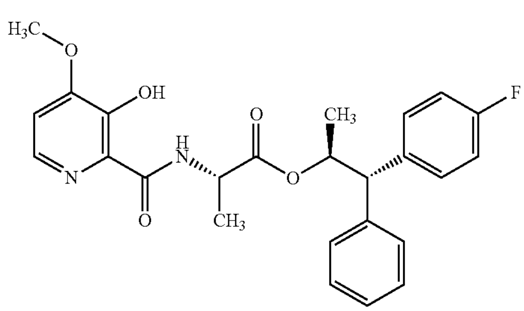 [SMILES: COc1ccnc(C(=O)N[C@@H](C)C(=O)O[C@@H](C)[C@@H](c2ccccc2)c2ccc(F)cc2)c1O] | Example 5, Step 2 | White Solid |

TABLE 1-continued

Compound Structure, Preparation Method, and Appearance

| *Cmpd. No. | Structure | Prepared According To Example | Appearance |
|---|---|---|---|
| 127 | 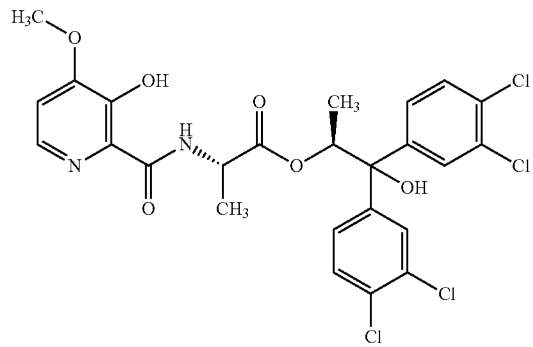 [SMILES: COc1ccnc(C(=O)N[C@@H](C)C(=O)O[C@@H](C)C(O)(c2ccc(Cl)c(Cl)c2)c2ccc(Cl)c(Cl)c2)c1O] | Example 5, Step 2 | White Solid |
| 128 | 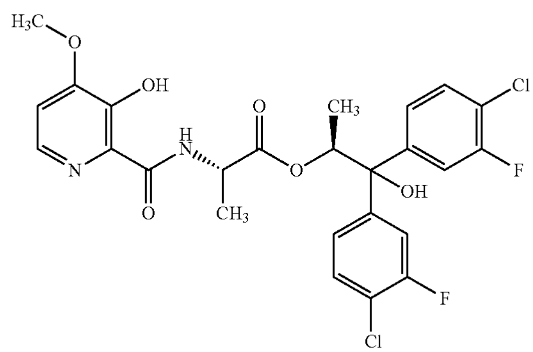 [SMILES: COc1ccnc(C(=O)N[C@@H](C)C(=O)O[C@@H](C)C(O)(c2ccc(Cl)c(F)c2)c2ccc(Cl)c(F)c2)c1O] | Example 5, Step 2 | White Solid |
| 129 | 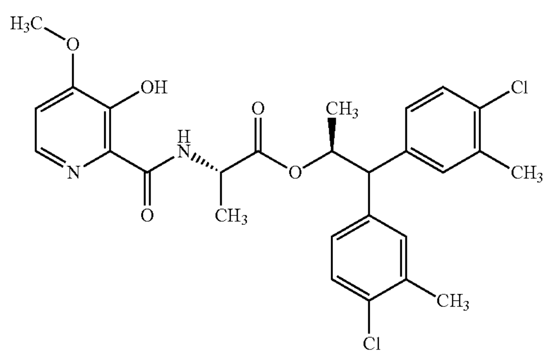 [SMILES: COc1ccnc(C(=O)N[C@@H](C)C(=O)O[C@@H](C)C(c2ccc(Cl)c(C)c2)c2ccc(Cl)c(C)c2)c1O] | Example 5, Step 2 | White Solid |
| 130 | 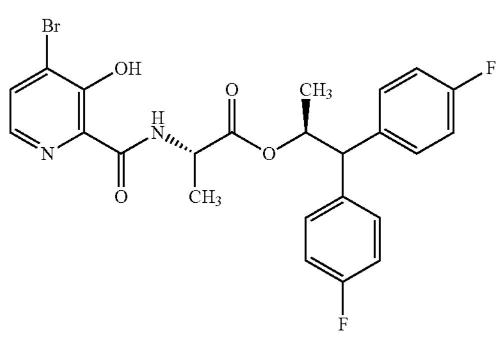 [SMILES: C[C@H](NC(=O)c1nccc(Br)c1O)C(=O)O[C@@H](C)C(c1ccc(F)cc1)c1ccc(F)cc1] | Example 5, Step 2 | Clear, Colorless Oil |

TABLE 1-continued

Compound Structure, Preparation Method, and Appearance

| *Cmpd. No. | Structure | Prepared According To Example | Appearance |
|---|---|---|---|
| 131 | 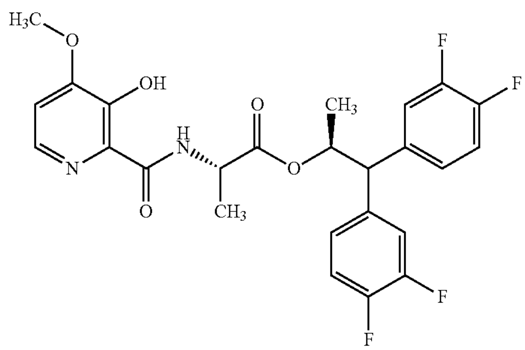 [SMILES: COc1ccnc(C(=O)N[C@@H](C)C(=O)O[C@@H](C)C(c2ccc(F)c(F)c2)c2ccc(F)c(F)c2)c1O] | Example 5, Step 2 | Clear, Colorless Oil |
| 132 | 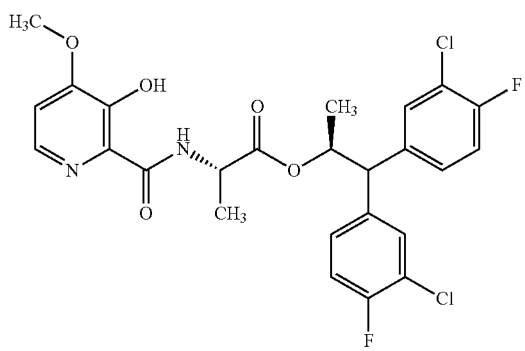 [SMILES: COc1ccnc(C(=O)N[C@@H](C)C(=O)O[C@@H](C)C(c2ccc(F)c(Cl)c2)c2ccc(F)c(Cl)c2)c1O] | Example 5, Step 2 | Colorless Foam |
| 133 | 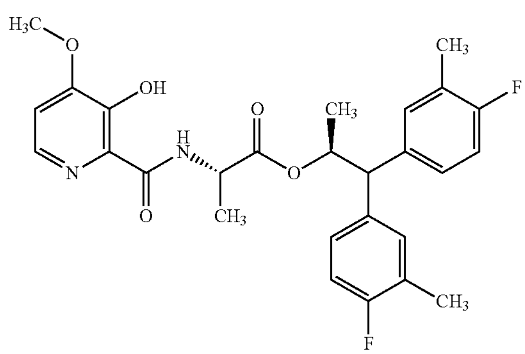 [SMILES: COc1ccnc(C(=O)N[C@@H](C)C(=O)O[C@@H](C)C(c2ccc(F)c(C)c2)c2ccc(F)c(C)c2)c1O] | Example 5, Step 2 | Colorless Foam |
| 135 | 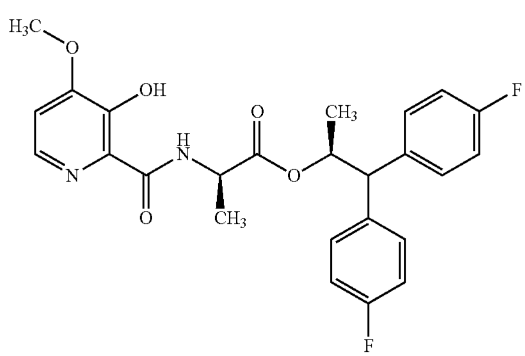 [SMILES: COc1ccnc(C(=O)N[C@H](C)C(=O)O[C@@H](C)C(c2ccc(F)cc2)c2ccc(F)cc2)c1O] | Example 5, Step 2 | Colorless Tacky Semi-Solid |

TABLE 1-continued

Compound Structure, Preparation Method, and Appearance

| *Cmpd. No. | Structure | Prepared According To Example | Appearance |
|---|---|---|---|
| 136 | 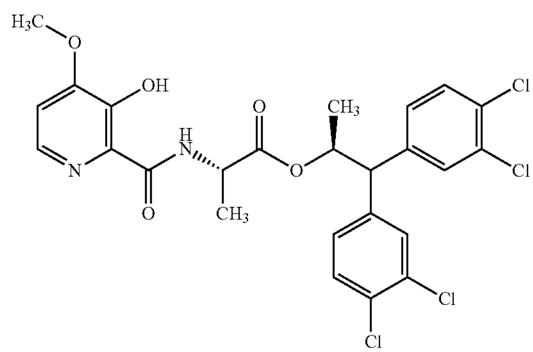 [SMILES: COc1ccnc(C(=O)N[C@@H](C)C(=O)O[C@@H](C)C(c2ccc(Cl)c(Cl)c2)c2ccc(Cl)c(Cl)c2)c1O] | Example 5, Step 2 | White Foam |
| 137 | 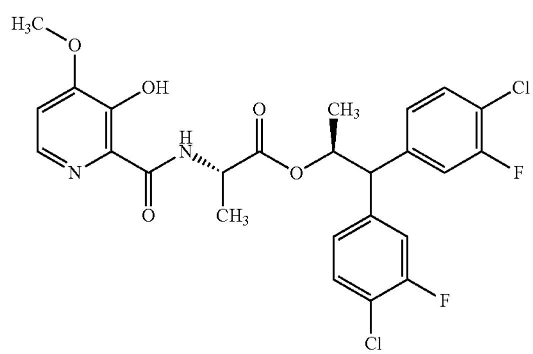 [SMILES: COc1ccnc(C(=O)N[C@@H](C)C(=O)O[C@@H](C)C(c2ccc(Cl)c(F)c2)c2ccc(Cl)c(F)c2)c1O] | Example 5, Step 2 | White Foam |
| 138 | 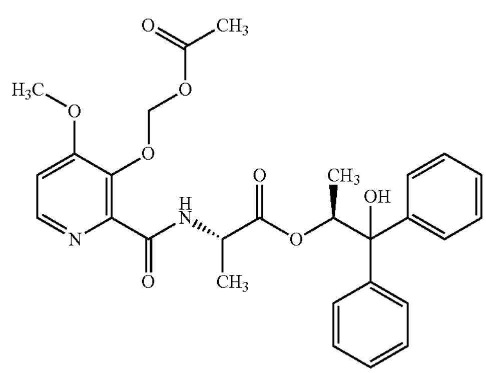 [SMILES: COc1ccnc(C(=O)N[C@@H](C)C(=O)O[C@@H](C)C(O)(c2ccccc2)c2ccccc2)c1OCOC(C)=O] | Example 6B | Colorless Semi-Solid |
| 139 | 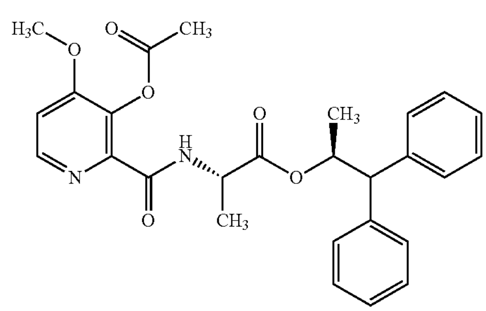 [SMILES: COc1ccnc(C(=O)N[C@@H](C)C(=O)O[C@@H](C)C(c2ccccc2)c2ccccc2)c1OC(C)=O] | Example 6A | Colorless Oil |

TABLE 1-continued

Compound Structure, Preparation Method, and Appearance

| *Cmpd. No. | Structure | Prepared According To Example | Appearance |
|---|---|---|---|
| 140 | 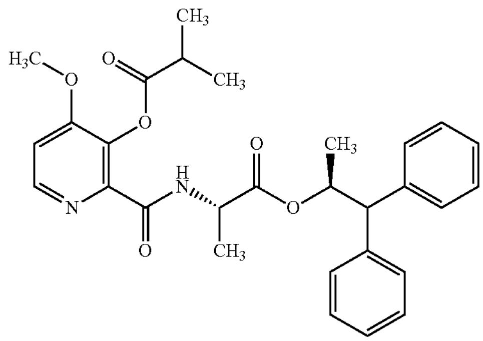 [SMILES: COc1ccnc(C(=O)N[C@@H](C)C(=O)O[C@@H](C)C(c2ccccc2)c2ccccc2)c1OC(=O)C(C)C] | Example 6A | White Foam |
| 141 | 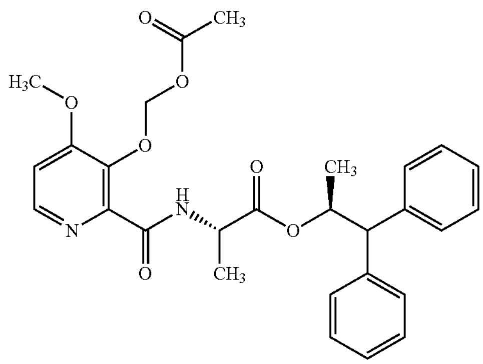 [SMILES: COc1ccnc(C(=O)N[C@@H](C)C(=O)O[C@@H](C)C(c2ccccc2)c2ccccc2)c1OCOC(C)=O] | Example 6B | White Foam |
| 142 | 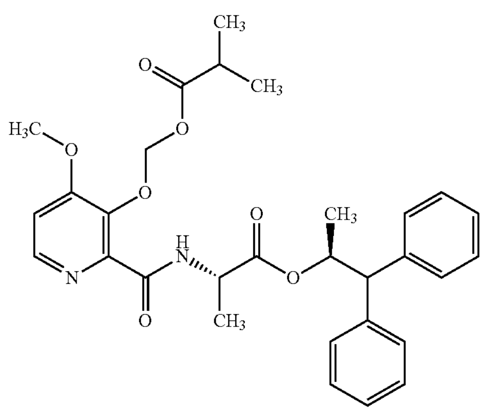 [SMILES: COc1ccnc(C(=O)N[C@@H](C)C(=O)O[C@@H](C)C(c2ccccc2)c2ccccc2)c1OCOC(=O)C(C)C] | Example 6C | White Foam |
| 143 | 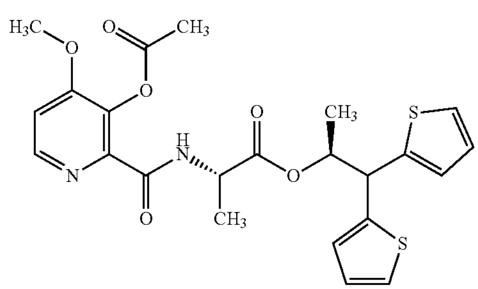 [SMILES: COc1ccnc(C(=O)N[C@@H](C)C(=O)O[C@@H](C)C(c2cccs2)c2cccs2)c1OC(C)=O] | Example 6A | Colorless Oil |

TABLE 1-continued
Compound Structure, Preparation Method, and Appearance
| *Cmpd. No. | Structure | Prepared According To Example | Appearance |
|---|---|---|---|
| 144 | 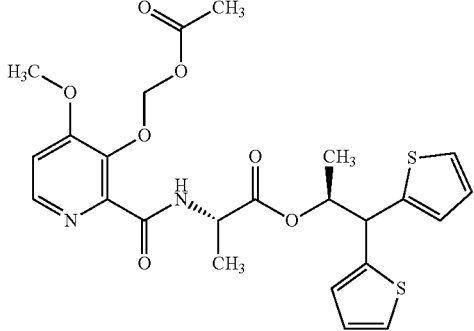 [SMILES: COc1ccnc(C(=O)N[C@@H](C)C(=O)O[C@@H](C)C(c2cccs2)c2cccs2)c1OCOC(C)=O] | Example 6B | Colorless Oil |
| 145 | 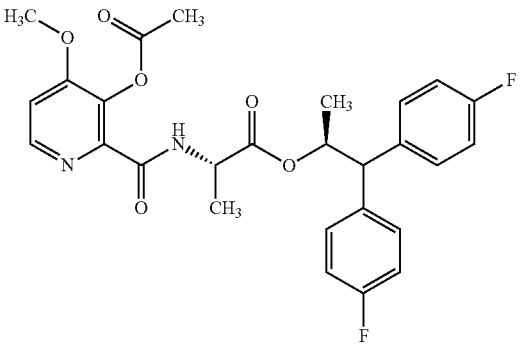 [SMILES: COc1ccnc(C(=O)N[C@@H](C)C(=O)O[C@@H](C)C(c2ccc(F)cc2)c2ccc(F)cc2)c1OC(C)=O] | Example 6A | Colorless Oil |
| 146 | 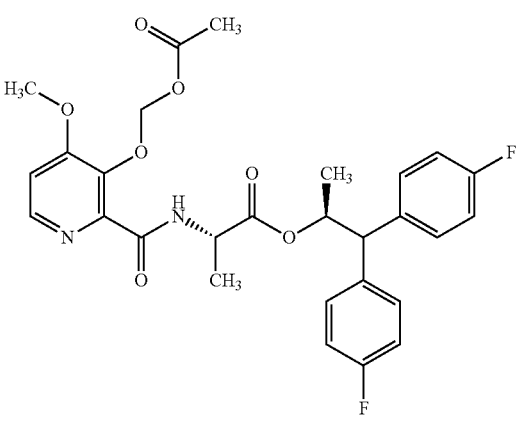 [SMILES: COc1ccnc(C(=O)N[C@@H](C)C(=O)O[C@@H](C)C(c2ccc(F)cc2)c2ccc(F)cc2)c1OCOC(C)=O] | Example 6B | Colorless Oil |
| 147 | 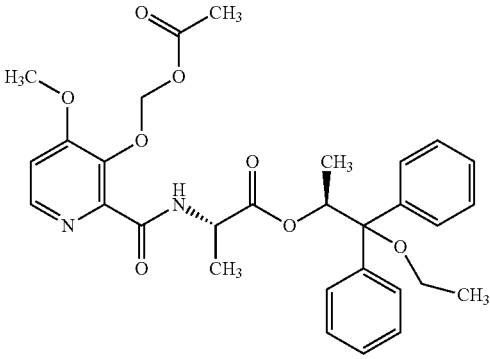 [SMILES: CCOC(c1ccccc1)(c1ccccc1)[C@H](C)OC(=O)[C@H](C)NC(=O)c1nccc(OC)c1OCOC(C)=O] | Example 6B | Colorless Oil |

TABLE 1-continued

Compound Structure, Preparation Method, and Appearance

| *Cmpd. No. | Structure | Prepared According To Example | Appearance |
|---|---|---|---|
| 148 | 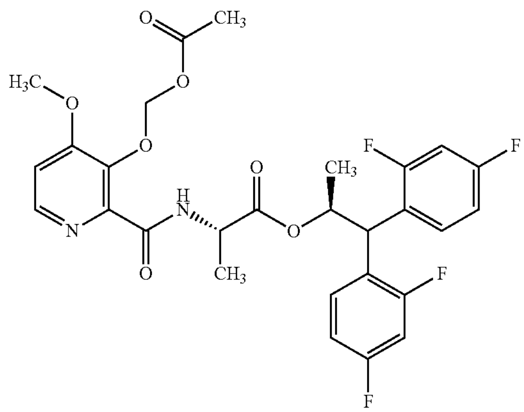 [SMILES: COc1ccnc(C(=O)N[C@@H](C)C(=O)O[C@@H](C)C(c2ccc(F)cc2F)c2ccc(F)cc2F)c1OCOC(C)=O] | Example 6B | Colorless Oil |
| 149 | 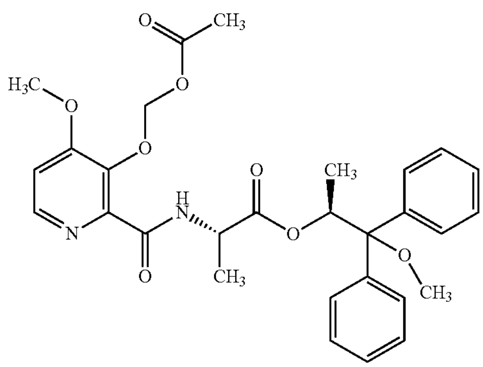 [SMILES: COc1ccnc(C(=O)N[C@@H](C)C(=O)O[C@@H](C)C(OC)(c2ccccc2)c2ccccc2)c1OCOC(C)=O] | Example 6B | Colorless Oil |
| 150 | 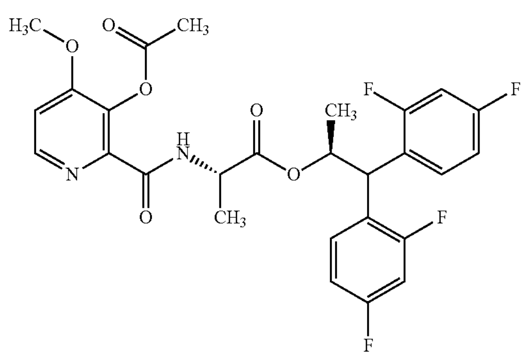 [SMILES: COc1ccnc(C(=O)N[C@@H](C)C(=O)O[C@@H](C)C(c2ccc(F)cc2F)c2ccc(F)cc2F)c1OC(C)=O] | Example 6A | Colorless Oil |
| 152 | 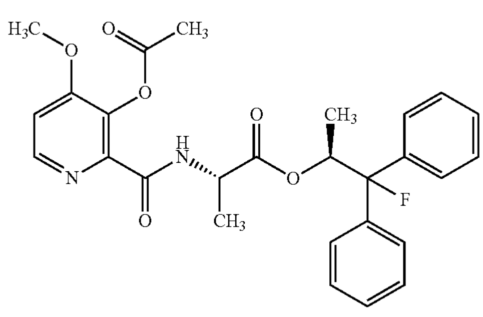 [SMILES: COc1ccnc(C(=O)N[C@@H](C)C(=O)O[C@@H](C)C(F)(c2ccccc2)c2ccccc2)c1OC(C)=O] | Example 6A | Colorless Oil |

TABLE 1-continued
Compound Structure, Preparation Method, and Appearance
| *Cmpd. No. | Structure | Prepared According To Example | Appearance |
| --- | --- | --- | --- |
| 153 | 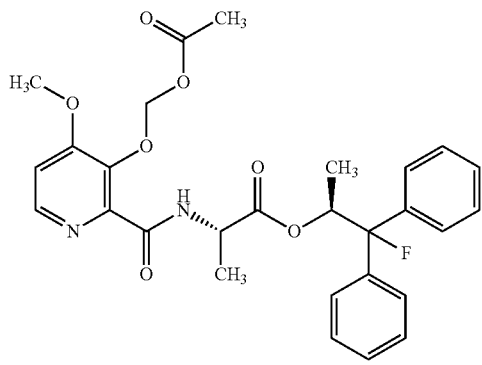 [SMILES: COc1ccnc(C(=O)N[C@@H](C)C(=O)O[C@@H](C)C(F)(c2ccccc2)c2ccccc2)c1OCOC(C)=O] | Example 6B | Colorless Oil |
| 155 | 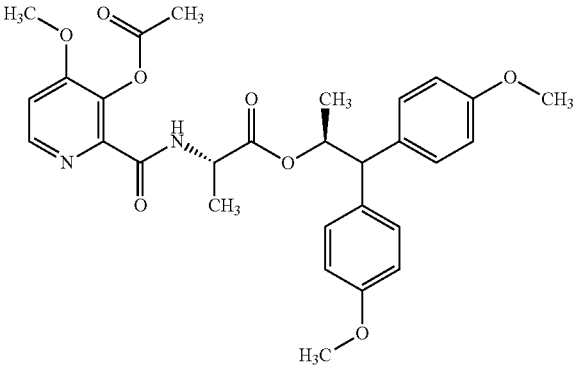 [SMILES: COc1ccc(C(c2ccc(OC)cc2)[C@H](C)OC(=O)[C@H](C)NC(=O)c2nccc(OC)c2OC(C)=O)cc1] | Example 6A | Colorless Oil |
| 156 | 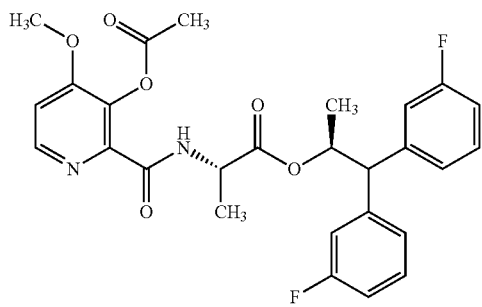 [SMILES: COc1ccnc(C(=O)N[C@@H](C)C(=O)O[C@@H](C)C(c2cccc(F)c2)c2cccc(F)c2)c1OC(C)=O] | Example 6A | Colorless Oil |
| 157 | 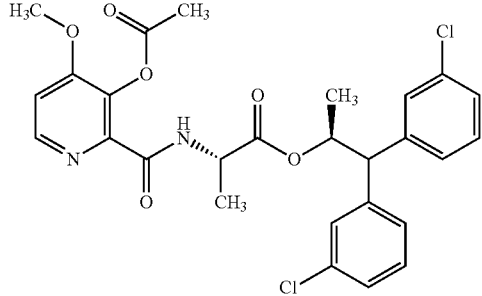 [SMILES: COc1ccnc(C(=O)N[C@@H](C)C(=O)O[C@@H](C)C(c2cccc(Cl)c2)c2cccc(Cl)c2)c1OC(C)=O] | Example 6A | Colorless Oil |

TABLE 1-continued

Compound Structure, Preparation Method, and Appearance

| *Cmpd. No. | Structure | Prepared According To Example | Appearance |
|---|---|---|---|
| 158 | 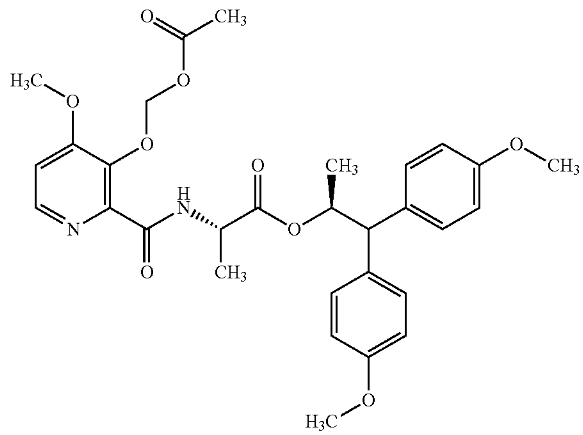 [SMILES: COc1ccc(C(c2ccc(OC)cc2)[C@H](C)OC(=O)[C@H](C)NC(=O)c2nccc(OC)c2OCOC(C)=O)cc1] | Example 6B | Colorless Oil |
| 159 | 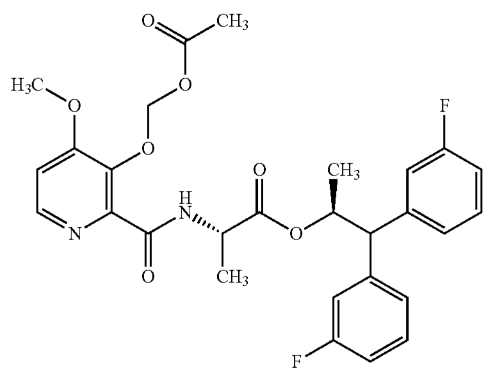 [SMILES: COc1ccnc(C(=O)N[C@@H](C)C(=O)O[C@@H](C)C(c2cccc(F)c2)c2cccc(F)c2)c1OCOC(C)=O] | Example 6B | Colorless Oil |
| 160 | 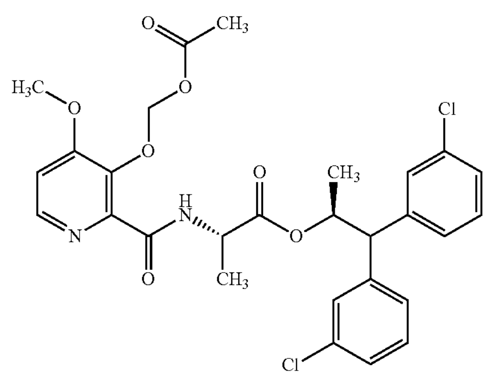 [SMILES: COc1ccnc(C(=O)N[C@@H](C)C(=O)O[C@@H](C)C(c2cccc(Cl)c2)c2cccc(Cl)c2)c1OCOC(C)=O] | Example 6B | Colorless Oil |
| 161 | 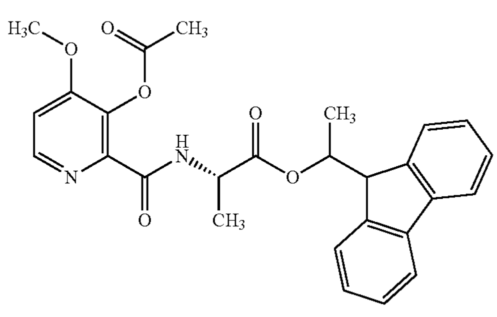 [SMILES: COc1ccnc(C(=O)N[C@@H](C)C(=O)OC(C)C2c3ccccc3-c3ccccc32)c1OC(C)=O] | Example 6A | Colorless Oil |

TABLE 1-continued

Compound Structure, Preparation Method, and Appearance

| *Cmpd. No. | Structure | Prepared According To Example | Appearance |
|---|---|---|---|
| 162 | 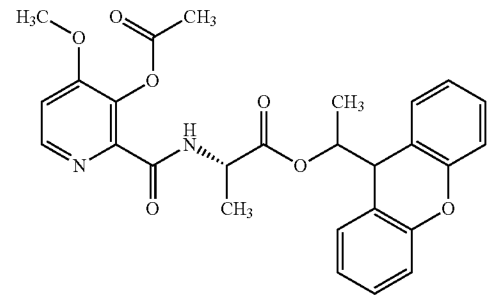 [SMILES: COc1ccnc(C(=O)N[C@@H](C)C(=O)OC(C)C2c3ccccc3Oc3ccccc32)c1OC(C)=O] | Example 6A | Colorless Oil |
| 163 | 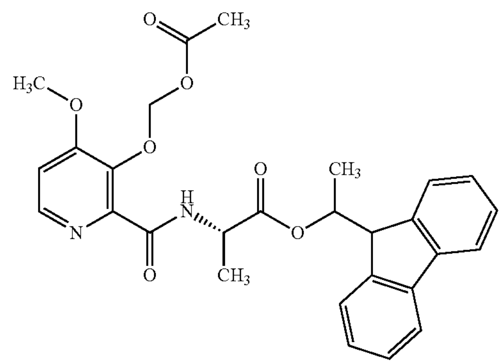 [SMILES: COc1ccnc(C(=O)N[C@@H](C)C(=O)OC(C)C2c3ccccc3-c3ccccc32)c1OCOC(C)=O] | Example 6B | Colorless Oil |
| 164 | 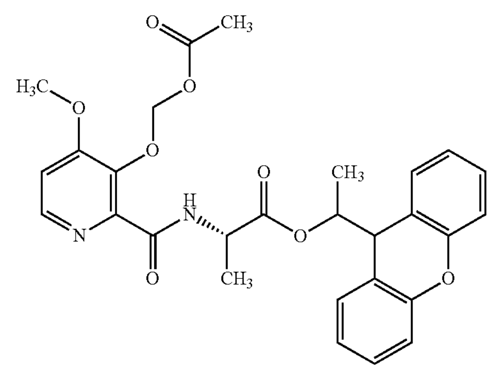 [SMILES: COc1ccnc(C(=O)N[C@@H](C)C(=O)OC(C)C2c3ccccc3Oc3ccccc32)c1OCOC(C)=O] | Example 6B | Colorless Oil |
| 165 | 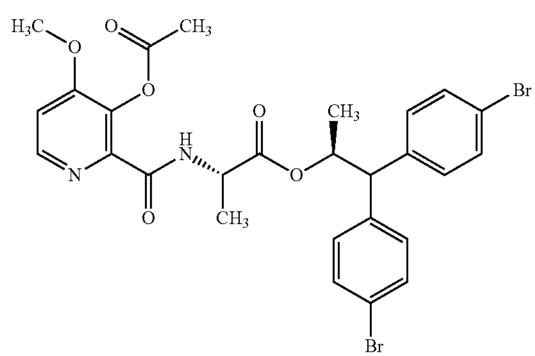 [SMILES: COc1ccnc(C(=O)N[C@@H](C)C(=O)O[C@@H](C)C(c2ccc(Br)cc2)c2ccc(Br)cc2)c1OC(C)=O] | Example 6A | Colorless Oil |

TABLE 1-continued

Compound Structure, Preparation Method, and Appearance

| *Cmpd. No. | Structure | Prepared According To Example | Appearance |
| --- | --- | --- | --- |
| 166 | 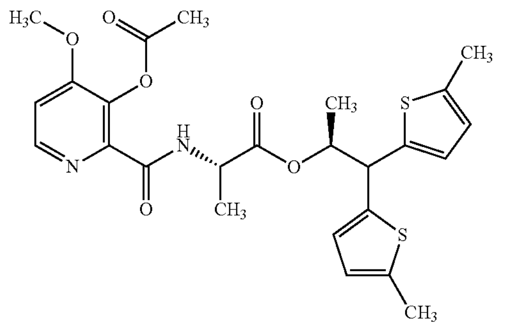 [SMILES: COc1ccnc(C(=O)N[C@@H](C)C(=O)O[C@@H](C)C(c2ccc(C)s2)c2ccc(C)s2)c1OC(C)=O] | Example 6A | Colorless Oil |
| 167 | 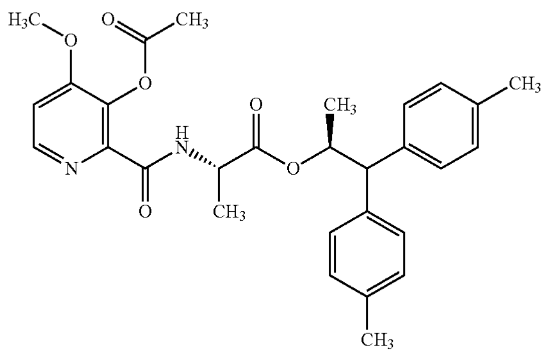 [SMILES: COc1ccnc(C(=O)N[C@@H](C)C(=O)O[C@@H](C)C(c2ccc(C)cc2)c2ccc(C)cc2)c1OC(C)=O] | Example 6A | Colorless Oil |
| 168 | 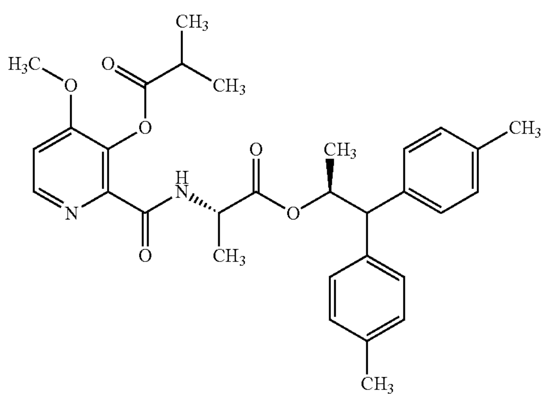 [SMILES: COc1ccnc(C(=O)N[C@@H](C)C(=O)O[C@@H](C)C(c2ccc(C)cc2)c2ccc(C)cc2)c1OC(=O)C(C)C] | Example 6A | Colorless Oil |
| 169 | 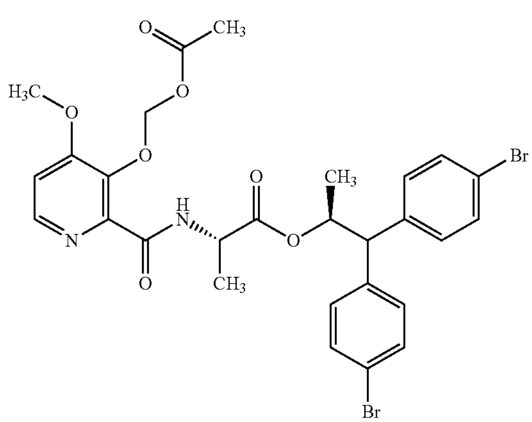 [SMILES: COc1ccnc(C(=O)N[C@@H](C)C(=O)O[C@@H](C)C(c2ccc(Br)cc2)c2ccc(Br)cc2)c1OCOC(C)=O] | Example 6B | Colorless Oil |

TABLE 1-continued

Compound Structure, Preparation Method, and Appearance

| *Cmpd. No. | Structure | Prepared According To Example | Appearance |
|---|---|---|---|
| 170 | 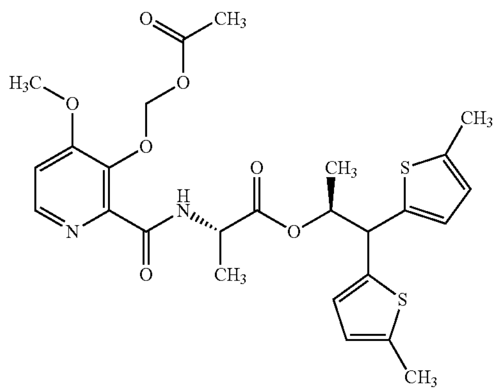 [SMILES: COc1ccnc(C(=O)N[C@@H](C)C(=O)O[C@@H](C)C(c2ccc(C)s2)c2ccc(C)s2)c1OCOC(C)=O] | Example 6B | Colorless Oil |
| 171 | 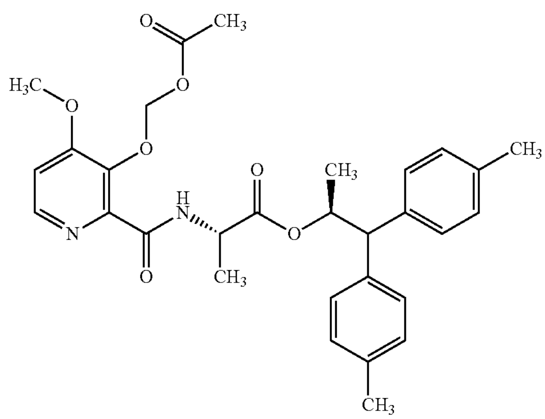 [SMILES: COc1ccnc(C(=O)N[C@@H](C)C(=O)O[C@@H](C)C(c2ccc(C)cc2)c2ccc(C)cc2)c1OCOC(C)=O] | Example 6B | Colorless Oil |
| 173 | 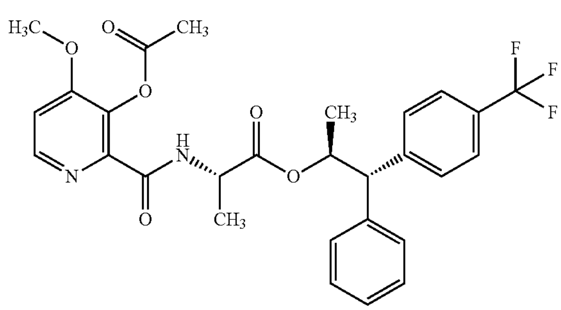 [SMILES: COc1ccnc(C(=O)N[C@@H](C)C(=O)O[C@@H](C)[C@@H](c2ccccc2)c2ccc(C(F)(F)F)cc2)c1OC(C)=O] | Example 6A | Colorless Oil |
| 174 | 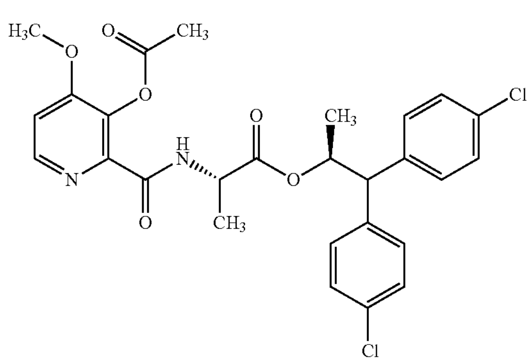 [SMILES: COc1ccnc(C(=O)N[C@@H](C)C(=O)O[C@@H](C)C(c2ccc(Cl)cc2)c2ccc(Cl)cc2)c1OC(C)=O] | Example 6A | Colorless Oil |

TABLE 1-continued

Compound Structure, Preparation Method, and Appearance

| *Cmpd. No. | Structure | Prepared According To Example | Appearance |
|---|---|---|---|
| 175 | 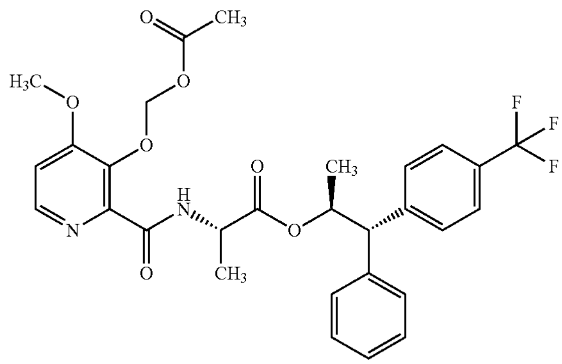 [SMILES: COc1ccnc(C(=O)N[C@@H](C)C(=O)O[C@@H](C)[C@@H](c2ccccc2)c2ccc(C(F)(F)F)cc2)c1OCOC(C)=O] | Example 6B | Colorless Oil |
| 176 | 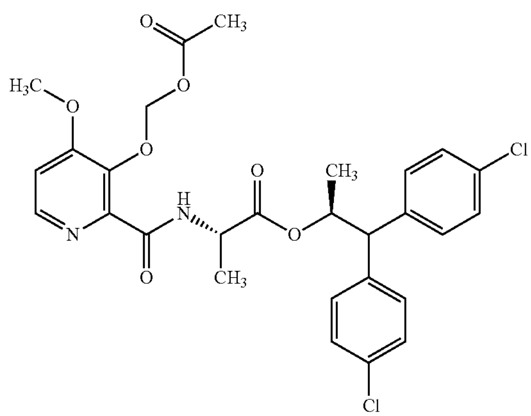 [SMILES: COc1ccnc(C(=O)N[C@@H](C)C(=O)O[C@@H](C)C(c2ccc(Cl)cc2)c2ccc(Cl)cc2)c1OCOC(C)=O] | Example 6B | Colorless Oil |
| 178 | 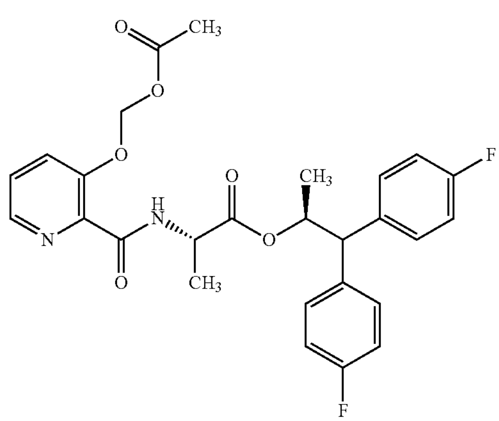 | Example 6B | Clear, Colorless Oil |

TABLE 1-continued

Compound Structure, Preparation Method, and Appearance

| *Cmpd. No. | Structure | Prepared According To Example | Appearance |
|---|---|---|---|
| 179 | 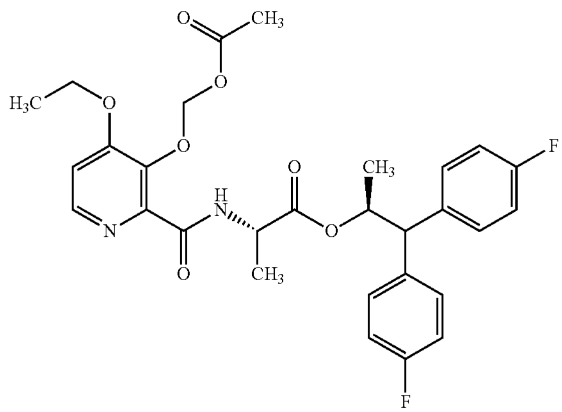 [SMILES: CCOc1ccnc(C(=O)N[C@@H](C)C(=O)O[C@@H](C)C(c2ccc(F)cc2)c2ccc(F)cc2)c1OCOC(C)=O] | Example 6B | Clear, Colorless Oil |
| 180 | 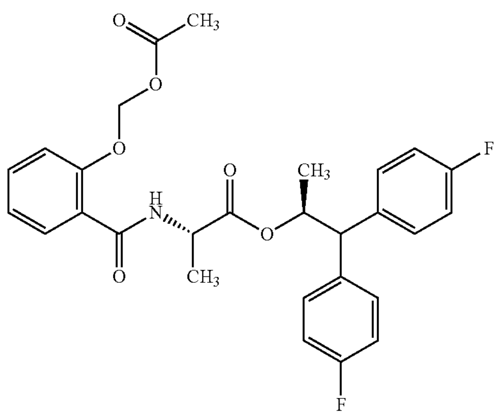 [SMILES: CC(=O)OCOc1ccccc1C(=O)N[C@@H](C)C(=O)O[C@@H](C)C(c1ccc(F)cc1)c1ccc(F)cc1] | Example 6B | Clear, Colorless Oil |
| 181 | 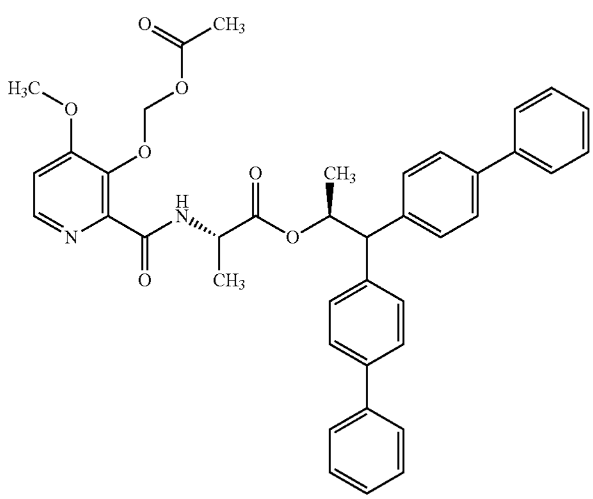 [SMILES: COc1ccnc(C(=O)N[C@@H](C)C(=O)O[C@@H](C)C(c2ccc(-c3ccccc3)cc2)c2ccc(-c3ccccc3)cc2)c1OCOC(C)=O] | Example 6B | White Foam |

TABLE 1-continued

Compound Structure, Preparation Method, and Appearance

| *Cmpd. No. | Structure | Prepared According To Example | Appearance |
|---|---|---|---|
| 182 | 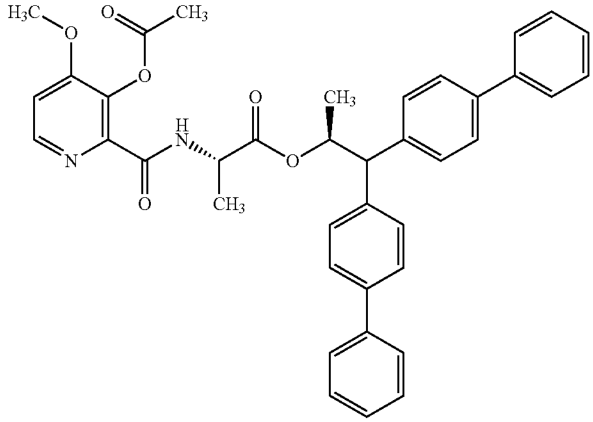 [SMILES: COc1ccnc(C(=O)N[C@@H](C)C(=O)O[C@@H](C)C(c2ccc(-c3ccccc3)cc2)c2ccc(-c3ccccc3)cc2)c1OC(C)=O] | Example 6A | Colorless Oil |
| 183 | 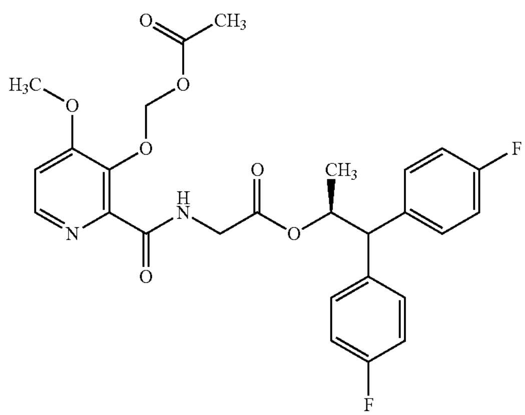 [SMILES: COc1ccnc(C(=O)NCC(=O)O[C@@H](C)C(c2ccc(F)cc2)c2ccc(F)cc2)c1OCOC(C)=O] | Example 6B | White Solid |
| 184 | 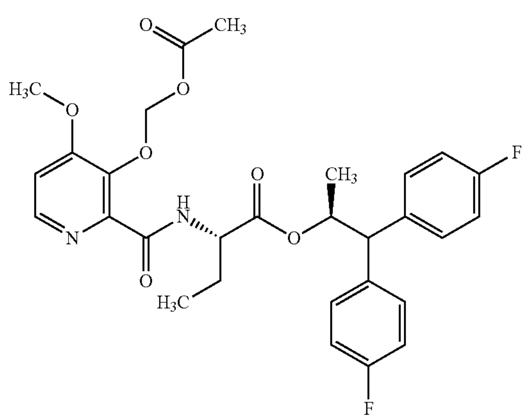 [SMILES: CC[C@H](NC(=O)c1nccc(OC)c1OCOC(C)=O)C(=O)O[C@@H](C)C(c1ccc(F)cc1)c1ccc(F)cc1] | Example 6B | White Solid |

TABLE 1-continued

Compound Structure, Preparation Method, and Appearance

| *Cmpd. No. | Structure | Prepared According To Example | Appearance |
|---|---|---|---|
| 185 | 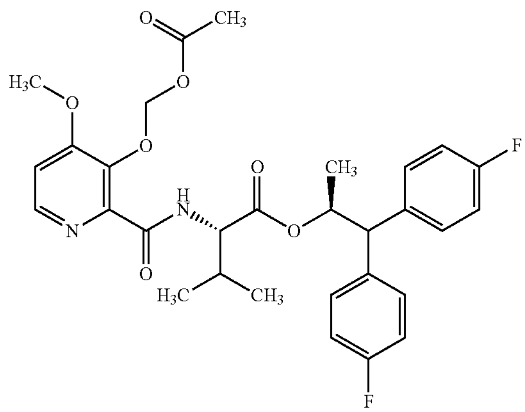 [SMILES: COc1ccnc(C(=O)N[C@H](C(=O)O[C@@H](C)C(c2ccc(F)cc2)c2ccc(F)cc2)C(C)C)c1OCOC(C)=O] | Example 6B | White Solid |
| 186 | 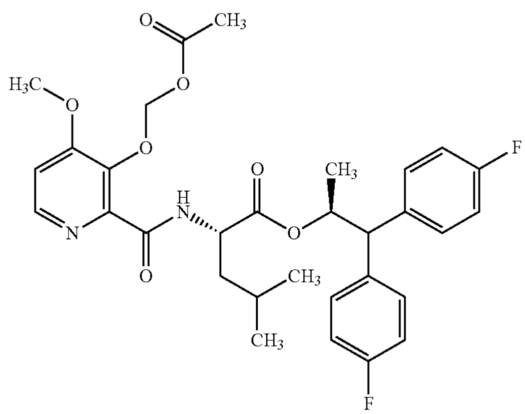 [SMILES: COc1ccnc(C(=O)N[C@@H](CC(C)C)C(=O)O[C@@H](C)C(c2ccc(F)cc2)c2ccc(F)cc2)c1OCOC(C)=O] | Example 6B | White Solid |
| 187 | 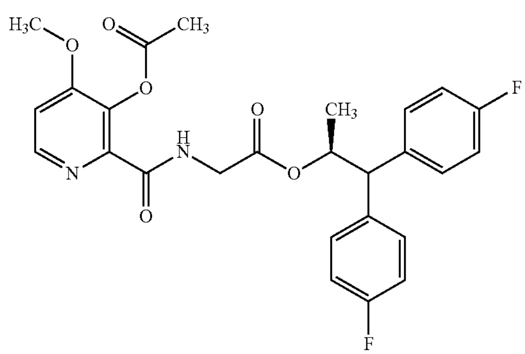 [SMILES: COc1ccnc(C(=O)NCC(=O)O[C@@H](C)C(c2ccc(F)cc2)c2ccc(F)cc2)c1OC(C)=O] | Example 6A | White Solid |
| 188 | 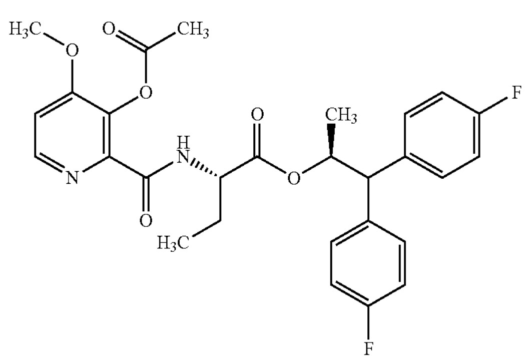 [SMILES: CC[C@H](NC(=O)c1nccc(OC)c1OC(C)=O)C(=O)O[C@@H](C)C(c1ccc(F)cc1)c1ccc(F)cc1] | Example 6A | White Solid |

TABLE 1-continued

Compound Structure, Preparation Method, and Appearance

| *Cmpd. No. | Structure | Prepared According To Example | Appearance |
|---|---|---|---|
| 189 | 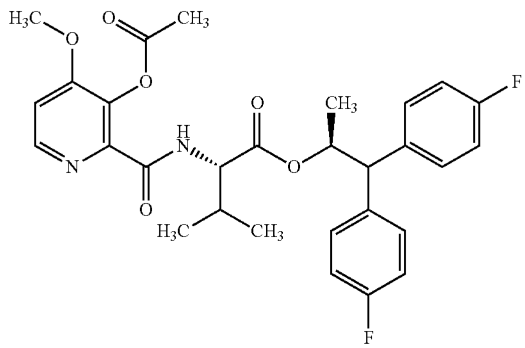 [SMILES: COc1ccnc(C(=O)N[C@H](C(=O)O[C@@H](C)C(c2ccc(F)cc2)c2ccc(F)cc2)C(C)C)c1OC(C)=O] | Example 6A | White Solid |
| 190 | 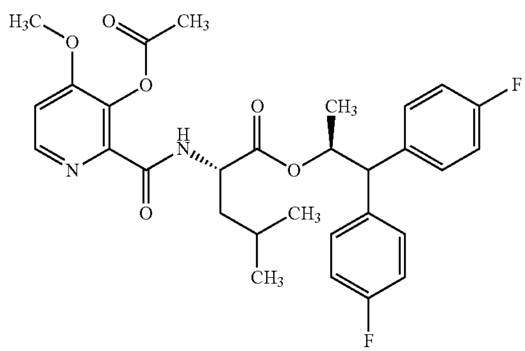 [SMILES: COc1ccnc(C(=O)N[C@@H](CC(C)C)C(=O)O[C@@H](C)C(c2ccc(F)cc2)c2ccc(F)cc2)c1OC(C)=O] | Example 6A | White Solid |
| 191 | 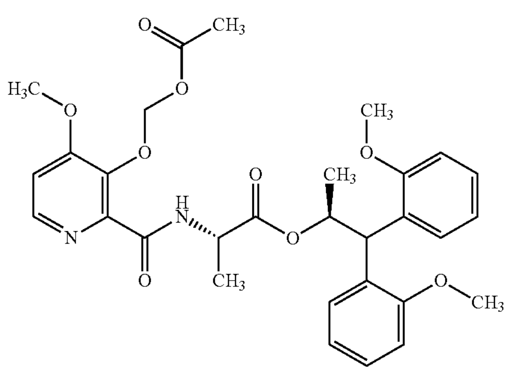 [SMILES: COc1ccccc1C(c1ccccc1OC)[C@H](C)OC(=O)[C@H](C)NC(=O)c1nccc(OC)c1OCOC(C)=O] | Example 6B | White Foam |
| 192 | 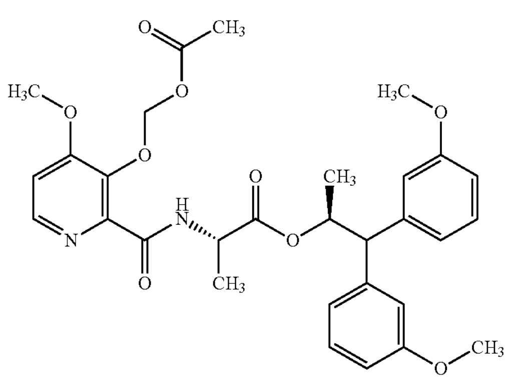 [SMILES: COc1cccc(C(c2cccc(OC)c2)[C@H](C)OC(=O)[C@H](C)NC(=O)c2nccc(OC)c2OCOC(C)=O)c1] | Example 6B | White Foam |

TABLE 1-continued

Compound Structure, Preparation Method, and Appearance

| *Cmpd. No. | Structure | Prepared According To Example | Appearance |
|---|---|---|---|
| 193 | 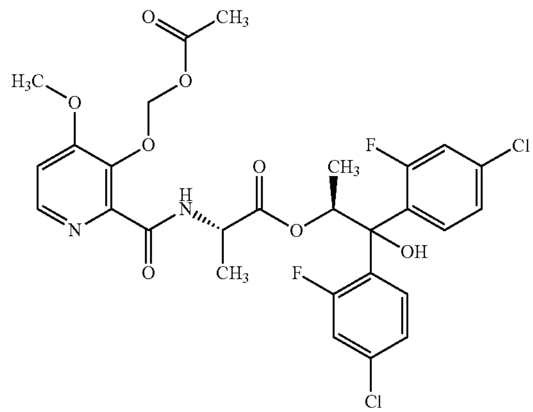 [SMILES: COc1ccnc(C(=O)N[C@@H](C)C(=O)O[C@@H](C)C(O)(c2ccc(Cl)cc2F)c2ccc(Cl)cc2F)c1OCOC(C)=O] | Example 6B | Sticky Wax |
| 194 | 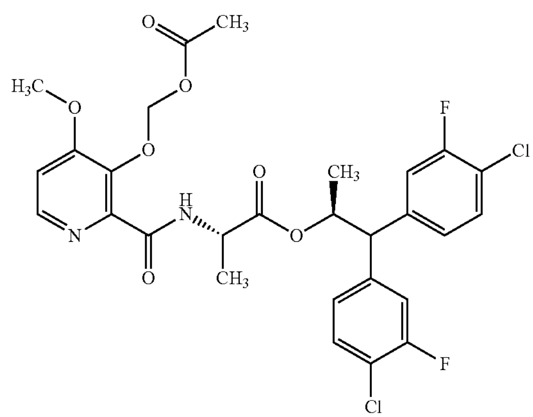 [SMILES: COc1ccnc(C(=O)N[C@@H](C)C(=O)O[C@@H](C)C(c2ccc(Cl)c(F)c2)c2ccc(Cl)c(F)c2)c1OCOC(C)=O] | Example 6B | White Foam |
| 195 | 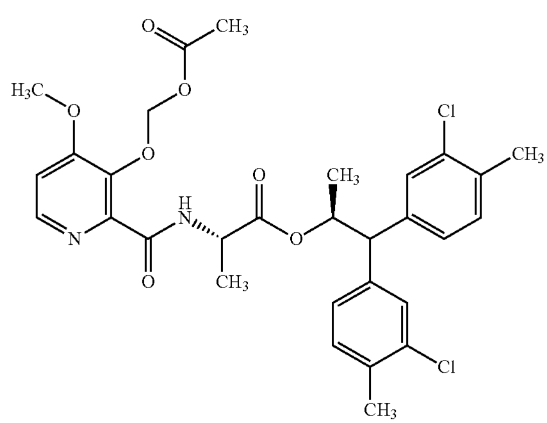 [SMILES: COc1ccnc(C(=O)N[C@@H](C)C(=O)O[C@@H](C)C(c2ccc(C)c(Cl)c2)c2ccc(C)c(Cl)c2)c1OCOC(C)=O] | Example 6B | White Foam |

TABLE 1-continued

Compound Structure, Preparation Method, and Appearance

| *Cmpd. No. | Structure | Prepared According To Example | Appearance |
|---|---|---|---|
| 196 | 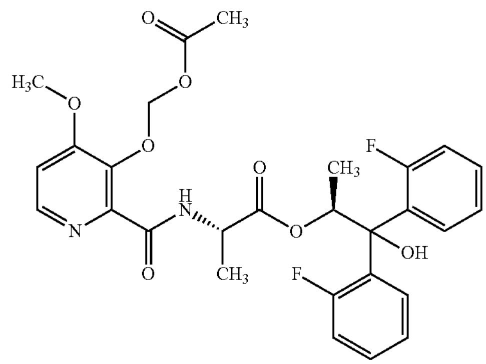 [SMILES: COc1ccnc(C(=O)N[C@@H](C)C(=O)O[C@@H](C)C(O)(c2ccccc2F)c2ccccc2F)c1OCOC(C)=O] | Example 6B | White Foam |
| 197 | 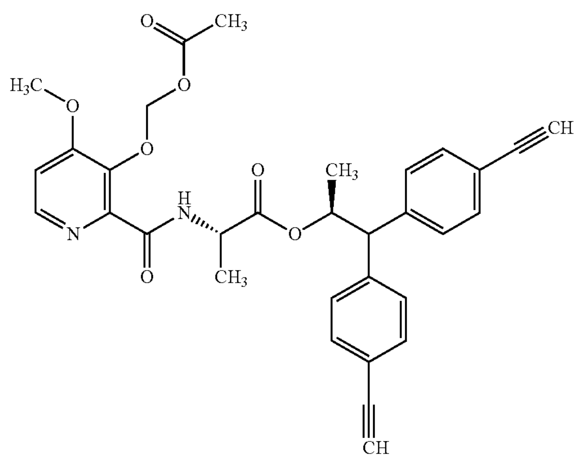 [SMILES: C#Cc1ccc(C(c2ccc(C#C)cc2)[C@H](C)OC(=O)[C@H](C)NC(=O)c2nccc(OC)c2OCOC(C)=O)cc1] | Example 6B | White Foam |
| 198 | 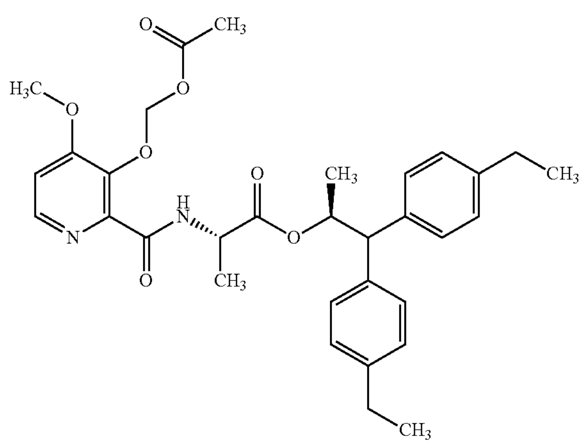 [SMILES: CCc1ccc(C(c2ccc(CC)cc2)[C@H](C)OC(=O)[C@H](C)NC(=O)c2nccc(OC)c2OCOC(C)=O)cc1] | Example 6B | Sticky Wax |

TABLE 1-continued

Compound Structure, Preparation Method, and Appearance

| *Cmpd. No. | Structure | Prepared According To Example | Appearance |
|---|---|---|---|
| 199 | 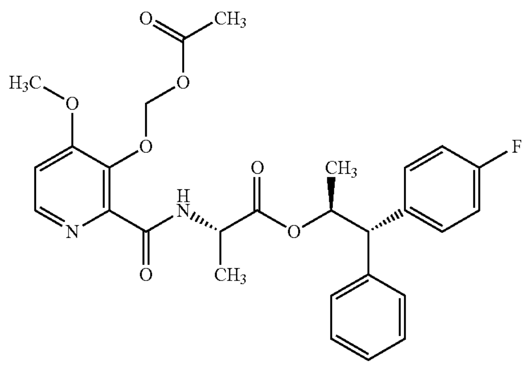 [SMILES: COc1ccnc(C(=O)N[C@@H](C)C(=O)O[C@@H](C)[C@@H](c2ccccc2)c2ccc(F)cc2)c1OCOC(C)=O] | Example 6B | White Solid |
| 201 | 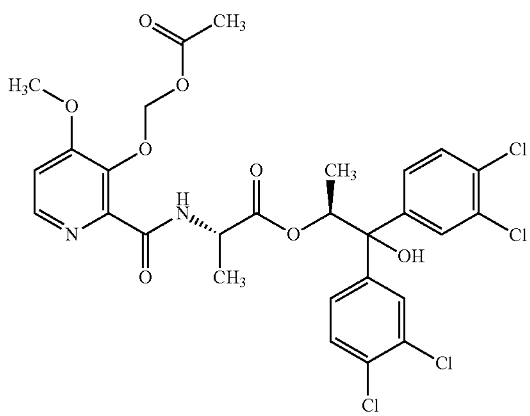 | Example 6B | White Solid |
| 202 | 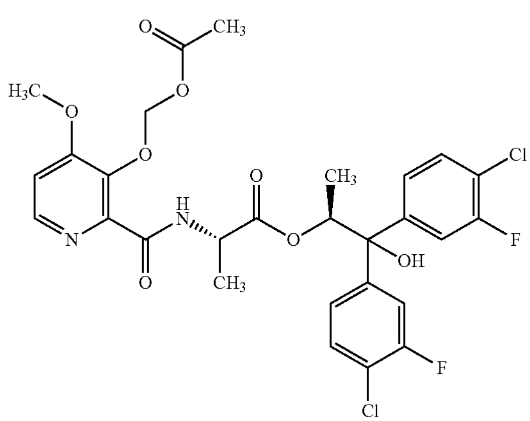 [SMILES: COc1ccnc(C(=O)N[C@@H](C)C(=O)O[C@@H](C)C(O)(c2ccc(Cl)c(F)c2)c2ccc(Cl)c(F)c2)c1OCOC(C)=O] | Example 6B | White Solid |

TABLE 1-continued

Compound Structure, Preparation Method, and Appearance

| *Cmpd. No. | Structure | Prepared According To Example | Appearance |
|---|---|---|---|
| 203 | 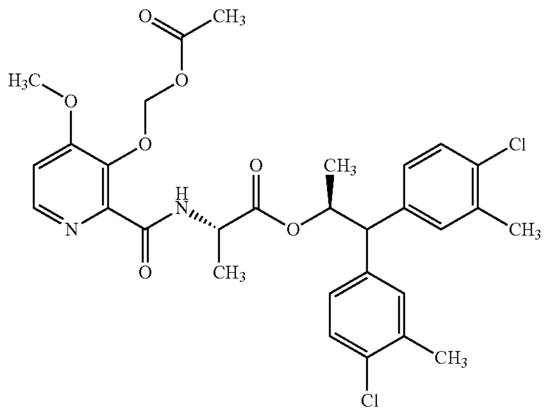 [SMILES: COc1ccnc(C(=O)N[C@@H](C)C(=O)O[C@@H](C)C(c2ccc(Cl)c(C)c2)c2ccc(Cl)c(C)c2)c1OCOC(C)=O] | Example 6B | White Solid |
| 204 | 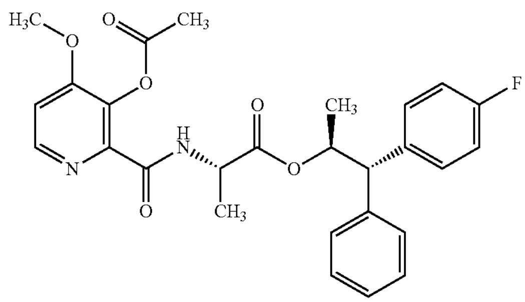 [SMILES: COc1ccnc(C(=O)N[C@@H](C)C(=O)O[C@@H](C)[C@@H](c2ccccc2)c2ccc(F)cc2)c1OC(C)=O] | Example 6A | White Solid |
| 206 | 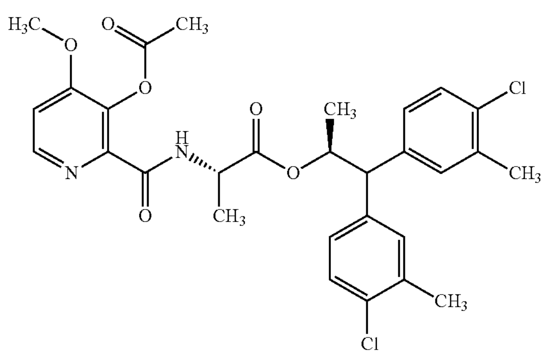 [SMILES: COc1ccnc(C(=O)N[C@@H](C)C(=O)O[C@@H](C)C(c2ccc(Cl)c(C)c2)c2ccc(Cl)c(C)c2)c1OC(C)=O] | Example 6A | White Solid |
| 207 | 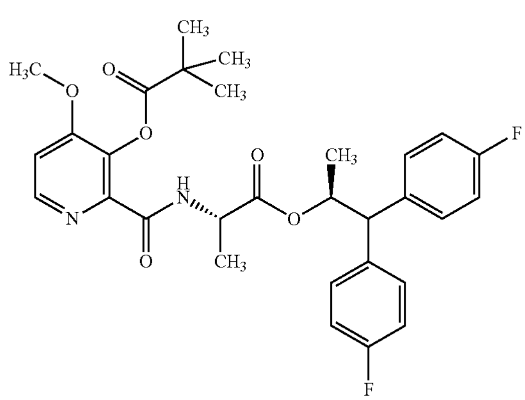 [SMILES: COc1ccnc(C(=O)N[C@@H](C)C(=O)O[C@@H](C)C(c2ccc(F)cc2)c2ccc(F)cc2)c1OC(=O)C(C)(C)C] | Example 6A | White Solid |

TABLE 1-continued
Compound Structure, Preparation Method, and Appearance
| *Cmpd. No. | Structure | Prepared According To Example | Appearance |
|---|---|---|---|
| 208 | 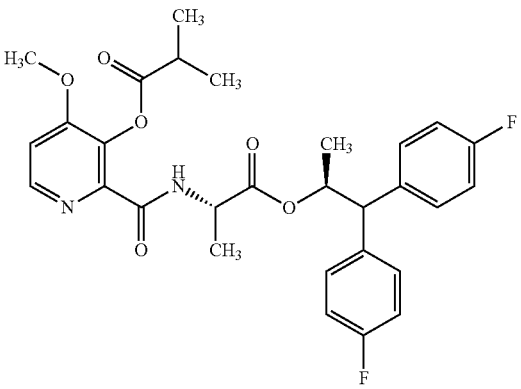 [SMILES: COc1ccnc(C(=O)N[C@@H](C)C(=O)O[C@@H](C)C(c2ccc(F)cc2)c2ccc(F)cc2)c1OC(=O)C(C)C] | Example 6A | Clear Colorless Oil |
| 209 | 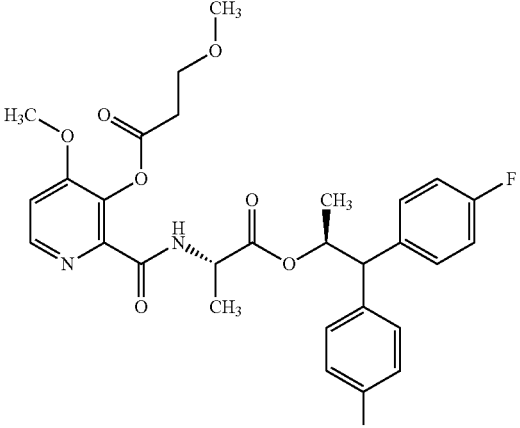 | Example 6A | Slightly Cloudy Colorless Oil |
| 210 | 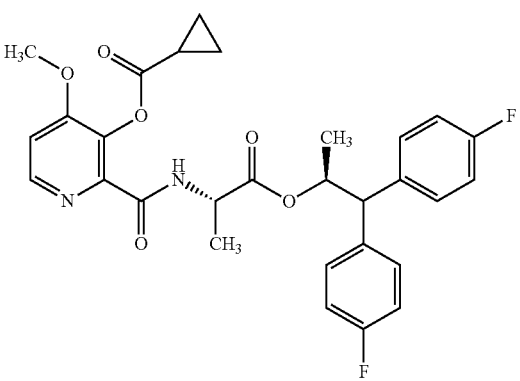 [SMILES: COc1ccnc(C(=O)N[C@@H](C)C(=O)O[C@@H](C)C(c2ccc(F)cc2)c2ccc(F)cc2)c1OC(=O)C1CC1] | Example 6A | Slightly Cloudy Colorless Oil |

TABLE 1-continued

Compound Structure, Preparation Method, and Appearance

| *Cmpd. No. | Structure | Prepared According To Example | Appearance |
|---|---|---|---|
| 211 | 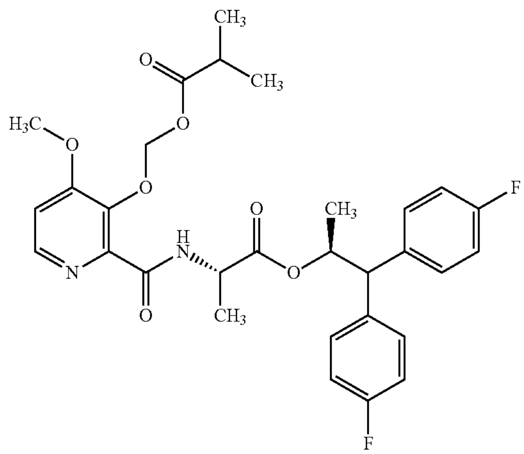 [SMILES: COc1ccnc(C(=O)N[C@@H](C)C(=O)O[C@@H](C)C(c2ccc(F)cc2)c2ccc(F)cc2)c1OCOC(=O)C(C)C] | Example 6C | Clear Colorless Oil |
| 212 | 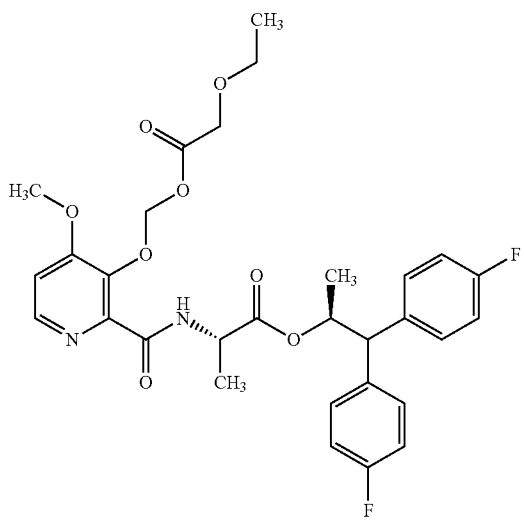 [SMILES: CCOCC(=O)OCOc1c(OC)ccnc1C(=O)N[C@@H](C)C(=O)O[C@@H](C)C(c1ccc(F)cc1)c1ccc(F)cc1] | Example 6C | Colorless Clear Film And Opaque Oil |
| 213 | 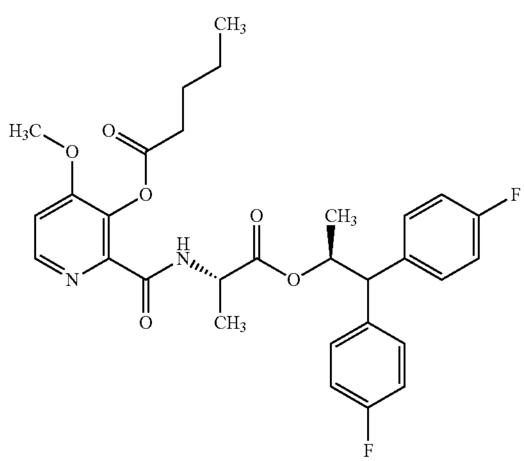 [SMILES: CCCCC(=O)Oc1c(OC)ccnc1C(=O)N[C@@H](C)C(=O)O[C@@H](C)C(c1ccc(F)cc1)c1ccc(F)cc1] | Example 6A | Clear Colorless Viscous Oil And Semi-Solid |

TABLE 1-continued

Compound Structure, Preparation Method, and Appearance

| *Cmpd. No. | Structure | Prepared According To Example | Appearance |
|---|---|---|---|
| 214 | 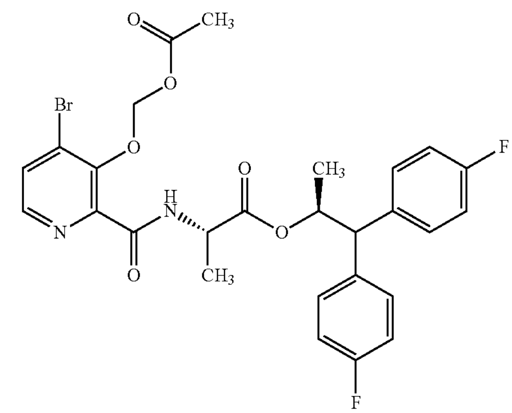 [SMILES: CC(=O)OCOc1c(Br)ccnc1C(=O)N[C@@H](C)C(=O)O[C@@H](C)C(c1ccc(F)cc1)c1ccc(F)cc1] | Example 6B | Clear, Colorless Oil |
| 215 | 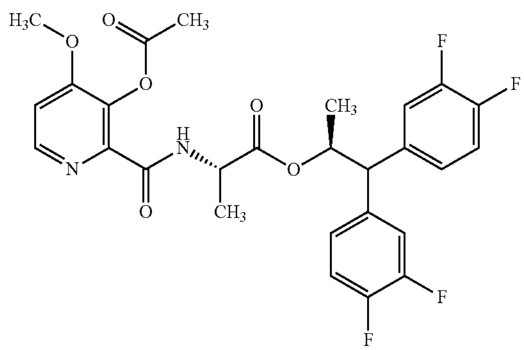 [SMILES: COc1ccnc(C(=O)N[C@@H](C)C(=O)O[C@@H](C)C(c2ccc(F)c(F)c2)c2ccc(F)c(F)c2)c1OC(C)=O] | Example 6A | Pale Yellow Oil |
| 216 | 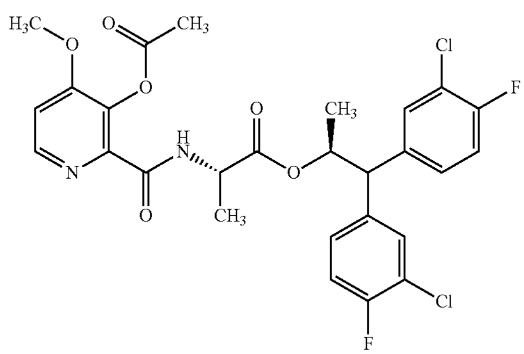 [SMILES: COc1ccnc(C(=O)N[C@@H](C)C(=O)O[C@@H](C)C(c2ccc(F)c(Cl)c2)c2ccc(F)c(Cl)c2)c1OC(C)=O] | Example 6A | Pale Yellow Oil |
| 217 | 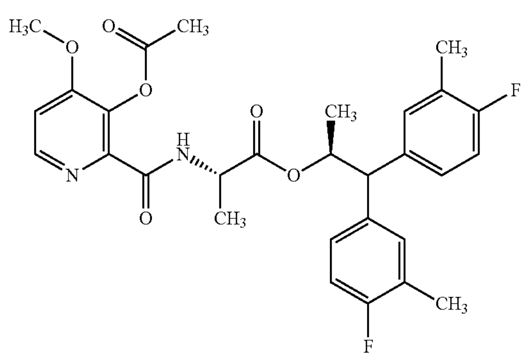 [SMILES: COc1ccnc(C(=O)N[C@@H](C)C(=O)O[C@@H](C)C(c2ccc(F)c(C)c2)c2ccc(F)c(C)c2)c1OC(C)=O] | Example 6A | Pale Yellow Oil |

TABLE 1-continued

Compound Structure, Preparation Method, and Appearance

| *Cmpd. No. | Structure | Prepared According To Example | Appearance |
|---|---|---|---|
| 218 | 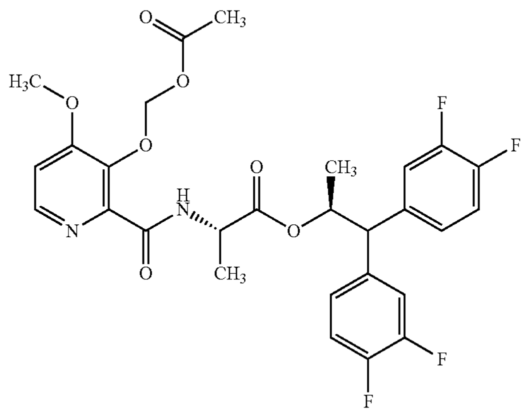 [SMILES: COc1ccnc(C(=O)N[C@@H](C)C(=O)O[C@@H](C)C(c2ccc(F)c(F)c2)c2ccc(F)c(F)c2)c1OCOC(C)=O] | Example 6B | Pale Yellow Oil |
| 219 | 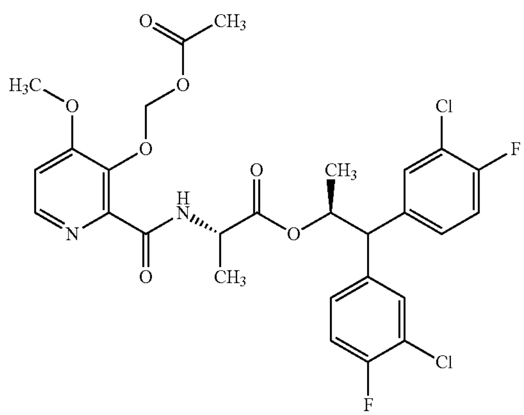 [SMILES: COc1ccnc(C(=O)N[C@@H](C)C(=O)O[C@@H](C)C(c2ccc(F)c(Cl)c2)c2ccc(F)c(Cl)c2)c1OCOC(C)=O] | Example 6B | Pale Yellow Oil |
| 220 | 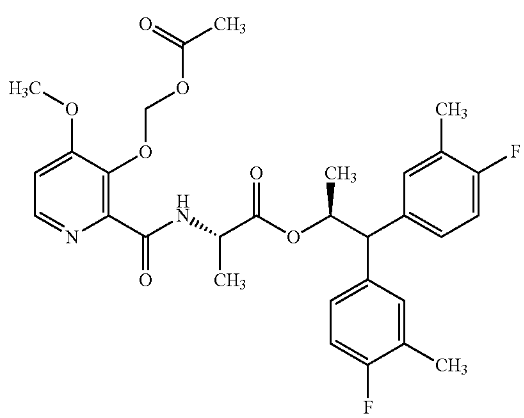 [SMILES: COc1ccnc(C(=O)N[C@@H](C)C(=O)O[C@@H](C)C(c2ccc(F)c(C)c2)c2ccc(F)c(C)c2)c1OCOC(C)=O] | Example 6B | Pale Yellow Oil |

TABLE 1-continued

Compound Structure, Preparation Method, and Appearance

| *Cmpd. No. | Structure | Prepared According To Example | Appearance |
|---|---|---|---|
| 221 | 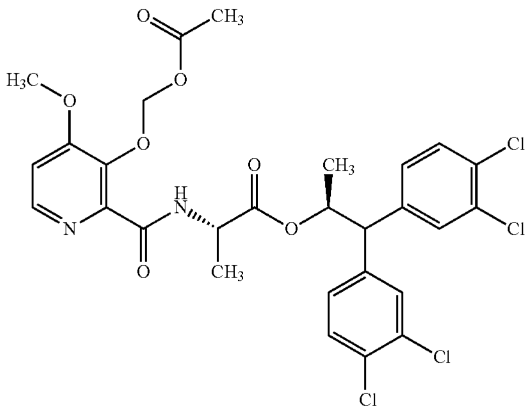 | Example 6B | White Foam |
| 222 | 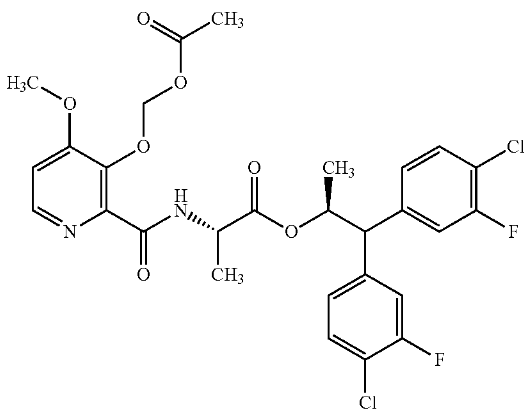 [SMILES: COc1ccnc(C(=O)N[C@@H](C)C(=O)O[C@@H](C)C(c2ccc(Cl)c(F)c2)c2ccc(Cl)c(F)c2)c1OCOC(C)=O] | Example 6B | White Foam |
| 223 | 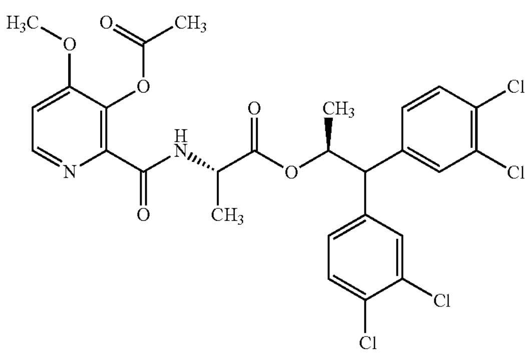 | Example 6A | White Foam |
| 224 | 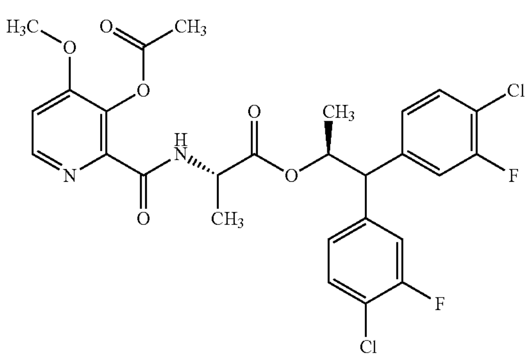 [SMILES: COc1ccnc(C(=O)N[C@@H](C)C(=O)O[C@@H](C)C(c2ccc(Cl)c(F)c2)c2ccc(Cl)c(F)c2)c1OC(C)=O] | Example 6A | White Foam |

TABLE 1-continued

Compound Structure, Preparation Method, and Appearance

| *Cmpd. No. | Structure | Prepared According To Example | Appearance |
|---|---|---|---|
| 225 | 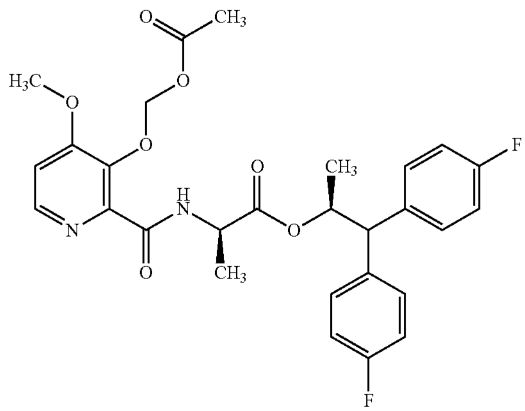 [SMILES: COc1ccnc(C(=O)N[C@H](C)C(=O)O[C@@H](C)C(c2ccc(F)cc2)c2ccc(F)cc2)c1OCOC(C)=O] | Example 6B | Slightly Opaque Colorless Oil |
| 226 | 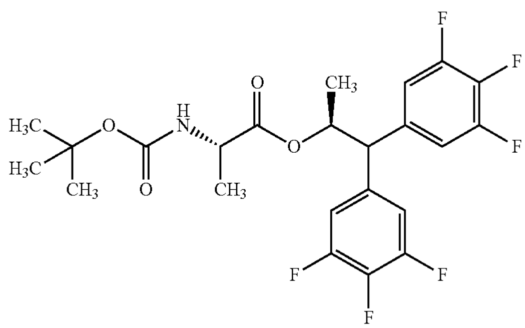 [SMILES: C[C@H](NC(=O)OC(C)(C)C)C(=O)O[C@@H](C)C(c1cc(F)c(F)c(F)c1)c1cc(F)c(F)c(F)c1] | Example 1; Example 2D, Steps 1-2; Example 3A; Example 4A | White Semi-Solid |
| 227 | 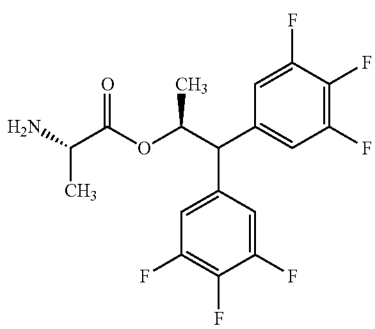 [SMILES: C[C@H](N)C(=O)O[C@@H](C)C(c1cc(F)c(F)c(F)c1)c1cc(F)c(F)c(F)c1] | Example 5, Step 1 | White Glass |
| 228 | 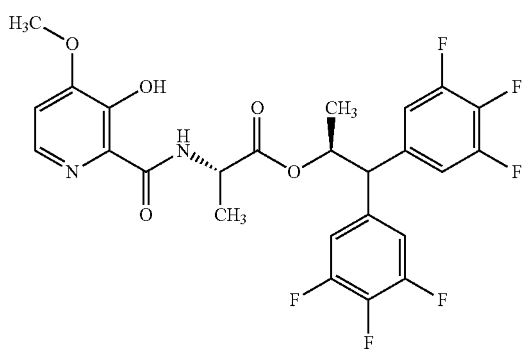 [SMILES: COc1ccnc(C(=O)N[C@@H](C)C(=O)O[C@@H](C)C(c2cc(F)c(F)c(F)c2)c2cc(F)c(F)c(F)c2)c1O] | Example 5, Step 2 | Colorless Foam |

TABLE 1-continued

Compound Structure, Preparation Method, and Appearance

| *Cmpd. No. | Structure | Prepared According To Example | Appearance |
|---|---|---|---|
| 229 | 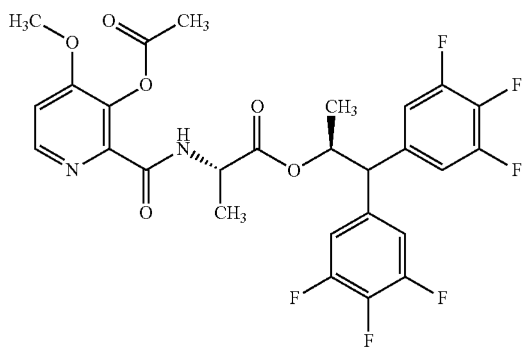 [SMILES: COc1ccnc(C(=O)N[C@@H](C)C(=O)O[C@@H](C)C(c2cc(F)c(F)c(F)c2)c2cc(F)c(F)c(F)c2)c1OC(C)=O] | Example 6A | Clear, Colorless Oil |
| 230 | 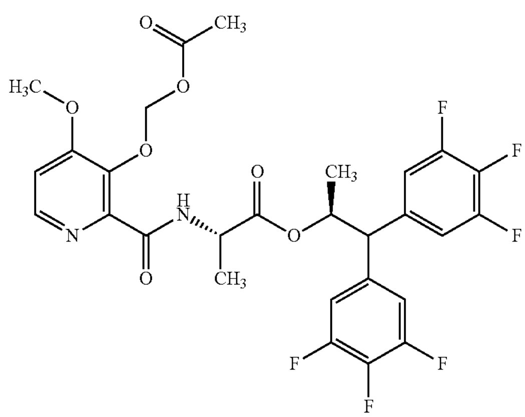 [SMILES: COc1ccnc(C(=O)N[C@@H](C)C(=O)O[C@@H](C)C(c2cc(F)c(F)c(F)c2)c2cc(F)c(F)c(F)c2)c1OCOC(C)=O] | Example 6B | Clear Colorless Oil |
| 232 | 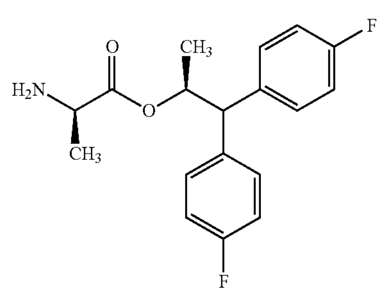 [SMILES: C[C@H](OC(=O)[C@@H](C)N)C(c1ccc(F)cc1)c1ccc(F)cc1] | Example 5, Step 1 | White Semi-Solid |
| 233 | 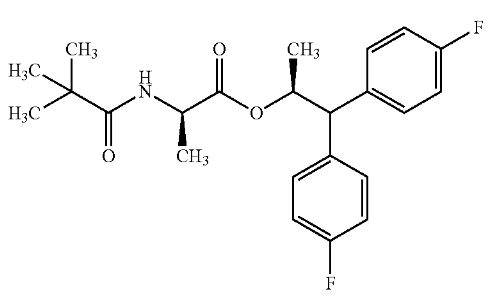 [SMILES: C[C@H](OC(=O)[C@@H](C)NC(=O)C(C)(C)C)C(c1ccc(F)cc1)c1ccc(F)cc1] | Example 1; Example 2A; Example 3A; Example 4A | Clear, Colorless Viscous Oil |

TABLE 1-continued

Compound Structure, Preparation Method, and Appearance

| *Cmpd. No. | Structure | Prepared According To Example | Appearance |
|---|---|---|---|
| 234 | 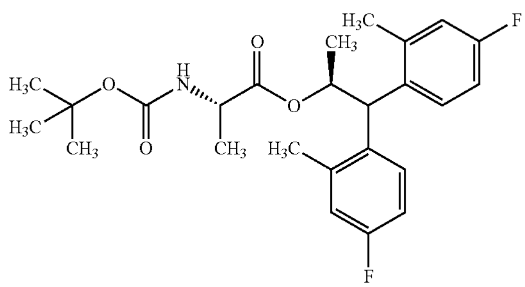 [SMILES: Cc1cc(F)ccc1C(c1ccc(F)cc1C)[C@H](C)OC(=O)[C@H](C)NC(=O)OC(C)(C)C] | Example 1; Example 2A; Example 3A; Example 4A. | Clear, Colorless Oil |
| 235 | 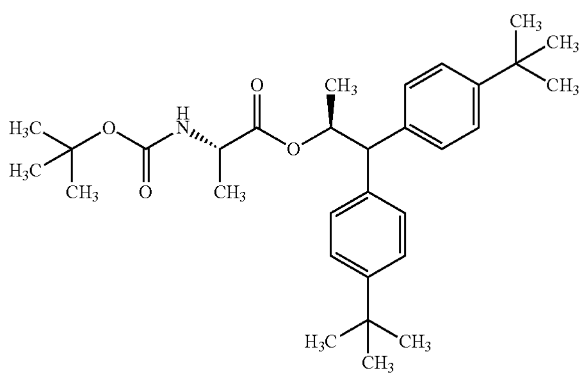 [SMILES: C[C@H](NC(=O)OC(C)(C)C)C(=O)O[C@@H](C)C(c1ccc(C(C)(C)C)cc1)c1ccc(C(C)(C)C)cc1] | Example 1; Example 2A; Example 3A; Example 4A. | Clear, Colorless Oil |
| 236 | 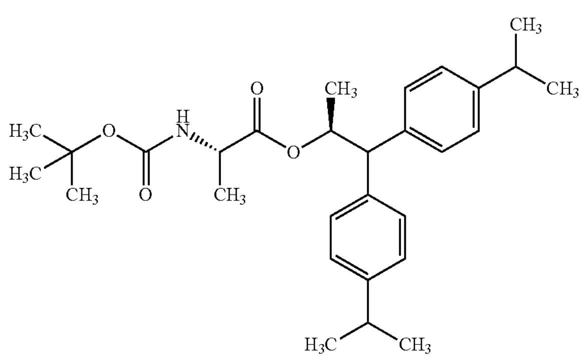 [SMILES: CC(C)c1ccc(C(c2ccc(C(C)C)cc2)[C@H](C)OC(=O)[C@H](C)NC(=O)OC(C)(C)C)cc1] | Example 1; Example 2A; Example 3A; Example 4A. | Clear, Colorless Oil |
| 237 | 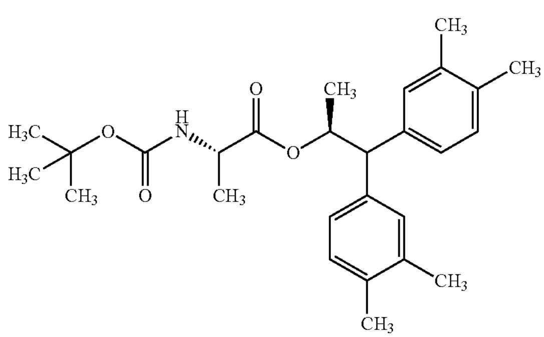 [SMILES: Cc1ccc(C(c2ccc(C)c(C)c2)[C@H](C)OC(=O)[C@H](C)NC(=O)OC(C)(C)C)cc1C] | Example 1; Example 2A; Example 3A; Example 4A. | Clear, Colorless Oil |

TABLE 1-continued

Compound Structure, Preparation Method, and Appearance

| *Cmpd. No. | Structure | Prepared According To Example | Appearance |
|---|---|---|---|
| 238 | 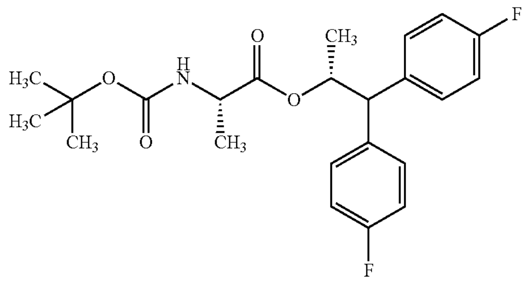 [SMILES: C[C@H](NC(=O)OC(C)(C)C)C(=O)O[C@H](C)C(c1ccc(F)cc1)c1ccc(F)cc1] | Example 1; Example 2A; Example 3A; Example 4A. | Slightly, Cloudy Colorless Viscous Oil |
| 239 | 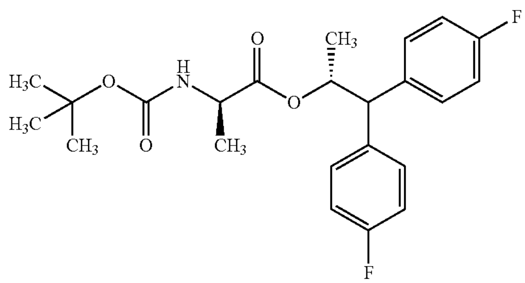 [SMILES: C[C@@H](NC(=O)OC(C)(C)C)C(=O)O[C@H](C)C(c1ccc(F)cc1)c1ccc(F)cc1] | Example 1; Example 2A; Example 3A; Example 4A. | Slightly, Cloudy Colorless Viscous Oil |
| 240 | 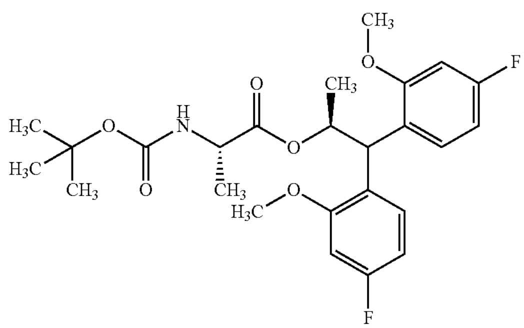 [SMILES: COc1cc(F)ccc1C(c1ccc(F)cc1OC)[C@H](C)OC(=O)[C@H](C)NC(=O)OC(C)(C)C] | Example 1; Example 2A; Example 3A; Example 4A. | White Foam |
| 241 | 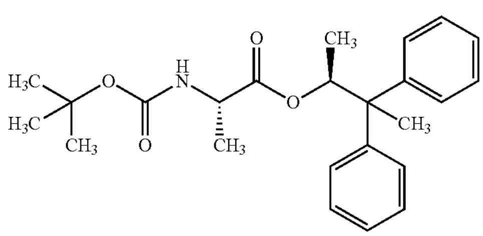 [SMILES: C[C@H](NC(=O)OC(C)(C)C)C(=O)O[C@@H](C)C(C)(c1ccccc1)c1ccccc1] | Example 3H Steps 1-2; Example 4A. | Colorless Oil |
| 242 | 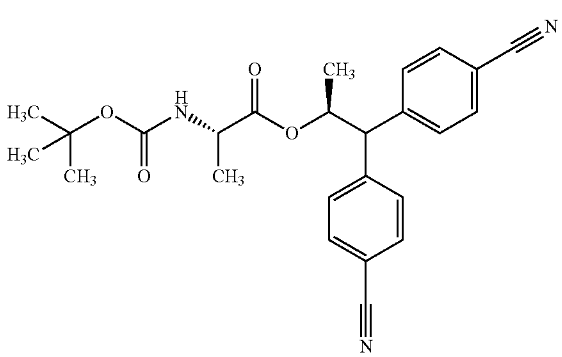 [SMILES: C[C@H](NC(=O)OC(C)(C)C)C(=O)O[C@@H](C)C(c1ccc(C#N)cc1)c1ccc(C#N)cc1] | Example 3G, Steps 1 and 2; Example 4A | Colorless Oil |

TABLE 1-continued

Compound Structure, Preparation Method, and Appearance

| *Cmpd. No. | Structure | Prepared According To Example | Appearance |
| --- | --- | --- | --- |
| 243 | 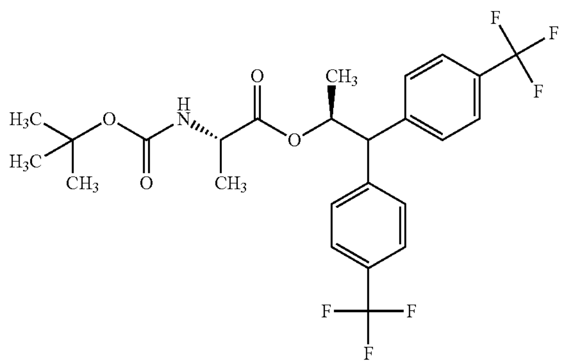 [SMILES: C[C@H](NC(=O)OC(C)(C)C)C(=O)O[C@@H](C)C(c1ccc(C(F)(F)F)cc1)c1ccc(C(F)(F)F)cc1] | Example 3G, Steps 1 and 2; Example 4A | Colorless Oil |
| 244 | 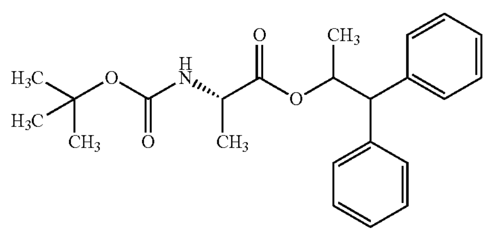 [SMILES: CC(OC(=O)[C@H](C)NC(=O)OC(C)(C)C)C(c1ccccc1)c1ccccc1] | Example 4A | Colorless Oil |
| 245 | 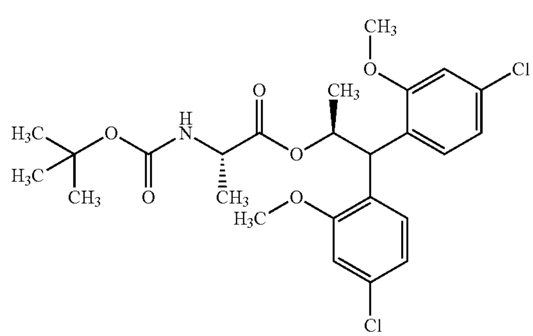 [SMILES: COc1cc(Cl)ccc1C(c1ccc(Cl)cc1OC)[C@H](C)OC(=O)[C@H](C)NC(=O)OC(C)(C)C] | Example 1; Example 3C; Example 4A. | White Foam |
| 246 | 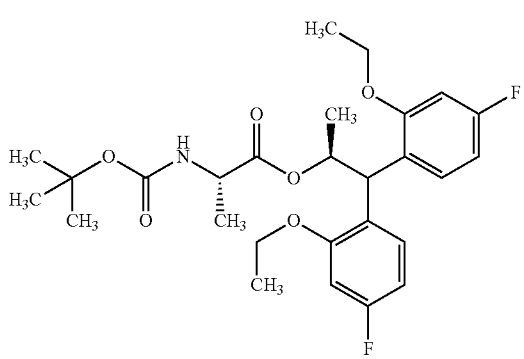 [SMILES: CCOc1cc(F)ccc1C(c1ccc(F)cc1OCC)[C@H](C)OC(=O)[C@H](C)NC(=O)OC(C)(C)C] | Example 1; Example 2A; Example 3A; Example 4A. | White Foam |

TABLE 1-continued

Compound Structure, Preparation Method, and Appearance

| *Cmpd. No. | Structure | Prepared According To Example | Appearance |
|---|---|---|---|
| 247 | 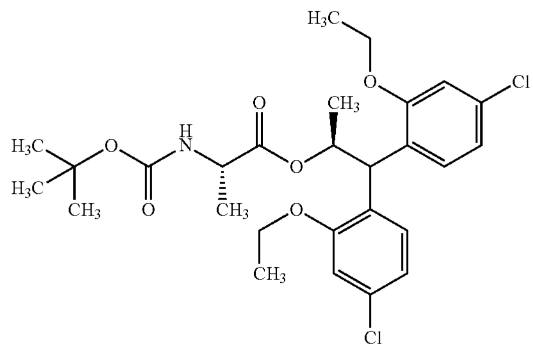 [SMILES: CCOc1cc(Cl)ccc1C(c1ccc(Cl)cc1OCC)[C@H](C)OC(=O)[C@H](C)NC(=O)OC(C)(C)C] | Example 1; Example 3C; Example 4A. | White Foam |
| 248 | 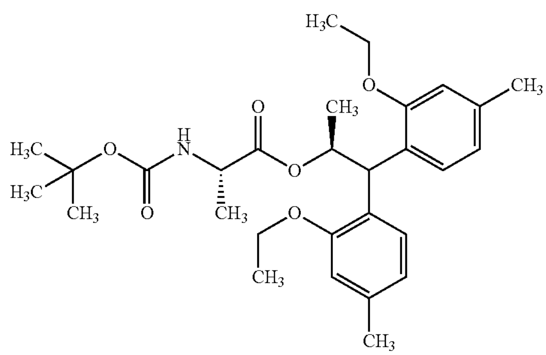 [SMILES: CCOc1cc(C)ccc1C(c1ccc(C)cc1OCC)[C@H](C)OC(=O)[C@H](C)NC(=O)OC(C)(C)C] | Example 1; Example 2A; Example 3A; Example 4A. | White Foam |
| 249 | 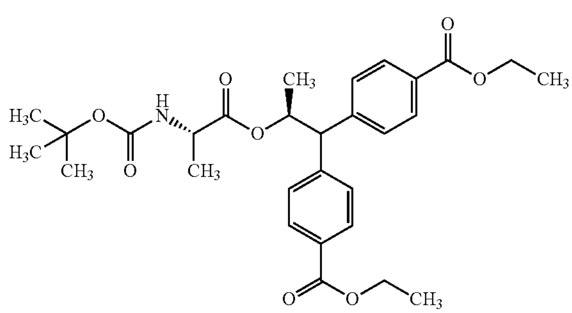 [SMILES: CCOC(=O)c1ccc(C(c2ccc(C(=O)OCC)cc2)[C@H](C)OC(=O)[C@H](C)NC(=O)OC(C)(C)C)cc1] | Example 3G, Steps 1 and 2; Example 4A | White Foam |
| 250 | 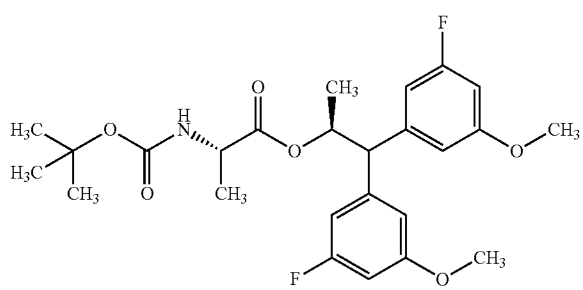 [SMILES: COc1cc(F)cc(C(c2cc(F)cc(OC)c2)[C@H](C)OC(=O)[C@H](C)NC(=O)OC(C)(C)C)c1] | Example 1; Example 2A; Example 3A; Example 4A. | White Semisolid |

TABLE 1-continued

Compound Structure, Preparation Method, and Appearance

| *Cmpd. No. | Structure | Prepared According To Example | Appearance |
|---|---|---|---|
| 251 | 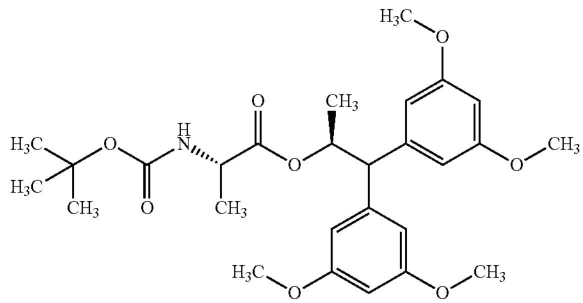 [SMILES: COc1cc(OC)cc(C(c2cc(OC)cc(OC)c2)[C@H](C)OC(=O)[C@H](C)NC(=O)OC(C)(C)C)c1] | Example 1; Example 2A; Example 3A; Example 4A. | White Semisolid |
| 252 | 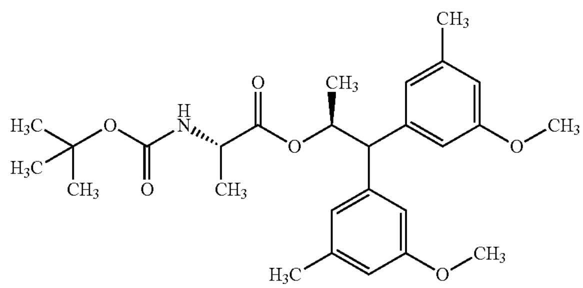 [SMILES: COc1cc(C)cc(C(c2cc(C)cc(OC)c2)[C@H](C)OC(=O)[C@H](C)NC(=O)OC(C)(C)C)c1] | Example 1; Example 2A; Example 3A; Example 4A. | White Semisolid |
| 253 | 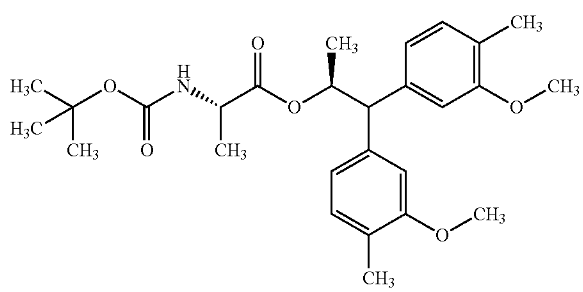 [SMILES: COc1cc(C(c2ccc(C)c(OC)c2)[C@H](C)OC(=O)[C@H](C)NC(=O)OC(C)(C)C)ccc1C] | Example 1; Example 2A; Example 3A; Example 4A. | Clear, Colorless Oil |
| 254 | 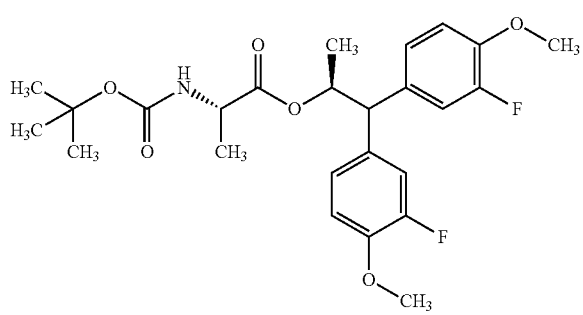 [SMILES: COc1ccc(C(c2ccc(OC)c(F)c2)[C@H](C)OC(=O)[C@H](C)NC(=O)OC(C)(C)C)cc1F] | Example 1; Example 2A; Example 3A; Example 4A. | Clear, Colorless Oil |
| 255 | 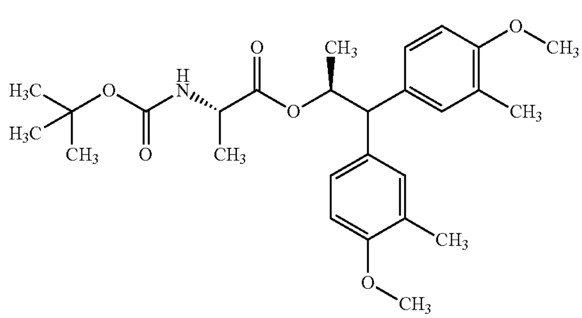 [SMILES: COc1ccc(C(c2ccc(OC)c(C)c2)[C@H](C)OC(=O)[C@H](C)NC(=O)OC(C)(C)C)cc1C] | Example 1; Example 2A; Example 3A; Example 4A. | Clear, Colorless Oil |

TABLE 1-continued

Compound Structure, Preparation Method, and Appearance

| *Cmpd. No. | Structure | Prepared According To Example | Appearance |
|---|---|---|---|
| 256 | 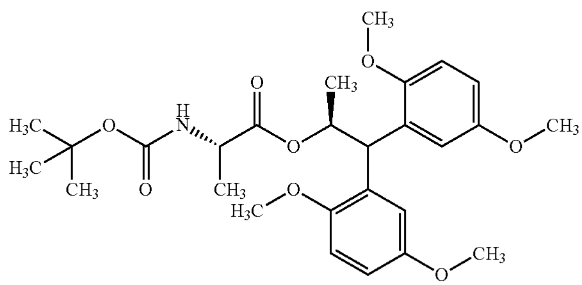 [SMILES: COc1ccc(OC)c(C(c2cc(OC)ccc2OC)[C@H](C)OC(=O)[C@H](C)NC(=O)OC(C)(C)C)c1] | Example 1; Example 2A; Example 3A; Example 4A. | Clear, Colorless Oil |
| 257 | 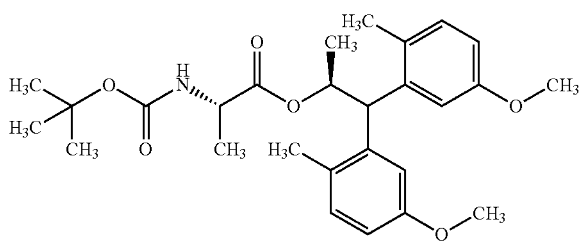 [SMILES: COc1ccc(C)c(C(c2cc(OC)ccc2C)[C@H](C)OC(=O)[C@H](C)NC(=O)OC(C)(C)C)c1] | Example 1; Example 2A; Example 3A; Example 4A. | Clear, Colorless Oil |
| 258 | 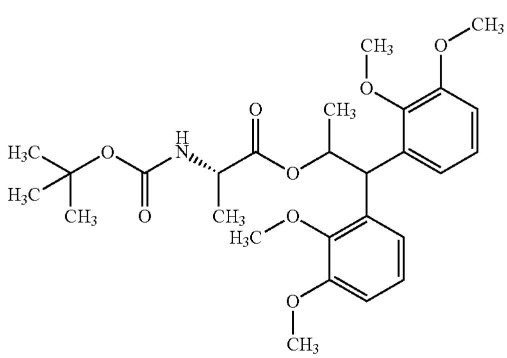 [SMILES: COc1cccc(C(c2cccc(OC)c2OC)C(C)OC(=O)[C@H](C)NC(=O)OC(C)(C)C)c1OC] | Example 3I; Example 4A | White Foam |
| 259 | 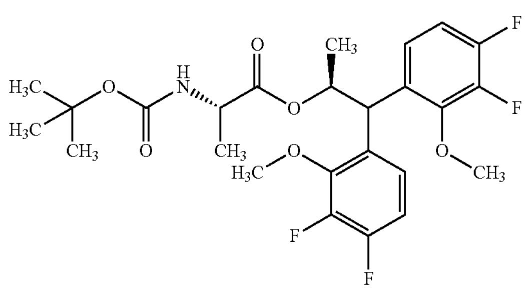 [SMILES: COc1c(C(c2ccc(F)c(F)c2OC)[C@H](C)OC(=O)[C@H](C)NC(=O)OC(C)(C)C)ccc(F)c1F] | Example 1; Example 2A; Example 3A; Example 4A. | White Foam |
| 260 | 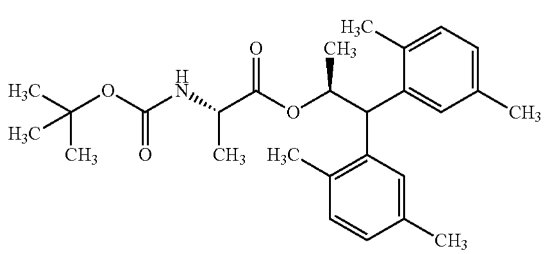 [SMILES: Cc1ccc(C)c(C(c2cc(C)ccc2C)[C@H](C)OC(=O)[C@H](C)NC(=O)OC(C)(C)C)c1] | Example 1; Example 2A; Example 3A; Example 4A. | Colorless Oil |

TABLE 1-continued

Compound Structure, Preparation Method, and Appearance

| *Cmpd. No. | Structure | Prepared According To Example | Appearance |
|---|---|---|---|
| 261 | 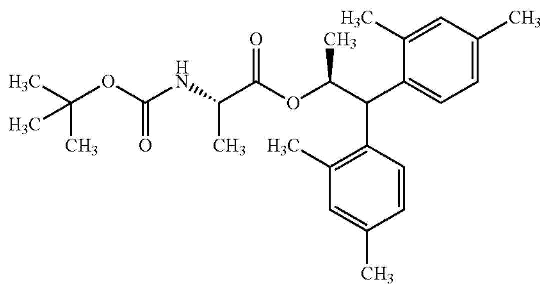 [SMILES: Cc1ccc(C(c2ccc(C)cc2C)[C@H](C)OC(=O)[C@H](C)NC(=O)OC(C)(C)C)c(C)c1] | Example 1; Example 2A; Example 3A; Example 4A. | Colorless Oil |
| 262 | 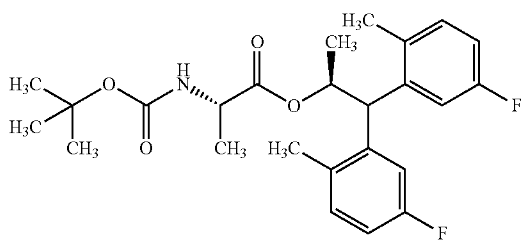 [SMILES: Cc1ccc(F)cc1C(c1cc(F)ccc1C)[C@H](C)OC(=O)[C@H](C)NC(=O)OC(C)(C)C] | Example 1; Example 2A; Example 3A; Example 4A. | Colorless Oil |
| 263 | 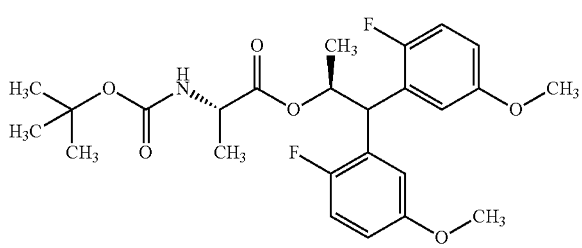 [SMILES: COc1ccc(F)c(C(c2cc(OC)ccc2F)[C@H](C)OC(=O)[C@H](C)NC(=O)OC(C)(C)C)c1] | Example 1; Example 2A; Example 3A; Example 4A. | Colorless Oil |
| 264 | 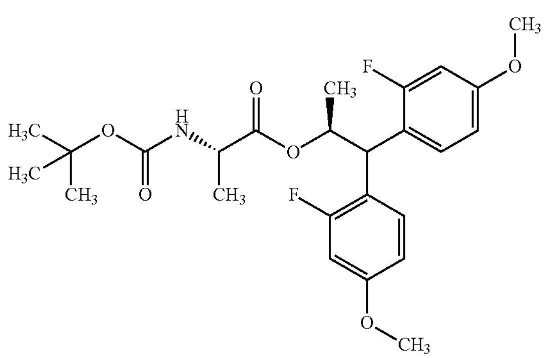 [SMILES: COc1ccc(C(c2ccc(OC)cc2F)[C@H](C)OC(=O)[C@H](C)NC(=O)OC(C)(C)C)c(F)c1] | Example 1; Example 2A; Example 3A; Example 4A. | White Foam |
| 265 | 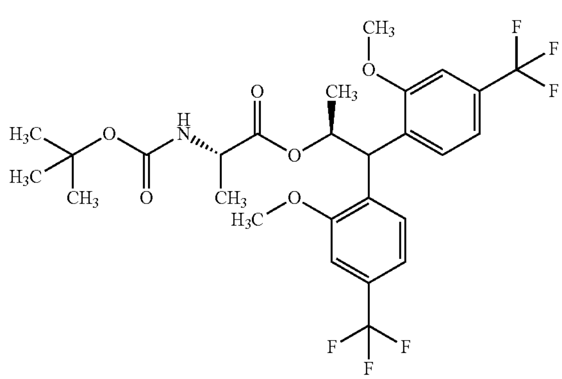 [SMILES: COc1cc(C(F)(F)F)ccc1C(c1ccc(C(F)(F)F)cc1OC)[C@H](C)OC(=O)[C@H](C)NC(=O)OC(C)(C)C] | Example 1; Example 2A; Example 3A; Example 4A. | Colorless Oil |

TABLE 1-continued

Compound Structure, Preparation Method, and Appearance

| *Cmpd. No. | Structure | Prepared According To Example | Appearance |
|---|---|---|---|
| 266 | 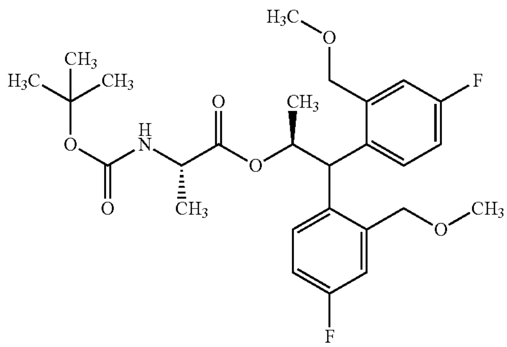 [SMILES: COCc1cc(F)ccc1C(c1ccc(F)cc1COC)[C@H](C)OC(=O)[C@H](C)NC(=O)OC(C)(C)C] | Example 1; Example 2A; Example 3A; Example 4A. | Sticky Wax |
| 267 | 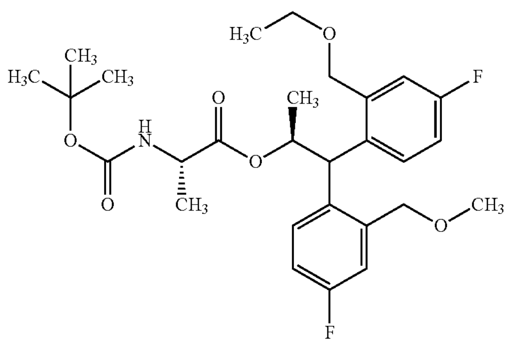 [SMILES: CCOCc1cc(F)ccc1C(c1ccc(F)cc1COC)[C@H](C)OC(=O)[C@H](C)NC(=O)OC(C)(C)C] | Example 1; Example 2A; Example 3A; Example 4A. | Sticky Wax. |
| 268 | 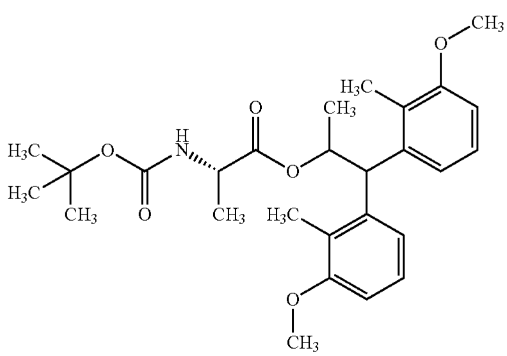 [SMILES: COc1cccc(C(c2cccc(OC)c2C)C(C)OC(=O)[C@H](C)NC(=O)OC(C)(C)C)c1C] | Example 3I, Example 4A | Oil |
| 269 | 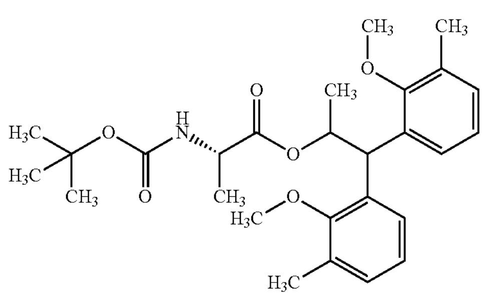 [SMILES: COc1c(C)cccc1C(c1cccc(C)c1OC)C(C)OC(=O)[C@H](C)NC(=O)OC(C)(C)C] | Example 3I, Example 4A | Oil |

TABLE 1-continued

Compound Structure, Preparation Method, and Appearance

| *Cmpd. No. | Structure | Prepared According To Example | Appearance |
|---|---|---|---|
| 270 | 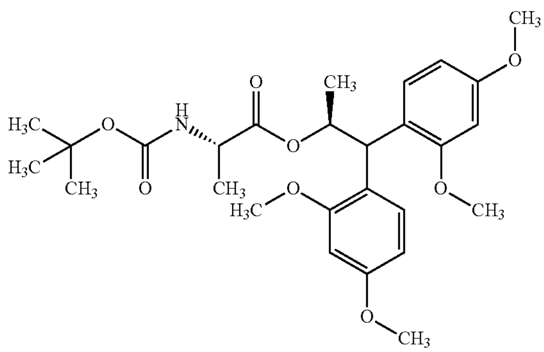 [SMILES: COc1ccc(C(c2ccc(OC)cc2OC)[C@H](C)OC(=O)[C@H](C)NC(=O)OC(C)(C)C)c(OC)c1] | Example 1; Example 2A; Example 3A; Example 4A | Colorless Oil |
| 271 | 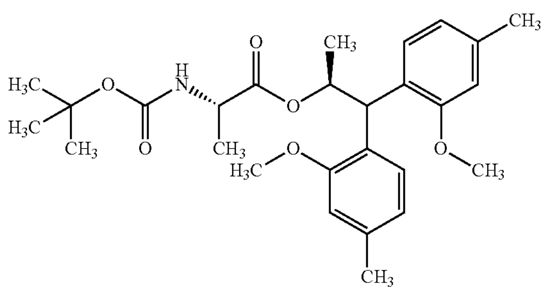 [SMILES: COc1cc(C)ccc1C(c1ccc(C)cc1OC)[C@H](C)OC(=O)[C@H](C)NC(=O)OC(C)(C)C] | Example 1; Example 2A; Example 3A; Example 4A | Colorless Oil |
| 272 | 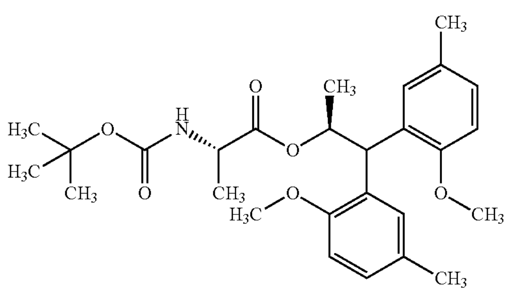 [SMILES: COc1ccc(C)cc1C(c1cc(C)ccc1OC)[C@H](C)OC(=O)[C@H](C)NC(=O)OC(C)(C)C] | Example 1; Example 2A; Example 3A; Example 4A | Colorless Oil |
| 273 | 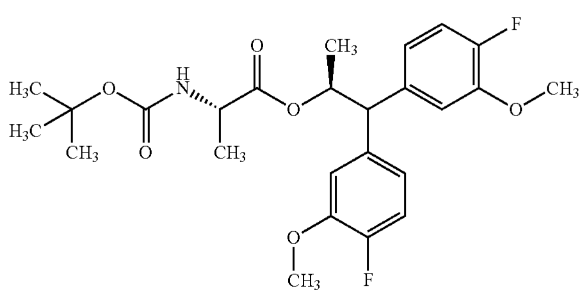 [SMILES: COc1cc(C(c2ccc(F)c(OC)c2)[C@H](C)OC(=O)[C@H](C)NC(=O)OC(C)(C)C)ccc1F] | Example 1; Example 2A; Example 3A; Example 4A | Colorless Oil |

TABLE 1-continued

Compound Structure, Preparation Method, and Appearance

| *Cmpd. No. | Structure | Prepared According To Example | Appearance |
|---|---|---|---|
| 274 | 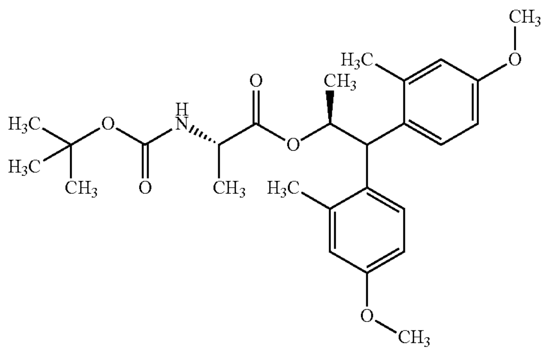 [SMILES: COc1ccc(C(c2ccc(OC)cc2C)[C@H](C)OC(=O)[C@H](C)NC(=O)OC(C)(C)C)c(C)c1] | Example 1; Example 2A; Example 3A; Example 4A | Colorless Oil |
| 275 | 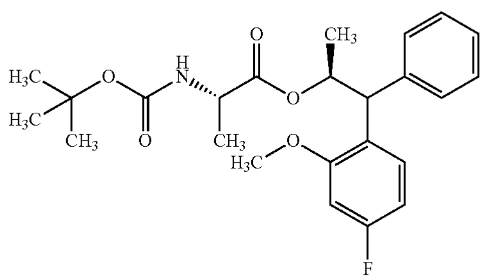 [SMILES: COc1cc(F)ccc1C(c1ccccc1)[C@H](C)OC(=O)[C@H](C)NC(=O)OC(C)(C)C] | Example 3F; Example 4A | Colorless Oil |
| 276 | 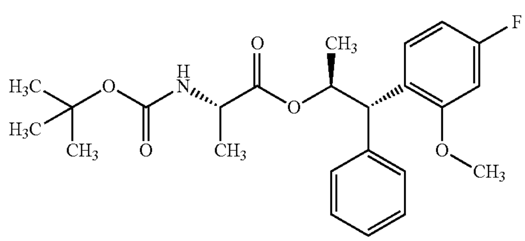 [SMILES: COc1cc(F)ccc1[C@H](c1ccccc1)[C@H](C)OC(=O)[C@H](C)NC(=O)OC(C)(C)C] | Example 3F; Example 4A | Colorless Oil |
| 277 | 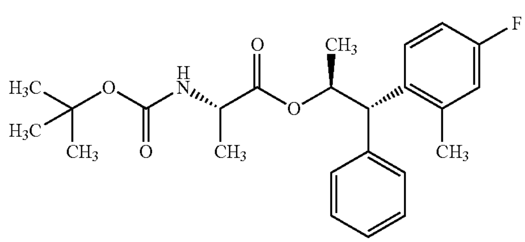 [SMILES: Cc1cc(F)ccc1[C@H](c1ccccc1)[C@H](C)OC(=O)[C@H](C)NC(=O)OC(C)(C)C] | Example 3F; Example 4A | Colorless Oil |
| 278 | 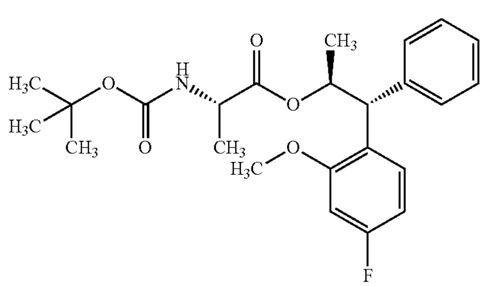 | Example 3F; Example 4A | Colorless Oil |

TABLE 1-continued

Compound Structure, Preparation Method, and Appearance

| *Cmpd. No. | Structure | Prepared According To Example | Appearance |
|---|---|---|---|
| 279 | 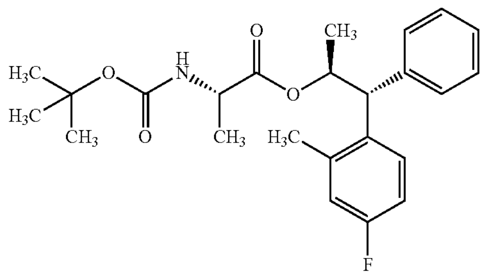 [SMILES: Cc1cc(F)ccc1[C@@H](c1ccccc1)[C@H](C)OC(=O)[C@H](C)NC(=O)OC(C)(C)C] | Example 3F; Example 4A | Colorless Oil |
| 280 | 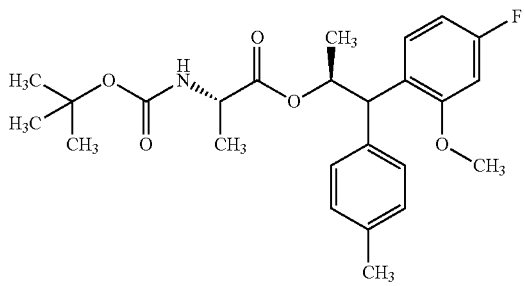 [SMILES: COc1cc(F)ccc1C(c1ccc(C)cc1)[C@H](C)OC(=O)[C@H](C)NC(=O)OC(C)(C)C] | Example 3F; Example 4A | Colorless Oil |
| 281 | 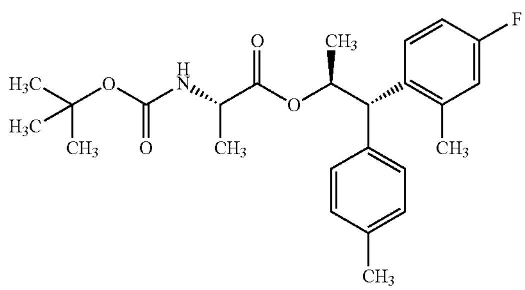 [SMILES: Cc1ccc([C@@H](c2ccc(F)cc2C)[C@H](C)OC(=O)[C@H](C)NC(=O)OC(C)(C)C)cc1] | Example 3F; Example 4A | Colorless Oil |
| 282 | 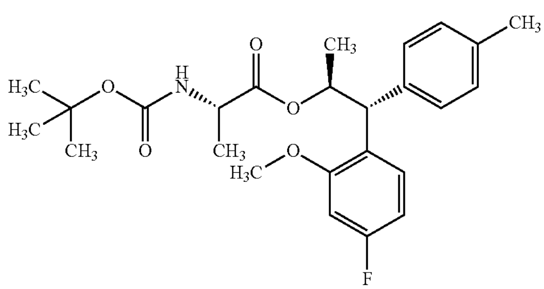 [SMILES: COc1cc(F)ccc1[C@@H](c1ccc(C)cc1)[C@H](C)OC(=O)[C@H](C)NC(=O)OC(C)(C)C] | Example 3F; Example 4A | Colorless Oil |
| 283 | 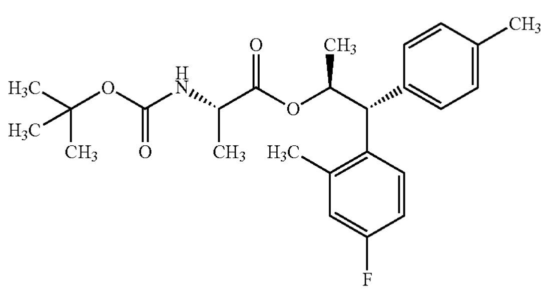 [SMILES: Cc1ccc([C@H](c2ccc(F)cc2C)[C@H](C)OC(=O)[C@H](C)NC(=O)OC(C)(C)C)cc1] | Example 3F; Example 4A | Colorless Oil |

TABLE 1-continued

Compound Structure, Preparation Method, and Appearance

| *Cmpd. No. | Structure | Prepared According To Example | Appearance |
|---|---|---|---|
| 284 | 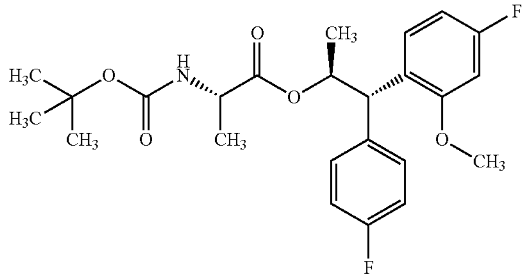 [SMILES: COc1cc(F)ccc1[C@H](c1ccc(F)cc1)[C@H](C)OC(=O)[C@H](C)NC(=O)OC(C)(C)C] | Example 3F; Example 4A | Colorless Oil |
| 285 | 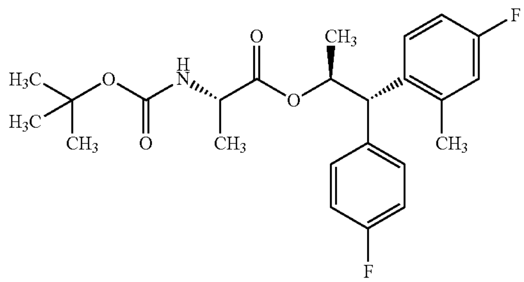 [SMILES: Cc1cc(F)ccc1[C@H](c1ccc(F)cc1)[C@H](C)OC(=O)[C@H](C)NC(=O)OC(C)(C)C] | Example 3F; Example 4A | Colorless Oil |
| 286 | 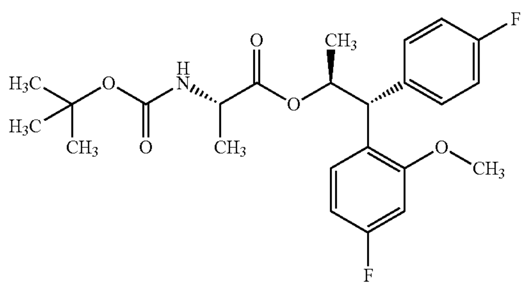 [SMILES: COc1cc(F)ccc1[C@@H](c1ccc(F)cc1)[C@H](C)OC(=O)[C@H](C)NC(=O)OC(C)(C)C] | Example 3F; Example 4A | Colorless Oil |
| 287 | 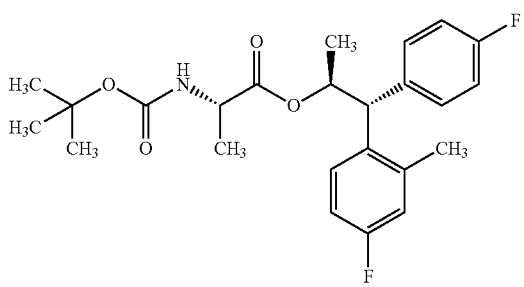 [SMILES: Cc1cc(F)ccc1[C@@H](c1ccc(F)cc1)[C@H](C)OC(=O)[C@H](C)NC(=O)OC(C)(C)C] | Example 3F; Example 4A | Colorless Oil |
| 288 | 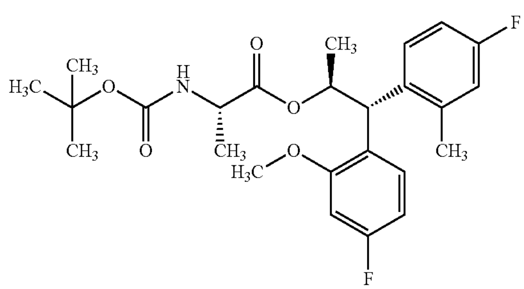 [SMILES: COc1cc(F)ccc1[C@@H](c1ccc(F)cc1C)[C@H](C)OC(=O)[C@H](C)NC(=O)OC(C)(C)C] | Example 3F; Example 4A | White Foam |

TABLE 1-continued

Compound Structure, Preparation Method, and Appearance

| *Cmpd. No. | Structure | Prepared According To Example | Appearance |
|---|---|---|---|
| 289 | 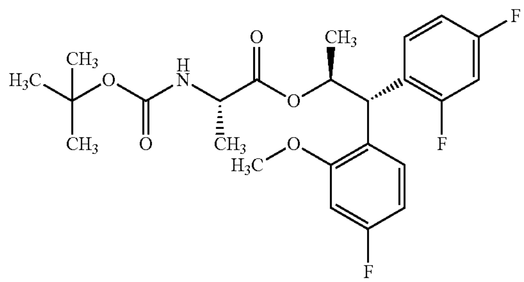 [SMILES: COc1cc(F)ccc1[C@@H](c1ccc(F)cc1F)[C@H](C)OC(=O)[C@H](C)NC(=O)OC(C)(C)C] | Example 3F; Example 4A | Yellow Sticky Wax |
| 290 | 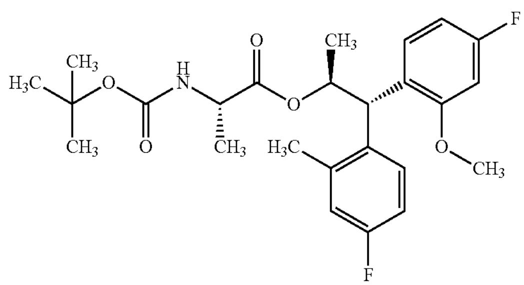 [SMILES: COc1cc(F)ccc1[C@H](c1ccc(F)cc1C)[C@H](C)OC(=O)[C@H](C)NC(=O)OC(C)(C)C] | Example 3F; Example 4A | White Foam |
| 291 | 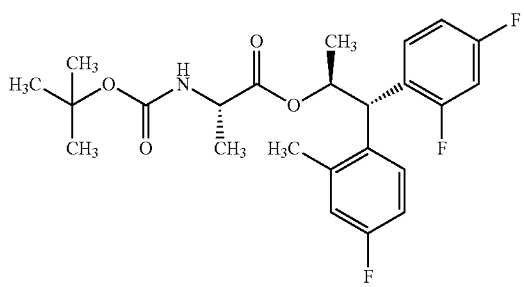 [SMILES: Cc1cc(F)ccc1[C@@H](c1ccc(F)cc1F)[C@H](C)OC(=O)[C@H](C)NC(=O)OC(C)(C)C] | Example 3F; Example 4A | Yellow Sticky Wax |
| 292 | 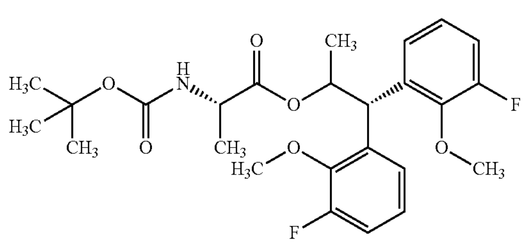 | Example 1; Example 2A; Example 3A; Example 4A | Colorless Oil |
| 293 | 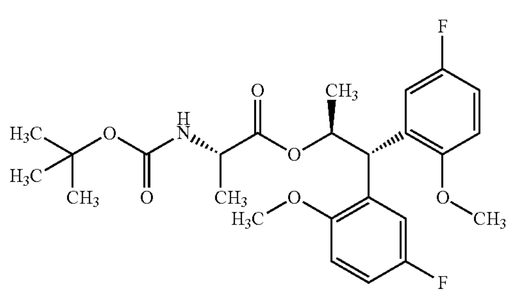 | Example 1; Example 2A; Example 3A; Example 4A | Colorless Oil |

TABLE 1-continued
Compound Structure, Preparation Method, and Appearance
| *Cmpd. No. | Structure | Prepared According To Example | Appearance |
|---|---|---|---|
| 294 | 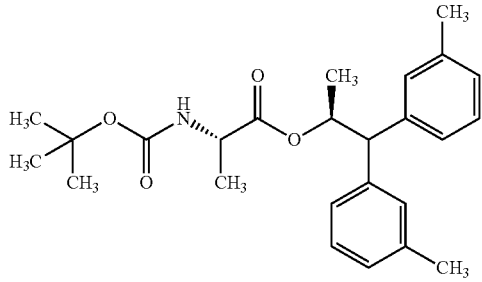 [SMILES: Cc1cccc(C(c2cccc(C)c2)[C@H](C)OC(=O)[C@H](C)NC(=O)OC(C)(C)C)c1] | Example 1; Example 2A; Example 3A; Example 4A | Colorless Oil |
| 295 | 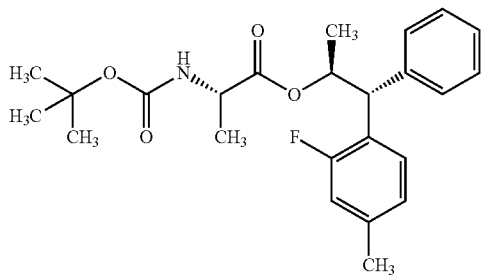 [SMILES: Cc1ccc([C@@H](c2ccccc2)[C@H](C)OC(=O)[C@H](C)NC(=O)OC(C)(C)C)c(F)c1] | Example 3F; Example 4A | Colorless Oil |
| 296 | 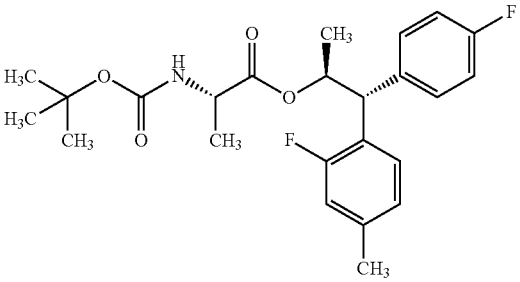 | Example 3F; Example 4A | Colorless Oil |
| 297 | 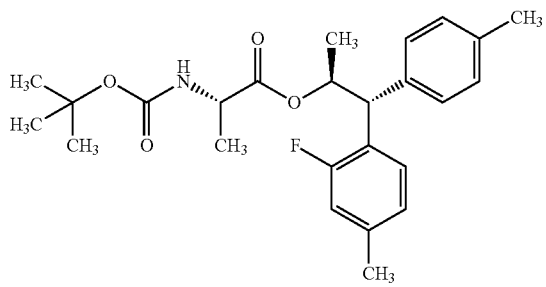 [SMILES: Cc1ccc([C@H](c2ccc(C)cc2F)[C@H](C)OC(=O)[C@H](C)NC(=O)OC(C)(C)C)cc1] | Example 3F; Example 4A | Colorless Oil |
| 298 | 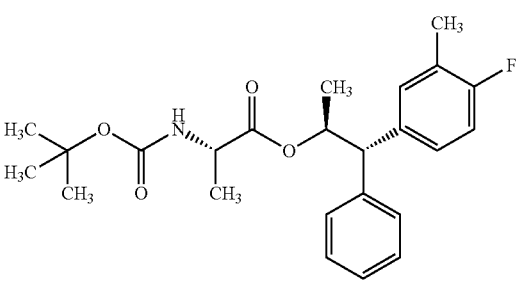 [SMILES: Cc1cc([C@H](c2ccccc2)[C@H](C)OC(=O)[C@H](C)NC(=O)OC(C)(C)C)ccc1F] | Example 3F; Example 4A | Colorless Oil |

TABLE 1-continued

Compound Structure, Preparation Method, and Appearance

| *Cmpd. No. | Structure | Prepared According To Example | Appearance |
|---|---|---|---|
| 299 | 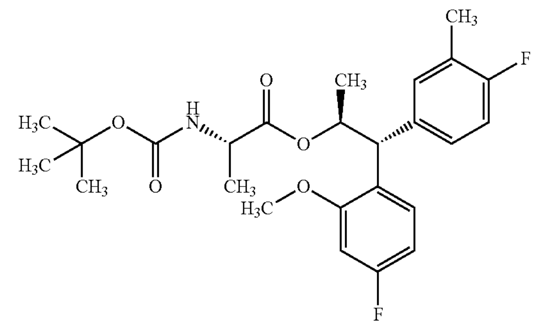 [SMILES: COc1cc(F)ccc1[C@@H](c1ccc(F)c(C)c1)[C@H](C)OC(=O)[C@H](C)NC(=O)OC(C)(C)C] | Example 3F; Example 4A | Colorless Oil |
| 300 | 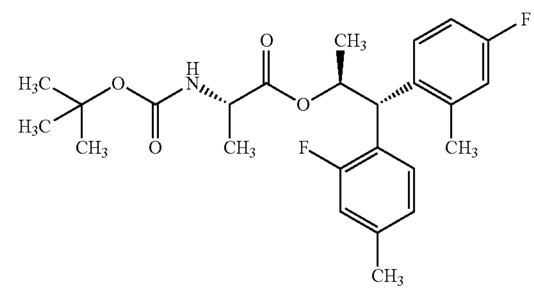 [SMILES: Cc1ccc([C@@H](c2ccc(F)cc2C)[C@H](C)OC(=O)[C@H](C)NC(=O)OC(C)(C)C)c(F)c1] | Example 3F; Example 4A | Colorless Oil |
| 301 | 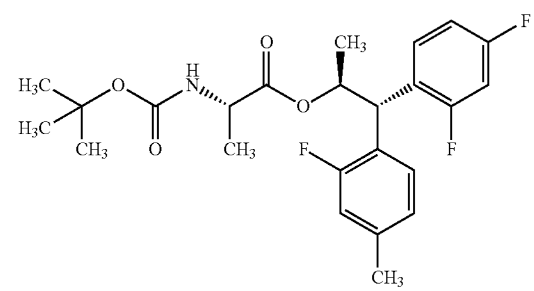 | Example 3F; Example 4A | Colorless Oil |
| 302 | 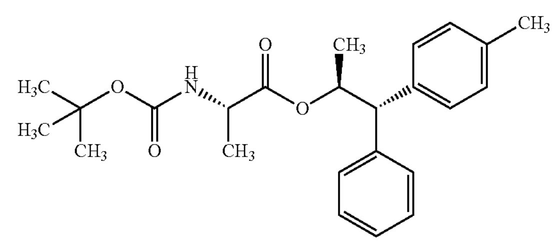 [SMILES: Cc1ccc([C@H](c2ccccc2)[C@H](C)OC(=O)[C@H](C)NC(=O)OC(C)(C)C)cc1] | Example 3F; Example 4A | Colorless Oil |
| 303 | 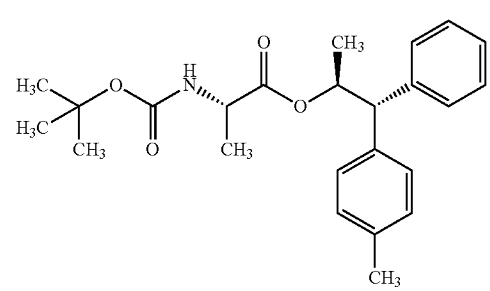 [SMILES: Cc1ccc([C@@H](c2ccccc2)[C@H](C)OC(=O)[C@H](C)NC(=O)OC(C)(C)C)cc1] | Example 3F; Example 4A | Colorless Oil |

TABLE 1-continued

Compound Structure, Preparation Method, and Appearance

| *Cmpd. No. | Structure | Prepared According To Example | Appearance |
| --- | --- | --- | --- |
| 304 | 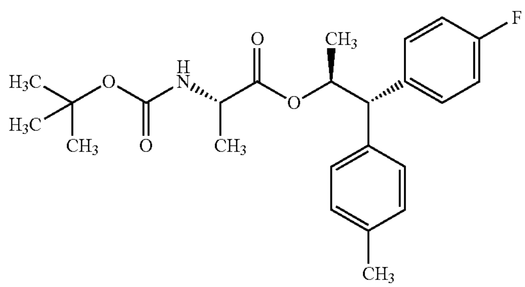 [SMILES: Cc1ccc([C@@H](c2ccc(F)cc2)[C@H](C)OC(=O)[C@H](C)NC(=O)OC(C)(C)C)cc1] | Example 3F; Example 4A | Colorless Oil |
| 305 | 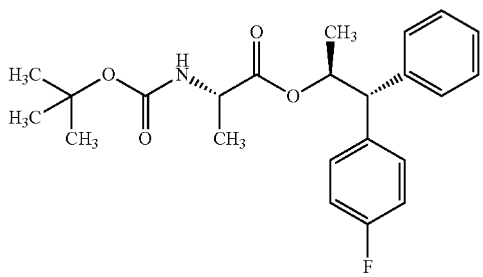 [SMILES: C[C@H](NC(=O)OC(C)(C)C)C(=O)O[C@@H](C)[C@H](c1ccccc1)c1ccc(F)cc1] | Example 3F; Example 4A | Colorless Oil |
| 306 | 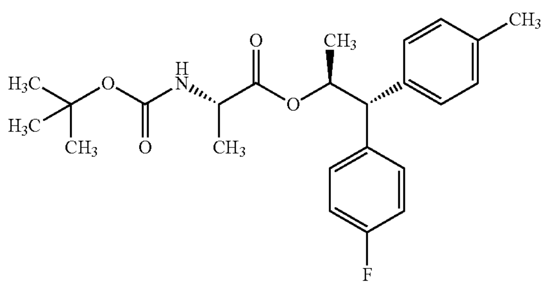 [SMILES: Cc1ccc([C@H](c2ccc(F)cc2)[C@H](C)OC(=O)[C@H](C)NC(=O)OC(C)(C)C)cc1] | Example 3F; Example 4A | Colorless Oil |
| 307 | 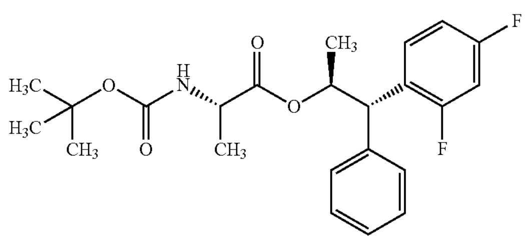 [SMILES: C[C@H](NC(=O)OC(C)(C)C)C(=O)O[C@@H](C)[C@@H](c1ccccc1)c1ccc(F)cc1F] | Example 3F; Example 4A | Colorless Oil |
| 308 | 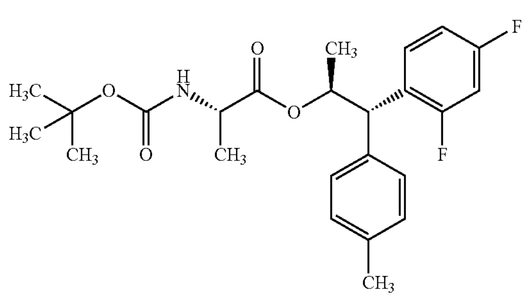 [SMILES: Cc1ccc([C@@H](c2ccc(F)cc2F)[C@H](C)OC(=O)[C@H](C)NC(=O)OC(C)(C)C)cc1] | Example 3F; Example 4A | Thick Oil |

TABLE 1-continued

Compound Structure, Preparation Method, and Appearance

| *Cmpd. No. | Structure | Prepared According To Example | Appearance |
|---|---|---|---|
| 309 | 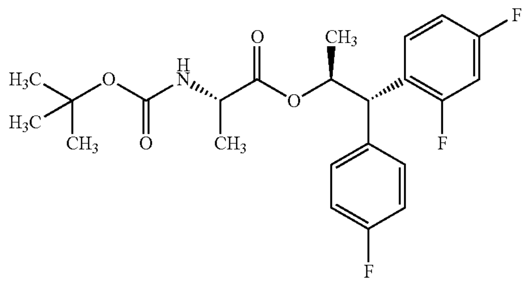 [SMILES: C[C@H](NC(=O)OC(C)(C)C)C(=O)O[C@@H](C)[C@@H](c1ccc(F)cc1)c1ccc(F)cc1F] | Example 3F; Example 4A | Colorless Oil |
| 310 | 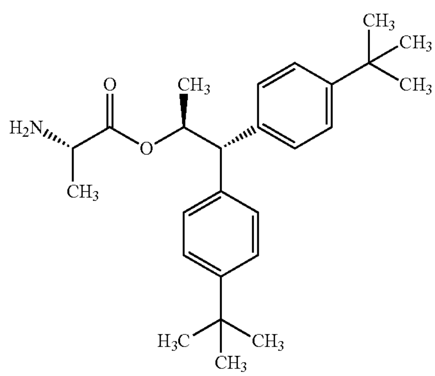 | Example 5, Step 1. | White Powder |
| 311 | 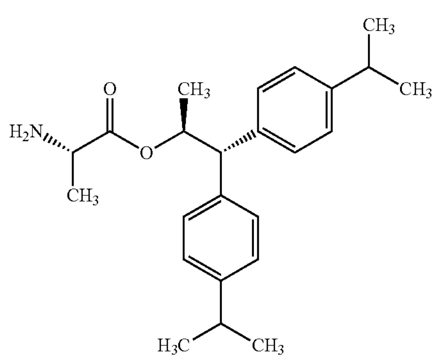 | Example 5, Step 1. | White Powder |
| 312 | 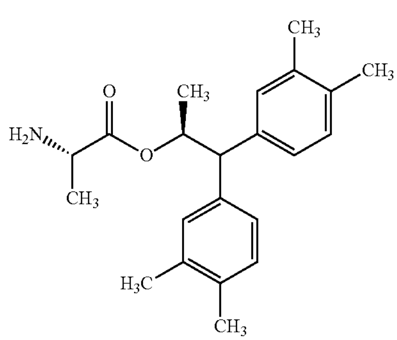 [SMILES: Cc1ccc(C(c2ccc(C)c(C)c2)[C@H](C)OC(=O)[C@H](C)N)cc1C] | Example 5, Step 1. | Clear, Colorless Thick Oil |

TABLE 1-continued

Compound Structure, Preparation Method, and Appearance

| *Cmpd. No. | Structure | Prepared According To Example | Appearance |
| --- | --- | --- | --- |
| 313 | 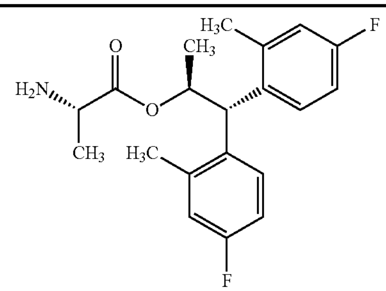 | Example 5, Step 1. | White Powder |
| 314 | 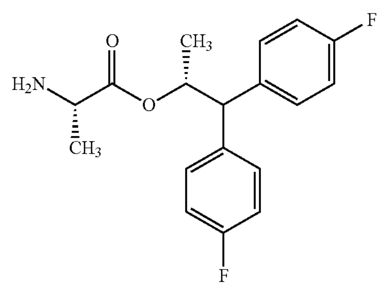 [SMILES: C[C@H](N)C(=O)O[C@H](C)C(c1ccc(F)cc1)c1ccc(F)cc1] | Example 5, Step 1. | White Semi-Solid |
| 315 | 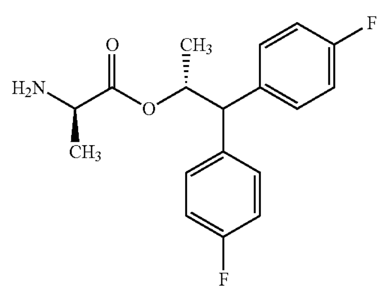 [SMILES: C[C@@H](N)C(=O)O[C@H](C)C(c1ccc(F)cc1)c1ccc(F)cc1] | Example 5, Step 1. | White Semi-Solid |
| 316 | 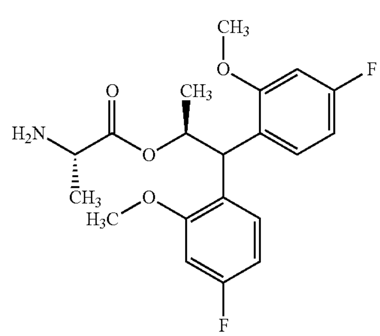 [SMILES: COc1cc(F)ccc1C(c1ccc(F)cc1OC)[C@H](C)OC(=O)[C@H](C)N] | Example 5, Step 1. | Clear Glass |
| 317 | 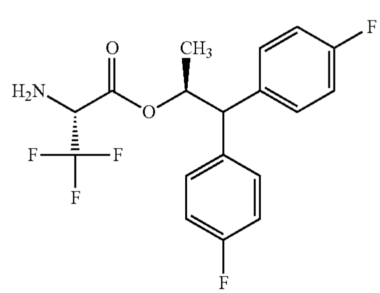 [SMILES: C[C@H](OC(=O)[C@@H](N)C(F)(F)F)C(c1ccc(F)cc1)c1ccc(F)cc1] | Example 1; Example 2A; Example 3A; Example 4A, Example 5, step 1. | Pale Purple Sticky Wax |

TABLE 1-continued

Compound Structure, Preparation Method, and Appearance

| *Cmpd. No. | Structure | Prepared According To Example | Appearance |
|---|---|---|---|
| 318 | 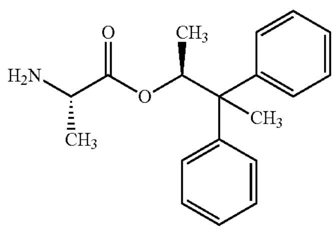 [SMILES: C[C@H](N)C(=O)O[C@@H](C)C(C)(c1ccccc1)c1ccccc1] | Example 5 Step 1. | Colorless Oil |
| 319 | 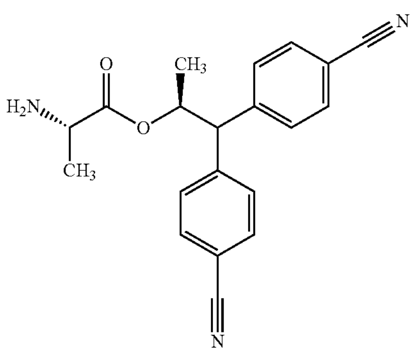 [SMILES: C[C@H](N)C(=O)O[C@@H](C)C(c1ccc(C#N)cc1)c1ccc(C#N)cc1] | Example 5, Step 1 | White Foam |
| 320 | 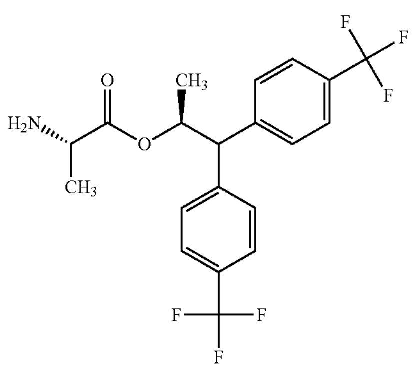 [SMILES: C[C@H](N)C(=O)O[C@@H](C)C(c1ccc(C(F)(F)F)cc1)c1ccc(C(F)(F)F)cc1] | Example 5, Step 1 | White Foam |
| 321 | 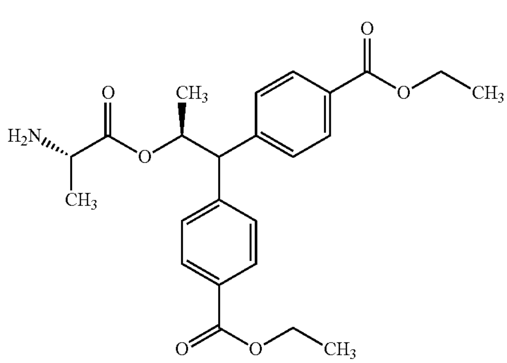 [SMILES: CCOC(=O)c1ccc(C(c2ccc(C(=O)OCC)cc2)[C@H](C)OC(=O)[C@H](C)N)cc1] | Example 5, Step 1 | White Solid |

TABLE 1-continued

Compound Structure, Preparation Method, and Appearance

| *Cmpd. No. | Structure | Prepared According To Example | Appearance |
|---|---|---|---|
| 322 | 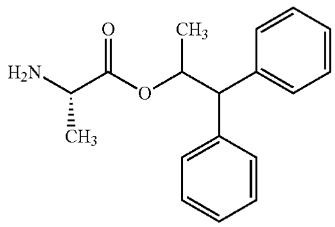 [SMILES: CC(OC(=O)[C@H](C)N)C(c1ccccc1)c1ccccc1] | Example 5, Step 1. | Colorless Oil |
| 323 | 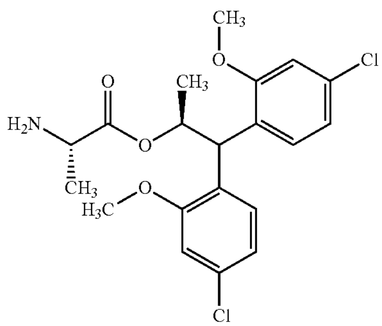 [SMILES: COc1cc(Cl)ccc1C(c1ccc(Cl)cc1OC)[C@H](C)OC(=O)[C@H](C)N] | Example 5, Step 1. | Yellow Oil |
| 324 | 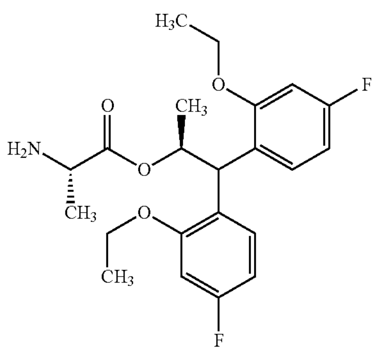 [SMILES: CCOc1cc(F)ccc1C(c1ccc(F)cc1OCC)[C@H](C)OC(=O)[C@H](C)N] | Example 5, Step 1. | Yellow Oil |
| 325 | 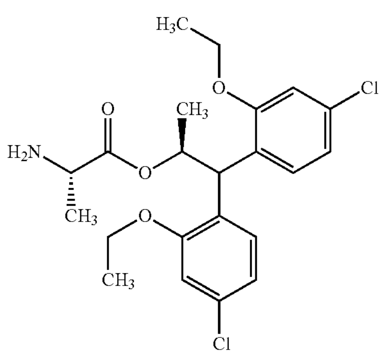 [SMILES: CCOc1cc(Cl)ccc1C(c1ccc(Cl)cc1OCC)[C@H](C)OC(=O)[C@H](C)N] | Example 5, Step 1. | Yellow Oil |

TABLE 1-continued

Compound Structure, Preparation Method, and Appearance

| *Cmpd. No. | Structure | Prepared According To Example | Appearance |
|---|---|---|---|
| 326 | 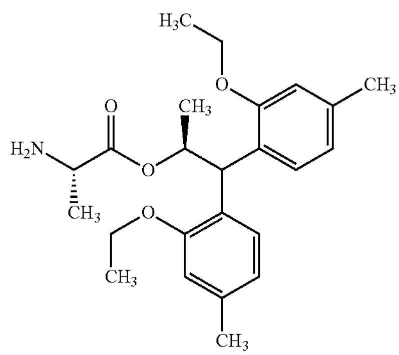 [SMILES: CCOc1cc(C)ccc1C(c1ccc(C)cc1OCC)[C@H](C)OC(=O)[C@H](C)N] | Example 5, Step 1. | Yellow Oil |
| 327 | 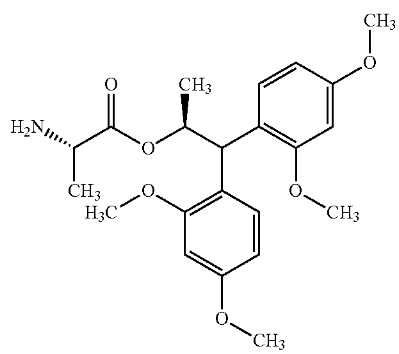 [SMILES: COc1ccc(C(c2ccc(OC)cc2OC)[C@H](C)OC(=O)[C@H](C)N)c(OC)c1] | Example 5, Step 1 | White Foam |
| 328 | 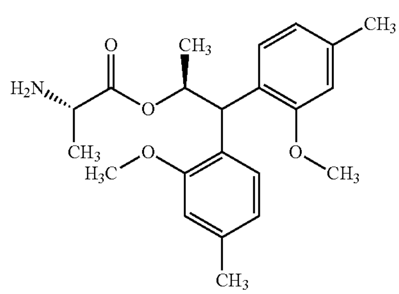 [SMILES: COc1cc(C)ccc1C(c1ccc(C)cc1OC)[C@H](C)OC(=O)[C@H](C)N] | Example 5, Step 1 | White Foam |
| 329 | 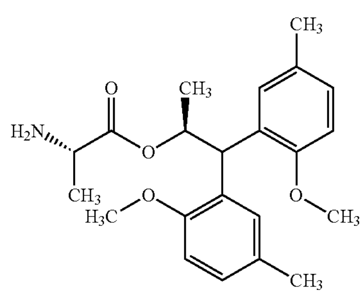 [SMILES: COc1ccc(C)cc1C(c1cc(C)ccc1OC)[C@H](C)OC(=O)[C@H](C)N] | Example 5, Step 1 | White Foam |

TABLE 1-continued

| *Cmpd. No. | Structure | Prepared According To Example | Appearance |
|---|---|---|---|
| 330 | 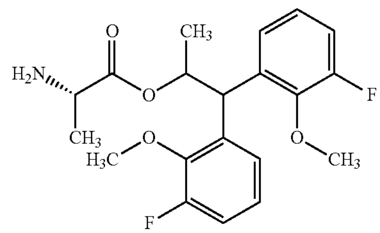 [SMILES: COc1c(F)cccc1C(c1cccc(F)c1OC)C(C)OC(=O)[C@H](C)N] | Example 5, Step 1 | White Foam |
| 331 | 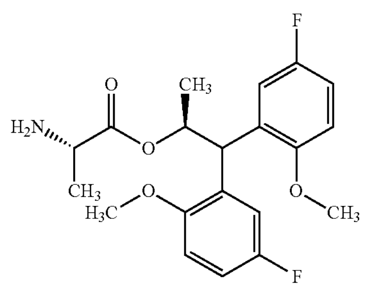 [SMILES: COc1ccc(F)cc1C(c1cc(F)ccc1OC)[C@H](C)OC(=O)[C@H](C)N] | Example 5, Step 1 | White Foam |
| 332 | 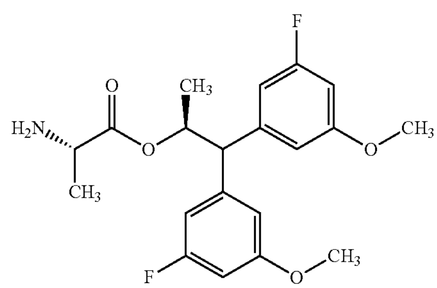 [SMILES: COc1cc(F)cc(C(c2cc(F)cc(OC)c2)[C@H](C)OC(=O)[C@H](C)N)c1] | Example 5, Step 1. | Clear, Colorless Oil |
| 333 | 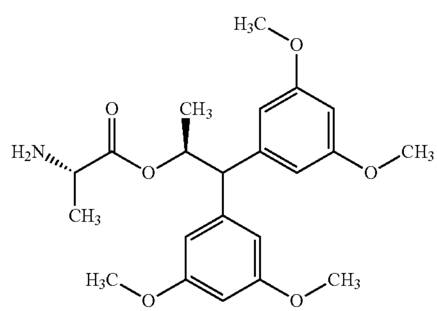 [SMILES: COc1cc(OC)cc(C(c2cc(OC)cc(OC)c2)[C@H](C)OC(=O)[C@H](C)N)c1] | Example 5, Step 1. | Light Brown Oil |
| 334 | 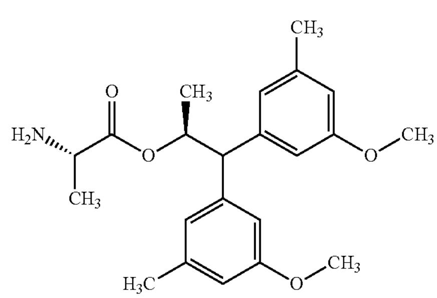 [SMILES: COc1cc(C)cc(C(c2cc(C)cc(OC)c2)[C@H](C)OC(=O)[C@H](C)N)c1] | Example 5, Step 1. | Pale Yellow Oil |

TABLE 1-continued

Compound Structure, Preparation Method, and Appearance

| *Cmpd. No. | Structure | Prepared According To Example | Appearance |
|---|---|---|---|
| 335 | 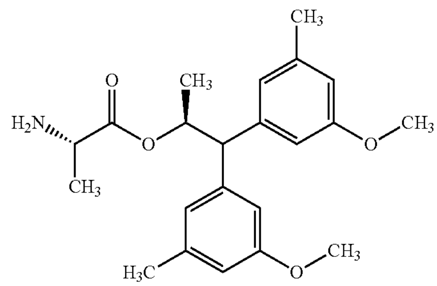 [SMILES: COc1cc(C)cc(C(c2cc(C)cc(OC)c2)[C@H](C)OC(=O)[C@H](C)N)c1] | Example 5, Step 1. | Pale Yellow Oil |
| 336 | 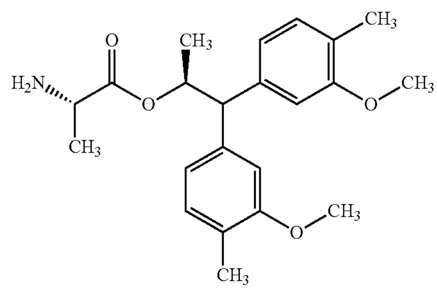 [SMILES: COc1cc(C(c2ccc(C)c(OC)c2)[C@H](C)OC(=O)[C@H](C)N)ccc1C] | Example 5, Step 1. | White Powdery Solid |
| 337 | 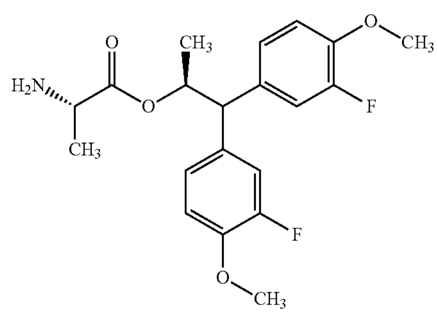 [SMILES: COc1ccc(C(c2ccc(OC)c(F)c2)[C@H](C)OC(=O)[C@H](C)N)cc1F] | Example 5, Step 1. | Clear, Colorless Oil |
| 338 | 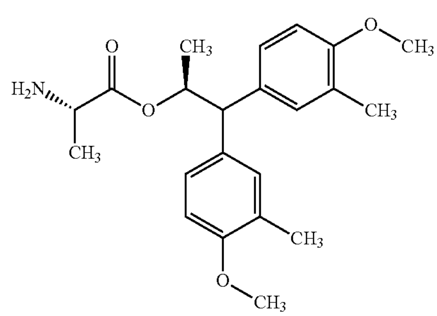 [SMILES: COc1ccc(C(c2ccc(OC)c(C)c2)[C@H](C)OC(=O)[C@H](C)N)cc1C] | Example 5, Step 1. | White Powdery Solid |
| 339 | 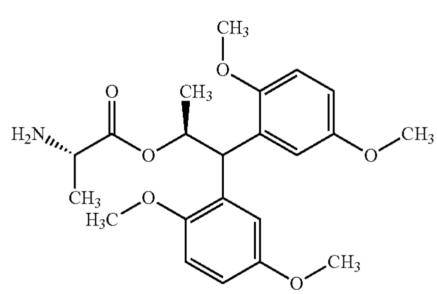 [SMILES: COc1ccc(OC)c(C(c2cc(OC)ccc2OC)[C@H](C)OC(=O)[C@H](C)N)c1] | Example 5, Step 1. | Clear, Colorless Oil |

TABLE 1-continued

Compound Structure, Preparation Method, and Appearance

| *Cmpd. No. | Structure | Prepared According To Example | Appearance |
|---|---|---|---|
| 340 | 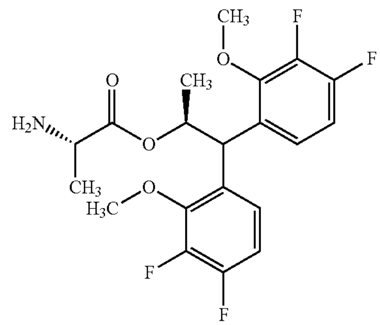 [SMILES: COc1c(C(c2ccc(F)c(F)c2OC)[C@H](C)OC(=O)[C@H](C)N)ccc(F)c1F] | Example 5, Step 1. | White Solid |
| 341 | 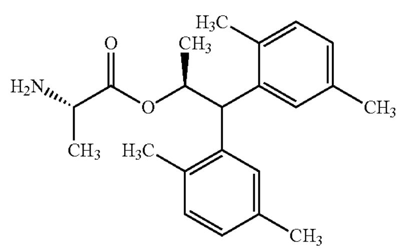 [SMILES: Cc1ccc(C)c(C(c2cc(C)ccc2C)[C@H](C)OC(=O)[C@H](C)N)c1] | Example 5, Step 1. | Thick Oil |
| 342 | 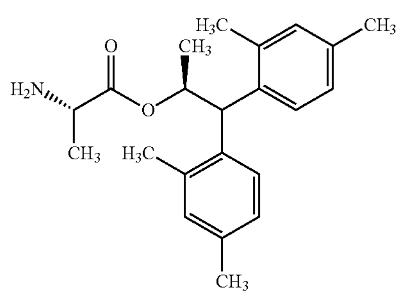 [SMILES: Cc1ccc(C(c2ccc(C)cc2C)[C@H](C)OC(=O)[C@H](C)N)c(C)c1] | Example 5, Step 1. | White Solid |
| 343 | 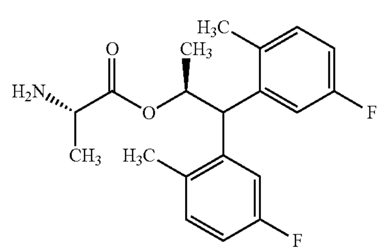 [SMILES: Cc1ccc(F)cc1C(c1cc(F)ccc1C)[C@H](C)OC(=O)[C@H](C)N] | Example 5, Step 1. | White Solid |
| 344 | 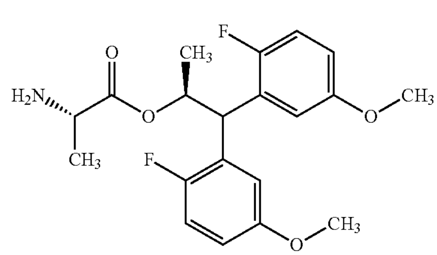 [SMILES: COc1ccc(F)c(C(c2cc(OC)ccc2F)[C@H](C)OC(=O)[C@H](C)N)c1] | Example 5, Step 1. | White Solid |

TABLE 1-continued

| *Cmpd. No. | Structure | Prepared According To Example | Appearance |
|---|---|---|---|
| 345 | 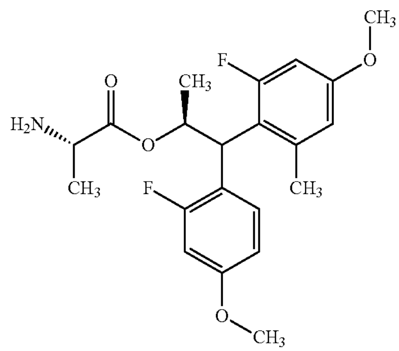 [SMILES: COc1ccc(C(c2c(C)cc(OC)cc2F)[C@H](C)OC(=O)[C@H](C)N)c(F)c1] | Example 5, Step 1. | White Solid |
| 346 | 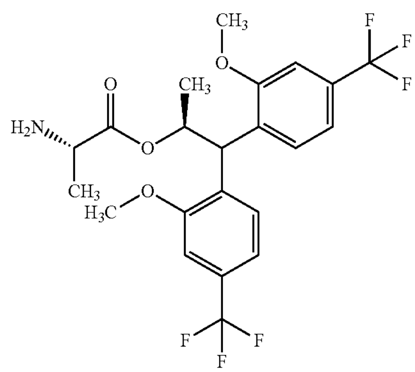 [SMILES: COc1cc(C(F)(F)F)ccc1C(c1ccc(C(F)(F)F)cc1OC)[C@H](C)OC(=O)[C@H](C)N] | Example 5, Step 1. | Thick Oil |
| 347 | 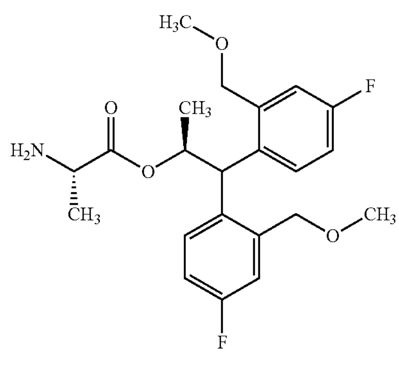 [SMILES: COCc1cc(F)ccc1C(c1ccc(F)cc1COC)[C@H](C)OC(=O)[C@H](C)N] | Example 5, Step 1. | White Solid |
| 348 | 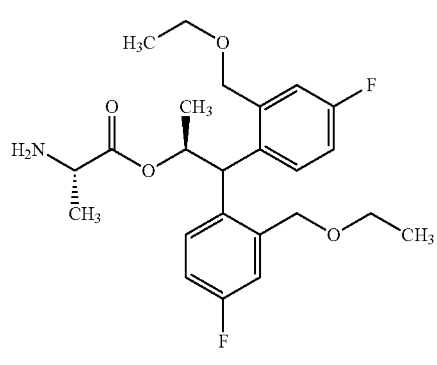 [SMILES: CCOCc1cc(F)ccc1C(c1ccc(F)cc1COCC)[C@H](C)OC(=O)[C@H](C)N] | Example 5, Step 1. | White Solid |

TABLE 1-continued

Compound Structure, Preparation Method, and Appearance

| *Cmpd. No. | Structure | Prepared According To Example | Appearance |
|---|---|---|---|
| 349 | 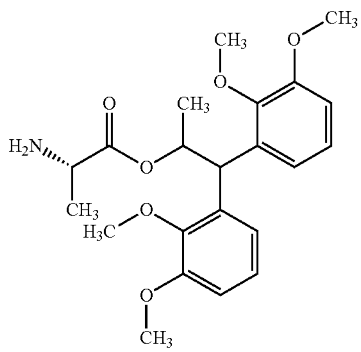 [SMILES: COc1cccc(C(c2cccc(OC)c2OC)C(C)OC(=O)[C@H](C)N)c1OC] | Example 5, Step 1 | Oil |
| 350 | 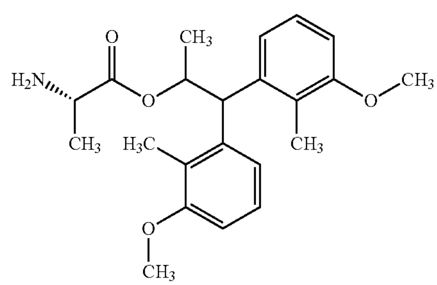 [SMILES: COc1cccc(C(c2cccc(OC)c2C)C(C)OC(=O)[C@H](C)N)c1C] | Example 5, Step 1 | Oil |
| 351 | 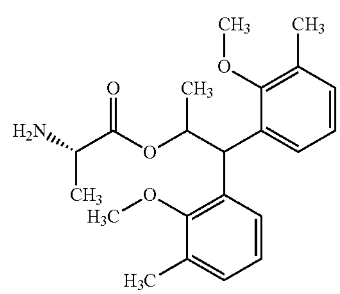 [SMILES: COc1c(C)cccc1C(c1cccc(C)c1OC)C(C)OC(=O)[C@H](C)N] | Example 5, Step 1 | Oil |
| 352 | 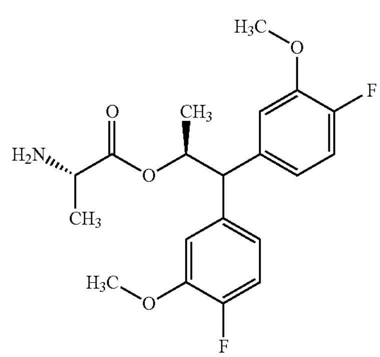 [SMILES: COc1cc(C(c2ccc(F)c(OC)c2)[C@H](C)OC(=O)[C@H](C)N)ccc1F] | Example 5, Step 1 | Colorless Oil |

TABLE 1-continued

Compound Structure, Preparation Method, and Appearance

| *Cmpd. No. | Structure | Prepared According To Example | Appearance |
|---|---|---|---|
| 353 | 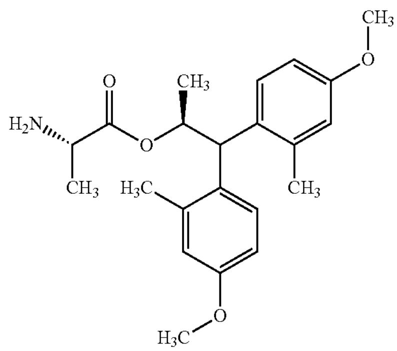 [SMILES: COc1ccc(C(c2ccc(OC)cc2C)[C@H](C)OC(=O)[C@H](C)N)c(C)c1] | Example 5, Step 1 | Colorless Oil |
| 354 | 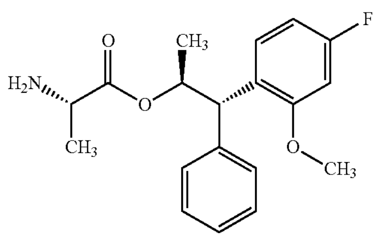 [SMILES: COc1cc(F)ccc1[C@H](c1ccccc1)[C@H](C)OC(=O)[C@H](C)N] | Example 5, Step 1 | Colorless Oil |
| 355 | 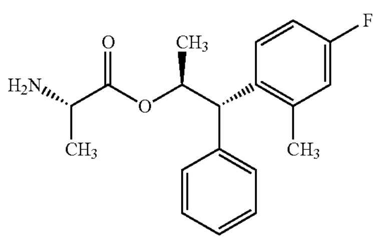 [SMILES: Cc1cc(F)ccc1[C@H](c1ccccc1)[C@H](C)OC(=O)[C@H](C)N] | Example 5, Step 1 | Colorless Oil |
| 356 | 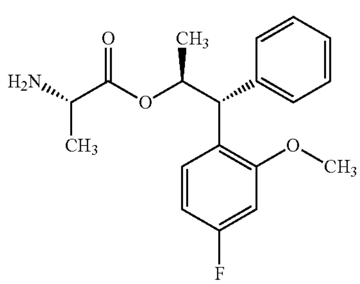 [SMILES: COc1cc(F)ccc1[C@@H](c1ccccc1)[C@H](C)OC(=O)[C@H](C)N] | Example 5, Step 1 | Colorless Oil |
| 357 | 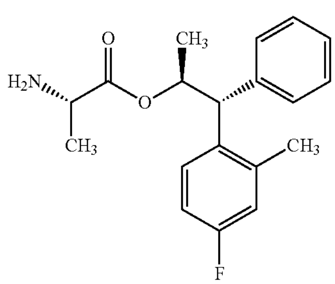 [SMILES: Cc1cc(F)ccc1[C@@H](c1ccccc1)[C@H](C)OC(=O)[C@H](C)N] | Example 5, Step 1 | Colorless Oil |

TABLE 1-continued

Compound Structure, Preparation Method, and Appearance

| *Cmpd. No. | Structure | Prepared According To Example | Appearance |
| --- | --- | --- | --- |
| 358 | 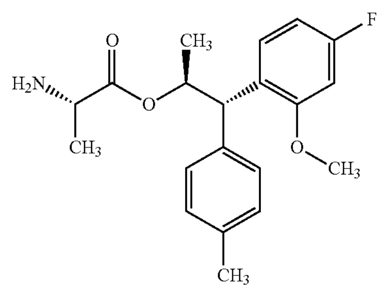 [SMILES: COc1cc(F)ccc1[C@H](c1ccc(C)cc1)[C@H](C)OC(=O)[C@H](C)N] | Example 5, Step 1 | Colorless Oil |
| 359 | 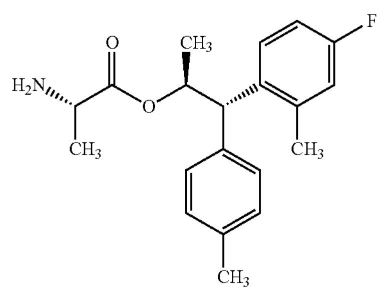 [SMILES: Cc1ccc([C@@H](c2ccc(F)cc2C)[C@H](C)OC(=O)[C@H](C)N)cc1] | Example 5, Step 1 | Colorless Oil |
| 360 | 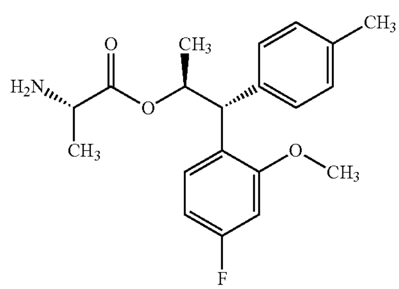 [SMILES: COc1cc(F)ccc1[C@@H](c1ccc(C)cc1)[C@H](C)OC(=O)[C@H](C)N] | Example 5, Step 1 | Colorless Oil |
| 361 | 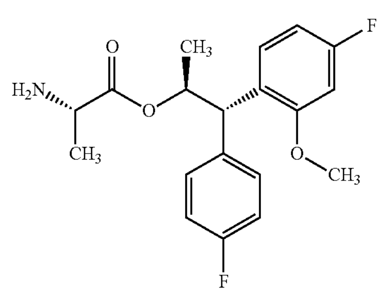 [SMILES: COc1cc(F)ccc1[C@H](c1ccc(F)cc1)[C@H](C)OC(=O)[C@H](C)N] | Example 5, Step 1 | Colorless Foam |
| 362 | 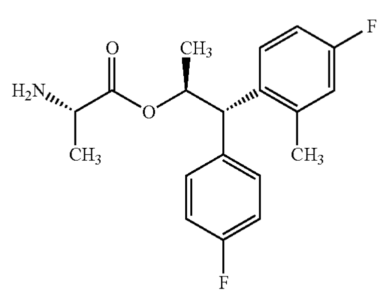 | Example 5, Step 1 | Colorless Foam |

TABLE 1-continued

Compound Structure, Preparation Method, and Appearance

| *Cmpd. No. | Structure | Prepared According To Example | Appearance |
|---|---|---|---|
| 363 | 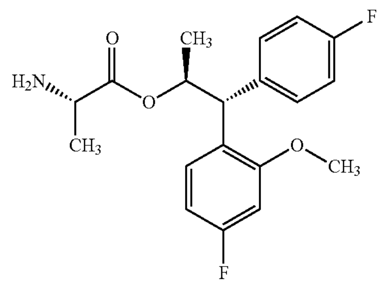 [SMILES: COc1cc(F)ccc1[C@@H](c1ccc(F)cc1)[C@H](C)OC(=O)[C@H](C)N] | Example 5, Step 1 | Colorless Oil |
| 364 | 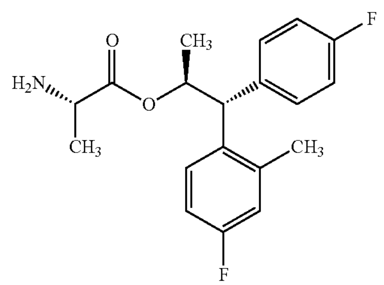 | Example 5, Step 1 | Colorless Oil |
| 365 | 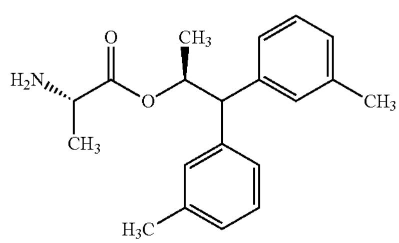 [SMILES: Cc1cccc(C(c2cccc(C)c2)[C@H](C)OC(=O)[C@H](C)N)c1] | Example 5, Step 1 | White Foam |
| 366 | 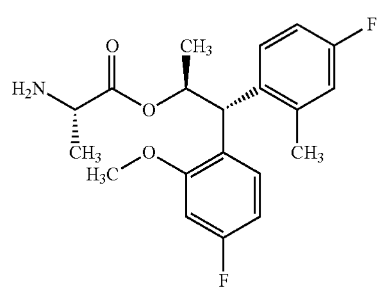 [SMILES: COc1cc(F)ccc1[C@@H](c1ccc(F)cc1C)[C@H](C)OC(=O)[C@H](C)N] | Example 5, Step 1. | Sticky Wax |
| 367 | 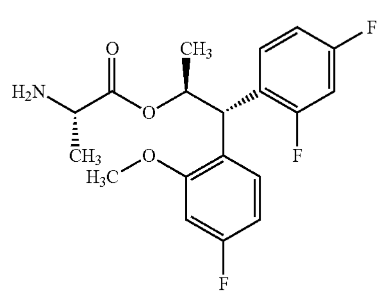 [SMILES: COc1cc(F)ccc1[C@@H](c1ccc(F)cc1F)[C@H](C)OC(=O)[C@H](C)N] | Example 5, Step 1. | Sticky Wax |

TABLE 1-continued

Compound Structure, Preparation Method, and Appearance

| *Cmpd. No. | Structure | Prepared According To Example | Appearance |
|---|---|---|---|
| 368 | 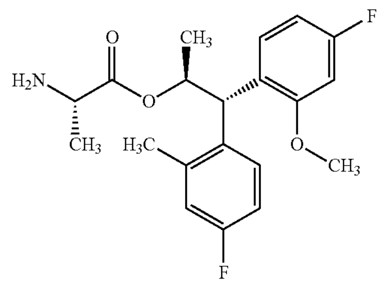 [SMILES: COc1cc(F)ccc1[C@H](c1ccc(F)cc1C)[C@H](C)OC(=O)[C@H](C)N] | Example 5, Step 1. | Sticky Wax |
| 369 | 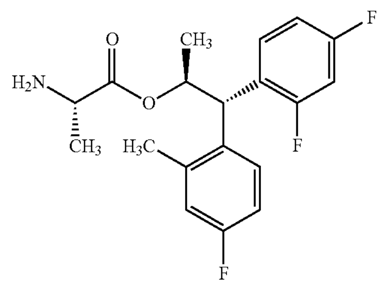 [SMILES: Cc1cc(F)ccc1[C@@H](c1ccc(F)cc1F)[C@H](C)OC(=O)[C@H](C)N] | Example 5, Step 1. | Sticky Wax |
| 370 | 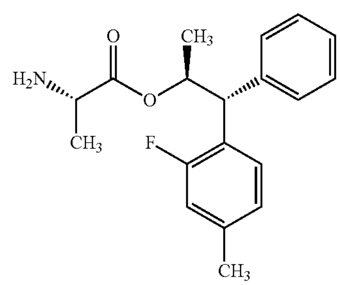 [SMILES: Cc1ccc([C@@H](c2ccccc2)[C@H](C)OC(=O)[C@H](C)N)c(F)c1] | Example 5, Step 1 | White Foam |
| 371 | 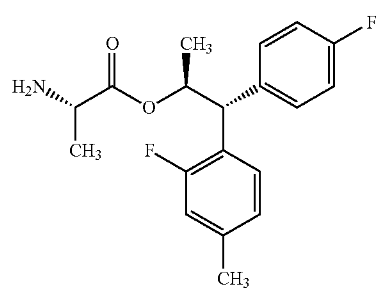 [SMILES: Cc1ccc([C@@H](c2ccc(F)cc2)[C@H](C)OC(=O)[C@H](C)N)c(F)c1] | Example 5, Step 1 | White Foam |
| 372 | 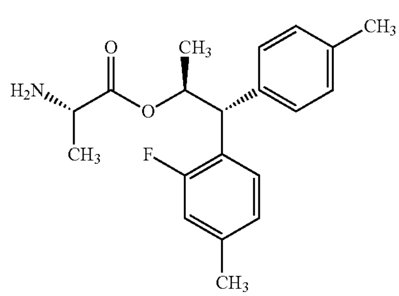 [SMILES: Cc1ccc([C@H](c2ccc(C)cc2F)[C@H](C)OC(=O)[C@H](C)N)cc1] | Example 5, Step 1 | White Foam |

TABLE 1-continued

Compound Structure, Preparation Method, and Appearance

| *Cmpd. No. | Structure | Prepared According To Example | Appearance |
|---|---|---|---|
| 373 | 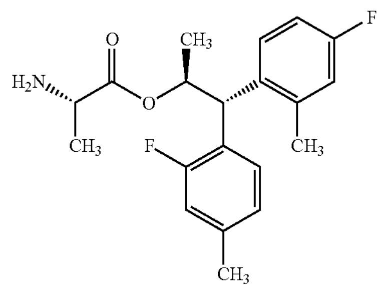 [SMILES: Cc1ccc([C@@H](c2ccc(F)cc2C)[C@H](C)OC(=O)[C@H](C)N)c(F)c1] | Example 5, Step 1 | White Foam |
| 374 | 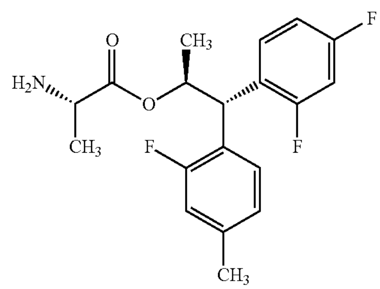 [SMILES: Cc1ccc([C@@H](c2ccc(F)cc2F)[C@H](C)OC(=O)[C@H](C)N)c(F)c1] | Example 5, Step 1 | White Foam |
| 375 | 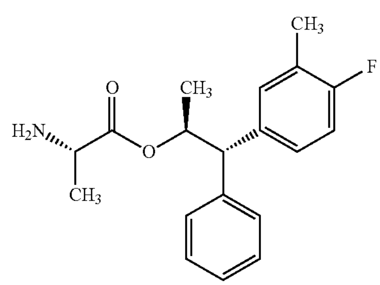 [SMILES: Cc1cc([C@H](c2ccccc2)[C@H](C)OC(=O)[C@H](C)N)ccc1F] | Example 5, Step 1 | Colorless Oil |
| 376 | 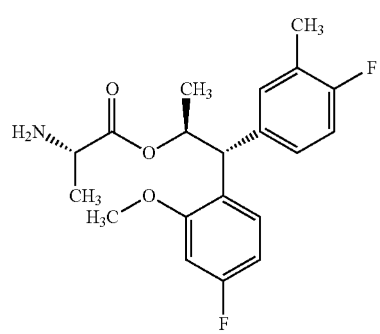 [SMILES: COc1cc(F)ccc1[C@@H](c1ccc(F)c(C)c1)[C@H](C)OC(=O)[C@H](C)N] | Example 5, Step 1 | Colorless Oil |
| 377 | 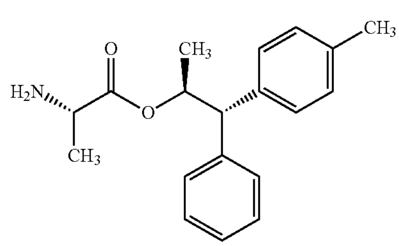 [SMILES: Cc1ccc([C@H](c2ccccc2)[C@H](C)OC(=O)[C@H](C)N)cc1] | Example 5, Step 1. | Thick Oil |

TABLE 1-continued

Compound Structure, Preparation Method, and Appearance

| *Cmpd. No. | Structure | Prepared According To Example | Appearance |
|---|---|---|---|
| 378 | 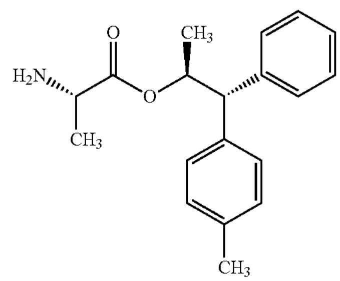 [SMILES: Cc1ccc([C@@H](c2ccccc2)[C@H](C)OC(=O)[C@H](C)N)cc1] | Example 5, Step 1. | Thick Oil |
| 379 | 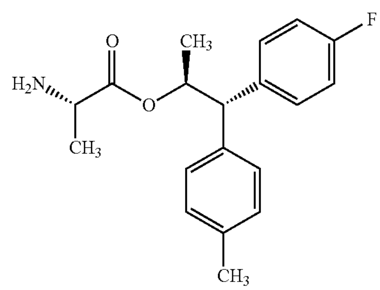 [SMILES: Cc1ccc([C@@H](c2ccc(F)cc2)[C@H](C)OC(=O)[C@H](C)N)cc1] | Example 5, Step 1. | White Solid |
| 380 | 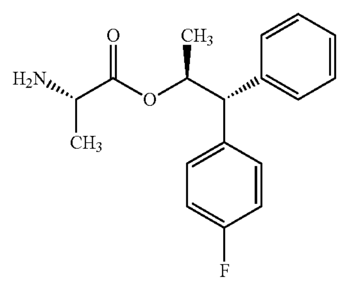 [SMILES: C[C@H](N)C(=O)O[C@@H](C)[C@H](c1ccccc1)c1ccc(F)cc1] | Example 5, Step 1. | Thick Oil |
| 381 | 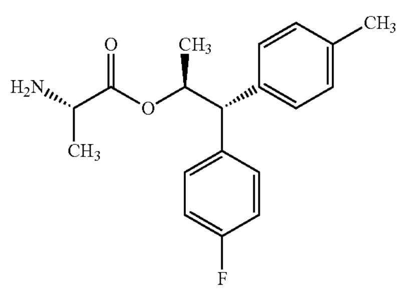 [SMILES: Cc1ccc([C@H](c2ccc(F)cc2)[C@H](C)OC(=O)[C@H](C)N)cc1] | Example 5, Step 1. | Thick Oil |
| 382 | 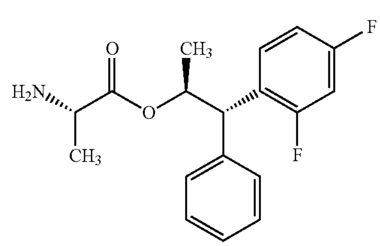 | Example 5, Step 1. | White Foam |

TABLE 1-continued

Compound Structure, Preparation Method, and Appearance

| *Cmpd. No. | Structure | Prepared According To Example | Appearance |
|---|---|---|---|
| 383 | 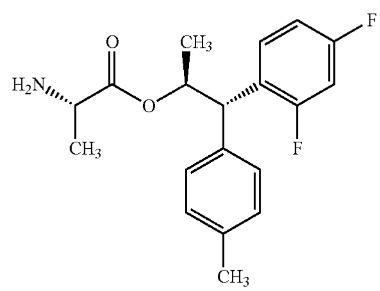 [SMILES: Cc1ccc([C@@H](c2ccc(F)cc2F)[C@H](C)OC(=O)[C@H](C)N)cc1] | Example 5, Step 1. | White Solid |
| 384 | 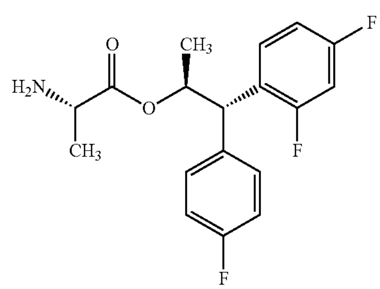 [SMILES: C[C@H](N)C(=O)O[C@@H](C)[C@@H](c1ccc(F)cc1)c1ccc(F)cc1F] | Example 5, Step 1. | White Foam |
| 385 | 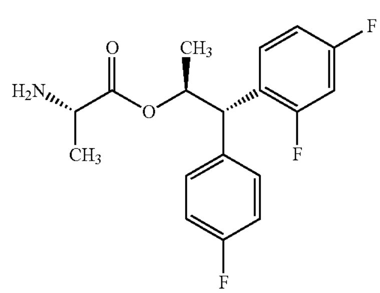 [SMILES: C[C@H](N)C(=O)O[C@@H](C)[C@@H](c1ccc(F)cc1)c1ccc(F)cc1F] | Example 5, Step 1. | White Foam |
| 386 | 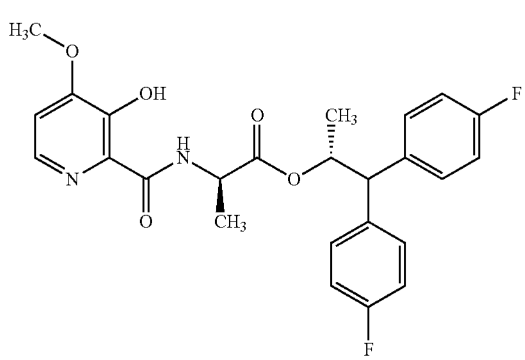 [SMILES: COc1ccnc(C(=O)N[C@H](C)C(=O)O[C@H](C)C(c2ccc(F)cc2)c2ccc(F)cc2)c1O] | Example 5, Step 2. | Matte White Solid And Clear Oil |

TABLE 1-continued

Compound Structure, Preparation Method, and Appearance

| *Cmpd. No. | Structure | Prepared According To Example | Appearance |
|---|---|---|---|
| 387 | 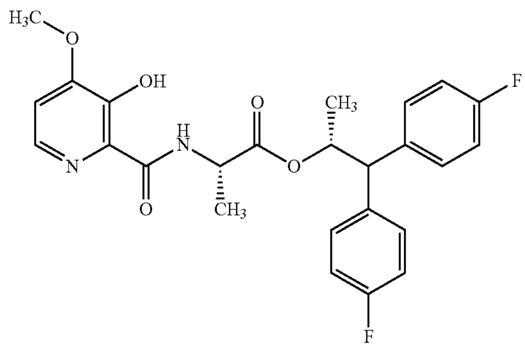 [SMILES: COc1ccnc(C(=O)N[C@@H](C)C(=O)O[C@H](C)C(c2ccc(F)cc2)c2ccc(F)cc2)c1O] | Example 5, Step 2. | Matte White Solid And Clear Oil |
| 388 | 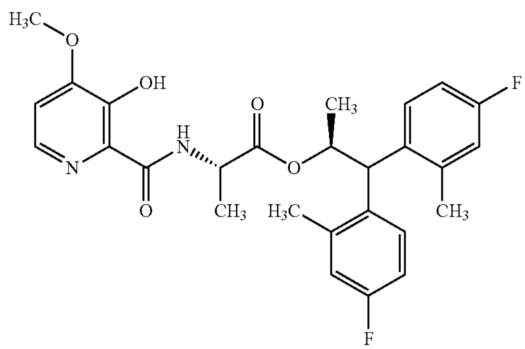 [SMILES: COc1ccnc(C(=O)N[C@@H](C)C(=O)O[C@@H](C)C(c2ccc(F)cc2C)c2ccc(F)cc2C)c1O] | Example 5, Step 2. | Clear, Colorless Oil |
| 389 | 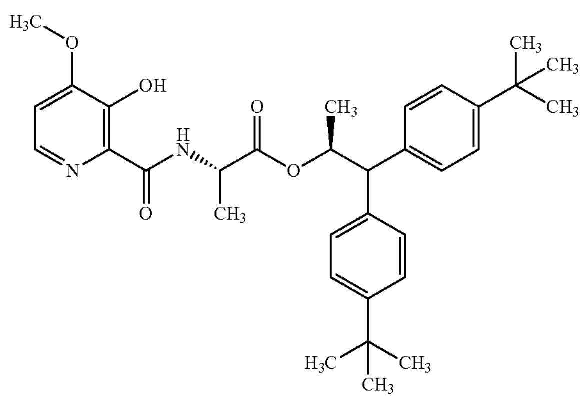 [SMILES: COc1ccnc(C(=O)N[C@@H](C)C(=O)O[C@@H](C)C(c2ccc(C(C)(C)C)cc2)c2ccc(C(C)(C)C)cc2)c1O] | Example 5, Step 2. | Colorless Foam |
| 390 | 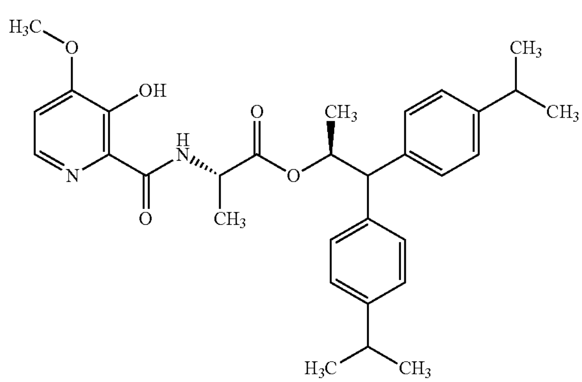 [SMILES: COc1ccnc(C(=O)N[C@@H](C)C(=O)O[C@@H](C)C(c2ccc(C(C)C)cc2)c2ccc(C(C)C)cc2)c1O] | Example 5, Step 2. | Colorless Foam |

TABLE 1-continued

Compound Structure, Preparation Method, and Appearance

| *Cmpd. No. | Structure | Prepared According To Example | Appearance |
| --- | --- | --- | --- |
| 391 | 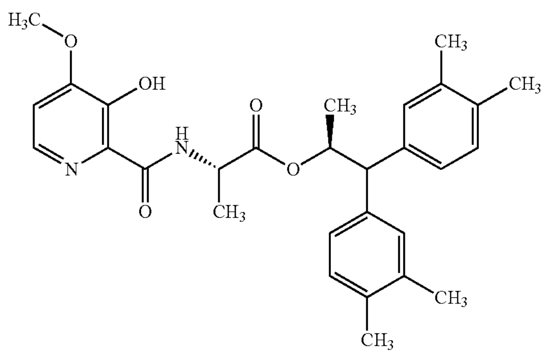 [SMILES: COc1ccnc(C(=O)N[C@@H](C)C(=O)O[C@@H](C)C(c2ccc(C)c(C)c2)c2ccc(C)c(C)c2)c1O] | Example 5, Step 2. | Clear, Colorless Oil |
| 392 | 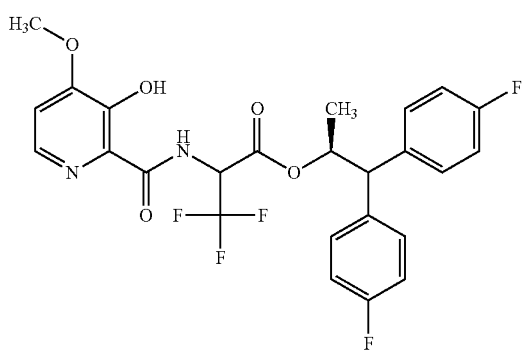 [SMILES: COc1ccnc(C(=O)NC(C(=O)O[C@@H](C)C(c2ccc(F)cc2)c2ccc(F)cc2)C(F)(F)F)c1O] | Example 5, Step 2. | Semi Solid |
| 393 | 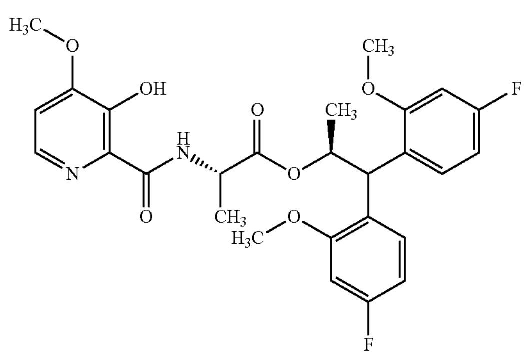 [SMILES: COc1cc(F)ccc1C(c1ccc(F)cc1OC)[C@H](C)OC(=O)[C@H](C)NC(=O)c1nccc(OC)c1O] | Example 5, Step 2. | White Foam |
| 394 | 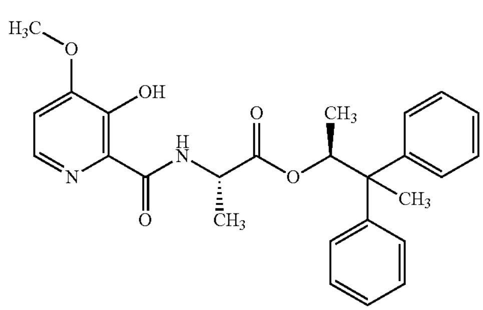 [SMILES: COc1ccnc(C(=O)N[C@@H](C)C(=O)O[C@@H](C)C(C)(c2ccccc2)c2ccccc2)c1O] | Example 5, Step 2. | Colorless Foamy Oil |

TABLE 1-continued

Compound Structure, Preparation Method, and Appearance

| *Cmpd. No. | Structure | Prepared According To Example | Appearance |
|---|---|---|---|
| 395 | 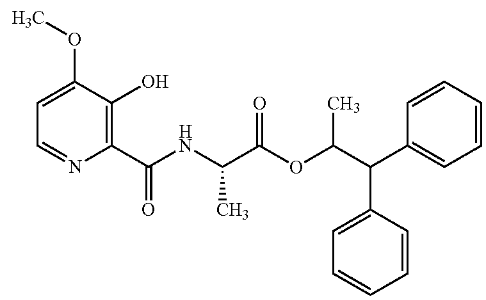 [SMILES: COc1ccnc(C(=O)N[C@@H](C)C(=O)OC(C)C(c2ccccc2)c2ccccc2)c1O] | Example 5, Step 2. | White Foam |
| 396 | 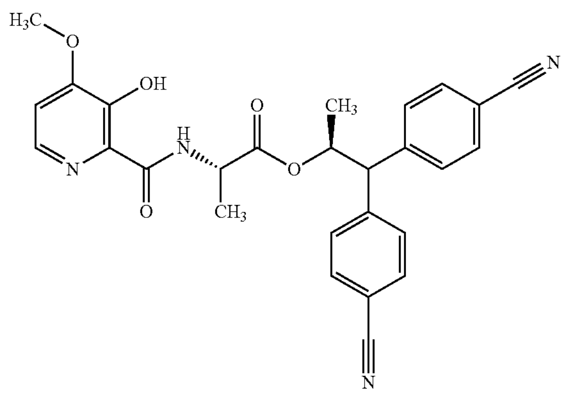 [SMILES: COc1ccnc(C(=O)N[C@@H](C)C(=O)O[C@@H](C)C(c2ccc(C#N)cc2)c2ccc(C#N)cc2)c1O] | Example 5, Step 2 | White Foam |
| 397 | 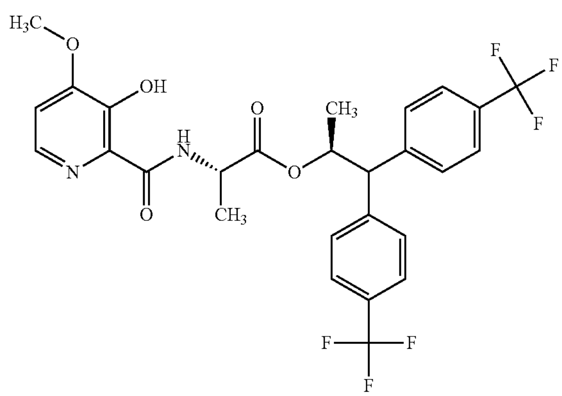 [SMILES: COc1ccnc(C(=O)N[C@@H](C)C(=O)O[C@@H](C)C(c2ccc(C(F)(F)F)cc2)c2ccc(C(F)(F)F)cc2)c1O] | Example 5, Step 2 | White Foam |
| 398 | 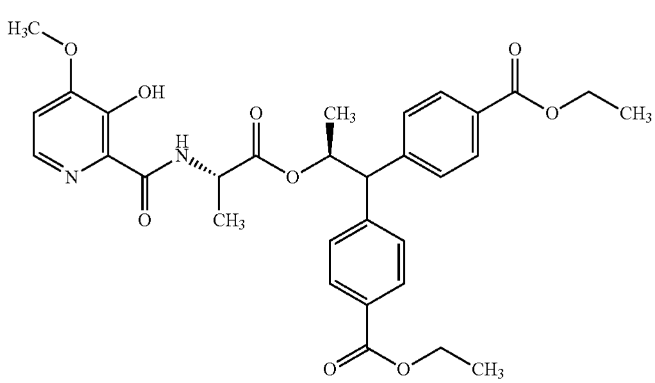 [SMILES: CCOC(=O)c1ccc(C(c2ccc(C(=O)OCC)cc2)[C@H](C)OC(=O)[C@H](C)NC(=O)c2nccc(OC)c2O)cc1] | Example 5, Step 2 | White Foam |

TABLE 1-continued

Compound Structure, Preparation Method, and Appearance

| *Cmpd. No. | Structure | Prepared According To Example | Appearance |
|---|---|---|---|
| 399 | 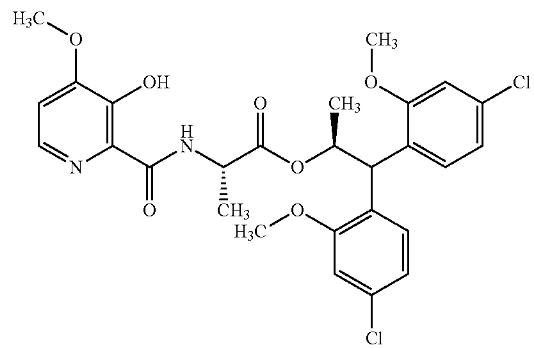 [SMILES: COc1cc(Cl)ccc1C(c1ccc(Cl)cc1OC)[C@H](C)OC(=O)[C@H](C)NC(=O)c1nccc(OC)c1O] | Example 5, Step 2. | White Foam |
| 400 | 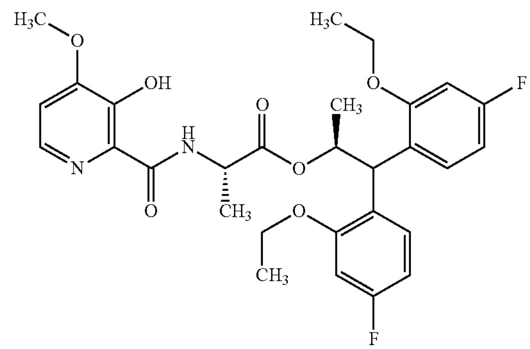 [SMILES: CCOc1cc(F)ccc1C(c1ccc(F)cc1OCC)[C@H](C)OC(=O)[C@H](C)NC(=O)c1nccc(OC)c1O] | Example 5, Step 2. | White Foam |
| 401 | 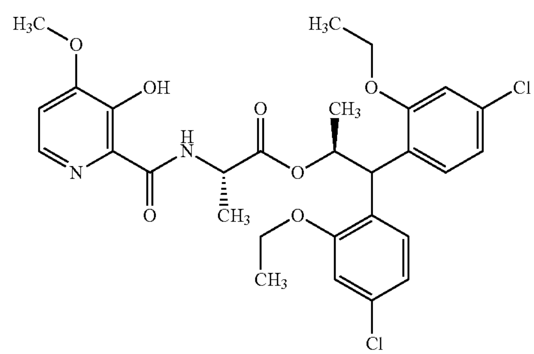 [SMILES: CCOc1cc(Cl)ccc1C(c1ccc(Cl)cc1OCC)[C@H](C)OC(=O)[C@H](C)NC(=O)c1nccc(OC)c1O] | Example 5, Step 2. | White Foam |
| 402 | 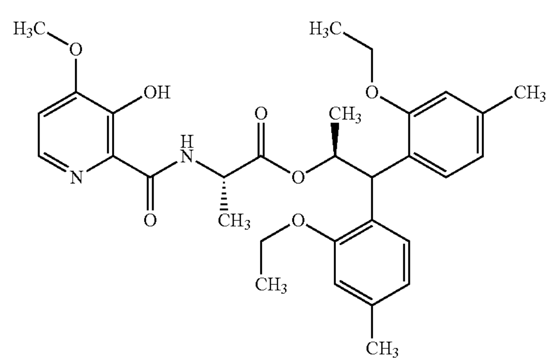 [SMILES: CCOc1cc(C)ccc1C(c1ccc(C)cc1OCC)[C@H](C)OC(=O)[C@H](C)NC(=O)c1nccc(OC)c1O] | Example 5, Step 2. | White Foam |

TABLE 1-continued

Compound Structure, Preparation Method, and Appearance

| *Cmpd. No. | Structure | Prepared According To Example | Appearance |
|---|---|---|---|
| 403 | 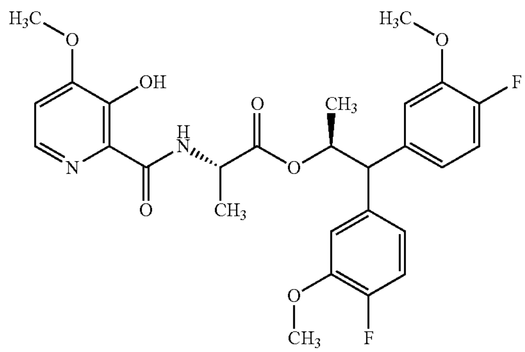 [SMILES: COc1cc(C(c2ccc(F)c(OC)c2)[C@H](C)OC(=O)[C@H](C)NC(=O)c2nccc(OC)c2O)ccc1F] | Example 5, Step 2 | Colorless Oil |
| 404 | 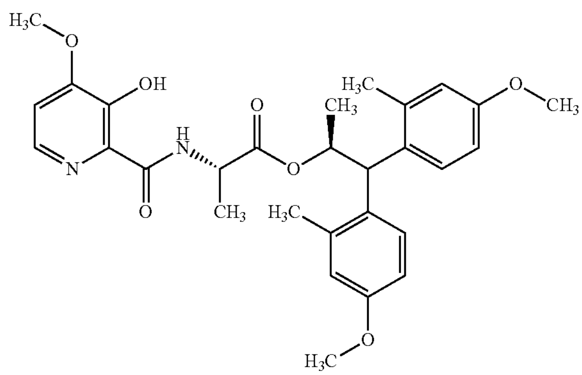 [SMILES: COc1ccc(C(c2ccc(OC)cc2C)[C@H](C)OC(=O)[C@H](C)NC(=O)c2nccc(OC)c2O)c(C)c1] | Example 5, Step 2 | Colorless Oil |
| 405 | 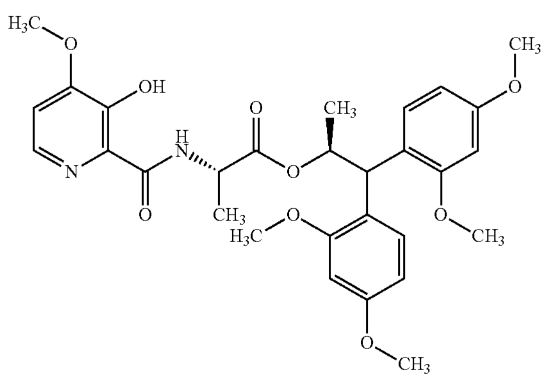 [SMILES: COc1ccc(C(c2ccc(OC)cc2OC)[C@H](C)OC(=O)[C@H](C)NC(=O)c2nccc(OC)c2O)c(OC)c1] | Example 5, Step 2 | White Foam |
| 406 | 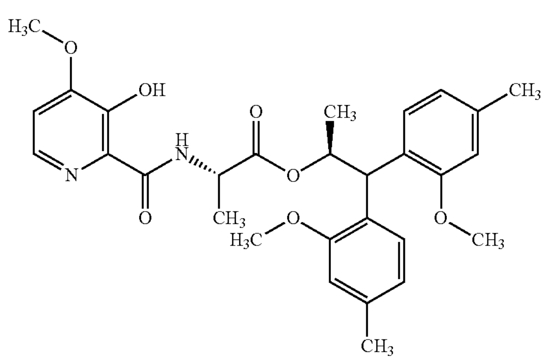 [SMILES: COc1cc(C)ccc1C(c1ccc(C)cc1OC)[C@H](C)OC(=O)[C@H](C)NC(=O)c1nccc(OC)c1O] | Example 5, Step 2 | White Foam |

TABLE 1-continued

Compound Structure, Preparation Method, and Appearance

| *Cmpd. No. | Structure | Prepared According To Example | Appearance |
|---|---|---|---|
| 407 | 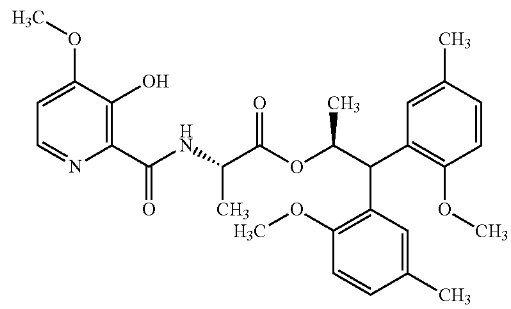 [SMILES: COc1ccc(C)cc1C(c1cc(C)ccc1OC)[C@H](C)OC(=O)[C@H](C)NC(=O)c1nccc(OC)c1O] | Example 5, Step 2 | White Foam |
| 408 | 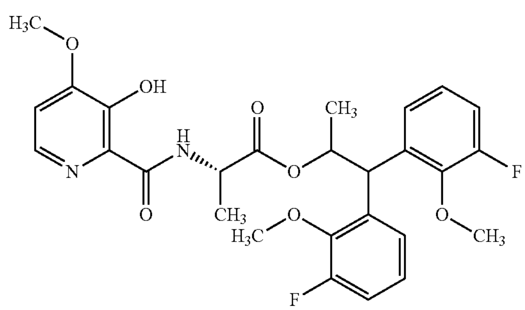 [SMILES: COc1ccnc(C(=O)N[C@@H](C)C(=O)OC(C)C(c2cccc(F)c2OC)c2cccc(F)c2OC)c1O] | Example 5, Step 2 | White Foam |
| 409 | 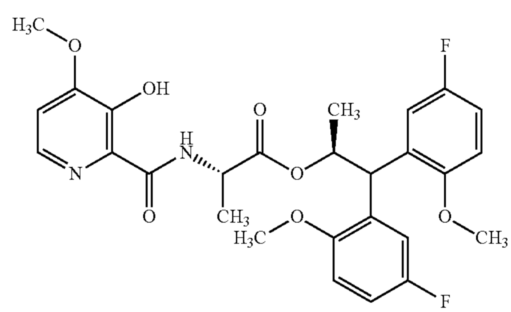 [SMILES: COc1ccc(F)cc1C(c1cc(F)ccc1OC)[C@H](C)OC(=O)[C@H](C)NC(=O)c1nccc(OC)c1O] | Example 5, Step 2 | White Foam |
| 410 | 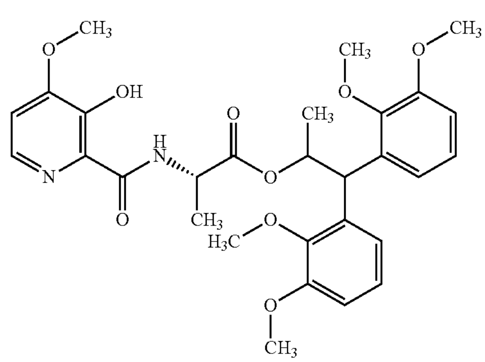 [SMILES: COc1ccnc(C(=O)N[C@@H](C)C(=O)OC(C)C(c2cccc(OC)c2OC)c2cccc(OC)c2OC)c1O] | Example 5, Step 2 | White Foam |

TABLE 1-continued

Compound Structure, Preparation Method, and Appearance

| *Cmpd. No. | Structure | Prepared According To Example | Appearance |
|---|---|---|---|
| 411 | 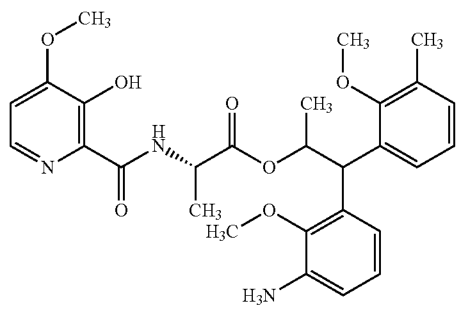 [SMILES: COc1ccnc(C(=O)N[C@@H](C)C(=O)OC(C)C(c2cccc(C)c2OC)c2cccc(N)c2OC)c1O] | Example 5, Step 2 | White Foam |
| 412 | 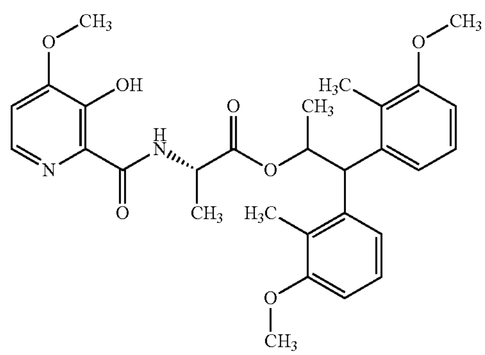 [SMILES: COc1cccc(C(c2cccc(OC)c2C)C(C)OC(=O)[C@H](C)NC(=O)c2nccc(OC)c2O)c1C] | Example 5, Step 2 | Oil |
| 413 | 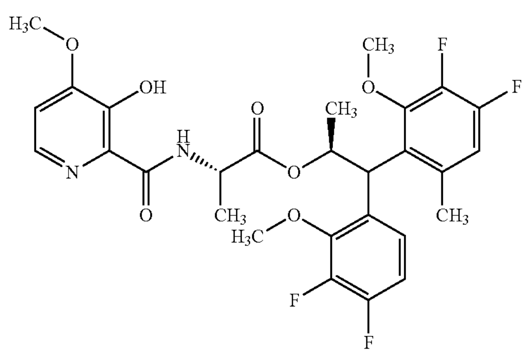 [SMILES: COc1ccnc(C(=O)N[C@@H](C)C(=O)O[C@@H](C)C(c2ccc(F)c(F)c2OC)c2c(C)cc(F)c(F)c2OC)c1O] | Example 5, Step 2. | White Foam |
| 414 | 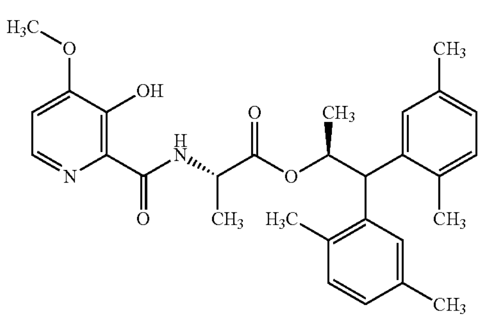 [SMILES: COc1ccnc(C(=O)N[C@@H](C)C(=O)O[C@@H](C)C(c2cc(C)ccc2C)c2cc(C)ccc2C)c1O] | Example 5, Step 2. | Thick Oil |

TABLE 1-continued

Compound Structure, Preparation Method, and Appearance

| *Cmpd. No. | Structure | Prepared According To Example | Appearance |
|---|---|---|---|
| 415 | 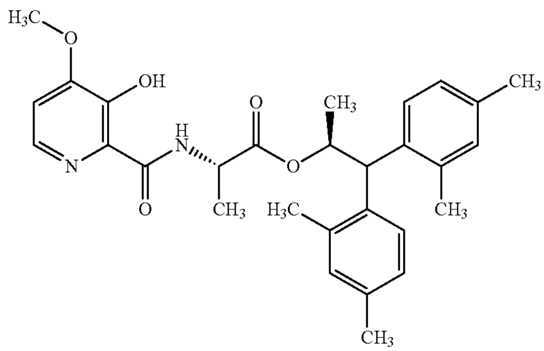 [SMILES: COc1ccnc(C(=O)N[C@@H](C)C(=O)O[C@@H](C)C(c2ccc(C)cc2C)c2ccc(C)cc2C)c1O] | Example 5, Step 2. | White Foam |
| 416 | 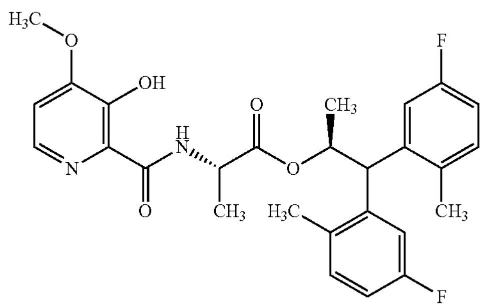 [SMILES: COc1ccnc(C(=O)N[C@@H](C)C(=O)O[C@@H](C)C(c2cc(F)ccc2C)c2cc(F)ccc2C)c1O] | Example 5, Step 2. | White Foam |
| 417 | 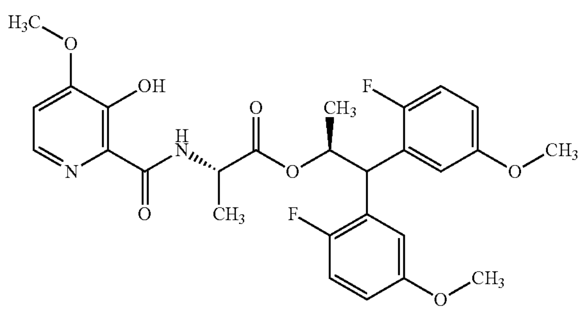 [SMILES: COc1ccc(F)c(C(c2cc(OC)ccc2F)[C@H](C)OC(=O)[C@H](C)NC(=O)c2nccc(OC)c2O)c1] | Example 5, Step 2. | White Foam |
| 418 | 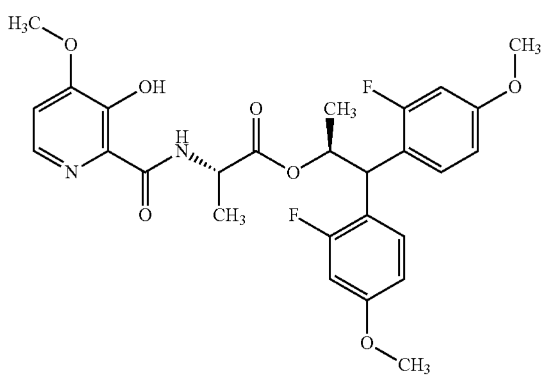 [SMILES: COc1ccc(C(c2ccc(OC)cc2F)[C@H](C)OC(=O)[C@H](C)NC(=O)c2nccc(OC)c2O)c(F)c1] | Example 5, Step 2. | White Foam |

TABLE 1-continued

Compound Structure, Preparation Method, and Appearance

| *Cmpd. No. | Structure | Prepared According To Example | Appearance |
|---|---|---|---|
| 419 | 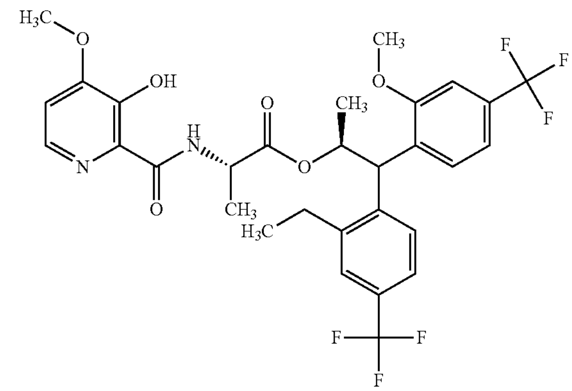 [SMILES: CCc1cc(C(F)(F)F)ccc1C(c1ccc(C(F)(F)F)cc1OC)[C@H](C)OC(=O)[C@H](C)NC(=O)c1nccc(OC)c1O] | Example 5, Step 2. | White Foam |
| 420 | 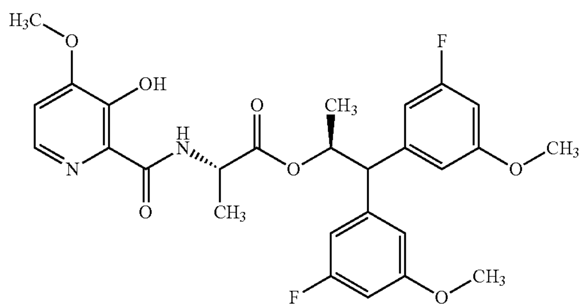 [SMILES: COc1cc(F)cc(C(c2cc(F)cc(OC)c2)[C@H](C)OC(=O)[C@H](C)NC(=O)c2nccc(OC)c2O)c1] | Example 5, Step 2. | Colorless Foam |
| 421 | 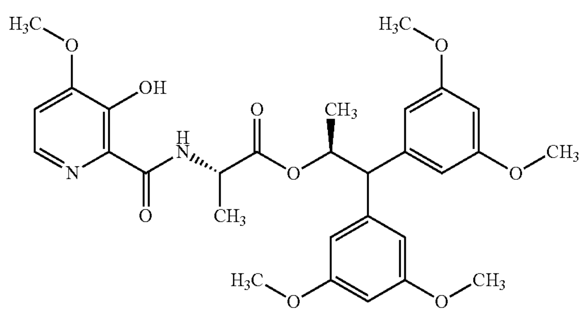 [SMILES: COc1cc(OC)cc(C(c2cc(OC)cc(OC)c2)[C@H](C)OC(=O)[C@H](C)NC(=O)c2nccc(OC)c2O)c1] | Example 5, Step 2. | Clear, Colorless Oil |
| 422 | 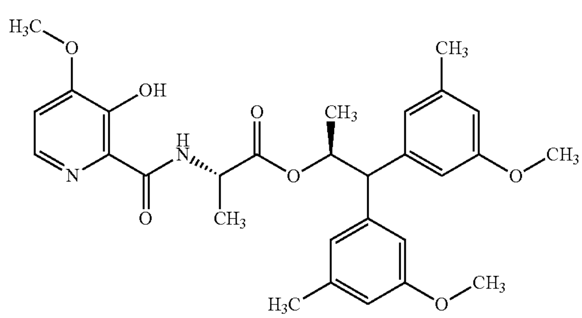 [SMILES: COc1cc(C)cc(C(c2cc(C)cc(OC)c2)[C@H](C)OC(=O)[C@H](C)NC(=O)c2nccc(OC)c2O)c1] | Example 5, Step 2. | Clear, Colorless Oil |

TABLE 1-continued
Compound Structure, Preparation Method, and Appearance
| *Cmpd. No. | Structure | Prepared According To Example | Appearance |
|---|---|---|---|
| 423 | 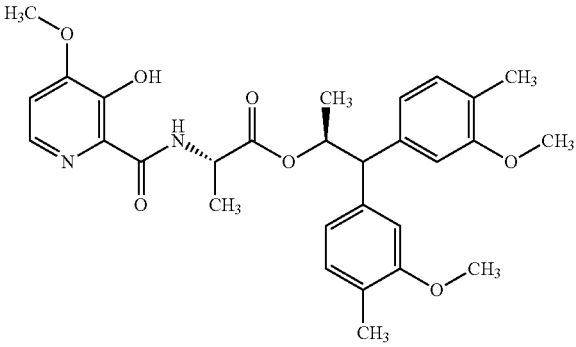 [SMILES: COc1cc(C(c2ccc(C)c(OC)c2)[C@H](C)OC(=O)[C@H](C)NC(=O)c2nccc(OC)c2O)ccc1C] | Example 5, Step 2. | Colorless Foam |
| 424 | 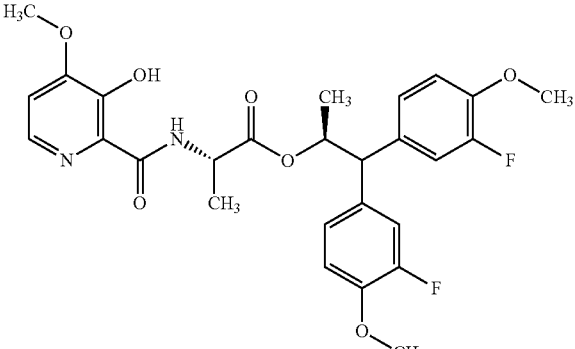 | Example 5, Step 2. | Colorless Foam |
| 425 | 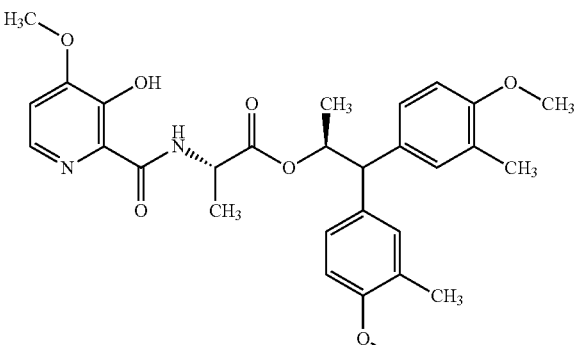 | Example 5, Step 2. | Clear, Colorless Oil |
| 426 | 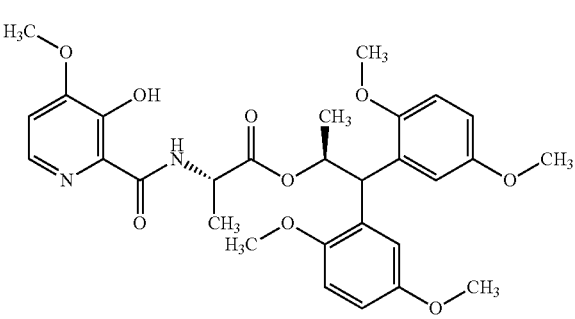 [SMILES: COc1ccc(OC)c(C(c2cc(OC)ccc2OC)[C@H](C)OC(=O)[C@H](C)NC(=O)c2nccc(OC)c2O)c1] | Example 5, Step 2. | Clear, Colorless Oil |

TABLE 1-continued

Compound Structure, Preparation Method, and Appearance

| *Cmpd. No. | Structure | Prepared According To Example | Appearance |
|---|---|---|---|
| 427 | 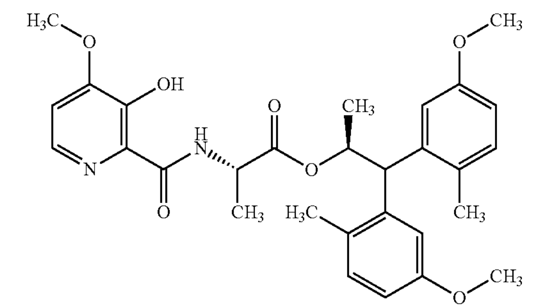 [SMILES: COc1ccc(C)c(C(c2cc(OC)ccc2C)[C@H](C)OC(=O)[C@H](C)NC(=O)c2nccc(OC)c2O)c1] | Example 5, Step 2. | Clear, Colorless Oil |
| 428 | 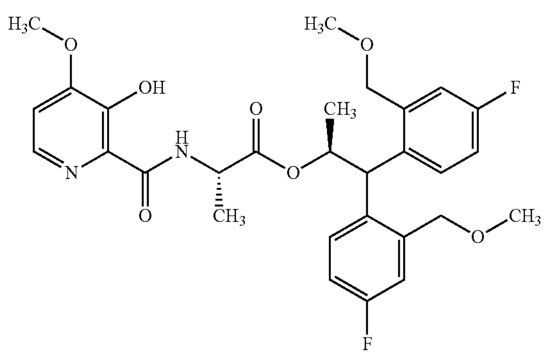 [SMILES: COCc1cc(F)ccc1C(c1ccc(F)cc1COC)[C@H](C)OC(=O)[C@H](C)NC(=O)c1nccc(OC)c1O] | Example 5, Step 2. | White Foam |
| 429 | 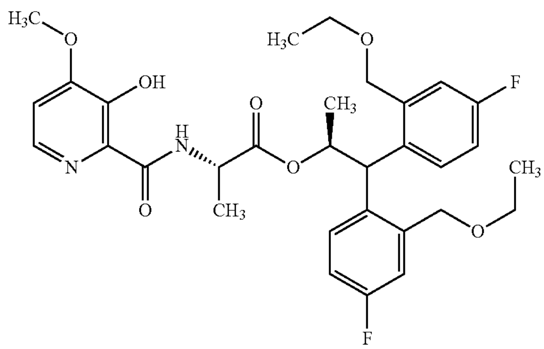 [SMILES: CCOCc1cc(F)ccc1C(c1ccc(F)cc1COCC)[C@H](C)OC(=O)[C@H](C)NC(=O)c1nccc(OC)c1O] | Example 5, Step 2. | Sticky Wax |
| 430 | 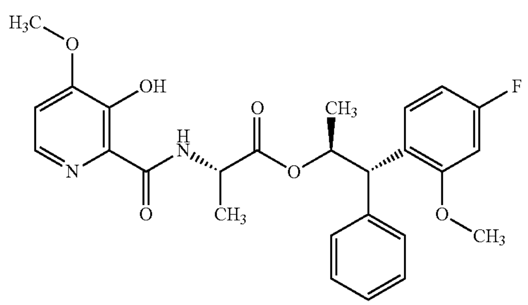 [SMILES: COc1cc(F)ccc1[C@H](c1ccccc1)[C@H](C)OC(=O)[C@H](C)NC(=O)c1nccc(OC)c1O] | Example 5, Step 2 | Colorless Gel |

TABLE 1-continued

Compound Structure, Preparation Method, and Appearance

| *Cmpd. No. | Structure | Prepared According To Example | Appearance |
| --- | --- | --- | --- |
| 431 | 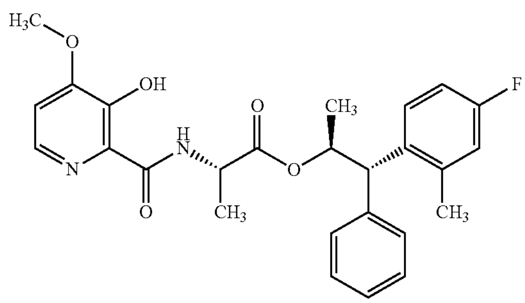 [SMILES: COc1ccnc(C(=O)N[C@@H](C)C(=O)O[C@@H](C)[C@@H](c2ccccc2)c2ccc(F)cc2C)c1O] | Example 5, Step 2 | Colorless Gel |
| 432 | 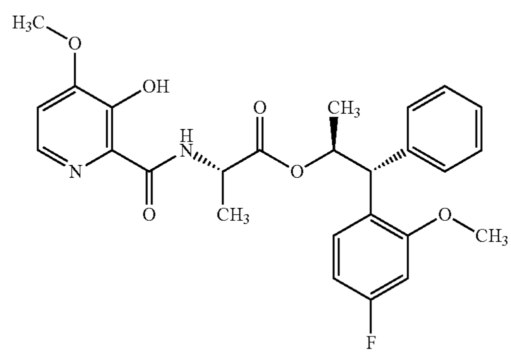 [SMILES: COc1cc(F)ccc1[C@@H](c1ccccc1)[C@H](C)OC(=O)[C@H](C)NC(=O)c1nccc(OC)c1O] | Example 5, Step 2 | Colorless Gel |
| 433 | 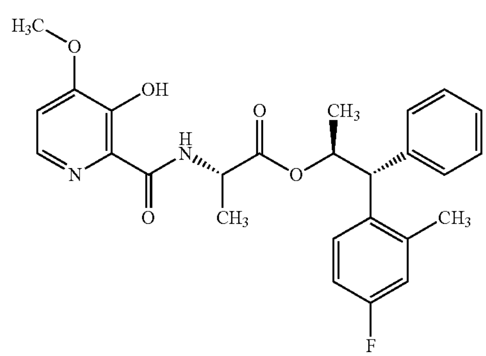 [SMILES: COc1ccnc(C(=O)N[C@@H](C)C(=O)O[C@@H](C)[C@H](c2ccccc2)c2ccc(F)cc2C)c1O] | Example 5, Step 2 | Colorless Gel |
| 434 | 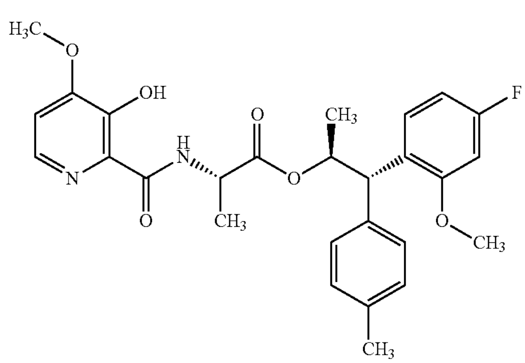 [SMILES: COc1cc(F)ccc1[C@H](c1ccc(C)cc1)[C@H](C)OC(=O)[C@H](C)NC(=O)c1nccc(OC)c1O] | Example 5, Step 2 | Colorless Oil |

TABLE 1-continued

Compound Structure, Preparation Method, and Appearance

| *Cmpd. No. | Structure | Prepared According To Example | Appearance |
|---|---|---|---|
| 435 | 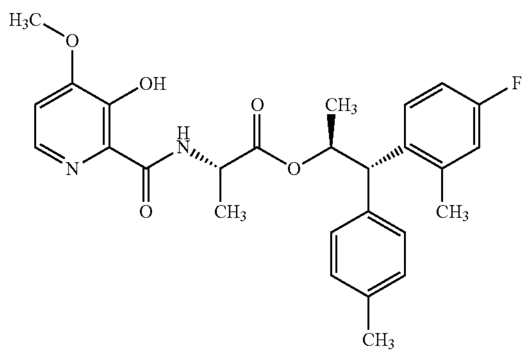 [SMILES: COc1ccnc(C(=O)N[C@@H](C)C(=O)O[C@@H](C)[C@@H](c2ccc(C)cc2)c2ccc(F)cc2C)c1O] | Example 5, Step 2 | Colorless Oil |
| 436 | 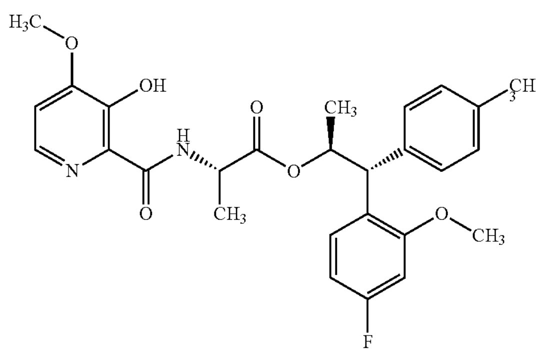 [SMILES: COc1cc(F)ccc1[C@@H](c1ccc(C)cc1)[C@H](C)OC(=O)[C@H](C)NC(=O)c1nccc(OC)c1O] | Example 5, Step 2 | Colorless Oil |
| 437 | 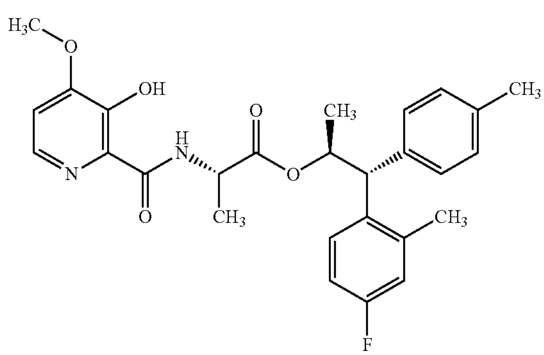 [SMILES: COc1ccnc(C(=O)N[C@@H](C)C(=O)O[C@@H](C)[C@H](c2ccc(C)cc2)c2ccc(F)cc2C)c1O] | Example 5, Step 2 | Colorless Oil |
| 438 | 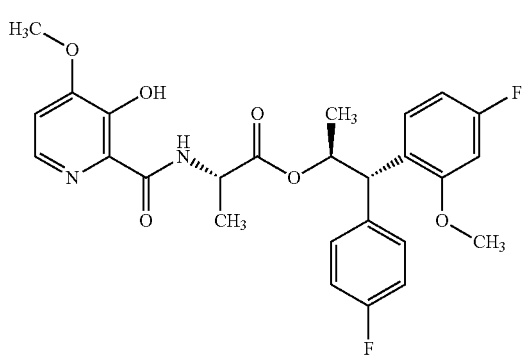 [SMILES: COc1cc(F)ccc1[C@H](c1ccc(F)cc1)[C@H](C)OC(=O)[C@H](C)NC(=O)c1nccc(OC)c1O] | Example 5, Step 2 | Colorless Foam |

TABLE 1-continued

Compound Structure, Preparation Method, and Appearance

| *Cmpd. No. | Structure | Prepared According To Example | Appearance |
| --- | --- | --- | --- |
| 439 | 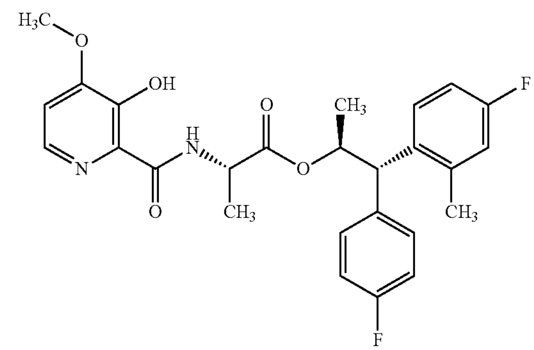 [SMILES: COc1ccnc(C(=O)N[C@@H](C)C(=O)O[C@@H](C)[C@@H](c2ccc(F)cc2)c2ccc(F)cc2C)c1O] | Example 5, Step 2 | Colorless Foam |
| 440 | 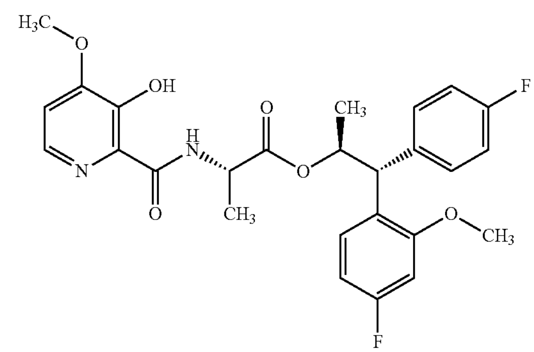 [SMILES: COc1cc(F)ccc1[C@@H](c1ccc(F)cc1)[C@H](C)OC(=O)[C@H](C)NC(=O)c1nccc(OC)c1O] | Example 5, Step 2 | Colorless Oil |
| 441 | 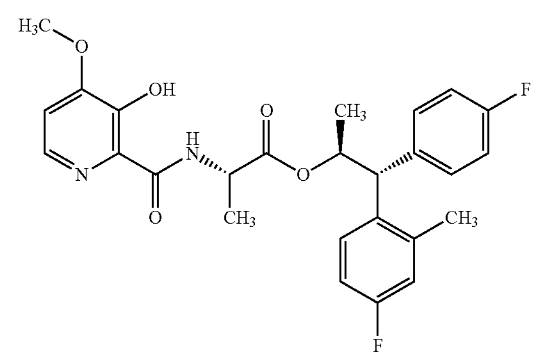 [SMILES: COc1ccnc(C(=O)N[C@@H](C)C(=O)O[C@@H](C)[C@H](c2ccc(F)cc2)c2ccc(F)cc2C)c1O] | Example 5, Step 2 | Colorless Oil |
| 442 | 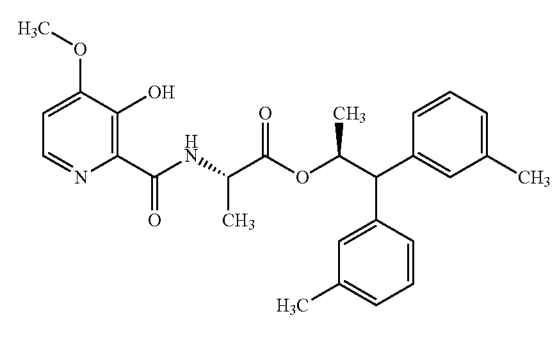 [SMILES: COc1ccnc(C(=O)N[C@@H](C)C(=O)O[C@@H](C)C(c2cccc(C)c2)c2cccc(C)c2)c1O] | Example 5, Step 2 | White Foam |

TABLE 1-continued

Compound Structure, Preparation Method, and Appearance

| *Cmpd. No. | Structure | Prepared According To Example | Appearance |
|---|---|---|---|
| 443 | 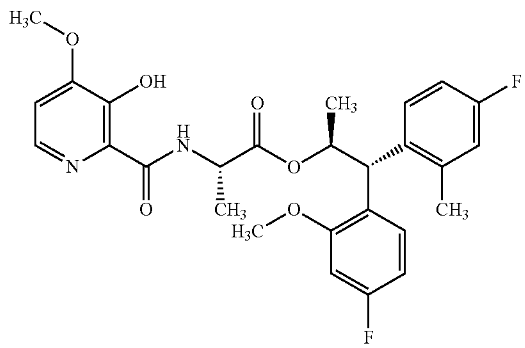 [SMILES: COc1cc(F)ccc1[C@@H](c1ccc(F)cc1C)[C@H](C)OC(=O)[C@H](C)NC(=O)c1nccc(OC)c1O] | Example 5, Step 2. | White Foam |
| 444 | 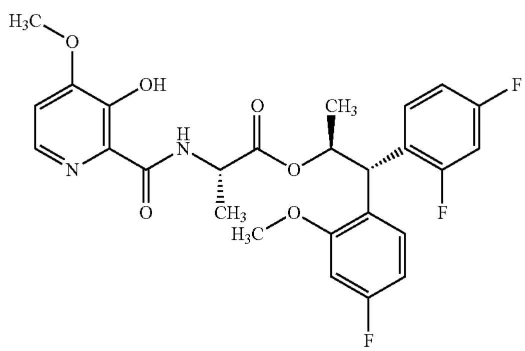 [SMILES: COc1cc(F)ccc1[C@@H](c1ccc(F)cc1F)[C@H](C)OC(=O)[C@H](C)NC(=O)c1nccc(OC)c1O] | Example 5, Step 2. | White Foam |
| 445 | 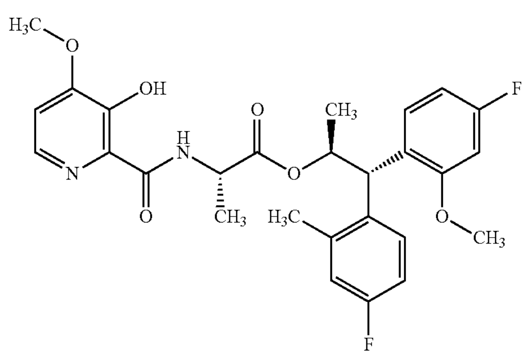 [SMILES: COc1cc(F)ccc1[C@H](c1ccc(F)cc1C)[C@H](C)OC(=O)[C@H](C)NC(=O)c1nccc(OC)c1O] | Example 5, Step 2. | White Foam |
| 446 | 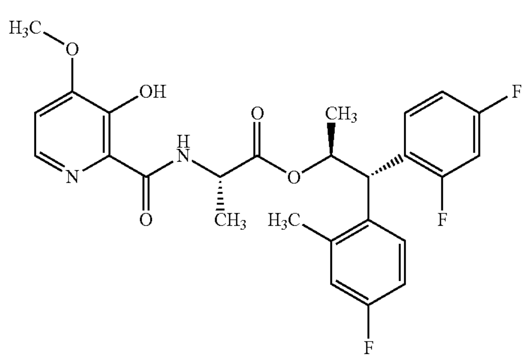 [SMILES: COc1ccnc(C(=O)N[C@@H](C)C(=O)O[C@@H](C)[C@@H](c2ccc(F)cc2C)c2ccc(F)cc2F)c1O] | Example 5, Step 2. | White Foam |

TABLE 1-continued

Compound Structure, Preparation Method, and Appearance

| *Cmpd. No. | Structure | Prepared According To Example | Appearance |
|---|---|---|---|
| 447 | 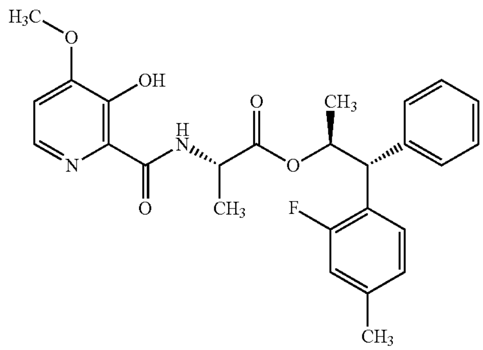 [SMILES: COc1ccnc(C(=O)N[C@@H](C)C(=O)O[C@@H](C)[C@H](c2ccccc2)c2ccc(C)cc2F)c1O] | Example 5, Step 2 | White Foam |
| 448 | 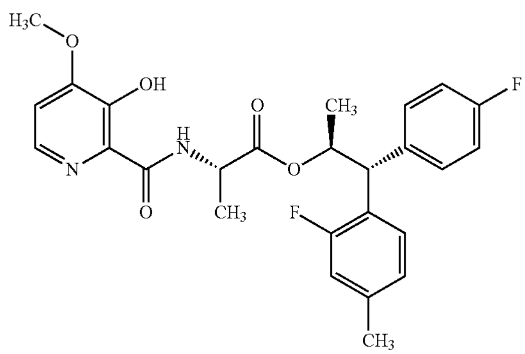 [SMILES: COc1ccnc(C(=O)N[C@@H](C)C(=O)O[C@@H](C)[C@H](c2ccc(F)cc2)c2ccc(C)cc2F)c1O] | Example 5, Step 2 | White Foam |
| 449 | 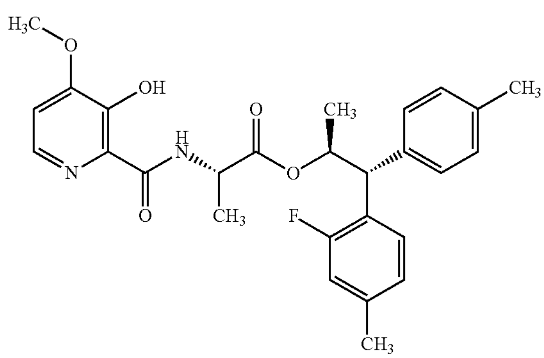 [SMILES: COc1ccnc(C(=O)N[C@@H](C)C(=O)O[C@@H](C)[C@H](c2ccc(C)cc2)c2ccc(C)cc2F)c1O] | Example 5, Step 2 | White Foam |
| 450 | 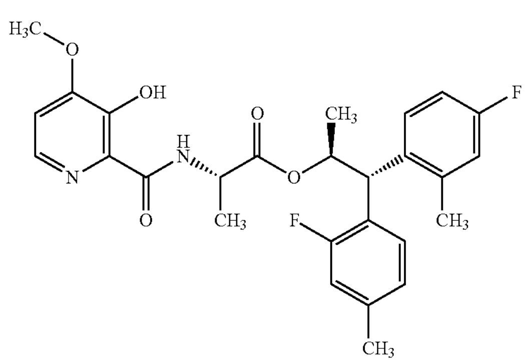 [SMILES: COc1ccnc(C(=O)N[C@@H](C)C(=O)O[C@@H](C)[C@H](c2ccc(F)cc2C)c2ccc(C)cc2F)c1O] | Example 5, Step 2 | White Foam |

TABLE 1-continued
Compound Structure, Preparation Method, and Appearance
| *Cmpd. No. | Structure | Prepared According To Example | Appearance |
|---|---|---|---|
| 451 | 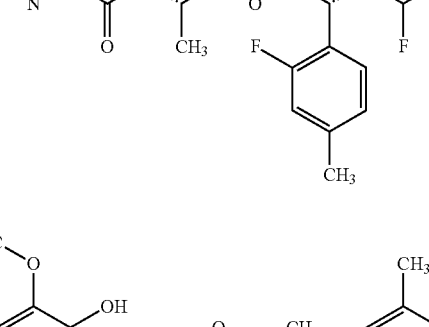 | Example 5, Step 2 | White Foam |
| 452 | 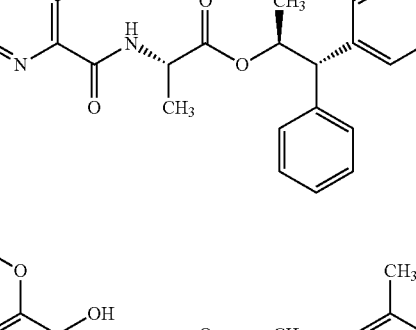 | Example 5, Step 2 | Colorless Oil |
| 453 | 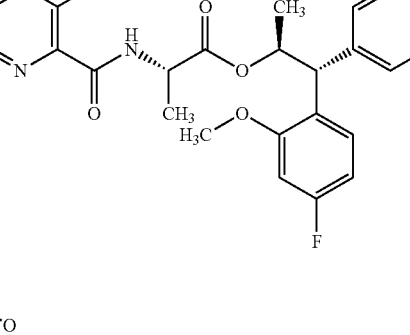 | Example 5, Step 2 | Colorless Oil |
| 454 | 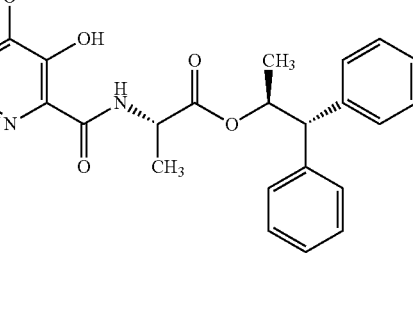 | Example 5, Step 2. | White Foam |

TABLE 1-continued

Compound Structure, Preparation Method, and Appearance

| *Cmpd. No. | Structure | Prepared According To Example | Appearance |
|---|---|---|---|
| 455 | 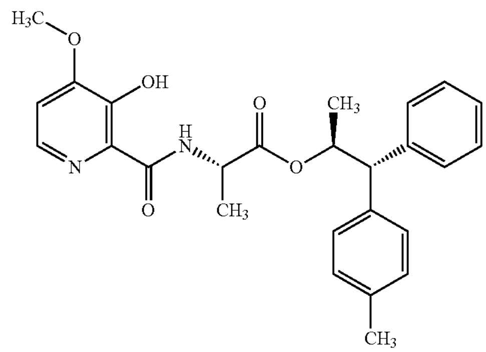 [SMILES: COc1ccnc(C(=O)N[C@@H](C)C(=O)O[C@@H](C)[C@H](c2ccccc2)c2ccc(C)cc2)c1O] | Example 5, Step 2. | White Foam |
| 456 | 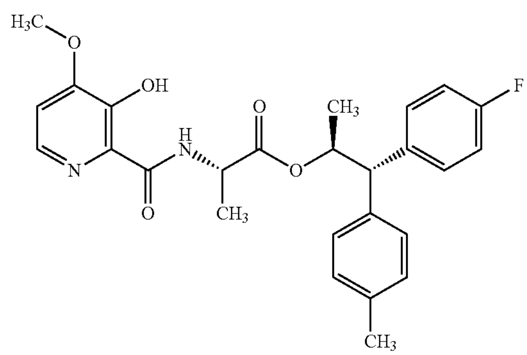 [SMILES: COc1ccnc(C(=O)N[C@@H](C)C(=O)O[C@@H](C)[C@@H](c2ccc(C)cc2)c2ccc(F)cc2)c1O] | Example 5, Step 2. | White Foam |
| 457 | 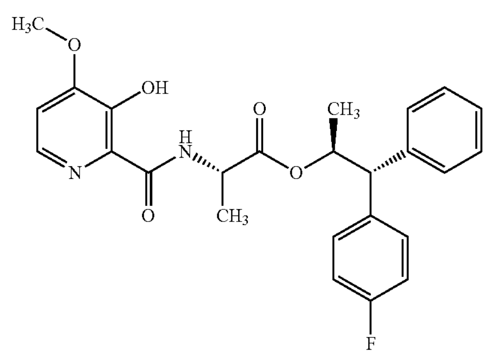 [SMILES: COc1ccnc(C(=O)N[C@@H](C)C(=O)O[C@@H](C)[C@H](c2ccccc2)c2ccc(F)cc2)c1O] | Example 5, Step 2. | White Foam |
| 458 | 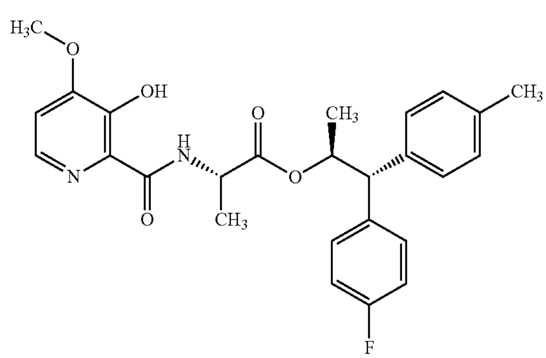 [SMILES: COc1ccnc(C(=O)N[C@@H](C)C(=O)O[C@@H](C)[C@H](c2ccc(C)cc2)c2ccc(F)cc2)c1O] | Example 5, Step 2. | White Foam |

TABLE 1-continued

Compound Structure, Preparation Method, and Appearance

| *Cmpd. No. | Structure | Prepared According To Example | Appearance |
|---|---|---|---|
| 459 | 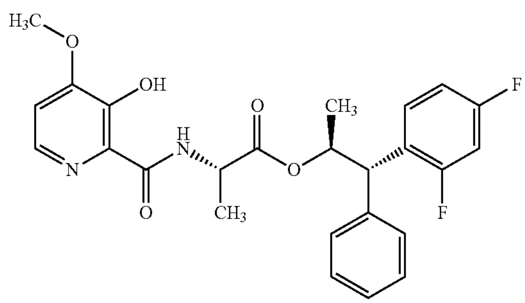 [SMILES: COc1ccnc(C(=O)N[C@@H](C)C(=O)O[C@@H](C)[C@@H](c2ccccc2)c2ccc(F)cc2F)c1O] | Example 5, Step 2. | White Foam |
| 460 | 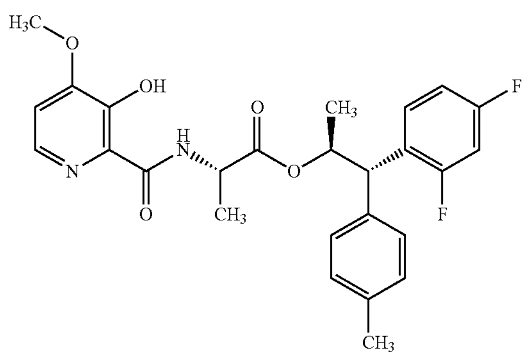 [SMILES: COc1ccnc(C(=O)N[C@@H](C)C(=O)O[C@@H](C)[C@@H](c2ccc(C)cc2)c2ccc(F)cc2F)c1O] | Example 5, Step 2. | White Foam |
| 461 | 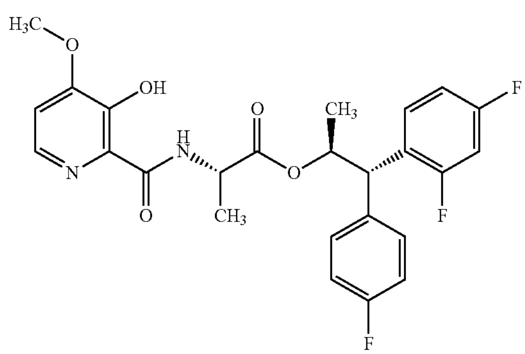 [SMILES: COc1ccnc(C(=O)N[C@@H](C)C(=O)O[C@@H](C)[C@@H](c2ccc(F)cc2)c2ccc(F)cc2F)c1O] | Example 5, Step 2. | White Foam |
| 462 | 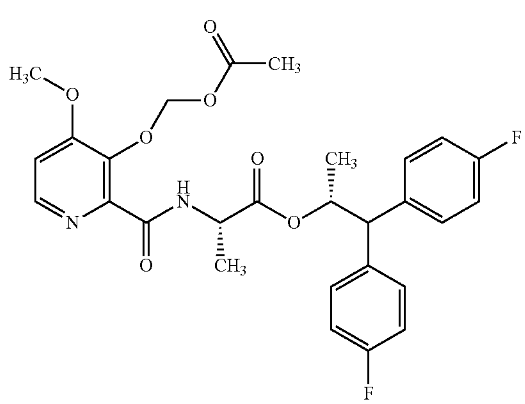 [SMILES: COc1ccnc(C(=O)N[C@@H](C)C(=O)O[C@H](C)C(c2ccc(F)cc2)c2ccc(F)cc2)c1OCOC(C)=O] | Example 6B. | Slightly Opaque Colorless Viscous Oil |

TABLE 1-continued

Compound Structure, Preparation Method, and Appearance

| *Cmpd. No. | Structure | Prepared According To Example | Appearance |
|---|---|---|---|
| 463 | 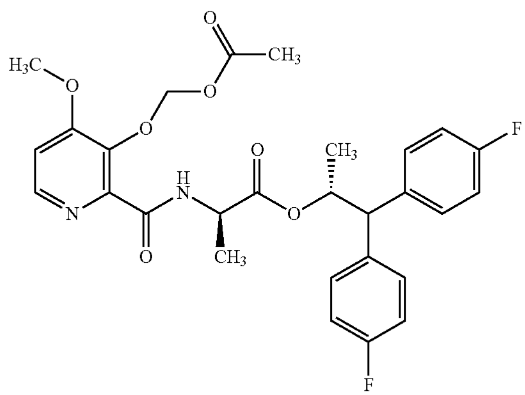 [SMILES: COc1ccnc(C(=O)N[C@H](C)C(=O)O[C@H](C)C(c2ccc(F)cc2)c2ccc(F)cc2)c1OCOC(C)=O] | Example 6B. | Slightly Opaque Colorless Viscous Oil |
| 464 | 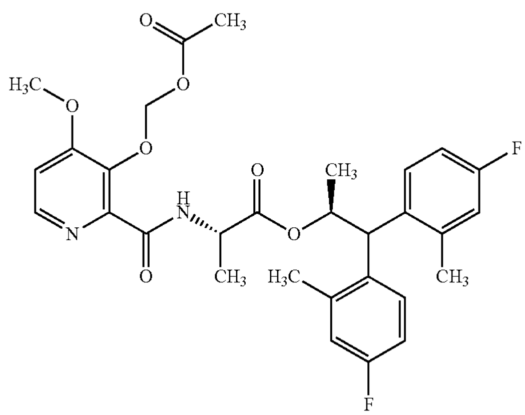 [SMILES: COc1ccnc(C(=O)N[C@@H](C)C(=O)O[C@@H](C)C(c2ccc(F)cc2C)c2ccc(F)cc2C)c1OCOC(C)=O] | Example 6B. | Yellow Oil |
| 465 | 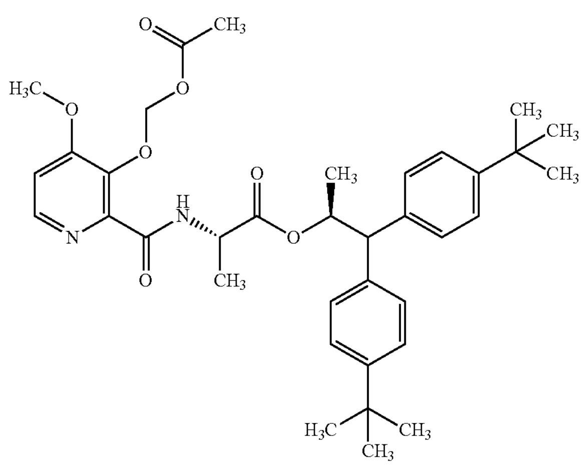 [SMILES: COc1ccnc(C(=O)N[C@@H](C)C(=O)O[C@@H](C)C(c2ccc(C(C)(C)C)cc2)c2ccc(C(C)(C)C)cc2)c1OCOC(C)=O] | Example 6B. | Clear, Colorless Oil |

TABLE 1-continued

Compound Structure, Preparation Method, and Appearance

| *Cmpd. No. | Structure | Prepared According To Example | Appearance |
|---|---|---|---|
| 466 | 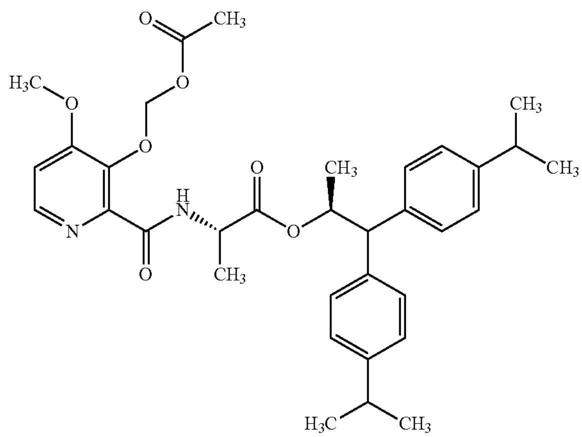 [SMILES: COc1ccnc(C(=O)N[C@@H](C)C(=O)O[C@@H](C)C(c2ccc(C(C)C)cc2)c2ccc(C(C)C)cc2)c1OCOC(C)=O] | Example 6B. | Pale Yellow Oil |
| 467 | 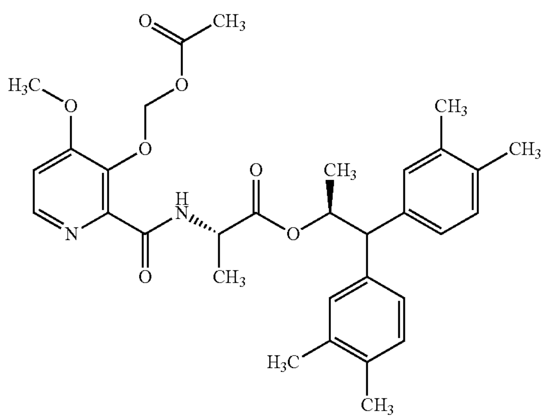 [SMILES: COc1ccnc(C(=O)N[C@@H](C)C(=O)O[C@@H](C)C(c2ccc(C)c(C)c2)c2ccc(C)c(C)c2)c1OCOC(C)=O] | Example 6B. | Pale Yellow Oil |
| 468 | 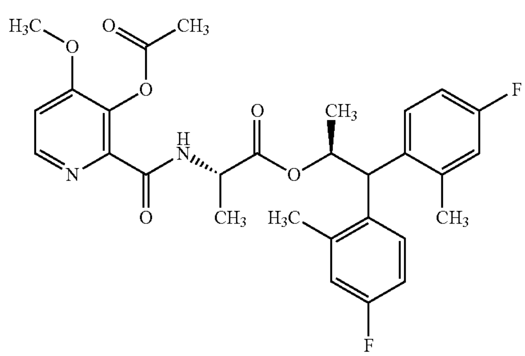 [SMILES: COc1ccnc(C(=O)N[C@@H](C)C(=O)O[C@@H](C)C(c2ccc(F)cc2C)c2ccc(F)cc2C)c1OC(C)=O] | Example 6A. | Fluffy White Powder |

TABLE 1-continued

Compound Structure, Preparation Method, and Appearance

| *Cmpd. No. | Structure | Prepared According To Example | Appearance |
| --- | --- | --- | --- |
| 469 | 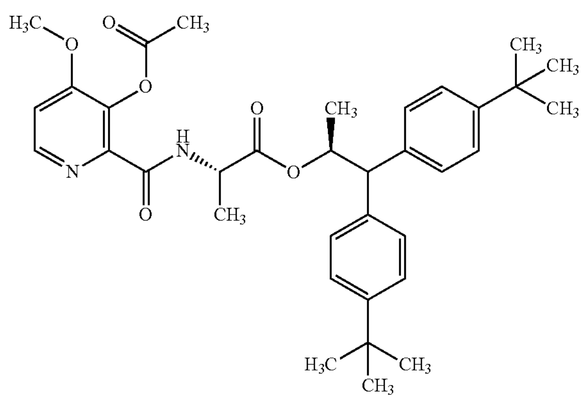 [SMILES: COc1ccnc(C(=O)N[C@@H](C)C(=O)O[C@@H](C)C(c2ccc(C(C)(C)C)cc2)c2ccc(C(C)(C)C)cc2)c1OC(C)=O] | Example 6A. | Clear, Colorless Oil |
| 470 | 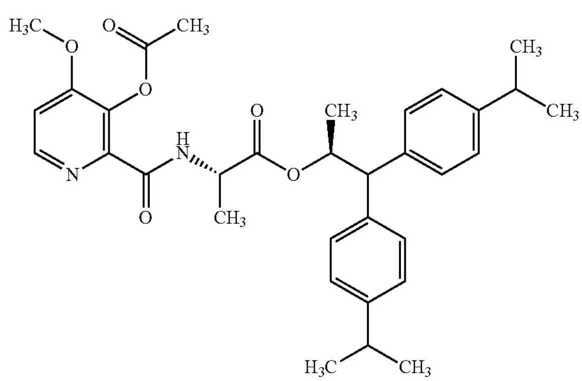 [SMILES: COc1ccnc(C(=O)N[C@@H](C)C(=O)O[C@@H](C)C(c2ccc(C(C)C)cc2)c2ccc(C(C)C)cc2)c1OC(C)=O] | Example 6A. | Clear, Colorless Oil |
| 471 | 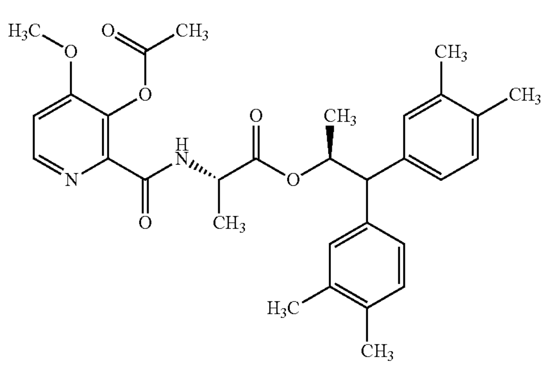 [SMILES: COc1ccnc(C(=O)N[C@@H](C)C(=O)O[C@@H](C)C(c2ccc(C)c(C)c2)c2ccc(C)c(C)c2)c1OC(C)=O] | Example 6A. | Clear, Colorless Oil |

TABLE 1-continued

Compound Structure, Preparation Method, and Appearance

| *Cmpd. No. | Structure | Prepared According To Example | Appearance |
|---|---|---|---|
| 472 | 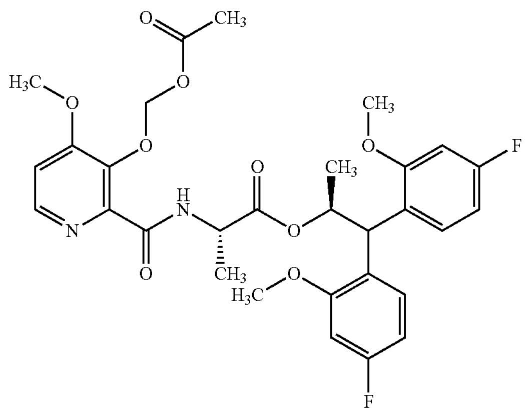 [SMILES: COc1cc(F)ccc1C(c1ccc(F)cc1OC)[C@H](C)OC(=O)[C@H](C)NC(=O)c1nccc(OC)c1OCOC(C)=O] | Example 6B. | White Foam |
| 473 | 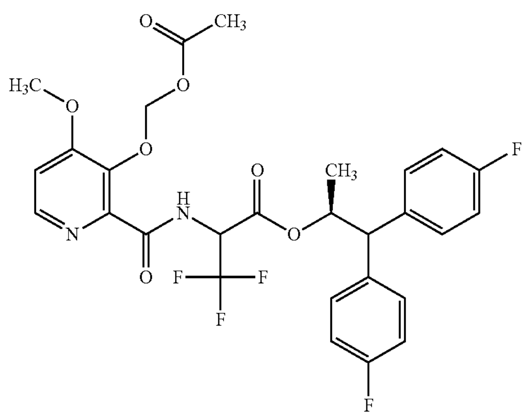 [SMILES: COc1ccnc(C(=O)NC(C(=O)O[C@@H](C)C(c2ccc(F)cc2)c2ccc(F)cc2)C(F)(F)F)c1OCOC(C)=O] | Example 6B. | Sticky Wax |
| 474 | 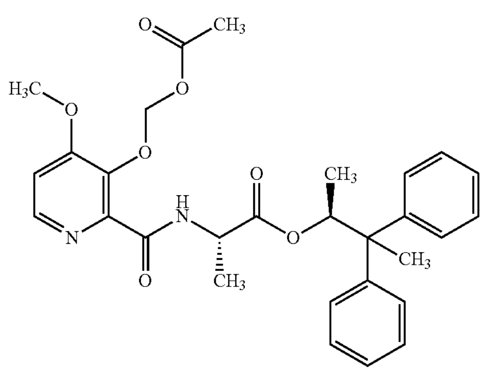 [SMILES: COc1ccnc(C(=O)N[C@@H](C)C(=O)O[C@@H](C)C(C)(c2ccccc2)c2ccccc2)c1OCOC(C)=O] | Example 6B. | Colorless Oil |

TABLE 1-continued

Compound Structure, Preparation Method, and Appearance

| *Cmpd. No. | Structure | Prepared According To Example | Appearance |
|---|---|---|---|
| 475 | 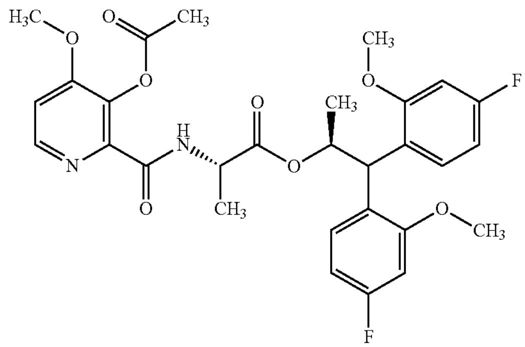 [SMILES: COc1cc(F)ccc1C(c1ccc(F)cc1OC)[C@H](C)OC(=O)[C@H](C)NC(=O)c1nccc(OC)c1OC(C)=O] | Example 6A. | White Foam |
| 476 | 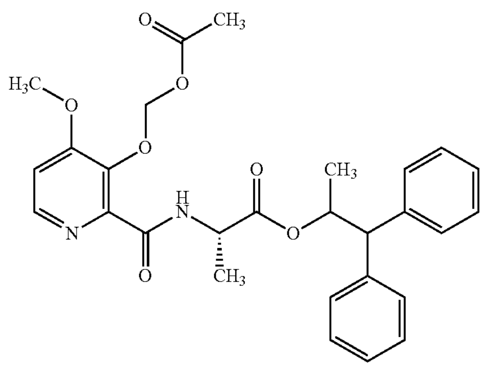 [SMILES: COc1ccnc(C(=O)N[C@@H](C)C(=O)OC(C)C(c2ccccc2)c2ccccc2)c1OCOC(C)=O] | Example 6B. | White Foam |
| 477 | 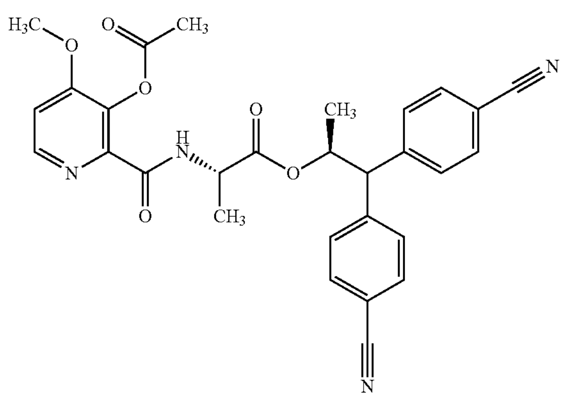 [SMILES: COc1ccnc(C(=O)N[C@@H](C)C(=O)O[C@@H](C)C(c2ccc(C#N)cc2)c2ccc(C#N)cc2)c1OC(C)=O] | Example 6A. | White Foam |
| 478 | 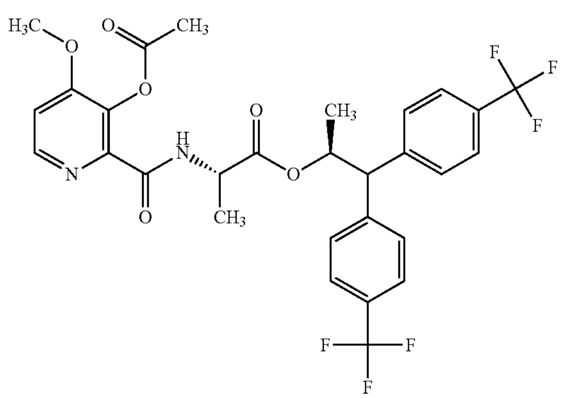 [SMILES: COc1ccnc(C(=O)N[C@@H](C)C(=O)O[C@@H](C)C(c2ccc(C(F)(F)F)cc2)c2ccc(C(F)(F)F)cc2)c1OC(C)=O] | Example 6A. | White Foam |

TABLE 1-continued

Compound Structure, Preparation Method, and Appearance

| *Cmpd. No. | Structure | Prepared According To Example | Appearance |
|---|---|---|---|
| 479 | 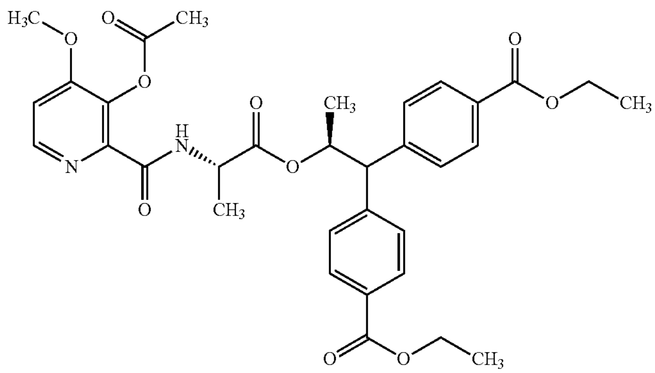 [SMILES: CCOC(=O)c1ccc(C(c2ccc(C(=O)OCC)cc2)[C@H](C)OC(=O)[C@H](C)NC(=O)c2nccc(OC)c2OC(C)=O)cc1] | Example 6A. | White Foam |
| 480 | 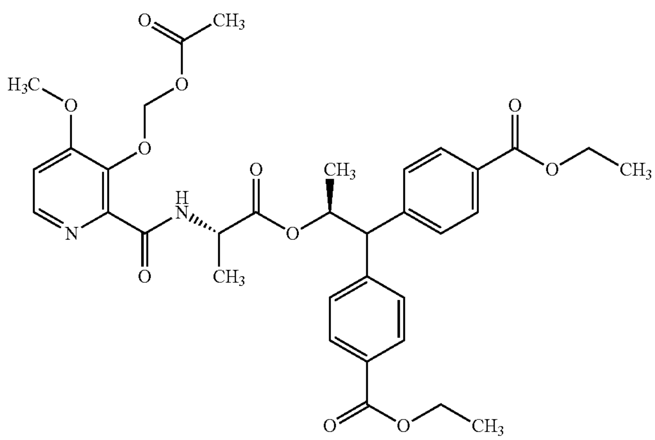 [SMILES: CCOC(=O)c1ccc(C(c2ccc(C(=O)OCC)cc2)[C@H](C)OC(=O)[C@H](C)NC(=O)c2nccc(OC)c2OCOC(C)=O)cc1] | Example 6B. | White Foam |
| 481 | 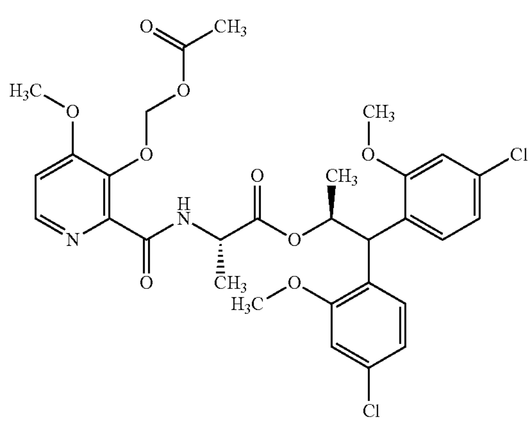 [SMILES: COc1cc(Cl)ccc1C(c1ccc(Cl)cc1OC)[C@H](C)OC(=O)[C@H](C)NC(=O)c1nccc(OC)c1OCOC(C)=O] | Example 6B. | White Foam |

TABLE 1-continued

Compound Structure, Preparation Method, and Appearance

| *Cmpd. No. | Structure | Prepared According To Example | Appearance |
|---|---|---|---|
| 482 | 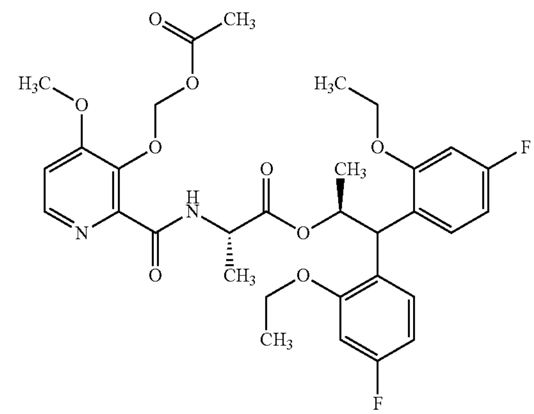 [SMILES: CCOc1cc(F)ccc1C(c1ccc(F)cc1OCC)[C@H](C)OC(=O)[C@H](C)NC(=O)c1nccc(OC)c1OCOC(C)=O] | Example 6B. | White Foam |
| 483 | 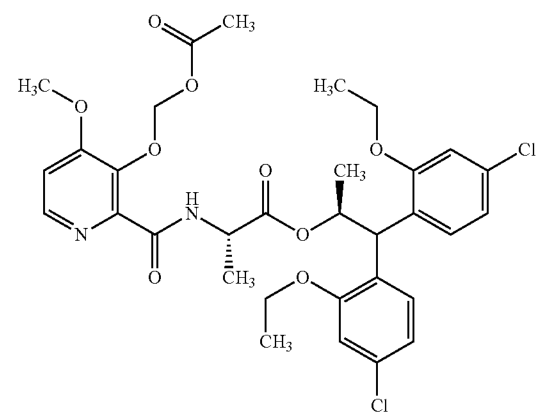 [SMILES: CCOc1cc(Cl)ccc1C(c1ccc(Cl)cc1OCC)[C@H](C)OC(=O)[C@H](C)NC(=O)c1nccc(OC)c1OCOC(C)=O] | Example 6B. | White Foam |
| 484 | 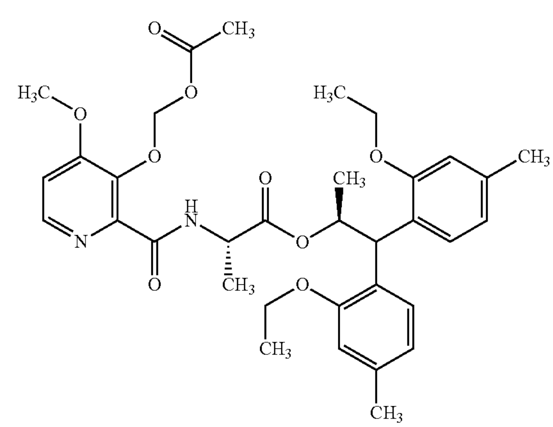 [SMILES: CCOc1cc(C)ccc1C(c1ccc(C)cc1OCC)[C@H](C)OC(=O)[C@H](C)NC(=O)c1nccc(OC)c1OCOC(C)=O] | Example 6B. | White Foam |

TABLE 1-continued

Compound Structure, Preparation Method, and Appearance

| *Cmpd. No. | Structure | Prepared According To Example | Appearance |
|---|---|---|---|
| 485 | 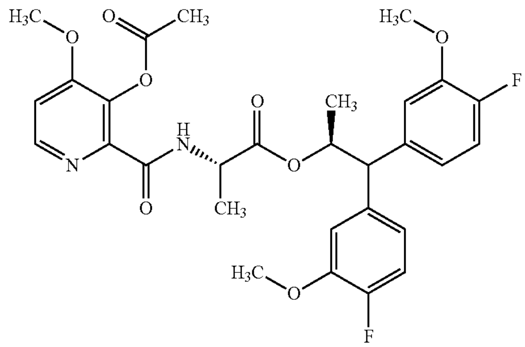 [SMILES: COc1cc(C(c2ccc(F)c(OC)c2)[C@H](C)OC(=O)[C@H](C)NC(=O)c2nccc(OC)c2OC(C)=O)ccc1F] | Example 6A | Colorless Oil |
| 486 | 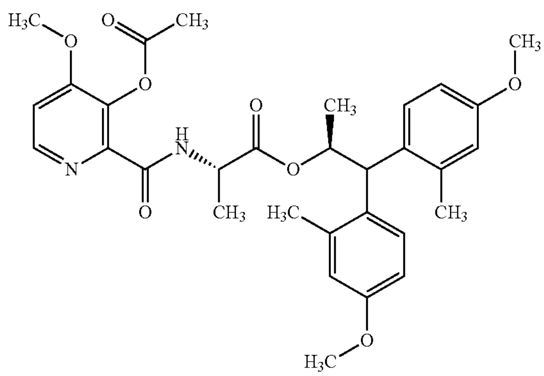 [SMILES: COc1ccc(C(c2ccc(OC)cc2C)[C@H](C)OC(=O)[C@H](C)NC(=O)c2nccc(OC)c2OC(C)=O)c(C)c1] | Example 6A | Colorless Oil |
| 487 | 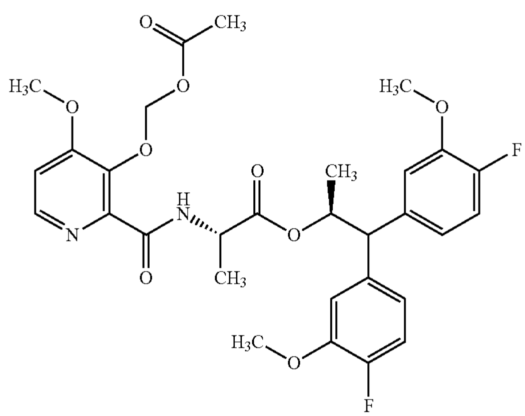 [SMILES: COc1cc(C(c2ccc(F)c(OC)c2)[C@H](C)OC(=O)[C@H](C)NC(=O)c2nccc(OC)c2OCOC(C)=O)ccc1F] | Example 6B | Colorless Oil |
| 488 | 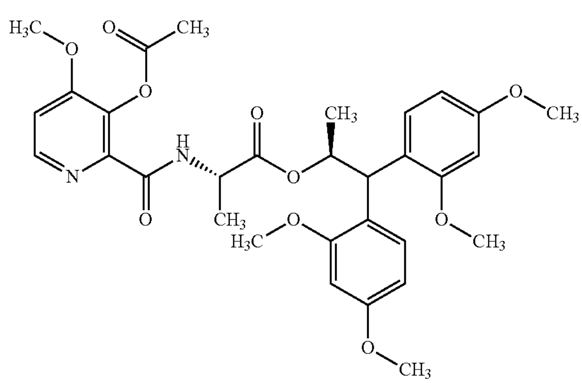 [SMILES: COc1ccc(C(c2ccc(OC)cc2OC)[C@H](C)OC(=O)[C@H](C)NC(=O)c2nccc(OC)c2OC(C)=O)c(OC)c1] | Example 6A. | White Foam |

TABLE 1-continued

Compound Structure, Preparation Method, and Appearance

| *Cmpd. No. | Structure | Prepared According To Example | Appearance |
|---|---|---|---|
| 489 | 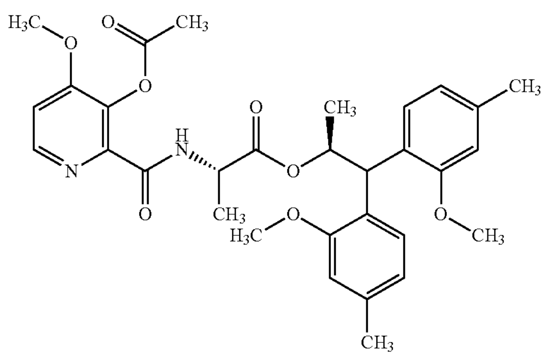 [SMILES: COc1cc(C)ccc1C(c1ccc(C)cc1OC)[C@H](C)OC(=O)[C@H](C)NC(=O)c1nccc(OC)c1OC(C)=O] | Example 6A. | White Foam |
| 490 | 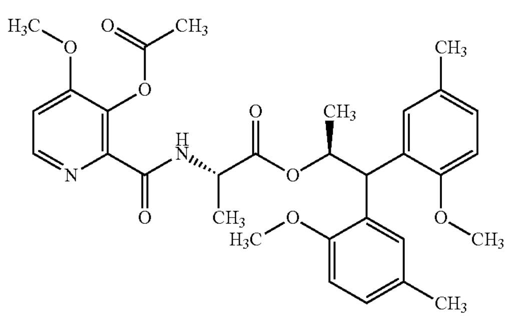 [SMILES: COc1ccc(C)cc1C(c1cc(C)ccc1OC)[C@H](C)OC(=O)[C@H](C)NC(=O)c1nccc(OC)c1OC(C)=O] | Example 6A. | White Wax |
| 491 | 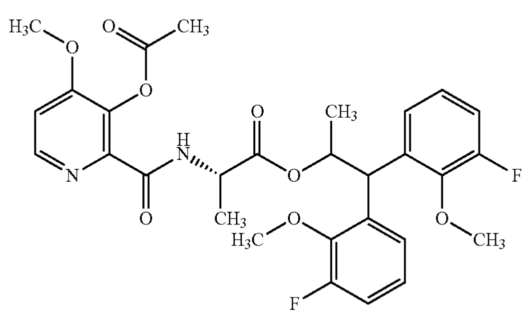 [SMILES: COc1ccnc(C(=O)N[C@@H](C)C(=O)OC(C)C(c2cccc(F)c2OC)c2cccc(F)c2OC)c1OC(C)=O] | Example 6A. | White Foam |
| 492 | 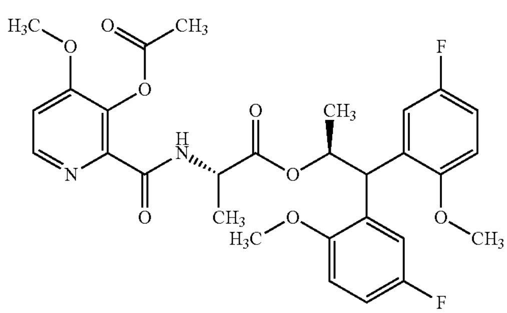 [SMILES: COc1ccc(F)cc1C(c1cc(F)ccc1OC)[C@H](C)OC(=O)[C@H](C)NC(=O)c1nccc(OC)c1OC(C)=O] | Example 6A. | White Foam |

TABLE 1-continued

Compound Structure, Preparation Method, and Appearance

| *Cmpd. No. | Structure | Prepared According To Example | Appearance |
|---|---|---|---|
| 493 | 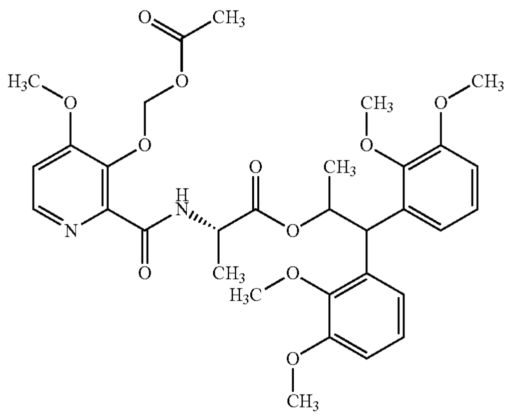 [SMILES: COc1cccc(C(c2cccc(OC)c2OC)C(C)OC(=O)[C@H](C)NC(=O)c2nccc(OC)c2OCOC(C)=O)c1OC] | Example 6B | White Foam |
| 494 | 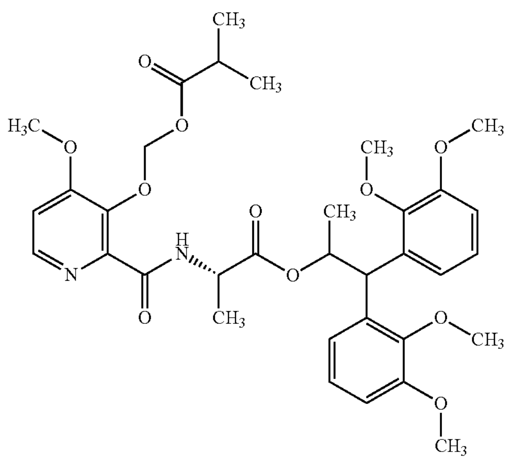 [SMILES: COc1cccc(C(c2cccc(OC)c2OC)C(C)OC(=O)[C@H](C)NC(=O)c2nccc(OC)c2OCOC(=O)C(C)C)c1OC] | Example 6C | White Foam |
| 495 | 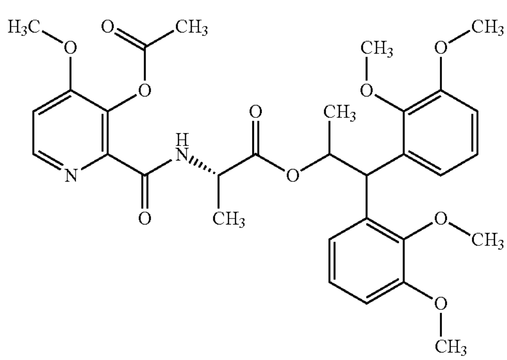 [SMILES: COc1cccc(C(c2cccc(OC)c2OC)C(C)OC(=O)[C@H](C)NC(=O)c2nccc(OC)c2OC(C)=O)c1OC] | Example 6A | White Foam |

TABLE 1-continued

Compound Structure, Preparation Method, and Appearance

| *Cmpd. No. | Structure | Prepared According To Example | Appearance |
|---|---|---|---|
| 496 | 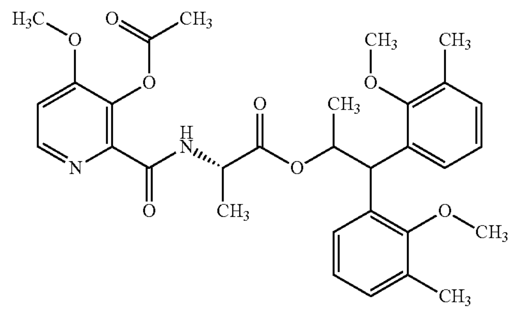 [SMILES: COc1ccnc(C(=O)N[C@@H](C)C(=O)OC(C)C(c2cccc(C)c2OC)c2cccc(C)c2OC)c1OC(C)=O] | Example 6A | White Foam |
| 497 | 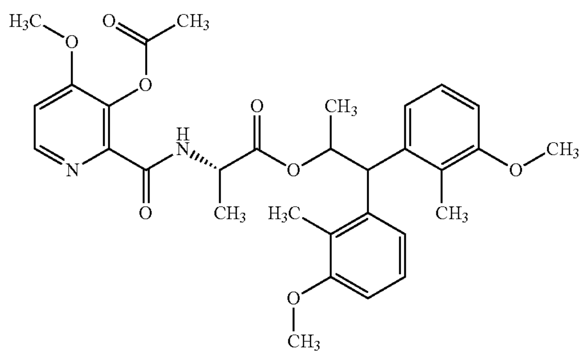 [SMILES: COc1cccc(C(c2cccc(OC)c2C)C(C)OC(=O)[C@H](C)NC(=O)c2nccc(OC)c2OC(C)=O)c1C] | Example 6A | Colorless Film |
| 498 | 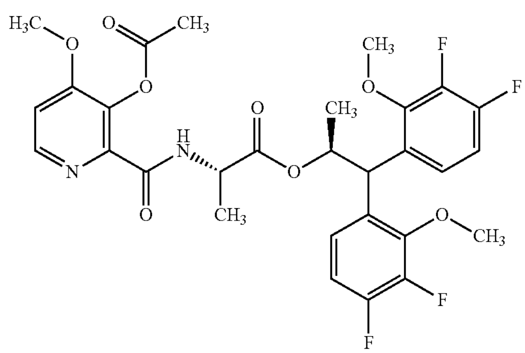 [SMILES: COc1ccnc(C(=O)N[C@@H](C)C(=O)O[C@@H](C)C(c2ccc(F)c(F)c2OC)c2ccc(F)c(F)c2OC)c1OC(C)=O] | Example 6A. | White Foam |
| 499 | 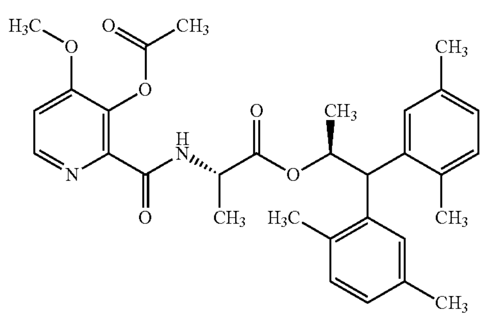 [SMILES: COc1ccnc(C(=O)N[C@@H](C)C(=O)O[C@@H](C)C(c2cc(C)ccc2C)c2cc(C)ccc2C)c1OC(C)=O] | Example 6A. | White Foam |

TABLE 1-continued

Compound Structure, Preparation Method, and Appearance

| *Cmpd. No. | Structure | Prepared According To Example | Appearance |
|---|---|---|---|
| 500 | 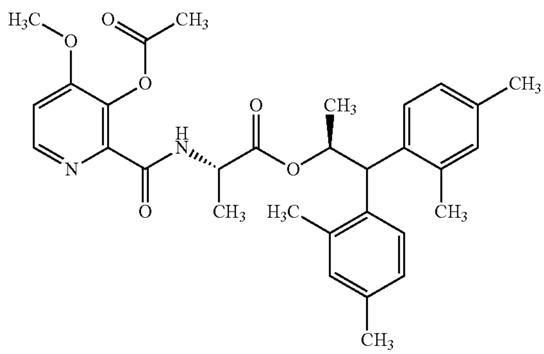 [SMILES: COc1ccnc(C(=O)N[C@@H](C)C(=O)O[C@@H](C)C(c2ccc(C)cc2C)c2ccc(C)cc2C)c1OC(C)=O] | Example 6A. | White Foam |
| 501 | 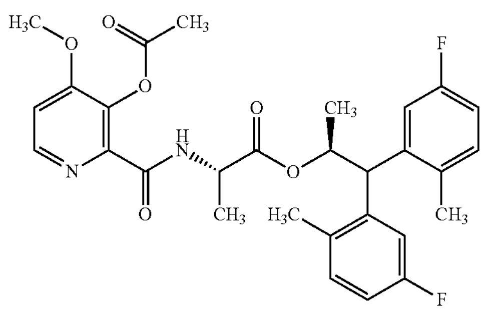 [SMILES: COc1ccnc(C(=O)N[C@@H](C)C(=O)O[C@@H](C)C(c2cc(F)ccc2C)c2cc(F)ccc2C)c1OC(C)=O] | Example 6A. | White Foam |
| 502 | 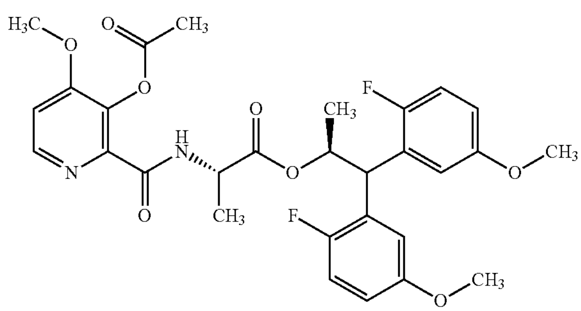 [SMILES: COc1ccc(F)c(C(c2cc(OC)ccc2F)[C@H](C)OC(=O)[C@H](C)NC(=O)c2nccc(OC)c2OC(C)=O)c1] | Example 6A. | White Foam |
| 503 | 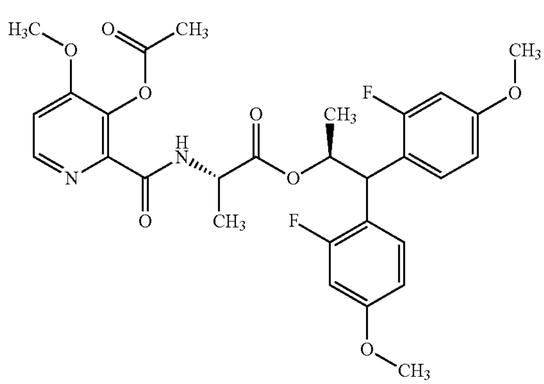 [SMILES: COc1ccc(C(c2ccc(OC)cc2F)[C@H](C)OC(=O)[C@H](C)NC(=O)c2nccc(OC)c2OC(C)=O)c(F)c1] | Example 6A. | White Foam |

TABLE 1-continued

Compound Structure, Preparation Method, and Appearance

| *Cmpd. No. | Structure | Prepared According To Example | Appearance |
|---|---|---|---|
| 504 | 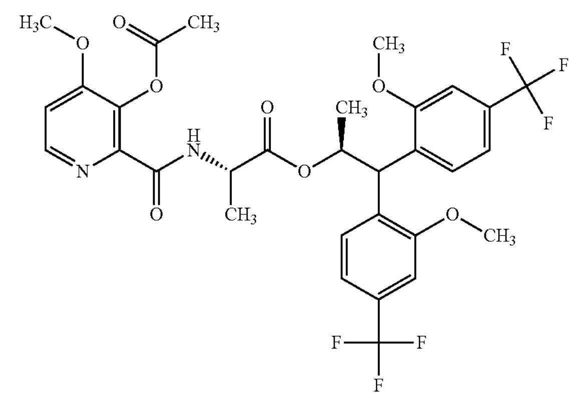 [SMILES: COc1cc(C(F)(F)F)ccc1C(c1ccc(C(F)(F)F)cc1OC)[C@H](C)OC(=O)[C@H](C)NC(=O)c1nccc(OC)c1OC(C)=O] | Example 6A. | White Foam |
| 505 | 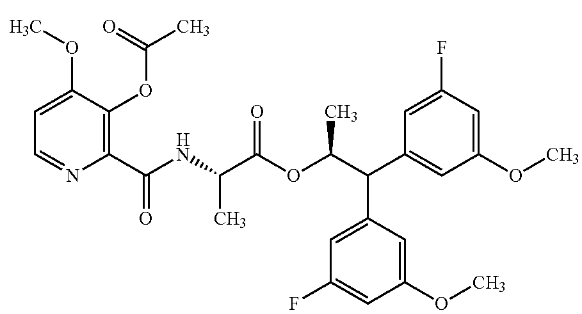 [SMILES: COc1cc(F)cc(C(c2cc(F)cc(OC)c2)[C@H](C)OC(=O)[C@H](C)NC(=O)c2nccc(OC)c2OC(C)=O)c1] | Example 6A. | Clear, Colorless Oil |
| 506 | 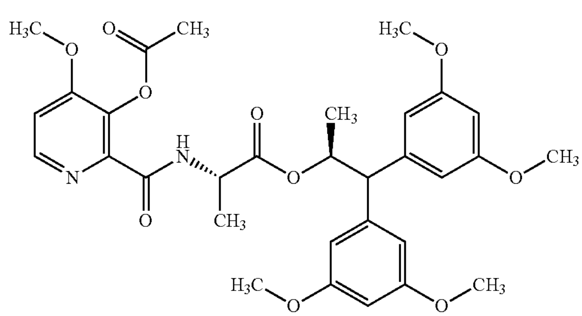 [SMILES: COc1cc(OC)cc(C(c2cc(OC)cc(OC)c2)[C@H](C)OC(=O)[C@H](C)NC(=O)c2nccc(OC)c2OC(C)=O)c1] | Example 6A. | Clear, Colorless Oil |
| 507 | 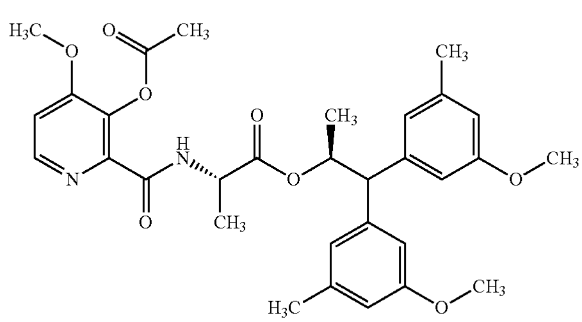 [SMILES: COc1cc(C)cc(C(c2cc(C)cc(OC)c2)[C@H](C)OC(=O)[C@H](C)NC(=O)c2nccc(OC)c2OC(C)=O)c1] | Example 6A. | Clear, Colorless Oil |

TABLE 1-continued

Compound Structure, Preparation Method, and Appearance

| *Cmpd. No. | Structure | Prepared According To Example | Appearance |
|---|---|---|---|
| 508 | 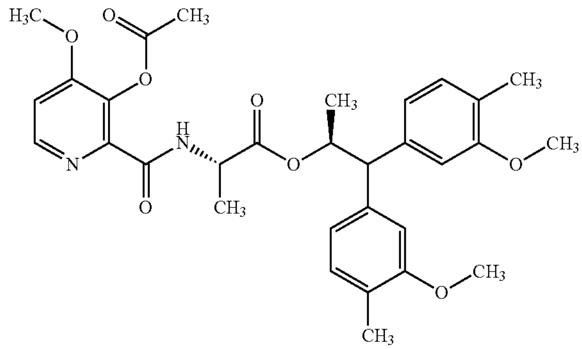 [SMILES: COc1cc(C(c2ccc(C)c(OC)c2)[C@H](C)OC(=O)[C@H](C)NC(=O)c2nccc(OC)c2OC(C)=O)ccc1C] | Example 6A. | Clear, Colorless Oil |
| 509 | 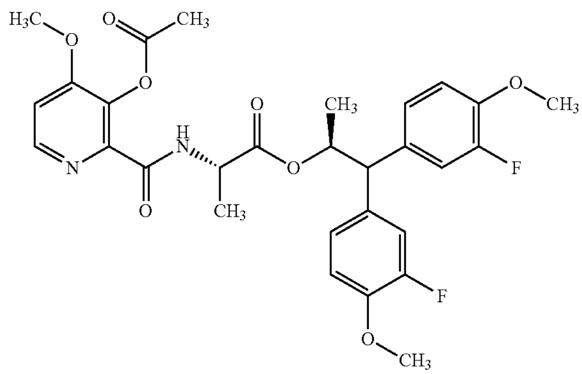 [SMILES: COc1ccc(C(c2ccc(OC)c(F)c2)[C@H](C)OC(=O)[C@H](C)NC(=O)c2nccc(OC)c2OC(C)=O)cc1F] | Example 6A. | Clear, Colorless Oil |
| 510 | 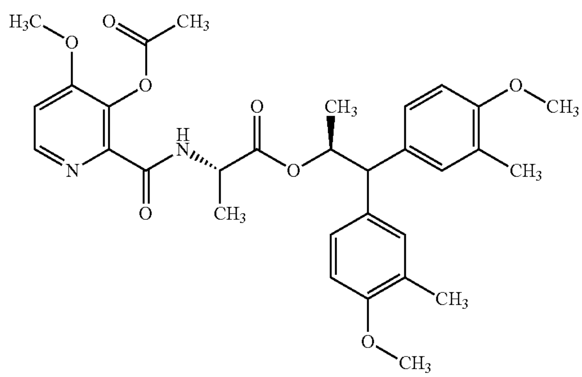 [SMILES: COc1ccc(C(c2ccc(OC)c(C)c2)[C@H](C)OC(=O)[C@H](C)NC(=O)c2nccc(OC)c2OC(C)=O)cc1C] | Example 6A. | Clear, Colorless Oil |
| 511 | 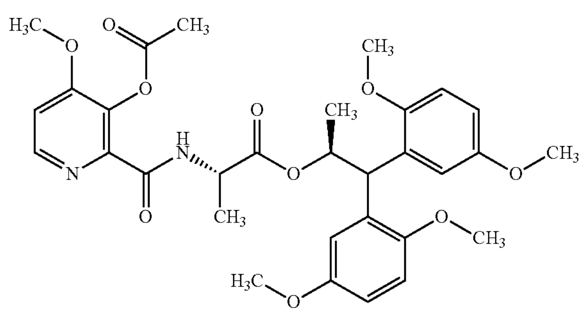 [SMILES: COc1ccc(OC)c(C(c2cc(OC)ccc2OC)[C@H](C)OC(=O)[C@H](C)NC(=O)c2nccc(OC)c2OC(C)=O)c1] | Example 6A. | Clear, Colorless Oil |

TABLE 1-continued

Compound Structure, Preparation Method, and Appearance

| *Cmpd. No. | Structure | Prepared According To Example | Appearance |
| --- | --- | --- | --- |
| 512 | 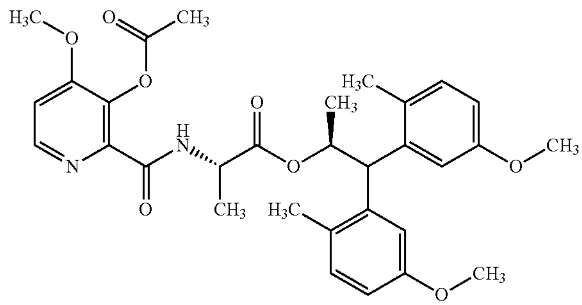 [SMILES: COc1ccc(C)c(C(c2cc(OC)ccc2C)[C@H](C)OC(=O)[C@H](C)NC(=O)c2nccc(OC)c2OC(C)=O)c1] | Example 6A. | Clear, Colorless Oil |
| 513 | 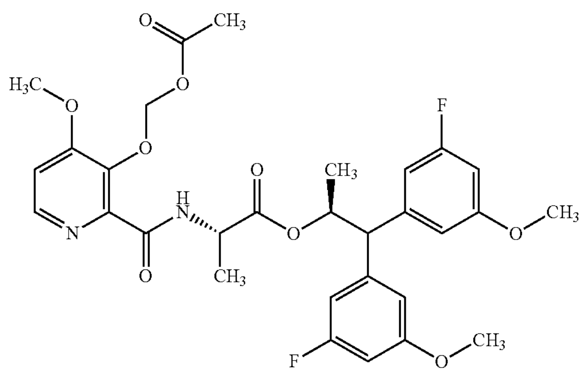 [SMILES: COc1cc(F)cc(C(c2cc(F)cc(OC)c2)[C@H](C)OC(=O)[C@H](C)NC(=O)c2nccc(OC)c2OCOC(C)=O)c1] | Example 6B. | Clear, Colorless Oil |
| 514 | 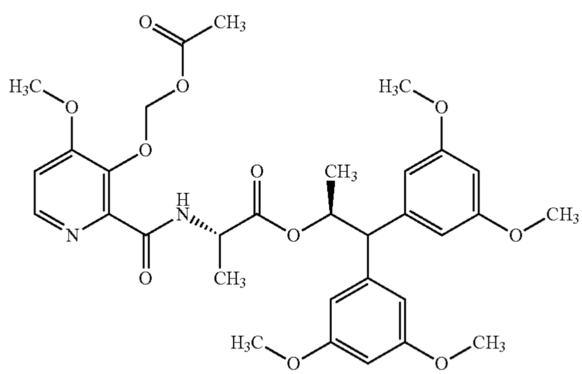 [SMILES: COc1cc(OC)cc(C(c2cc(OC)cc(OC)c2)[C@H](C)OC(=O)[C@H](C)NC(=O)c2nccc(OC)c2OCOC(C)=O)c1] | Example 6B. | Clear, Colorless Oil |
| 515 | 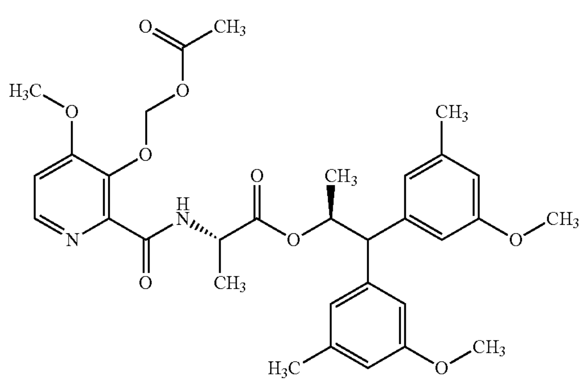 [SMILES: COc1cc(C)cc(C(c2cc(C)cc(OC)c2)[C@H](C)OC(=O)[C@H](C)NC(=O)c2nccc(OC)c2OCOC(C)=O)c1] | Example 6B. | Clear, Colorless Oil |

TABLE 1-continued
Compound Structure, Preparation Method, and Appearance
| *Cmpd. No. | Structure | Prepared According To Example | Appearance |
|---|---|---|---|
| 516 | 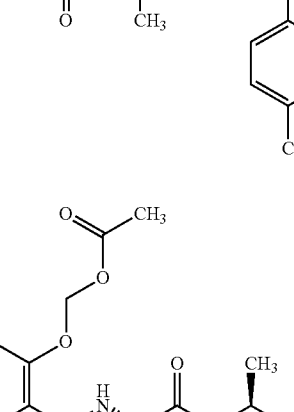 | Example 6B. | Clear, Colorless Oil |
| 517 | 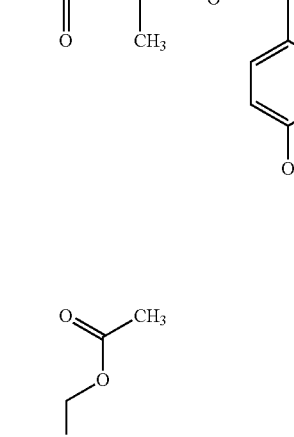 | Example 6B. | Clear, Colorless Oil |
| 518 | 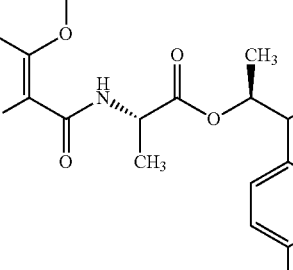 | Example 6B. | Clear, Colorless Oil |

TABLE 1-continued

Compound Structure, Preparation Method, and Appearance

| *Cmpd. No. | Structure | Prepared According To Example | Appearance |
| --- | --- | --- | --- |
| 519 | 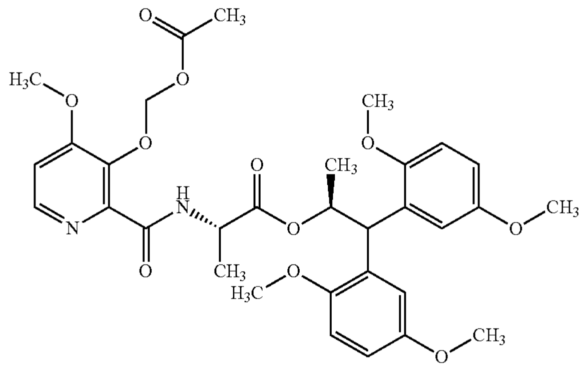 [SMILES: COc1ccc(OC)c(C(c2cc(OC)ccc2OC)[C@H](C)OC(=O)[C@H](C)NC(=O)c2nccc(OC)c2OCOC(C)=O)c1] | Example 6B. | Clear, Colorless Oil |
| 520 | 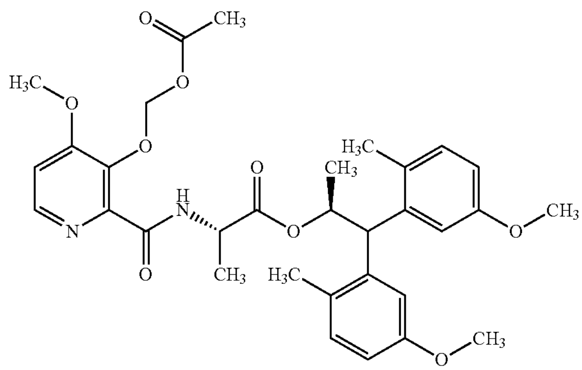 [SMILES: COc1ccc(C)c(C(c2cc(OC)ccc2C)[C@H](C)OC(=O)[C@H](C)NC(=O)c2nccc(OC)c2OCOC(C)=O)c1] | Example 6B. | Clear, Colorless Oil |
| 521 | 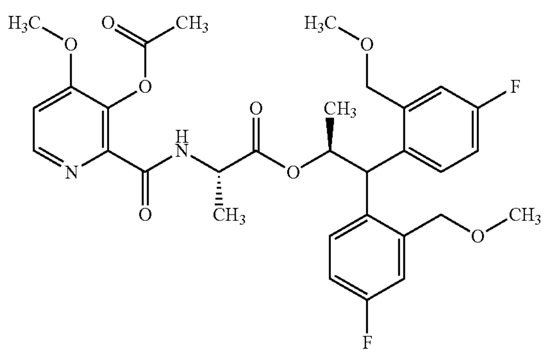 [SMILES: COCc1cc(F)ccc1C(c1ccc(F)cc1COC)[C@H](C)OC(=O)[C@H](C)NC(=O)c1nccc(OC)c1OC(C)=O] | Example 6A. | White Foam. |
| 522 | 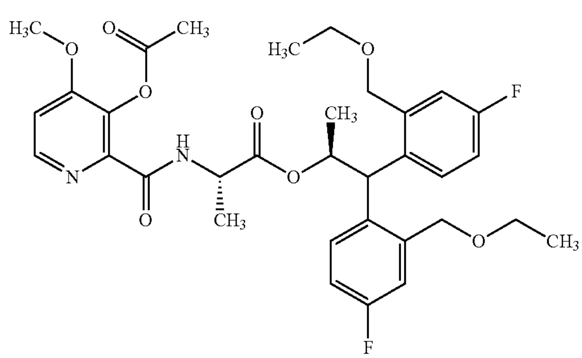 [SMILES: CCOCc1cc(F)ccc1C(c1ccc(F)cc1COCC)[C@H](C)OC(=O)[C@H](C)NC(=O)c1nccc(OC)c1OC(C)=O] | Example 6A. | Sticky White Foam |

TABLE 1-continued

Compound Structure, Preparation Method, and Appearance

| *Cmpd. No. | Structure | Prepared According To Example | Appearance |
|---|---|---|---|
| 523 | 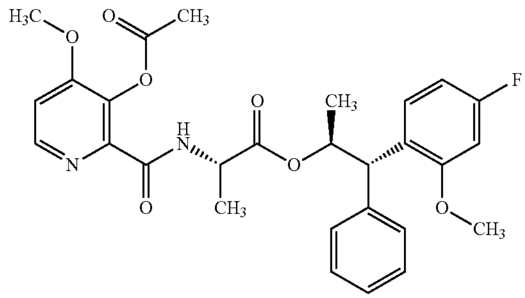 [SMILES: COc1cc(F)ccc1[C@H](c1ccccc1)[C@H](C)OC(=O)[C@H](C)NC(=O)c1nccc(OC)c1OC(C)=O] | Example 6A | Colorless Oil |
| 524 | 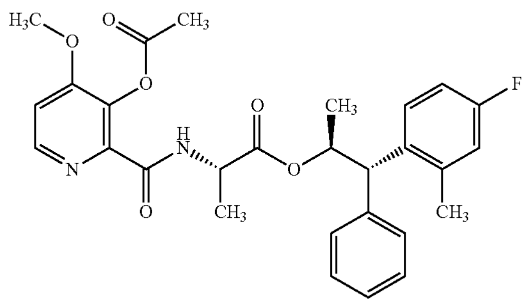 [SMILES: COc1ccnc(C(=O)N[C@@H](C)C(=O)O[C@@H](C)[C@@H](c2ccccc2)c2ccc(F)cc2C)c1OC(C)=O] | Example 6A | Colorless Oil |
| 525 | 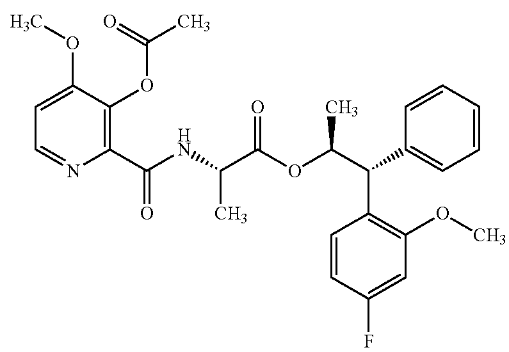 [SMILES: COc1cc(F)ccc1[C@@H](c1ccccc1)[C@H](C)OC(=O)[C@H](C)NC(=O)c1nccc(OC)c1OC(C)=O] | Example 6A | Colorless Oil |
| 526 | 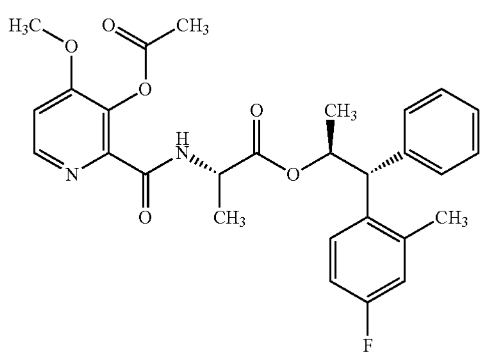 [SMILES: COc1ccnc(C(=O)N[C@@H](C)C(=O)O[C@@H](C)[C@H](c2ccccc2)c2ccc(F)cc2C)c1OC(C)=O] | Example 6A | Colorless Oil |

TABLE 1-continued

Compound Structure, Preparation Method, and Appearance

| *Cmpd. No. | Structure | Prepared According To Example | Appearance |
|---|---|---|---|
| 527 | 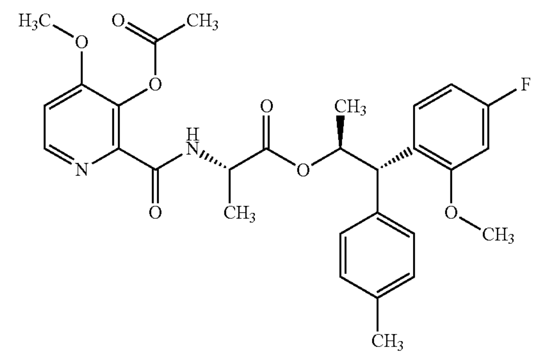 [SMILES: COc1cc(F)ccc1[C@H](c1ccc(C)cc1)[C@H](C)OC(=O)[C@H](C)NC(=O)c1nccc(OC)c1OC(C)=O] | Example 6A | Colorless Foam |
| 528 | 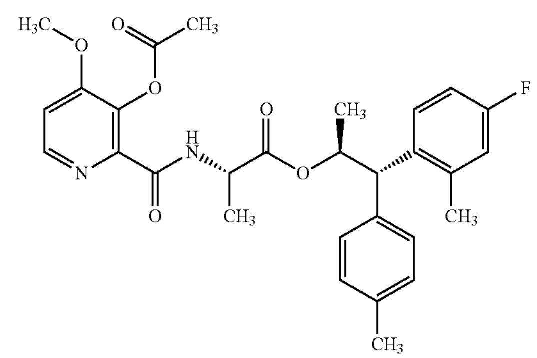 [SMILES: COc1ccnc(C(=O)N[C@@H](C)C(=O)O[C@@H](C)[C@@H](c2ccc(C)cc2)c2ccc(F)cc2C)c1OC(C)=O] | Example 6A | Colorless Foam |
| 529 | 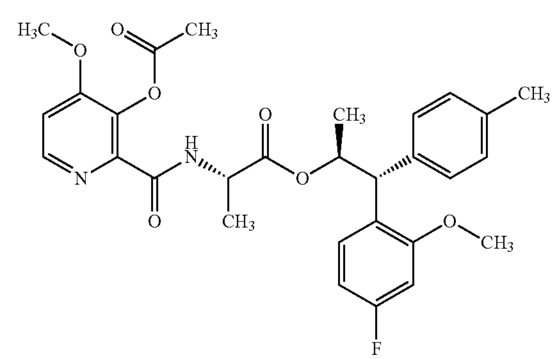 [SMILES: COc1cc(F)ccc1[C@@H](c1ccc(C)cc1)[C@H](C)OC(=O)[C@H](C)NC(=O)c1nccc(OC)c1OC(C)=O] | Example 6A | Colorless Foam |
| 530 | 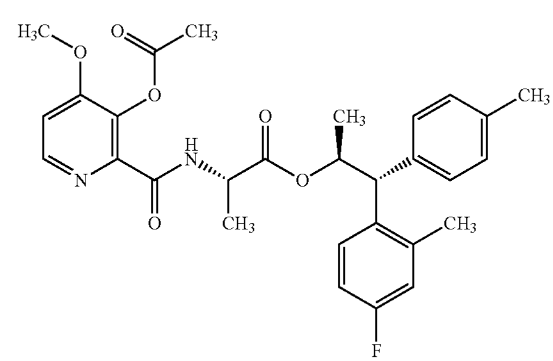 [SMILES: COc1ccnc(C(=O)N[C@@H](C)C(=O)O[C@@H](C)[C@H](c2ccc(C)cc2)c2ccc(F)cc2C)c1OC(C)=O] | Example 6A | Colorless Foam |

TABLE 1-continued

Compound Structure, Preparation Method, and Appearance

| *Cmpd. No. | Structure | Prepared According To Example | Appearance |
|---|---|---|---|
| 531 | 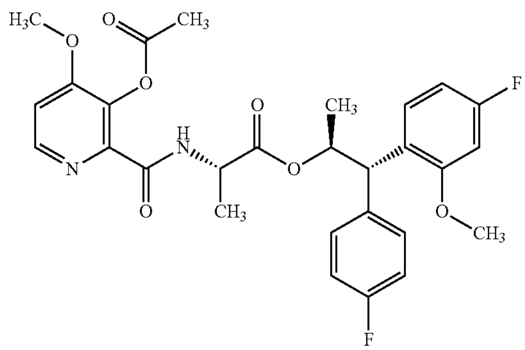 [SMILES: COc1cc(F)ccc1[C@H](c1ccc(F)cc1)[C@H](C)OC(=O)[C@H](C)NC(=O)c1nccc(OC)c1OC(C)=O] | Example 6A | Colorless Oil |
| 532 | 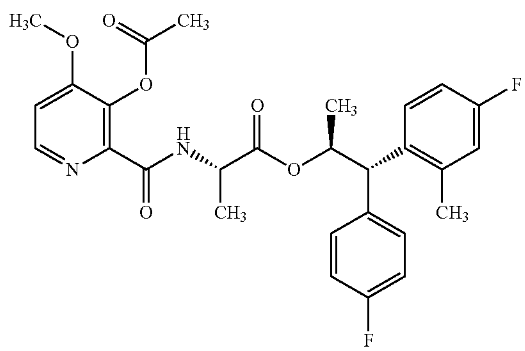 [SMILES: COc1ccnc(C(=O)N[C@@H](C)C(=O)O[C@@H](C)[C@@H](c2ccc(F)cc2)c2ccc(F)cc2C)c1OC(C)=O] | Example 6A | Colorless Oil |
| 533 | 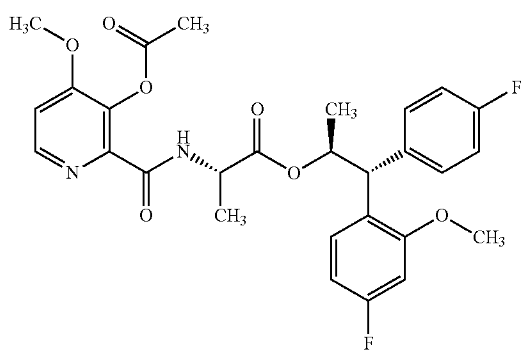 [SMILES: COc1cc(F)ccc1[C@@H](c1ccc(F)cc1)[C@H](C)OC(=O)[C@H](C)NC(=O)c1nccc(OC)c1OC(C)=O] | Example 6A | Colorless Oil |
| 534 | 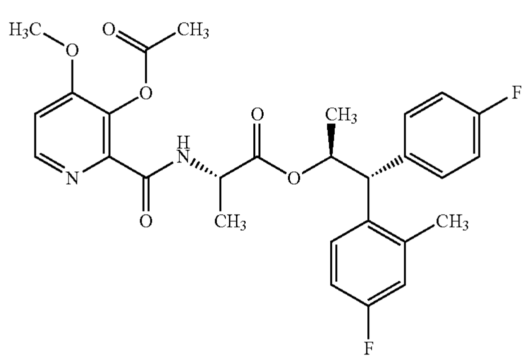 [SMILES: COc1ccnc(C(=O)N[C@@H](C)C(=O)O[C@@H](C)[C@H](c2ccc(F)cc2)c2ccc(F)cc2C)c1OC(C)=O] | Example 6A | Colorless Oil |

TABLE 1-continued

Compound Structure, Preparation Method, and Appearance

| *Cmpd. No. | Structure | Prepared According To Example | Appearance |
|---|---|---|---|
| 535 | 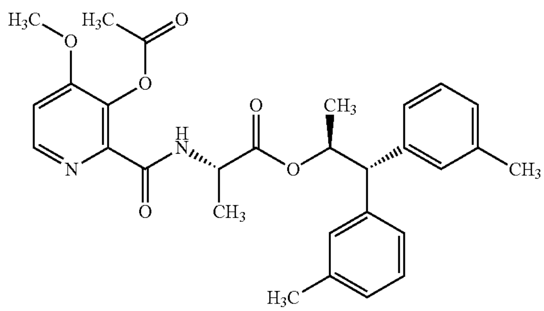 | Example 6A. | White Foam |
| 536 | 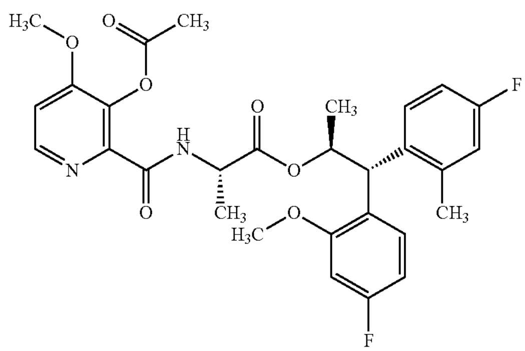 [SMILES: COc1cc(F)ccc1[C@@H](c1ccc(F)cc1C)[C@H](C)OC(=O)[C@H](C)NC(=O)c1nccc(OC)c1OC(C)=O] | Example 6A. | White Foam |
| 537 | 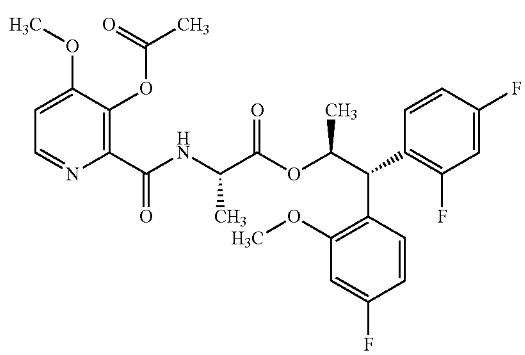 [SMILES: COc1cc(F)ccc1[C@@H](c1ccc(F)cc1F)[C@H](C)OC(=O)[C@H](C)NC(=O)c1nccc(OC)c1OC(C)=O] | Example 6A. | White Foam |
| 538 | 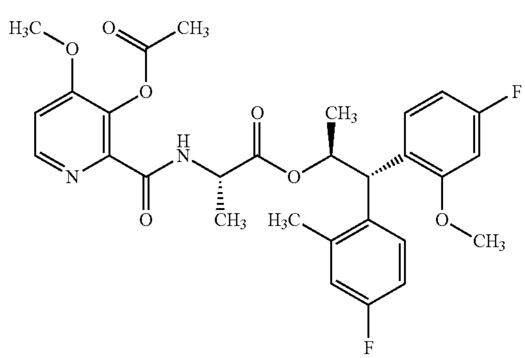 [SMILES: COc1cc(F)ccc1[C@H](c1ccc(F)cc1C)[C@H](C)OC(=O)[C@H](C)NC(=O)c1nccc(OC)c1OC(C)=O] | Example 6A. | White Foam |

TABLE 1-continued

Compound Structure, Preparation Method, and Appearance

| *Cmpd. No. | Structure | Prepared According To Example | Appearance |
|---|---|---|---|
| 539 | 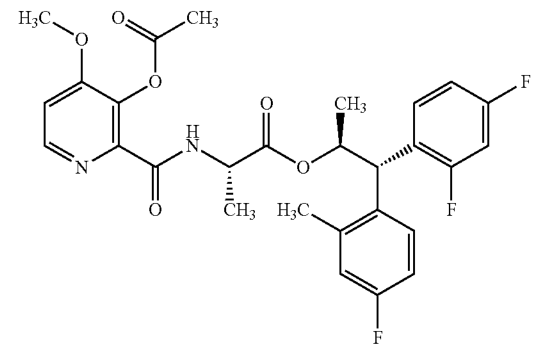 [SMILES: COc1ccnc(C(=O)N[C@@H](C)C(=O)O[C@@H](C)[C@@H](c2ccc(F)cc2C)c2ccc(F)cc2F)c1OC(C)=O] | Example 6A. | White Foam |
| 540 | 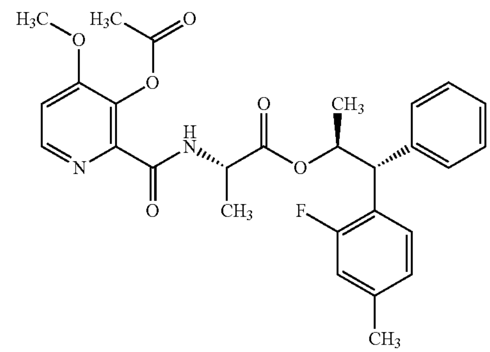 [SMILES: COc1ccnc(C(=O)N[C@@H](C)C(=O)O[C@@H](C)[C@H](c2ccccc2)c2ccc(C)cc2F)c1OC(C)=O] | Example 6A. | White Foam |
| 541 | 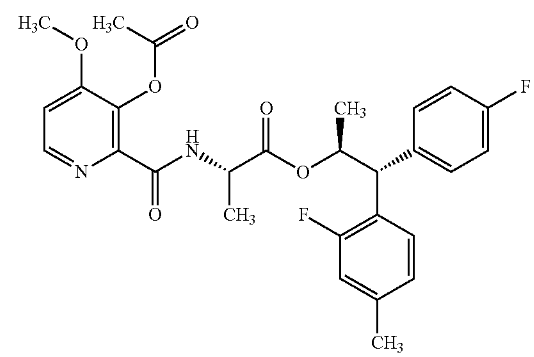 [SMILES: COc1ccnc(C(=O)N[C@@H](C)C(=O)O[C@@H](C)[C@H](c2ccc(F)cc2)c2ccc(C)cc2F)c1OC(C)=O] | Example 6A. | White Foam |
| 542 | 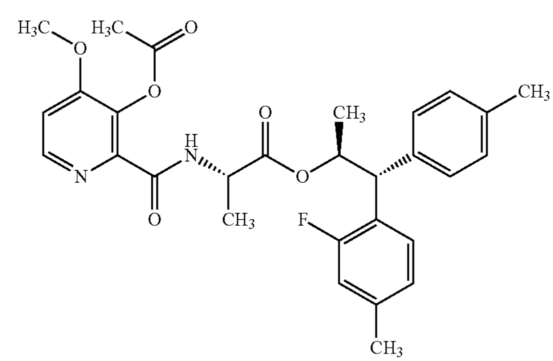 [SMILES: COc1ccnc(C(=O)N[C@@H](C)C(=O)O[C@@H](C)[C@H](c2ccc(C)cc2)c2ccc(C)cc2F)c1OC(C)=O] | Example 6A. | White Foam |

TABLE 1-continued

Compound Structure, Preparation Method, and Appearance

| *Cmpd. No. | Structure | Prepared According To Example | Appearance |
|---|---|---|---|
| 543 | 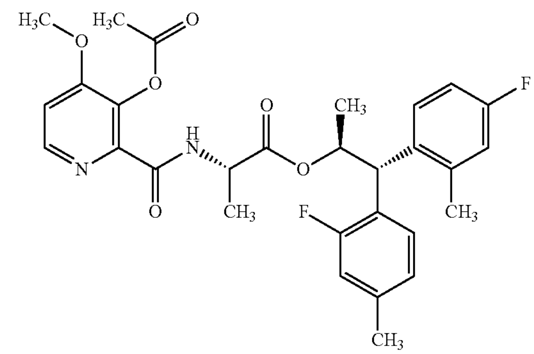 [SMILES: COc1ccnc(C(=O)N[C@@H](C)C(=O)O[C@@H](C)[C@H](c2ccc(F)cc2C)c2ccc(C)cc2F)c1OC(C)=O] | Example 6A. | White Foam |
| 544 | 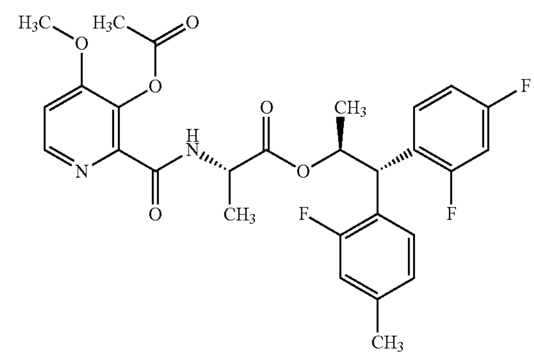 [SMILES: COc1ccnc(C(=O)N[C@@H](C)C(=O)O[C@@H](C)[C@@H](c2ccc(C)cc2F)c2ccc(F)cc2F)c1OC(C)=O] | Example 6A. | White Foam |
| 545 | 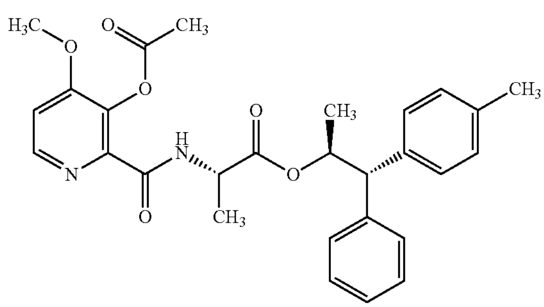 [SMILES: COc1ccnc(C(=O)N[C@@H](C)C(=O)O[C@@H](C)[C@@H](c2ccccc2)c2ccc(C)cc2)c1OC(C)=O] | Example 6A. | White Foam |
| 546 | 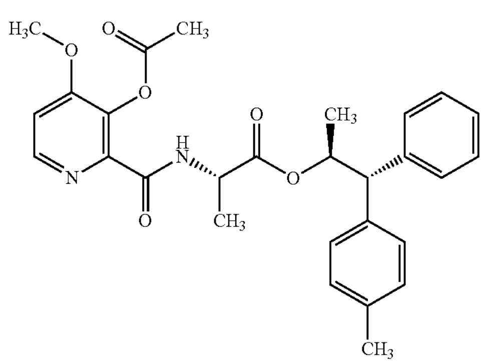 [SMILES: COc1ccnc(C(=O)N[C@@H](C)C(=O)O[C@@H](C)[C@H](c2ccccc2)c2ccc(C)cc2)c1OC(C)=O] | Example 6A. | White Foam |

TABLE 1-continued

Compound Structure, Preparation Method, and Appearance

| *Cmpd. No. | Structure | Prepared According To Example | Appearance |
|---|---|---|---|
| 547 | 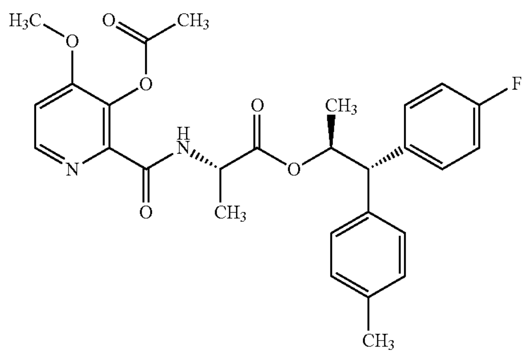 [SMILES: COc1ccnc(C(=O)N[C@@H](C)C(=O)O[C@@H](C)[C@@H](c2ccc(C)cc2)c2ccc(F)cc2)c1OC(C)=O] | Example 6A. | White Foam |
| 548 | 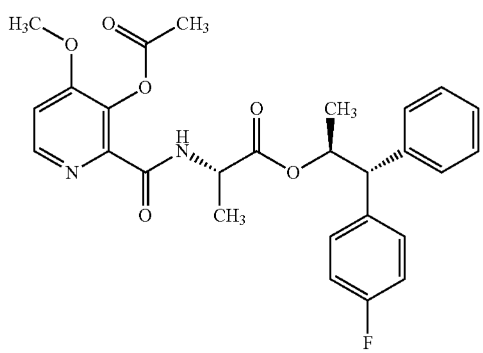 [SMILES: COc1ccnc(C(=O)N[C@@H](C)C(=O)O[C@@H](C)[C@H](c2ccccc2)c2ccc(F)cc2)c1OC(C)=O] | Example 6A. | White Foam |
| 549 | 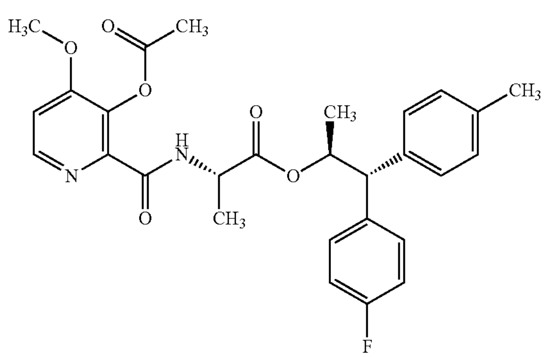 [SMILES: COc1ccnc(C(=O)N[C@@H](C)C(=O)O[C@@H](C)[C@H](c2ccc(C)cc2)c2ccc(F)cc2)c1OC(C)=O] | Example 6A. | White Foam |
| 550 | 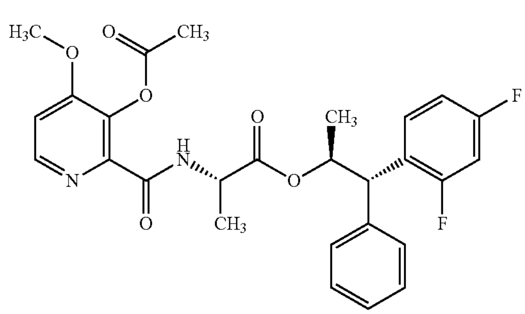 | Example 6A. | White Foam |

TABLE 1-continued
Compound Structure, Preparation Method, and Appearance
| *Cmpd. No. | Structure | Prepared According To Example | Appearance |
|---|---|---|---|
| 551 | 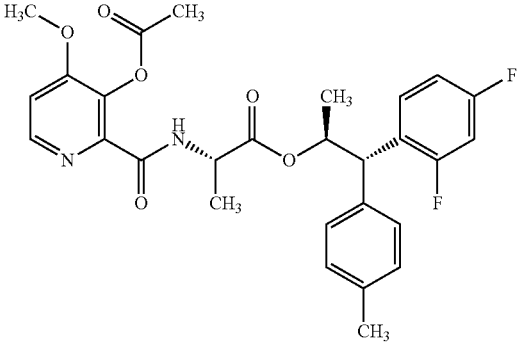 | Example 6A. | White Foam |
| 552 | 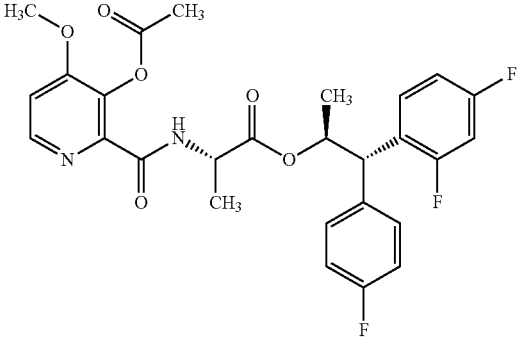 [SMILES: COc1ccnc(C(=O)N[C@@H](C)C(=O)O[C@@H](C)[C@@H](c2ccc(F)cc2)c2ccc(F)cc2F)c1OC(C)=O] | Example 6A. | White Foam |
| 553 | 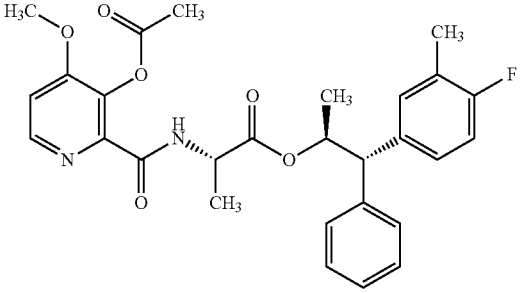 [SMILES: COc1ccnc(C(=O)N[C@@H](C)C(=O)O[C@@H](C)[C@@H](c2ccccc2)c2ccc(F)c(C)c2)c1OC(C)=O] | Example 6A | Colorless Foam |
| 554 | 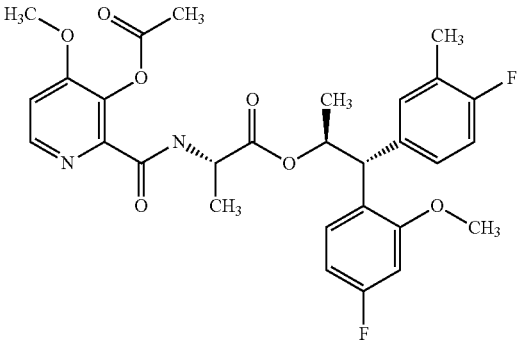 [SMILES: COc1cc(F)ccc1[C@@H](c1ccc(F)c(C)c1)[C@H](C)OC(=O)[C@H](C)NC(=O)c1nccc(OC)c1OC(C)=O] | Example 6A | Colorless Foam |
*Cmpd. No. - Compound Number

| Lengthy table referenced here | | Lengthy table referenced here |
|---|---|---|
| US10182568-20190122-T00001 | | US10182568-20190122-T00004 |
| Please refer to the end of the specification for access instructions. | | Please refer to the end of the specification for access instructions. |
| Lengthy table referenced here | | Lengthy table referenced here |
| US10182568-20190122-T00002 | | US10182568-20190122-T00005 |
| Please refer to the end of the specification for access instructions. | | Please refer to the end of the specification for access instructions. |
| Lengthy table referenced here | | Lengthy table referenced here |
| US10182568-20190122-T00003 | | US10182568-20190122-T00006 |
| Please refer to the end of the specification for access instructions. | | Please refer to the end of the specification for access instructions. |

LENGTHY TABLES

The patent contains a lengthy table section. A copy of the table is available in electronic form from the USPTO web site (http://seqdata.uspto.gov/?pageRequest=docDetail&DocID=US10182568B2). An electronic copy of the table will also be available from the USPTO upon request and payment of the fee set forth in 37 CFR 1.19(b)(3).

What is claimed is:

1. A composition for the control of a fungal pathogen including mixtures of at least one of the compounds of Formula 1

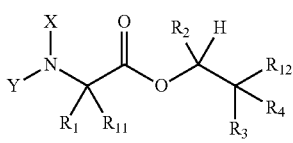

wherein:
X is hydrogen or $C(O)R_5$;
Y is hydrogen, $C(O)R_5$, or Q;
Q is

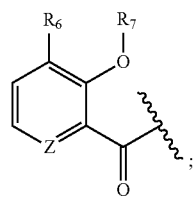

wherein: Z is N;
$R_1$ is hydrogen or alkyl, substituted with 0, 1 or multiple $R_8$;
$R_2$ is methyl;
$R_3$ is chosen from aryl or heteroaryl, each optionally substituted with 0, 1 or multiple $R_8$;
$R_4$ is chosen from hydrogen, halo, hydroxyl, alkyl or alkoxy;
$R_5$ is chosen from alkoxy or benzyloxy, each optionally substituted with 0, 1, or multiple $R_8$;
$R_6$ is chosen from hydrogen, alkoxy, or halo, each optionally substituted with 0, 1, or multiple $R_8$;
$R_7$ is chosen from hydrogen, —$C(O)R_9$, or —$CH_2OC(O)R_9$;
$R_8$ is chosen from hydrogen, alkyl, aryl, acyl, halo, alkenyl, alkynyl, alkoxy, cyano, or heterocyclyl, each optionally substituted with 0, 1, or multiple $R_{10}$,
$R_9$ is chosen from alkyl, alkoxy, or aryl, each optionally substituted with 0, 1, or multiple $R_8$;
$R_{10}$ is chosen from hydrogen, alkyl, aryl, acyl, halo, alkenyl, alkoxy, or heterocyclyl;
$R_{11}$ is chosen from hydrogen or alkyl, substituted with 0, 1 or multiple $R_8$;
$R_{12}$ is chosen from aryl or heteroaryl, each optionally substituted with 0, 1 or multiple $R_8$; and
a phytologically acceptable carrier material.

2. The composition according to claim 1, wherein X is hydrogen and Y is Q.

3. The composition according to claim 2, wherein $R_6$ is alkoxy.

4. The composition according to claim 3, wherein $R_7$ is hydrogen.

5. The composition according to claim 4, wherein $R_1$ and $R_{11}$ are independently chosen from hydrogen or alkyl, $R_3$ and $R_{12}$ are independently aryl, each optionally substituted with 0, 1 or multiple $R_8$, and $R_4$ is H.

6. The composition according to claim 3, wherein $R_7$ is chosen from —$C(O)R_9$, or —$CH_2OC(O)R_9$.

7. The composition according to claim 6, wherein $R_9$ is alkyl, optionally substituted with 0, 1 or multiple $R_8$.

8. The composition according to claim 7, wherein $R_1$ and $R_{11}$ are independently chosen from hydrogen or alkyl, $R_3$ and $R_{12}$ are independently aryl, each optionally substituted with 0, 1 or multiple $R_8$, and $R_4$ is H.

9. The composition according to claim 8, wherein $R_9$ is chosen from —$CH_3$, —$CH_2OCH_2CH_3$, —$CH_2CH_2OCH_3$, —$CH(CH_3)_2$, —$CH_2CH_2CH_2CH_3$, -cyclopropyl.

10. The composition according to claim 1 wherein the fungal pathogen is one of Leaf Blotch of Wheat (*Zymoseptoria tritici*), Wheat Brown Rust (*Puccinia triticina*), Stripe Rust (*Puccinia striiformis*), Scab of Apple (*Venturia inaequalis*), Blister Smut of Maize (*Ustilago maydis*), Powdery Mildew of Grapevine (*Uncinula necator*), Barley scald (*Rhynchosporium secalis*), Blast of Rice (*Pyricularia oryzae*), Rust of Soybean (*Phakopsora pachyrhizi*), Glume Blotch of Wheat (*Leptosphaeria nodorum*), Powdery Mildew of Wheat (*Blumeria graminis* f. sp. *tritici*), Powdery Mildew of Barley (*Blumeria graminis* f. sp. *hordei*), Powdery Mildew of Cucurbits (*Erysiphe cichoracearum*), Anthracnose of Cucurbits (*Colletotrichum lagenarium*), Leaf Spot of Beet (*Cercospora beticola*), Early Blight of Tomato (*Alternaria solani*), and Net Blotch of Barley (*Pyrenophora teres*).

11. The composition according to claim 5 wherein the fungal pathogen is one of Leaf Blotch of Wheat (*Zymoseptoria tritici*), Wheat Brown Rust (*Puccinia triticina*), Scab of Apple (*Venturia inaequalis*), Barley scald (*Rhynchosporium secalis*), Blast of Rice (*Pyricularia oryzae*), Rust of Soybean (*Phakopsora pachyrhizi*), Glume Blotch of Wheat (*Leptosphaeria nodorum*), Anthracnose of Cucurbits (*Colletotrichum lagenarium*), Leaf Spot of Beet (*Cercospora beticola*), and Early Blight of Tomato (*Alternaria solani*).

12. The composition according to claim 6 wherein the fungal pathogen is one Leaf Blotch of Wheat (*Zymoseptoria tritici*), Wheat Brown Rust (*Puccinia triticina*), Scab of Apple (*Venturia inaequalis*), Barley scald (*Rhynchosporium secalis*), Blast of Rice (*Pyricularia oryzae*), Rust of Soybean (*Phakopsora pachyrhizi*), Glume Blotch of Wheat (*Leptosphaeria nodorum*), Anthracnose of Cucurbits (*Colletotrichum lagenarium*), Leaf Spot of Beet (*Cercospora beticola*), and Early Blight of Tomato (*Alternaria solani*).

13. The composition according to claim 8 wherein the fungal pathogen is one of Leaf Blotch of Wheat (*Zymoseptoria tritici*), Wheat Brown Rust (*Puccinia triticina*), Scab of Apple (*Venturia inaequalis*), Barley scald (*Rhynchosporium secalis*), Blast of Rice (*Pyricularia oryzae*), Rust of Soybean (*Phakopsora pachyrhizi*), Glume Blotch of Wheat (*Leptosphaeria nodorum*), Anthracnose of Cucurbits (*Colletotrichum lagenarium*), Leaf Spot of Beet (*Cercospora beticola*), and Early Blight of Tomato (*Alternaria solani*).

14. The composition according to claim 9 wherein the fungal pathogen is one of Leaf Blotch of Wheat (*Zymoseptoria tritici*), Wheat Brown Rust (*Puccinia triticina*), Scab of Apple (*Venturia inaequalis*), Barley scald (*Rhynchosporium secalis*), Blast of Rice (*Pyricularia oryzae*), Rust of Soybean (*Phakopsora pachyrhizi*), Glume Blotch of Wheat (*Leptosphaeria nodorum*), Anthracnose of Cucurbits (*Colletotrichum lagenarium*), Leaf Spot of Beet (*Cercospora beticola*), and Early Blight of Tomato (*Alternaria solani*).

15. A method for the control and prevention of fungal attack on a plant, the method including the step of:
applying a fungicidally effective amount of at least one of the compositions of claim 5 to at least one of the plant, an area adjacent to the plant, soil adapted to support growth of the plant, a root of the plant, and foliage of the plant.

16. A method for the control and prevention of fungal attack on a plant, the method including the step of:
applying a fungicidally effective amount of at least one of the compositions of claim 8 to at least one of the plant, an area adjacent to the plant, soil adapted to support growth of the plant, a root of the plant, and foliage of the plant.

17. A method for the control and prevention of fungal attack on a plant, the method including the step of:
applying a fungicidally effective amount of at least one of the compositions of claim 9 to at least one of the plant, an area adjacent to the plant, soil adapted to support growth of the plant, a root of the plant, and foliage of the plant.

18. A method for the control and prevention of fungal attack on a plant, the method including the step of:
applying a fungicidally effective amount of at least one of the compositions of claim 10 to at least one of the plant, an area adjacent to the plant, soil adapted to support growth of the plant, a root of the plant, and foliage of the plant.

19. A method for the control and prevention of fungal attack on a plant, the method including the step of:
applying a fungicidally effective amount of at least one of the compositions of claim 14 to at least one of the plant, an area adjacent to the plant, soil adapted to support growth of the plant, a root of the plant, and foliage of the plant.

* * * * *